United States Patent
Li et al.

(10) Patent No.: US 10,874,679 B2
(45) Date of Patent: *Dec. 29, 2020

(54) BORON-CONTAINING SMALL MOLECULES

(71) Applicant: Bill & Melinda Gates Foundation, Seattle, WA (US)

(72) Inventors: Xianfeng Li, Cupertino, CA (US); Christopher S Lunde, Belmont, CA (US); Robert T Jacobs, Wake Forest, NC (US); Yasheen Zhou, Moraga, CA (US)

(73) Assignee: Bill & Melinda Gates Foundation, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/840,239

(22) Filed: Apr. 3, 2020

(65) Prior Publication Data

US 2020/0230160 A1   Jul. 23, 2020

Related U.S. Application Data

(63) Continuation of application No. 16/081,904, filed as application No. PCT/US2017/019658 on Feb. 27, 2017, now Pat. No. 10,611,781.

(60) Provisional application No. 62/302,591, filed on Mar. 2, 2016.

(51) Int. Cl.
*A61K 31/69* (2006.01)
*A61P 31/04* (2006.01)
*C07F 5/02* (2006.01)
*A61K 45/06* (2006.01)

(52) U.S. Cl.
CPC ............. *A61K 31/69* (2013.01); *A61K 45/06* (2013.01); *A61P 31/04* (2018.01); *C07F 5/027* (2013.01)

(58) Field of Classification Search
CPC .................................. C07F 5/025; C07F 5/02
USPC ......................................................... 514/64
See application file for complete search history.

(56) References Cited

U.S. PATENT DOCUMENTS

| 6,239,175 B1 * | 5/2001 | Hinks ............... C07D 285/125 514/480 |
| 10,611,781 B2 * | 4/2020 | Li ..................... C07F 5/025 |

| 2006/0234981 A1 | 10/2006 | Baker et al. |
| 2007/0155699 A1 | 7/2007 | Baker et al. |
| 2007/0293457 A1 | 12/2007 | Baker et al. |
| 2009/0227541 A1 | 9/2009 | Baker et al. |
| 2011/0212918 A1 | 9/2011 | Hernandez et al. |
| 2013/0231304 A1 | 9/2013 | Jacobs et al. |
| 2016/0340369 A1 | 11/2016 | Chen et al. |

FOREIGN PATENT DOCUMENTS

| CN | 1283197 A | 2/2001 |
| CN | 101160124 A | 4/2008 |
| WO | 9921855 A1 | 5/1999 |
| WO | 2006/089067 A2 | 8/2006 |
| WO | 2011/017125 A1 | 2/2011 |
| WO | 2014/176634 A1 | 11/2014 |
| WO | 2017/151492 A1 | 9/2017 |

OTHER PUBLICATIONS

Berge, S. et al. "Pharmaceutical Salts" Journal of Pharmaceutical Sciences, Jan. 1977; vol. 66, No. 1; 19 pages.
Clare, R. et al. "Development and Validation of a High-Throughput Anti-Wolbachia Whole-Cell Screen: A Route to Macrofilaricidal Drugs against Onchocerciasis and Lymphatic Filariasi" Journal of Biomolecular Screening, 2015; vol. 20, No. 1; pp. 64-69.
EPO, Extended European Search Report for European Application No. 17760540.9. dated Oct. 7, 2019. 10 pages.
Hunt, E. "Pleuromutilin antibiotics" Drugs of the Future, Jan. 2000, vol. 25, No. 11, pp. 1163-1168.
ISA, International Search Report for International Patent Application No. PCT/US2017/019658. dated Jul. 31, 2017. 4 pages.
Maehr, H. "A proposed new convention for graphic presentation of molecular geometry and topography" Journal of Chemical Education, 1985; vol. 62, No. 2, pp. 114-120.
National Center for Biotechnology Information. PubChem Database. SID 124342424, Source=Thomson Pharma, SID=124342424, https://pubchem.ncbi.nlm.nih.gov/substance/124342424.
Eccleston, et al. "2 Fluorescence-Based Assays," Progress in Medicinal chemistry, vol. 43, 2005, pp. 19-48.
Plumb, "Plumb's Veterinary Drug Handbook" Fifth Edition, 4 pages.
Office Action for Cn 201780027717.7, dated Aug. 4, 2020, 10 pages.

* cited by examiner

*Primary Examiner* — Kahsay Habte
(74) *Attorney, Agent, or Firm* — Perkins Coie LLP

(57) ABSTRACT

Compounds, pharmaceutical formulations, and methods of treating bacterial infections are disclosed.

21 Claims, No Drawings

BORON-CONTAINING SMALL MOLECULES

CROSS-REFERENCE TO RELATED APPLICATIONS

This is a continuation application of U.S. application Ser. No. 16/081,904, filed Sep. 1, 2018, which is a national phase application of International Patent Application No. PCT/US2017/019658, filed Feb. 27, 2017, which claims the benefit of U.S. Provisional Patent Application No. 62/302,591, filed Mar. 2, 2016, which is incorporated by reference in its entirety for all purpose.

BACKGROUND OF THE INVENTION

The present invention relates to organic compounds, such as pleuromutilins. Pleuromutilin, a compound having the following formula:

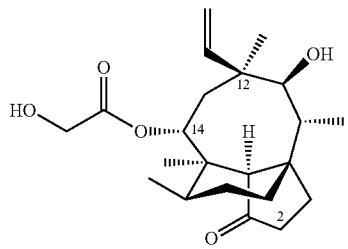

is a naturally occurring antibacterial, e.g. produced by the basidomycetes *Pleurotus mutilus* and *P. passeckerianus*, see e.g. The Merck Index, 13th edition, item 7617. Further modified pleuromutilins are also known.

Surprisingly, it has now been discovered that certain classes of pleuromutilins modified with boron are surprisingly effective antibacterials. This, and other uses of these compounds, are described herein.

SUMMARY OF THE INVENTION

In a first aspect, the invention provides a compound having a structure which is a salt or a hydrate or a solvate thereof, having a structure which is:

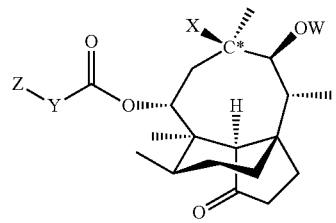

(I)

wherein the variables are as defined herein.

In a second aspect, the invention provides a combination comprising a compound of the invention together with at least one other therapeutically active agent.

In a third aspect, the invention provides a pharmaceutical formulation comprising: a) a compound of the invention; and b) a pharmaceutically acceptable excipient.

In a fourth aspect, the invention provides a method of inhibiting protein synthesis in a bacteria, the method comprising contacting the bacteria with a compound of the invention, thereby inhibiting protein synthesis in the bacteria.

In a fifth aspect, the invention provides a method of inhibiting the growth and/or killing a bacteria, the method comprising contacting the bacteria with the compound of the invention, thereby inhibiting the growth and/or killing the bacteria.

In a sixth aspect, the invention provides a method of treating a microbial disease and/or a worm disease in an animal, the method comprising administering to the animal a therapeutically effective amount of a compound of the invention, thereby treating the microbial disease and/or the worm disease.

DETAILED DESCRIPTION OF THE INVENTION

I. Definitions and Abbreviations

As used herein, the singular forms "a," "an", and "the" include plural references unless the context clearly dictates otherwise. For example, reference to "an active agent" includes a single active agent as well as two or more different active agents in combination. It is to be understood that present teaching is not limited to the specific dosage forms, carriers, or the like, disclosed herein and as such may vary.

The abbreviations used herein generally have their conventional meaning within the chemical and biological arts.

The following abbreviations have been used: Ac is acetyl; AcOH is acetic acid; ACTBr is cetyltrimethylammonium bromide; AIBN is azobisisobutyronitrile or 2,2 azobisisobutyronitrile; aq. is aqueous; Ar is aryl; $B_2pin_2$ is bis(pinacolato)diboron; Bn is, in general, benzyl [see Cbz for one example of an exception]; $(BnS)_2$ is benzyl disulfide; BnSH is benzyl thiol or benzyl mercaptan; BnBr is benzyl bromide; Boc is tert-butoxy carbonyl; $Boc_2O$ is di-tert-butyl dicarbonate; Bz is, in general, benzoyl; BzOOH is benzoyl peroxide; Cbz or Z is benzyloxycarbonyl or carboxybenzyl; $Cs_2CO_3$ is cesium carbonate; CSA is camphor sulfonic acid; CTAB is cetyltrimethylammonium bromide; Cy is cyclohexyl; DABCO is 1,4-diazabicyclo[2.2.2]octane; DCM is dichloromethane or methylene chloride; DHP is dihydropyran; DIAD is diisopropyl azodicarboxylate; DIEA or DIPEA is N,N-diisopropylethylamine; DMAP is 4-(dimethylamino)pyridine; DME is 1,2-dimethoxyethane; DMF is N,N-dimethylformamide; DMSO is dimethylsulfoxide; equiv or eq. is equivalent; EtOAc is ethyl acetate; EtOH is ethanol; $Et_2O$ is diethyl ether; EDCI is N-(3-dimethylaminopropyl)-N'-ethylcarbodiimide hydrochloride; ELS is evaporative light scattering; equiv or eq is equivalent; h is hours; HATU is O-(7-azabenzotriazol-1-yl)-N,N,N,N-tetramethyluronium hexafluorophosphate; HOBt is N-hydroxybenzotriazole; HCl is hydrochloric acid; HPLC is high pressure liquid chromatography; ISCO Companion is automated flash chromatography equipment with fraction analysis by UV absorption available from Presearch; KOAc or AcOK is potassium acetate; $K_2CO_3$ is potassium carbonate; LiAlH4 or LAH is lithium aluminum hydride; LDA is lithium diisopropylamide; LHMDS is lithium bis(trimethylsilyl) amide; KHMDS is potassium bis(trimethylsilyl) amide; LiOH is lithium hydroxide; m-CPBA is 3-chloroperoxybenzoic acid; MeCN or ACN is methyl cyanide or cyanomethane or ethanenitrile or acetonitrile which are all names for the same compound; MeOH is methanol; $MgSO_4$ is magnesium sulfate; mins or min is minutes; Mp or MP is melting point; $NaCNBH_3$ is sodium cyanoborohydride; NaOH is sodium hydroxide; $Na_2SO_4$ is sodium sulfate; NBS is N-bromosuccinimide; $NH_4Cl$ is ammonium chloride; NIS is N-iodosuccinimide; $N_2$ is nitrogen; NMM is N-methylmorpholine; n-BuLi is n-butyllithium; overnight is O/N; $PdCl_2$(pddf) is 1,1'-Bis (diphenylphosphino) ferroceneldichloropalladium(II); Pd/C is the catalyst known as palladium on carbon; $Pd_2(dba)_3$ is an organometallic catalyst known as tris(dibenzylideneacetone) dipalladium(0); Ra Ni or Raney Ni is Raney nickel; Ph is phenyl; PMB is p-methoxybenzyl; PrOH is 1-propanol; iPrOH is 2-propanol; $POCl_3$ is phosphorus chloride oxide; PTSA is para-toluene sulfonic acid; Pyr. or Pyr or Py as used herein means Pyridine; RT or rt or r.t. is room temperature; sat. is saturated; Si-amine or Si—$NH_2$ is amino-functionalized silica, available from SiliCycle; Si-pyr is pyridyl-functionalized silica, available from SiliCycle; TEA or $Et_3N$ is triethylamine; TFA is trifluoroacetic acid; $Tf_2O$ is trifluoromethanesulfonic anhydride; THF is tetrahydrofuran; TFAA is trifluoroacetic anhydride; THP is tetrahydropyranyl; TMSI is trimethylsilyl iodide; $H_2O$ is water; $diNO_2PhSO_2Cl$ is dinitrophenyl sulfonyl chloride; 3-F-4-$NO_2$-$PhSO_2Cl$ is 3-fluoro-4-nitrophenylsulfonyl chloride; 2-MeO-4-$NO_2$-$PhSO_2Cl$ is 2-methoxy-4-nitrophenylsulfonyl chloride; and $(EtO)_2POCH_2COOEt$ is a triethylester of phosphonoacetic acid known as triethyl phosphonoacetate.

"Compound of the invention," as used herein, refers to the compounds discussed herein, salts (e.g. pharmaceutically acceptable salts), prodrugs, solvates and hydrates of these compounds.

"Combination of the invention," as used herein, refers to the compounds and antiinflammatories discussed herein as well as acids, bases, salt forms (such as pharmaceutically acceptable salts), prodrugs, solvates and hydrates of these compounds and antiinflammatories.

"Boron containing compounds", as used herein, refers to the compounds of the invention that contain boron as part of their chemical formula.

The term "poly" as used herein means at least 2. For example, a polyvalent metal ion is a metal ion having a valency of at least 2.

"Moiety" refers to a radical of a molecule that is attached to the remainder of the molecule.

The symbol , whether utilized as a bond or displayed perpendicular to a bond, indicates the point at which the displayed moiety is attached to the remainder of the molecule.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). In some embodiments, the term "alkyl" means a straight or branched chain, or combinations thereof, which may be fully saturated, mono- or polyunsaturated and can include di- and multivalent radicals. Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "alkylene" by itself or as part of another substituent means a divalent radical derived from an alkane, as exemplified, but not limited, by —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the invention. A "lower alkyl" or "lower alkylene" is a shorter chain alkyl or alkylene group, generally having eight or fewer carbon atoms.

The term "alkenylene" by itself or as part of another substituent means a divalent radical derived from an alkene.

The term "cycloalkylene" by itself or as part of another substituent means a divalent radical derived from a cycloalkane.

The term "heteroalkylene" by itself or as part of another substituent means a divalent radical derived from an heteroalkane.

The term "heterocycloalkylene" by itself or as part of another substituent means a divalent radical derived from an heterocycloalkane.

The term "arylene" by itself or as part of another substituent means a divalent radical derived from an aryl.

The term "heteroarylene" by itself or as part of another substituent means a divalent radical derived from heteroaryl.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom. In some embodiments, the term "heteroalkyl," by itself or in combination with another term, means a stable straight or branched chain, or combinations thereof, consisting of the stated number of carbon atoms and at least one heteroatom. In an exemplary embodiment, the heteroatoms can be selected from the group consisting of B, O, N and S, and wherein the nitrogen and sulfur atoms may optionally be oxidized and the nitrogen heteroatom may optionally be quaternized. The heteroatom(s) B, O, N and S may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—$S(O)_2$—$CH_3$, —CH=CH—O—$CH_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)₂R'— represents both —C(O)₂R'— and —R' C(O)₂—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1 (1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1 piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 or 2 or 3 rings), which are fused together or linked covalently. The term "heteroaryl" refers to aryl groups (or rings) that contain from one to four heteroatoms. In an exemplary embodiment, the heteroatom is selected from B, N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —R', —OR', =O, =NR', =N—OR', —NR'R", —SR', -halogen, —SiR'R"R'", —OC(O)R', —C(O)R', —CO₂R', —CONR'R", —OC(O)NR'R", —NR"C(O)R', —NR'—C(O)NR"R'", —NR"C(O)₂R', —NR""-C(NR'R"R'")=NR"", —NR""—C(NR'R")=NR'", —S(O)R', —S(O)₂R', —S(O)₂NR'R", —NR"SO₂R', —CN, —NO₂, —N₃, —CH(Ph)₂, fluoro($C_1$-$C_4$)alkoxy, and fluoro($C_1$-$C_4$)alkyl, in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'", R"" and R"'" groups when more than one of these groups is present. When R' and R" are attached to the same nitrogen atom, they can be combined with the nitrogen atom to form a 5-, 6-, or 7-membered ring. For example, —NR'R" is meant to include, but not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF₃ and —CH₂CF₃) and acyl (e.g., —C(O)CH₃, —C(O)CF₃, —C(O)CH₂OCH₃, and the like).

Similar to the substituents described for the alkyl radical, substituents for the aryl and heteroaryl groups are generically referred to as "aryl group substituents." The substituents are selected from, for example: —R', —OR', =O, =NR', =N—OR', —NR'R", —SR', -halogen, —SiR'R"R'", —OC(O)R', —C(O)R', —CO₂R', —CONR'R", —OC(O)NR'R", —NR"C(O)R', —NR'—C(O)NR"R'", —NR"C(O)₂R', —NR""-C(NR'R"R'")=NR"", —NR""—C(NR'R")=NR'", —S(O)R', —S(O)₂R', —S(O)₂NR'R", —NR"SO₂R', —CN, —NO₂, —N₃, —CH(Ph)₂, fluoro($C_1$-$C_4$)alkoxy, and fluoro($C_1$-$C_4$)alkyl, in a number ranging from zero to the total number of open valences on the aromatic ring system; and where R', R", R'" and R"" are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R'", R"" and R"'" groups when more than one of these groups is present.

Two of the substituents on adjacent atoms of the aryl or heteroaryl ring may optionally be replaced with a substituent of the formula T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula A-(CH₂)$_r$—B—, wherein A and B are independently —CRR'—, —O—, —NR—, —S—, —S(O)—, —S(O)₂—, —S(O)₂NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula (CRR')$_s$—X—(CR"R'")$_d$—, where s and d are independently integers of from 0 to 3, and X is —O—, —NR'—, —S—, —S(O)—, —S(O)$_2$—, or —S(O)$_2$NR'—. The substituents R, R', R" and R''' are preferably independently selected from hydrogen or substituted or unsubstituted C$_1$ or C$_2$ or C$_3$ or C$_4$ or C$_5$ or C$_6$ alkyl.

"Ring" as used herein, means a substituted or unsubstituted cycloalkyl, substituted or unsubstituted heterocycloalkyl, substituted or unsubstituted aryl, or substituted or unsubstituted heteroaryl. A ring includes fused ring moieties. The number of atoms in a ring is typically defined by the number of members in the ring. For example, a "5- to 7-membered ring" means there are 5 or 6 or 7 atoms in the encircling arrangement. Unless otherwise specified, the ring optionally includes a heteroatom. Thus, the term "5- to 7-membered ring" includes, for example phenyl, pyridinyl and piperidinyl. The term "5- to 7-membered heterocycloalkyl ring", on the other hand, would include pyridinyl and piperidinyl, but not phenyl. The term "ring" further includes a ring system comprising more than one "ring", wherein each "ring" is independently defined as above.

As used herein, the term "heteroatom" includes atoms other than carbon (C) and hydrogen (H). Examples include oxygen (O), nitrogen (N), sulfur (S), silicon (Si), germanium (Ge), aluminum (Al) and boron (B).

The term "leaving group" means a functional group or atom which can be displaced by another functional group or atom in a substitution reaction, such as a nucleophilic substitution reaction. By way of example, representative leaving groups include triflate, chloro, bromo and iodo groups; sulfonic ester groups, such as mesylate, tosylate, brosylate, nosylate and the like; and acyloxy groups, such as acetoxy, trifluoroacetoxy and the like.

The symbol "R" is a general abbreviation that represents a substituent group that is selected from substituted or unsubstituted alkyl, substituted or unsubstituted heteroalkyl, substituted or unsubstituted aryl, substituted or unsubstituted heteroaryl, substituted or unsubstituted cycloalkyl and substituted or unsubstituted heterocycloalkyl groups.

By "effective" amount of a drug, formulation, or permeant is meant a sufficient amount of an active agent to provide the desired local or systemic effect. A "Topically effective," "pharmaceutically effective," or "therapeutically effective" amount refers to the amount of drug needed to effect the desired therapeutic result.

"Topically effective" refers to a material that, when applied to the skin, nail, hair, claw or hoof produces a desired pharmacological result either locally at the place of application or systemically as a result of transdermal passage of an active ingredient in the material.

The term "pharmaceutically acceptable salt" is meant to include a salt of a compound of the invention which is prepared with relatively nontoxic acids or bases, depending on the particular substituents found on the compounds described herein.

When compounds of the invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino (such as choline or diethylamine or amino acids such as d-arginine, l-arginine, d-lysine, l-lysine), or magnesium salt, or a similar salt. When compounds of the invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", Journal of Pharmaceutical Science 66: 1-19 (1977)). Certain specific compounds of the invention contain both basic and acidic functionalities that allow the compounds to be converted into either base or acid addition salts.

The neutral forms of the compounds are preferably regenerated by contacting the salt with a base or acid and isolating the parent compounds in the conventional manner. The parent form of the compound differs from the various salt forms in certain physical properties, such as solubility in polar solvents.

In addition to salt forms, the invention provides compounds which are in a prodrug form. Prodrugs of the compounds described herein readily undergo chemical changes under physiological conditions to provide the compounds of the invention. Additionally, prodrugs can be converted to the compounds of the invention by chemical or biochemical methods in an ex vivo environment.

Certain compounds of the invention can exist in unsolvated forms as well as solvated forms, including hydrated forms. In general, the solvated forms are equivalent to unsolvated forms and are encompassed within the scope of the invention. Certain compounds of the invention may exist in multiple crystalline or amorphous forms.

Certain compounds of the invention possess asymmetric carbon atoms (optical centers) or double bonds; the racemates, diastereomers, geometric isomers and individual isomers are encompassed within the scope of the invention. The graphic representations of racemic, ambiscalemic and scalemic or enantiomerically pure compounds used herein are taken from Maehr, J. Chem. Ed. 1985, 62: 114-120. Solid and broken wedges are used to denote the absolute configuration of a stereocenter unless otherwise noted. When the compounds described herein contain olefinic double bonds or other centers of geometric asymmetry, and unless specified otherwise, it is intended that the compounds include both E and Z geometric isomers. Likewise, all tautomeric forms are included.

Compounds of the invention can exist in particular geometric or stereoisomeric forms. The invention contemplates all such compounds, including cis- and trans-isomers, (−)- and (+)-enantiomers, (R)- and (S)-enantiomers, diastereomers, (D)-isomers, (L)-isomers, the racemic mixtures thereof, and other mixtures thereof, such as enantiomerically or diastereomerically enriched mixtures, as falling within the scope of the invention. Additional asymmetric carbon atoms can be present in a substituent such as an alkyl group. All such isomers, as well as mixtures thereof, are intended to be included in this invention.

Optically active (R)- and (S)-isomers and d and/isomers can be prepared using chiral synthons or chiral reagents, or resolved using conventional techniques. If, for instance, a particular enantiomer of a compound of the invention is desired, it can be prepared by asymmetric synthesis, or by derivatization with a chiral auxiliary, where the resulting diastereomeric mixture is separated and the auxiliary group cleaved to provide the pure desired enantiomers. Alternatively, where the molecule contains a basic functional group, such as an amino group, or an acidic functional group, such as a carboxyl group, diastereomeric salts can be formed with an appropriate optically active acid or base, followed by resolution of the diastereomers thus formed by fractional crystallization or chromatographic means known in the art, and subsequent recovery of the pure enantiomers. In addition, separation of enantiomers and diastereomers is frequently accomplished using chromatography employing chiral, stationary phases, optionally in combination with chemical derivatization (e.g., formation of carbamates from amines).

The compounds of the invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). The compounds may also be labeled with stable isotopes such as deuterium. All isotopic variations of the compounds of the invention, whether radioactive or not, are intended to be encompassed within the scope of the invention.

The term "pharmaceutically acceptable carrier" or "pharmaceutically acceptable vehicle" refers to any formulation or carrier medium that provides the appropriate delivery of an effective amount of an active agent as defined herein, does not interfere with the effectiveness of the biological activity of the active agent, and that is sufficiently non-toxic to the animal. Representative carriers include water, oils, both vegetable and mineral, cream bases, lotion bases, ointment bases and the like. These bases include suspending agents, thickeners, penetration enhancers, and the like. Their formulation is well known to those in the pharmaceutical arts. Additional information concerning carriers can be found in *Remington: The Science and Practice of Pharmacy*, 21st Ed., Lippincott, Williams & Wilkins (2005) which is incorporated herein by reference.

The term "pharmaceutically acceptable additive" refers to preservatives, antioxidants, fragrances, emulsifiers, dyes and excipients known or used in the field of drug formulation and that do not unduly interfere with the effectiveness of the biological activity of the active agent, and that is sufficiently non-toxic to the animal. Additives for topical formulations are well-known in the art, and may be added to the topical composition, as long as they are pharmaceutically acceptable and not deleterious to the epithelial cells or their function. Further, they should not cause deterioration in the stability of the composition. For example, inert fillers, anti-irritants, tackifiers, excipients, fragrances, opacifiers, antioxidants, gelling agents, stabilizers, surfactant, emollients, coloring agents, preservatives, buffering agents, other permeation enhancers, and other conventional components of topical or transdermal delivery formulations as are known in the art.

The term "excipients" is conventionally known to mean carriers, diluents, vehicles, and or additives used in formulating drug compositions effective for the desired use.

The terms "effective amount" or a "therapeutically effective amount" of a drug or pharmacologically active agent refers to a nontoxic but sufficient amount of the drug or agent to provide the desired effect. In the oral dosage forms of the present disclosure, an "effective amount" of one active of the combination is the amount of that active that is effective to provide the desired effect when used in combination with the other active of the combination. The amount that is "effective" will vary from subject to subject, depending on the age and general condition of the individual, the particular active agent or agents, and the appropriate "effective" amount in any individual case may be determined by one of ordinary skill in the art using routine experimentation.

The phrases "active ingredient", "therapeutic agent", "active", or "active agent" mean a chemical entity which can be effective in treating a targeted disorder, disease or condition.

The phrase "pharmaceutically acceptable" means moieties or compounds that are, within the scope of medical judgment, suitable for use in humans without causing undesirable biological effects such as undue toxicity, irritation, allergic response, and the like, for example.

The phrase "unit", as used herein, refers to the number of discrete objects to be administered which comprise the dosage form. In some embodiments, the dosage form includes a compound of the invention in one capsule. This is a single unit. In some embodiments, the dosage form includes a compound of the invention as part of a therapeutically effective dosage of a cream or ointment. This is also a single unit.

In some embodiments, the dosage form includes a compound of the invention and another active ingredient contained within one capsule, or as part of a therapeutically effective dosage of a topical formulation, such as a cream or an ointment, for example. This is a single unit, whether or not the interior of the capsule includes multiple discrete granules of the active ingredient. In some embodiments, the dosage form includes a compound of the invention in one capsule, and the active ingredient in a second capsule. This is a two unit dosage form, such as two capsules or tablets, and so such units are contained in a single package. Thus the term 'unit' refers to the object which is administered to the animal, not to the interior components of the object.

The term, "prodrug", as defined herein, is a derivative of a parent drug molecule that exerts its pharmacological effect only after chemical and/or enzymatic conversion to its active form in vivo. Prodrugs include those designed to circumvent problems associated with delivery of the parent drug. This may be due to poor physicochemical properties, such as poor chemical stability or low aqueous solubility, and may also be due to poor pharmacokinetic properties, such as poor bioavailability or poor half-life. Thus, certain advantages of prodrugs may include improved chemical stability, absorption, and/or PK properties of the parent carboxylic acids. Prodrugs may also be used to make drugs more amenable to the animal, by minimizing the frequency (e.g., once daily) or route of dosing (e.g., oral), or to improve the taste or odor if given orally, or to minimize pain if given parenterally.

"Biological medium," as used herein refers to both in vitro and in vivo biological milieus. Exemplary in vitro "biological media" include, but are not limited to, cell culture, tissue culture, homogenates, plasma and blood. In vivo applications are generally performed in mammals, preferably humans.

"Inhibiting" and "blocking," are used interchangeably herein to refer to the partial or full blockade of an enzyme, such as a beta-lactamase or a leucyl t-RNA synthetase or a phosphodiesterase.

Boron is able to form additional covalent or dative bonds with oxygen, sulfur or nitrogen under some circumstances in this invention.

Embodiments of the invention also encompass compounds that are poly- or multi-valent species, including, for example, species such as dimers, trimers, tetramers and higher homologs of the compounds of use in the invention or reactive analogues thereof.

"Salt counterion", as used herein, refers to positively charged ions that associate with a compound of the invention when the boron is fully negatively or partially negatively charged. Examples of salt counterions include $H^+$, $H_3O^+$, ammonium, potassium, calcium, magnesium, organic amino (such as choline or diethylamine or amino acids such as d-arginine, l-arginine, d-lysine, l-lysine), and sodium.

The compounds comprising a boron bonded to a carbon and three heteroatoms (such as three oxygens described in this section) can optionally contain a fully negatively charged boron or partially negatively charged boron. Due to the negative charge, a positively charged counterion may associate with this compound, thus forming a salt. Examples of positively charged counterions include $H^+$, $H_3O^+$, ammonium, potassium, calcium, magnesium, organic amino (such as choline or diethylamine or amino acids such as d-arginine, l-arginine, d-lysine, l-lysine), and sodium. These salts of the compounds are implicitly contained in descriptions of these compounds.

II. Introduction

The invention provides novel boron compounds and methods for the preparation of these molecules. The invention further provides methods of treating bacterial infections, killing and/or inhibiting the growth of bacteria in part or wholly through the use of the compounds described herein. In another aspect, the invention is a combination of a compound of the invention and an antibacterial. In another aspect, the invention is a pharmaceutical formulation comprising a pharmaceutically acceptable excipient and a compound of the invention. In another aspect, the invention is a pharmaceutical formulation comprising a compound of the invention, an antibacterial, and a pharmaceutically acceptable excipient.

III. a) Compounds

In one aspect the invention provides a compound of the invention. In an exemplary embodiment, the invention provides a compound described herein, or a salt or a hydrate or a solvate thereof. In an exemplary embodiment, the salt of a compound described herein is a pharmaceutically acceptable salt. In an exemplary embodiment, the invention provides a compound described herein, or a pharmaceutically acceptable salt thereof. In an exemplary embodiment, the invention provides a compound described in a formula provided herein. In an exemplary embodiment, the invention provides a compound described herein.

In an exemplary embodiment, the compound has a structure which is

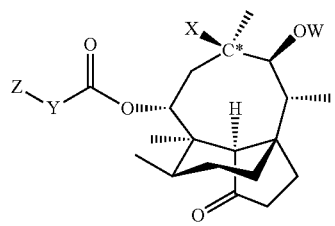

(I)

wherein W is H or a bond to X; X is

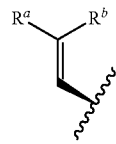

wherein $R^a$ and $R^b$ are each independently selected from the group consisting of $R^{15}$, —$OR^{15}$, —$NR^{15}R^{16}$, —$SR^{15}$, —$S(O)R^{15}$, —$S(O)_2R^{15}$, —$S(O)_2NR^{15}R^{16}$, —$C(O)R^{15}$, —$C(O)OR^{15}$, and —$C(O)NR^{15}R^{16}$ wherein $R^{15}$ and $R^{16}$ are each independently selected from the group consisting of H, halogen, cyano, nitro, —$OR^{17}$, —$NR^{17}R^{18}$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, wherein $R^{17}$ and $R^{18}$ are each independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, and wherein $R^{15}$ and $R^{16}$, and/or $R^{17}$ and $R^{18}$, along with the nitrogen to which they are connected, are optionally joined to form a substituted or unsubstituted 4- to 8-membered ring, with the proviso that $R^a$ and $R^b$ are not both H; or X is

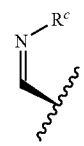

wherein $R^c$ is —$OR^{15}$, —$NR^{15}R^{16}$, —$SR^{15}$, —$S(O)R^{15}$, —$S(O)_2R^{15}$, —$S(O)_2NR^{15}R^{16}$, —$C(O)R^{15}$, —$C(O)OR^{15}$, and —$C(O)NR^{15}R^{16}$, wherein $R^{15}$ and $R^{16}$ are each independently selected from the group consisting of H, halogen, cyano, nitro, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, and wherein $R^{15}$ and $R^{16}$, along with the nitrogen to which they are connected, are optionally joined to form a substituted or unsubstituted 4- to 8-membered ring, or X is

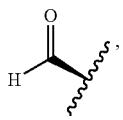

or X is

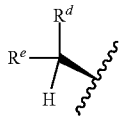

wherein $R^d$ and $R^e$ are each independently selected from the group consisting of H, halogen, cyano, nitro, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, —$OR^{15}$, —$NR^{15}R^{16}$, —$SR^{15}$, —$S(O)R^{15}$, —$S(O)_2R^{15}$, —$S(O)_2NR^{15}R^{16}$, —$C(O)R^{15}$, —$C(O)OR^{15}$, and —$C(O)NR^{15}R^{16}$, wherein $R^{15}$ and $R^{16}$ are each independently selected from the group consisting of H, halogen, cyano, nitro, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, and wherein $R^d$ and $R^e$, along with the atom to which they are connected, are optionally joined to form a substituted or unsubstituted 3- to 8-membered ring, and wherein $R^{15}$ and $R^{16}$, along with the nitrogen to which they are connected, are optionally joined to form a substituted or unsubstituted 4- to 8-membered ring with the proviso that $R^d$ and $R^e$ are not both H, wherein X optionally comprises an attachment point to W; Y is selected from the group consisting of a bond, O, S, NH, substituted or unsubstituted alkylene, and substituted or unsubstituted heteroalkylene; and Z is a substituted or unsubstituted heterocyclic ring or ring system containing at least one endocyclic boron.

In an exemplary embodiment, the compound is Formula (I), W, Y and Z are as described herein, and X is

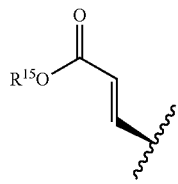

wherein $R^{15}$ is selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, Y and Z are as described herein, and X is

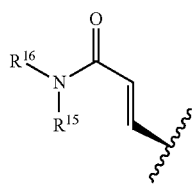

wherein $R^{15}$ and $R^{16}$ are each independently selected from the group consisting of H, —$OR^{17}$, —$NR^{17}R^{18}$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, wherein $R^{17}$ and $R^{18}$ are each independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, and wherein $R^{15}$ and $R^{16}$, and/or $R^{17}$ and $R^{18}$, along with the nitrogen to which they are connected, are optionally joined to form a substituted or unsubstituted 4- to 8-membered ring. In an exemplary embodiment, the compound is Formula (I), W, Y and Z are as described herein, and X is

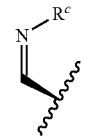

wherein $R^c$ is selected from the group consisting of H, substituted or unsubstituted alkyl, and —$OR^{15}$ wherein $R^{15}$ is H or substituted or unsubstituted alkyl. In an exemplary embodiment, the compound is Formula (I), W, Y and Z are as described herein, and X is

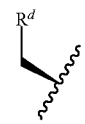

wherein $R^d$ is selected from the group consisting of halogen, substituted or unsubstituted alkyl, substituted or unsubstituted heterocycloalkyl, substituted or unsubstituted aryl, —$OR^{15}$, —$SR^{15}$, —$S(O)R^{15}$, —$NR^{15}R^{16}$, —$C(O)R^{15}$, —$CH_2C(O)OR^{15}$, and —$CH_2C(O)NR^{15}R^{16}$, wherein $R^{15}$ and $R^{16}$ are each independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, and wherein $R^{15}$ and $R^{16}$, along with the nitrogen to which they are connected, are optionally joined to form a substituted or unsubstituted 4- to 8-membered ring.

In an exemplary embodiment, the compound is Formula (I), W, Y and Z are as described herein, and X is

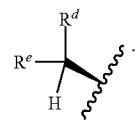

In an exemplary embodiment, the compound is Formula (I), W, X and Z are as described herein, and Y is substituted alkylene. In an exemplary embodiment, the compound is Formula (I), W, X and Z are as described herein, and Y is unsubstituted alkylene. In an exemplary embodiment, the compound is Formula (I), W, X and Z are as described herein, and Y is methylene. In an exemplary embodiment, the compound is Formula (I), W, X and Z are as described herein, and Y is ethylene. In an exemplary embodiment, the compound is Formula (I), W, X and Z are as described herein, and Y is propylene. In an exemplary embodiment, the compound is Formula (I), W, X and Z are as described herein, and Y is substituted heteroalkylene. In an exemplary embodiment, the compound is Formula (I), W, X and Z are as described herein, and Y is unsubstituted heteroalkylene.

In an exemplary embodiment, the compound is Formula (I), W, X and Z are as described herein, and Y is *—OCH$_2$—.
In an exemplary embodiment, the compound is Formula (I), W, X and Z are as described herein, and Y is *—SCH$_2$—.
In an exemplary embodiment, the compound is Formula (I), W, X and Z are as described herein, and Y is *—NHCH$_2$—.
In an exemplary embodiment, the compound is Formula (I), W, X and Z are as described herein, and Y is *—CH$_2$NH—.
In an exemplary embodiment, the compound is Formula (I), W, X and Z are as described herein, and Y is *—C(O)NH—.
In an exemplary embodiment, the compound is Formula (I), W, X and Z are as described herein, and Y is *—CH$_2$NHCH$_2$— or 1-piperazinyl or *—S(O)CH$_2$— or *—S(O)$_2$—. In an exemplary embodiment, the compound is Formula (I), W, X and Z are as described herein, and Y is 1-piperazinyl. In an exemplary embodiment, the compound is Formula (I), W, X and Z are as described herein, and Y is *—S(O)CH$_2$—. In an exemplary embodiment, the compound is Formula (I), W, X and Z are as described herein, and Y is *—S(O)$_2$—. In an exemplary embodiment, the compound is Formula (I), W, X and Z are as described herein, and Y is *—S(O)$_2$CH$_2$—. In an exemplary embodiment, the compound is Formula (I), W, X and Z are as described herein, and Y is *—NHC(O)OCH$_2$—. In this paragraph, * represents the point of attachment to Z.

In an exemplary embodiment, the compound is Formula (I), W, X and Y are as described herein, and Z is substituted or unsubstituted heteroaryl, wherein said heteroaryl comprises an endocyclic boron. In an exemplary embodiment, the compound is Formula (I), W, X and Y are as described herein, and Z is substituted or unsubstituted heteroaryl, wherein said heteroaryl has one ring, and said ring comprises an endocyclic boron. In an exemplary embodiment, the compound is Formula (I), W, X and Y are as described herein, and Z is substituted or unsubstituted heteroaryl, wherein said heteroaryl has two rings, and one of the two rings comprises an endocyclic boron.

In an exemplary embodiment, the compound is Formula (I), W, X and Y are as described herein, and Z is substituted or unsubstituted heterocycloalkyl, wherein said heterocycloalkyl comprises an endocyclic boron. In an exemplary embodiment, the compound is Formula (I), W, X and Y are as described herein, and Z is substituted or unsubstituted heterocycloalkyl, wherein said heterocycloalkyl has one ring, and said ring comprises an endocyclic boron. In an exemplary embodiment, the compound is Formula (I), W, X and Y are as described herein, and Z is substituted or unsubstituted heterocycloalkyl, wherein said heterocycloalkyl has two rings, and one of the two rings comprises an endocyclic boron.

In an exemplary embodiment, the compound is Formula (I), W, X and Y are as described herein, and Z is substituted or unsubstituted benzoxaborole. In an exemplary embodiment, the compound is Formula (I), W, X and Y are as described herein, and Z is substituted or unsubstituted pyridinyloxaborole. In an exemplary embodiment, the compound is Formula (I), W, X and Y are as described herein, and Z is substituted or unsubstituted benzoxaborininol. In an exemplary embodiment, the compound is Formula (I), W, X and Y are as described herein, and Z is substituted or unsubstituted benzoxazaborininol. In an exemplary embodiment, the compound is Formula (I), W, X and Y are as described herein, and Z is substituted or unsubstituted benzodiazaborininol. In an exemplary embodiment, the compound is Formula (I), W, X and Y are as described herein, and Z is substituted or unsubstituted oxaborole. In an exemplary embodiment, X the compound is Formula (I), and W and Y are as described herein, and Z is substituted or unsubstituted dihydrobenzoazaborinine.

In an exemplary embodiment, the compound is Formula (I), W, X and Y are as described herein, and said Z is

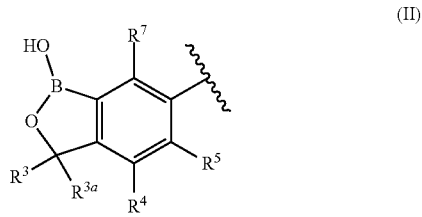

(II)

wherein $R^3$, $R^{3a}$, $R^4$, $R^5$, and $R^7$ are each independently selected from the group consisting of $R^{10}$, —$OR^{10}$, —$NR^{10}R^{11}$, —$S(O)R^{10}$, —$S(O)_2R^{10}$, —$S(O)_2NR^{10}R^{11}$, —$C(O)R^{10}$, —$C(O)OR^{10}$, and —$C(O)NR^{10}R^{11}$ wherein $R^{10}$ and $R^{11}$ are each independently selected from the group consisting of H, halogen, cyano, nitro, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

In an exemplary embodiment, the compound is Formula (I), W, X and Y are as described herein, and said Z is

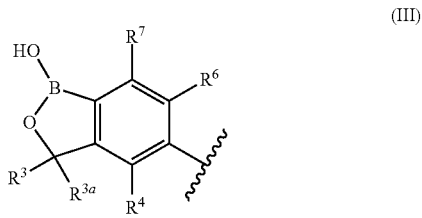

(III)

wherein $R^3$, $R^{3a}$, $R^4$, $R^6$, and $R^7$ are each independently selected from the group consisting of $R^{10}$, —$OR^{10}$, —$NR^{10}R^{11}$, —$R^{10}$, —$S(O)R^{10}$, —$S(O)_2R^{10}$, —$S(O)_2NR^{10}R^{11}$, —$C(O)R^{10}$, —$C(O)OR^{10}$, and —$C(O)NR^{10}R^{11}$ wherein $R^{10}$ and $R^{11}$ are each independently selected from the group consisting of H, halogen, cyano, nitro, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

In an exemplary embodiment, the compound is Formula (I), W, X and Y are as described herein, and said Z is

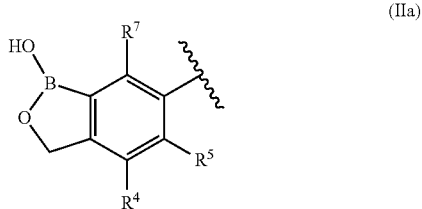

(IIa)

wherein $R^4$, $R^5$, and $R^7$ are each independently selected from the group consisting of $R^{10}$, —$OR^{10}$, —$NR^{10}R^{11}$ wherein $R^{10}$ and $R^{11}$ are each independently selected from the group consisting of H, halogen, cyano, nitro, substituted or unsubstituted alkyl, and substituted or unsubstituted heteroalkyl. In an exemplary embodiment, the compound is Formula (I), W, X and Y are as described herein, and said Z is

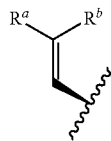

In an exemplary embodiment, the compound is (3aR,4R, 5R,7S,8S,9R,9aS,12R)-8-hydroxy-7-(hydroxymethyl)-4,7, 9,12-tetramethyl-3-oxodecahydro-4,9a-propanocyclopenta [8]annulen-5-yl 2-((7-fluoro-1-hydroxy-1,3-dihydrobenzo [c][1,2]oxaborol-6-yl)oxy)acetate. In an exemplary embodiment, the compound is (3aR,4R,5R,7R,8S,9R,9aS, 12R)-8-hydroxy-4,7,9,12-tetramethyl-7-((R)-oxiran-2-yl)-3-oxodecahydro-4,9a-propanocyclopenta[8]annulen-5-yl 2-((7-fluoro-1-hydroxy-1,3-dihydrobenzo[c][1,2]oxaborol-6-yl)oxy)acetate. In an exemplary embodiment, the compound is (3aR,4R,5R,7S,8S,9R,9aS,12R)-8-hydroxy-4,7,9, 12-tetramethyl-7-((E)-2-(3-methyl-1,2,4-oxadiazol-5-yl) vinyl)-3-oxodecahydro-4,9a-propanocyclopenta[8]annulen-5-yl 2-((7-fluoro-1-hydroxy-1,3-dihydrobenzo[c][1,2] oxaborol-6-yl)oxy)acetate.

In an exemplary embodiment, the compound is Formula (I), W, Y and Z are as described herein, and said X is

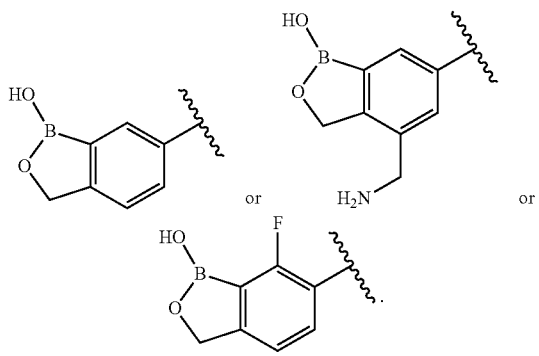

wherein $R^a$ and $R^b$ are each independently selected from the group consisting of $R^{15}$, —$OR^{15}$, —$NR^{15}R^{16}$, —$SR^{15}$, —$S(O)R^{15}$, —$S(O)_2R^{15}$, —$S(O)_2NR^{15}R^{16}$, —$C(O)R^{15}$, —$C(O)OR^{15}$, and —$C(O)NR^{15}R^{16}$ wherein $R^{15}$ and $R^{16}$ are each independently selected from the group consisting of H, halogen, cyano, nitro, —$OR^{17}$, —$NR^{17}R^{18}$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, wherein $R^{17}$ and $R^{18}$ are each independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, and wherein $R^{15}$ and $R^{16}$, and/or $R^{17}$ and $R^{18}$, along with the nitrogen to which they are connected, are optionally joined to form a substituted or unsubstituted 4- to 8-membered ring, with the proviso that $R^a$ and $R^b$ are not both H. In an exemplary embodiment, the compound is Formula (I), W, Y and Z are as described herein, and said X is

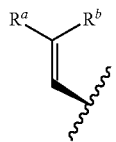

wherein one of $R^a$ and $R^b$ is H, and the other of $R^a$ and $R^b$ is selected from the group consisting of $R^{15}$, —$OR^{15}$, —$NR^{15}R^{16}$, —$SR^{15}$, —$S(O)R^{15}$, —$S(O)_2R^{15}$, —$S(O)_2NR^{15}R^{16}$, —$C(O)R^{15}$, —$C(O)OR^{15}$, and —$C(O)NR^{15}R^{16}$ wherein $R^{15}$ and $R^{16}$ are each independently selected from the group consisting of H, halogen, cyano, nitro, —$OR^{17}$, —$NR^{17}R^{18}$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, wherein $R^{17}$ and $R^{18}$ are each independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, and wherein $R^{15}$ and $R^{16}$, and/or $R^{17}$ and $R^{18}$, along with the nitrogen to which they are connected, are optionally joined to form a substituted or unsubstituted 4- to 8-membered ring. In an exemplary embodiment, the compound is Formula (I), W, Y and Z are as described herein, and said X is

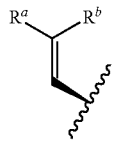

wherein one of $R^a$ and $R^b$ is H, and the other of $R^a$ and $R^b$ is substituted or unsubstituted heteroaryl. In an exemplary embodiment, the compound is Formula (I), W, Y and Z are as described herein, and said X is

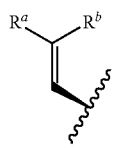

wherein one of $R^a$ and $R^b$ is H, and the other of $R^a$ and $R^b$ is unsubstituted oxadiazolyl. In an exemplary embodiment, the compound is Formula (I), W, Y and Z are as described herein, and said X is

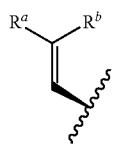

wherein one of $R^a$ and $R^b$ is H, and the other of $R^a$ and $R^b$ is 1,2,4-oxadiazolyl. In an exemplary embodiment, the compound is Formula (I), W, Y and Z are as described herein, and said X is

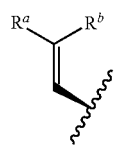

wherein one of $R^a$ and $R^b$ is H, and the other of $R^a$ and $R^b$ is 1,2,4-oxadiazol-5-yl. In an exemplary embodiment, the compound is Formula (I), W, Y and Z are as described herein, and said X is

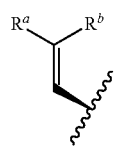

wherein one of $R^a$ and $R^b$ is H, and the other of $R^a$ and $R^b$ is substituted oxadiazolyl. In an exemplary embodiment, the compound is Formula (I), W, Y and Z are as described herein, and said X is

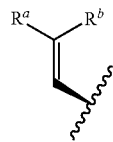

wherein one of $R^a$ and $R^b$ is H, and the other of $R^a$ and $R^b$ is oxadiazolyl, substituted with unsubstituted $C_1$-$C_6$ alkyl. In an exemplary embodiment, the compound is Formula (I), W, Y and Z are as described herein, and said X is

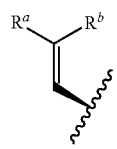

wherein one of $R^a$ and $R^b$ is H, and the other of $R^a$ and $R^b$ is oxadiazolyl, substituted with unsubstituted $C_1$-$C_3$ alkyl. In an exemplary embodiment, the compound is Formula (I), W, Y and Z are as described herein, and said X is

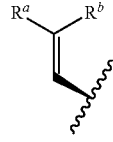

wherein one of $R^a$ and $R^b$ is H, and the other of $R^a$ and $R^b$ is oxadiazolyl, substituted with methyl. In an exemplary embodiment, the compound is Formula (I), W, Y and Z are as described herein, and said X is

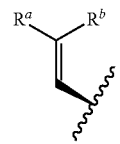

wherein one of $R^a$ and $R^b$ is H, and the other of $R^a$ and $R^b$ is 3-methyl 1,2,4-oxadiazol-5-yl.

In an exemplary embodiment, the compound is Formula (I), W, Y and Z are as described herein, and said X is

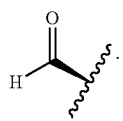

In an exemplary embodiment, the compound is Formula (I), W, Y and Z are as described herein, and X is

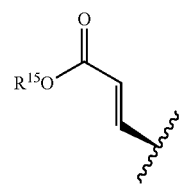

wherein $R^{15}$ is selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, the compound is Formula (I), W, Y and Z are as described herein, and X is

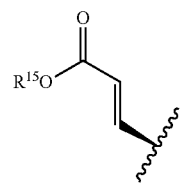

wherein $R^{15}$ is H. In an exemplary embodiment, the compound is Formula (I), W, Y and Z are as described herein, and X is

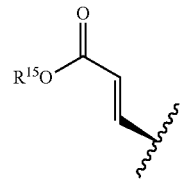

wherein $R^{15}$ is substituted alkyl. In an exemplary embodiment, the compound is Formula (I), W, Y and Z are as described herein, and X is

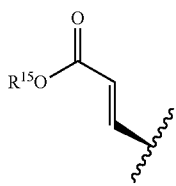

wherein R[15] is unsubstituted $C_1$-$C_6$ alkyl. In an exemplary embodiment, the compound is Formula (I), W, Y and Z are as described herein, and X is

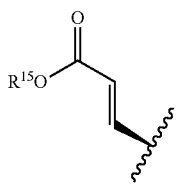

wherein R[15] is unsubstituted $C_2$-$C_4$ alkyl.

In an exemplary embodiment, the compound is Formula (I), W, Y and Z are as described herein, and X is

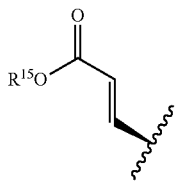

wherein R[15] is methyl.

In an exemplary embodiment, the compound is Formula (I), W, Y and Z are as described herein, and X is

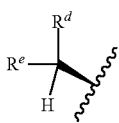

wherein R[d] and R[e] are each independently selected from the group consisting of H, halogen, cyano, nitro, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, —OR[15], —NR[15]R[16], —SR[15], —S(O)R[15], —S(O)$_2$R[15], —S(O)$_2$NR[15]R[16], —C(O)R[15], —C(O)OR[15], and —C(O)NR[15]R[16], wherein R[15] and R[16] are each independently selected from the group consisting of H, halogen, cyano, nitro, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, and wherein R[d] and R[e], along with the atom to which they are connected, are optionally joined to form a substituted or unsubstituted 3- to 8-membered ring, and wherein R[15] and R[16], along with the nitrogen to which they are connected, are optionally joined to form a substituted or unsubstituted 4- to 8-membered ring with the proviso that R[d] and R[e] are not both H. In an exemplary embodiment, the compound is Formula (I), W, Y and Z are as described herein, and X is

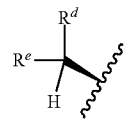

wherein R[d] and R[e] are each independently selected from $C_1$-$C_3$ alkyl.

In an exemplary embodiment, the compound is Formula (I), W, Y and Z are as described herein, and X is

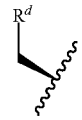

wherein R[d] is selected from the group consisting of halogen, substituted or unsubstituted alkyl, substituted or unsubstituted heterocycloalkyl, substituted or unsubstituted aryl, —OR[15], —SR[15], —S(O)R[15], —NR[15]R[16], —C(O)R[15], —CH$_2$C(O)OR[15], and —CH$_2$C(O)NR[15]R[16], wherein R[15] and R[16] are each independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, and wherein R[15] and R[16], along with the nitrogen to which they are connected, are optionally joined to form a substituted or unsubstituted 4- to 8-membered ring.

In an exemplary embodiment, the compound is Formula (I), W, Y and Z are as described herein, and said X is

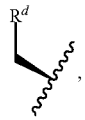

wherein R[d] is OH. In an exemplary embodiment, the compound is Formula (I), W, Y and Z are as described herein, and said X is

wherein R[d] is —OR[15], wherein R[15] is substituted or unsubstituted alkyl. In an exemplary embodiment, the compound is Formula (I), W, Y and Z are as described herein, and said X is

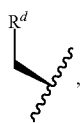

wherein $R^d$ is —$OR^{15}$, wherein $R^{15}$ is unsubstituted $C_1$-$C_6$ alkyl. In an exemplary embodiment, the compound is Formula (I), W, Y and Z are as described herein, and said X is

wherein $R^d$ is —$OR^{15}$, wherein $R^{15}$ is methyl. In an exemplary embodiment, the compound is Formula (I), W, Y and Z are as described herein, and said X is

wherein $R^d$ is —$OR^{15}$, wherein $R^{15}$ is ethyl or propyl or isopropyl. In an exemplary embodiment, the compound is Formula (I), W, Y and Z are as described herein, and said X is $C_1$-$C_6$ alkyl substituted with at least one hydroxy. In an exemplary embodiment, the compound is Formula (I), W, Y and Z are as described herein, and said X is $C_3$ alkyl substituted with at least one hydroxy. In an exemplary embodiment, the compound is Formula (I), W, Y and Z are as described herein, and said X is ethyl substituted with at least one hydroxy. In an exemplary embodiment, the compound is Formula (I), W, Y and Z are as described herein, and said X is methyl substituted with at least one hydroxy. In an exemplary embodiment, the compound is Formula (I), W, Y and Z are as described herein, and said X is hydroxymethyl.

In an exemplary embodiment, the compound is Formula (I), W, Y and Z are as described herein, and said X is

wherein $R^d$ is SH. In an exemplary embodiment, the compound is Formula (I), W, Y and Z are as described herein, and said X is

wherein $R^d$ is —$SR^{15}$, wherein $R^{15}$ is substituted or unsubstituted alkyl. In an exemplary embodiment, the compound is Formula (I), W, Y and Z are as described herein, and said X is

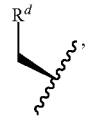

wherein $R^d$ is —$SR^{15}$, wherein $R^{15}$ is unsubstituted $C_1$-$C_6$ alkyl. In an exemplary embodiment, the compound is Formula (I), W, Y and Z are as described herein, and said X is

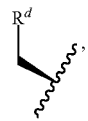

wherein $R^d$ is —$SR^{15}$, wherein $R^{15}$ is methyl. In an exemplary embodiment, the compound is Formula (I), W, Y and Z are as described herein, and said X is

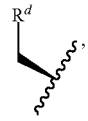

wherein $R^d$ is —$SR^{15}$, wherein $R^{15}$ is ethyl or propyl or isopropyl.

In an exemplary embodiment, the compound is Formula (I), W, Y and Z are as described herein, and said X is

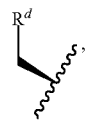

wherein $R^d$ is substituted or unsubstituted alkyl. In an exemplary embodiment, the compound is Formula (I), W, Y and Z are as described herein, and said X is

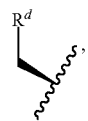

wherein $R^d$ is unsubstituted $C_4$-$C_6$ alkyl. In an exemplary embodiment, the compound is Formula (I), W, Y and Z are as described herein, and said X is wherein $R^d$ is unsubstituted $C_2$-$C_3$ alkyl. In an exemplary embodiment, the compound is Formula (I), W, Y and Z are as described herein, and said X is

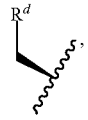

wherein $R^d$ is methyl. In an exemplary embodiment, the compound is Formula (I), W, Y and Z are as described herein, and said X is

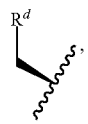

wherein $R^d$ is ethyl or propyl or isopropyl. In an exemplary embodiment, the compound is Formula (I), W, Y and Z are as described herein, and said X is

wherein $R^d$ is butyl, isobutyl, or t-butyl. In an exemplary embodiment, the compound is Formula (I), W, Y and Z are as described herein, and said X is

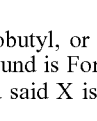

wherein $R^d$ is $C_1$-$C_6$ alkyl, substituted with hydroxy. In an exemplary embodiment, the compound is Formula (I), W, Y and Z are as described herein, and said X is

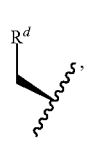

wherein $R^d$ is $C_1$-$C_6$ alkyl, substituted with hydroxy.

In an exemplary embodiment, the compound is Formula (I), W, Y and Z are as described herein, and said X is

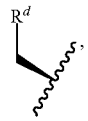

wherein $R^d$ is $C_1$-$C_6$ alkyl, substituted with —$OR^{20}$ or —$SR^{20}$, wherein $R^{20}$ is unsubstituted $C_1$-$C_6$ alkyl. In an exemplary embodiment, the compound is Formula (I), W, Y and Z are as described herein, and said X is

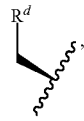

wherein $R^d$ is $C_1$-$C_2$ alkyl, substituted with —$OR^{20}$ or —$SR^{20}$, wherein $R^{20}$ is unsubstituted $C_1$-$C_6$ alkyl. In an exemplary embodiment, the compound is Formula (I), W, Y and Z are as described herein, and said X is

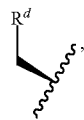

wherein $R^d$ is methyl, substituted with —$OR^{20}$ or —$SR^{20}$, wherein $R^{20}$ is unsubstituted $C_1$-$C_6$ alkyl. In an exemplary embodiment, the compound is Formula (I), W, Y and Z are as described herein, and said X is

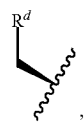

wherein $R^d$ is $C_1$-$C_6$ alkyl, substituted with —$OR^{20}$ or —$SR^{20}$, wherein $R^{20}$ is unsubstituted $C_1$-$C_3$ alkyl. In an exemplary embodiment, the compound is Formula (I), W, Y and Z are as described herein, and said X is

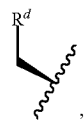

wherein $R^d$ is $C_1$-$C_6$ alkyl, substituted with —$OR^{20}$ or —$SR^{20}$, wherein $R^{20}$ is unsubstituted $C_1$-$C_2$ alkyl. In an exemplary embodiment, the compound is Formula (I), W, Y and Z are as described herein, and said X is

wherein $R^d$ is $C_1$-$C_6$ alkyl, substituted with —$OR^{20}$ or —$SR^{20}$, wherein $R^{20}$ is methyl. In an exemplary embodiment, the compound is Formula (I), W, Y and Z are as described herein, and said X is

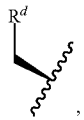

wherein $R^d$ is methyl, substituted with —$OR^{20}$ or —$SR^{20}$, wherein $R^{20}$ is methyl.

In an exemplary embodiment, the compound is Formula (I), W, Y and Z are as described herein, and said X is

wherein $R^d$ is substituted alkenyl. In an exemplary embodiment, the compound is Formula (I), W, Y and Z are as described herein, and said X is unsubstituted alkenyl. In an exemplary embodiment, the compound is Formula (I), W, Y and Z are as described herein, and said $R^d$ is ethene. In an exemplary embodiment, the compound is Formula (I), W, Y and Z are as described herein, and said X is allyl.

In an exemplary embodiment, the compound is Formula (I), W, Y and Z are as described herein, and said X is

wherein $R^d$ is substituted alkynyl. In an exemplary embodiment, the compound is Formula (I), W, Y and Z are as described herein, and said X is

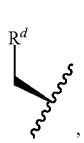

wherein $R^d$ is ethynyl. In an exemplary embodiment, the compound is Formula (I), W, Y and Z are as described herein, and said X is unsubstituted alkynyl. In an exemplary embodiment, the compound is Formula (I), W, Y and Z are as described herein, and said X is propynyl. In an exemplary embodiment, the compound is Formula (I), W, Y and Z are as described herein, and said X is ethynyl.

In an exemplary embodiment, the compound is Formula (I), W, Y and Z are as described herein, and said X is

wherein $R^d$ is halogen. In an exemplary embodiment, the compound is Formula (I), W, Y and Z are as described herein, and said X is

wherein $R^d$ is fluoro. In an exemplary embodiment, the compound is Formula (I), W, Y and Z are as described herein, and said X is

wherein $R^d$ is chloro. In an exemplary embodiment, the compound is Formula (I), W, Y and Z are as described herein, and said X is

wherein $R^d$ is bromo.

In an exemplary embodiment, the compound is Formula (I), W, Y and Z are as described herein, and said X is

wherein $R^d$ is substituted phenyl. In an exemplary embodiment, the compound is Formula (I), W, Y and Z are as described herein, and said X is

wherein $R^d$ is unsubstituted phenyl.

In an exemplary embodiment, the compound is Formula (I), W, Y and Z are as described herein, and said X is

wherein $R^d$ and $R^e$, along with the atom to which they are connected, are optionally joined to form a substituted or unsubstituted 3- to 8-membered ring. In an exemplary embodiment, the compound is Formula (I), W, Y and Z are as described herein, and said X is

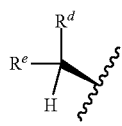

wherein $R^d$ and $R^e$, along with the atom to which they are connected, are optionally joined to form a substituted or unsubstituted 3- to 6-membered ring. In an exemplary embodiment, the compound is Formula (I), W, Y and Z are as described herein, and said X is

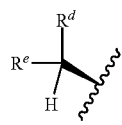

wherein $R^d$ and $R^e$, along with the atom to which they are connected, are optionally joined to form a unsubstituted 3- to 6-membered ring. In an exemplary embodiment, the compound is Formula (I), W, Y and Z are as described herein, and said X is

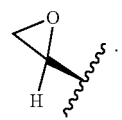

In an exemplary embodiment, the compound is Formula (I), W, Y and Z are as described herein, and said X is

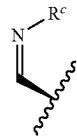

wherein $R^c$ is —$OR^{15}$, —$NR^{15}R^{16}$, —$SR^{15}$, —$S(O)R^{15}$, —$S(O)_2R^{15}$, —$S(O)_2NR^{15}R^{16}$, —$C(O)R^{15}$, —$C(O)OR^{15}$, and —$C(O)NR^{15}R^{16}$, wherein $R^{15}$ and $R^{16}$ are each independently selected from the group consisting of H, halogen, cyano, nitro, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, and wherein $R^{15}$ and $R^{16}$, along with the nitrogen to which they are connected, are optionally joined to form a substituted or unsubstituted 4- to 8-membered ring. In an exemplary embodiment, the compound is Formula (I), W, Y and Z are as described herein, and said X is

wherein W is —$OR^{15}$, wherein $R^{15}$ is selected from the group consisting of H, halogen, cyano, nitro, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, the compound is Formula (I), W, Y and Z are as described herein, and said X is

wherein W is —$OR^{15}$, wherein $R^{15}$ is selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In an exemplary embodiment, the compound is Formula (I), W, Y and Z are as described herein, and said X is

wherein $R^c$ is —$OR^{15}$, wherein $R^{15}$ is H. In an exemplary embodiment, the compound is Formula (I), W, Y and Z are as described herein, and said X is

wherein $R^c$ is —$OR^{15}$, wherein $R^{15}$ is substituted $C_1$-$C_6$ alkyl. In an exemplary embodiment, the compound is Formula (I), W, Y and Z are as described herein, and said X is

wherein $R^c$ is —$OR^{15}$, wherein $R^{15}$ is unsubstituted $C_1$-$C_6$ alkyl. In an exemplary embodiment, the compound is Formula (I), W, Y and Z are as described herein, and said X is

wherein $R^c$ is —$OR^{15}$, wherein $R^{15}$ is unsubstituted $C_1$-$C_3$ alkyl. In an exemplary embodiment, the compound is Formula (I), W, Y and Z are as described herein, and said X is

[structure]

wherein $R^c$ is —$OR^{15}$, wherein $R^{15}$ is methyl.

In an exemplary embodiment, the compound is Formula (I), $R^4$, $R^5$, $R^6$, $R^7$, W, X and Y are as described herein, Z is Formula (II) or (III), and $R^3$ is H and $R^{3a}$ is H. In an exemplary embodiment, the compound is Formula (I), $R^4$, $R^5$, $R^6$, $R^7$, W, X and Y are as described herein, Z is Formula (II) or (III), and $R^3$ is unsubstituted $C_1$-$C_3$ alkyl and $R^{3a}$ is unsubstituted $C_1$-$C_3$ alkyl. In an exemplary embodiment, the compound is Formula (I), $R^4$, $R^5$, $R^6$, $R^7$, W, X and Y are as described herein, Z is Formula (II) or (III), and $R^3$ is unsubstituted $C_1$-$C_3$ alkyl and $R^{3a}$ is H. In an exemplary embodiment, the compound is Formula (I), $R^4$, $R^5$, $R^6$, $R^7$, W, X and Y are as described herein, Z is Formula (II) or (III), and $R^3$ is methyl and $R^{3a}$ is methyl. In an exemplary embodiment, the compound is Formula (I), $R^4$, $R^5$, $R^6$, $R^7$, W, X and Y are as described herein, Z is Formula (II) or (III), and $R^3$ is methyl and $R^{3a}$ is H. In an exemplary embodiment, the compound is Formula (I), $R^4$, $R^5$, $R^6$, $R^7$, W, X and Y are as described herein, Z is Formula (II) or (III), and $R^3$ is $C_1$-$C_3$ alkyl substituted with substituted or unsubstituted amino and $R^{3a}$ is H. In an exemplary embodiment, the compound is Formula (I), $R^4$, $R^5$, $R^6$, $R^7$, W, X and Y are as described herein, Z is Formula (II) or (III), and $R^3$ is —$CH_2NH_2$ and $R^{3a}$ is H.

In an exemplary embodiment, the compound is Formula (I), $R^3$, $R^{3a}$, W, X and Y are as described herein, Z is Formula (II), $R^4$ is H or halogen, $R^5$ is H or halogen, and $R^7$ is H or halogen. In an exemplary embodiment, the compound is Formula (I), $R^3$, $R^{3a}$, W, X and Y are as described herein, Z is Formula (II), $R^4$ is halogen, $R^5$ is H, and $R^7$ is H. In an exemplary embodiment, the compound is Formula (I), $R^3$, $R^{3a}$, W, X and Y are as described herein, Z is Formula (II), $R^4$ is Cl, $R^5$ is H, and $R^7$ is H. In an exemplary embodiment, the compound is Formula (I), $R^3$, $R^{3a}$, W, X and Y are as described herein, Z is Formula (II), $R^4$ is F, $R^5$ is H, and $R^7$ is H. In an exemplary embodiment, the compound is Formula (I), $R^3$, $R^{3a}$, W, X and Y are as described herein, the compound is Formula (I), Z is Formula (II), $R^4$ is H, $R^5$ is halogen, and $R^7$ is H. In an exemplary embodiment, the compound is Formula (I), $R^3$, $R^{3a}$, W, X and Y are as described herein, Z is Formula (II), $R^4$ is H, $R^5$ is Cl, and $R^7$ is H. In an exemplary embodiment, the compound is Formula (I), $R^3$, $R^{3a}$, W, X and Y are as described herein, Z is Formula (II), $R^4$ is H, $R^5$ is F, and $R^7$ is H. In an exemplary embodiment, the compound is Formula (I), $R^3$, $R^{3a}$, W, X and Y are as described herein, Z is Formula (II), $R^4$ is H, $R^5$ is H, and $R^7$ is halogen. In an exemplary embodiment, the compound is Formula (I), $R^3$, $R^{3a}$, W, X and Y are as described herein, the compound is Formula (I), Z is Formula (II), $R^4$ is H, $R^5$ is H, and $R^7$ is Cl. In an exemplary embodiment, the compound is Formula (I), $R^3$, $R^{3a}$, W, X and Y are as described herein, Z is Formula (II), $R^4$ is H, $R^5$ is H, and $R^7$ is F. In an exemplary embodiment, the compound is Formula (I), $R^3$, $R^{3a}$, W, X and Y are as described herein, Z is Formula (II), $R^4$ is H, $R^5$ is halogen, and $R^7$ is halogen. In an exemplary embodiment, the compound is Formula (I), $R^3$, $R^{3a}$, W, X and Y are as described herein, Z is Formula (II), $R^4$ is H, $R^5$ is Cl, and $R^7$ is Cl. In an exemplary embodiment, the compound is Formula (I), $R^3$, $R^{3a}$, W, X and Y are as described herein, Z is Formula (II), $R^4$ is H, $R^5$ is F, and $R^7$ is F.

In an exemplary embodiment, the compound is Formula (I), $R^3$, $R^{3a}$, W, X and Y are as described herein, Z is Formula (III), $R^4$ is H or halogen, $R^6$ is H or halogen, and $R^7$ is H or halogen. In an exemplary embodiment, the compound is Formula (I), $R^3$, $R^{3a}$, W, X and Y are as described herein, Z is Formula (III), $R^4$ is halogen, $R^6$ is H, and $R^7$ is H. In an exemplary embodiment, the compound is Formula (I), $R^3$, $R^{3a}$, W, X and Y are as described herein, Z is Formula (III), $R^4$ is Cl, $R^6$ is H, and $R^7$ is H. In an exemplary embodiment, the compound is Formula (I), $R^3$, $R^{3a}$, W, X and Y are as described herein, Z is Formula (III), $R^4$ is F, $R^6$ is H, and $R^7$ is H. In an exemplary embodiment, the compound is Formula (I), $R^3$, $R^{3a}$, W, X and Y are as described herein, Z is Formula (III), $R^4$ is H, $R^6$ is halogen, and $R^7$ is H. In an exemplary embodiment, the compound is Formula (I), $R^3$, $R^{3a}$, W, X and Y are as described herein, Z is Formula (III), $R^4$ is H, $R^6$ is Cl, and $R^7$ is H. In an exemplary embodiment, the compound is Formula (I), $R^3$, $R^{3a}$, W, X and Y are as described herein, Z is Formula (III), $R^4$ is H, $R^6$ is F, and $R^7$ is H. In an exemplary embodiment, the compound is Formula (I), $R^3$, $R^{3a}$, W, X and Y are as described herein, Z is Formula (III), $R^4$ is H, $R^6$ is H, and $R^7$ is halogen. In an exemplary embodiment, the compound is Formula (I), $R^3$, $R^{3a}$, W, X and Y are as described herein, Z is Formula (III), $R^4$ is H, $R^6$ is H, and $R^7$ is Cl. In an exemplary embodiment, the compound is Formula (I), $R^3$, $R^{3a}$, W, X and Y are as described herein, Z is Formula (III), $R^4$ is H, $R^6$ is H, and $R^7$ is F. In an exemplary embodiment, the compound is Formula (I), $R^3$, $R^{3a}$, W, X and Y are as described herein, Z is Formula (III), $R^4$ is H, $R^6$ is halogen, and $R^7$ is halogen. In an exemplary embodiment, the compound is Formula (I), $R^3$, $R^{3a}$, W, X and Y are as described herein, Z is Formula (III), $R^4$ is H, $R^6$ is Cl, and $R^7$ is Cl. In an exemplary embodiment, the compound is Formula (I), $R^3$, $R^{3a}$, W, X and Y are as described herein, Z is Formula (III), $R^4$ is H, $R^6$ is F, and $R^7$ is F.

In an exemplary embodiment, the compound is Formula (I), $R^3$, $R^{3a}$, W, X and Y are as described herein, Z is Formula (II), $R^4$ is H or cyano, $R^5$ is H or cyano, and $R^7$ is H or cyano. In an exemplary embodiment, the compound is Formula (I), $R^3$, $R^{3a}$, W, X and Y are as described herein, Z is Formula (II), $R^4$ is cyano, $R^5$ is H, and $R^7$ is H. In an exemplary embodiment, the compound is Formula (I), $R^3$, $R^{3a}$, W, X and Y are as described herein, Z is Formula (II), $R^4$ is H, $R^5$ is cyano, and $R^7$ is H. In an exemplary embodiment, the compound is Formula (I), $R^3$, $R^{3a}$, W, X and Y are as described herein, Z is Formula (II), $R^4$ is H, $R^5$ is H, and $R^7$ is cyano.

In an exemplary embodiment, the compound is Formula (I), $R^3$, $R^{3a}$, W, X and Y are as described herein, Z is Formula (III), $R^4$ is H or cyano, $R^6$ is H or cyano, and $R^7$ is H or cyano. In an exemplary embodiment, the compound is Formula (I), $R^3$, $R^{3a}$, W, X and Y are as described herein, Z is Formula (III), $R^4$ is cyano, $R^6$ is H, and $R^7$ is H. In an exemplary embodiment, the compound is Formula (I), $R^3$, $R^{3a}$, W, X and Y are as described herein, Z is Formula (III), $R^4$ is H, $R^6$ is cyano, and $R^7$ is H. In an exemplary embodiment, the compound is Formula (I), $R^3$, $R^{3a}$, W, X and Y are as described herein, Z is Formula (III), $R^4$ is H, $R^6$ is H, and $R^7$ is cyano.

In an exemplary embodiment, the compound is Formula (I), $R^3$, $R^{3a}$, W, X and Y are as described herein, Z is Formula (II), $R^4$, $R^5$, and $R^7$ are each independently selected from H or $C_1$-$C_3$ alkyl substituted with amino. In an exemplary embodiment, the compound is Formula (I), $R^3$, $R^{3a}$, W, X and Y are as described herein, Z is Formula (II), $R^4$, $R^5$, and $R^7$ are each independently selected from H or —$CH_2NH_2$. In an exemplary embodiment, the compound is Formula (I), $R^3$, $R^{3a}$, W, X and Y are as described herein, Z is Formula (II), $R^4$ is —$CH_2NH_2$, $R^5$ is H, and $R^7$ is H. In an exemplary embodiment, the compound is Formula (I), $R^3$, $R^{3a}$, W, X and Y are as described herein, Z is Formula (II), $R^4$ is H, $R^5$ is —$CH_2NH_2$, and $R^7$ is H. In an exemplary embodiment, the compound is Formula (I), $R^3$, $R^{3a}$, W, X and Y are as described herein, Z is Formula (II), $R^4$ is H, $R^5$ is H, and $R^7$ is —$CH_2NH_2$.

In an exemplary embodiment, the compound is Formula (I), $R^3$, $R^{3a}$, W, X and Y are as described herein, Z is Formula (III), $R^4$, $R^6$, and $R^7$ are each independently selected from H or $C_1$-$C_3$ alkyl substituted with amino. In an exemplary embodiment, the compound is Formula (I), $R^3$, $R^{3a}$, W, X and Y are as described herein, Z is Formula (III), $R^4$, $R^6$, and $R^7$ are each independently selected from H or —$CH_2NH_2$. In an exemplary embodiment, the compound is Formula (I), $R^3$, $R^{3a}$, W, X and Y are as described herein, Z is Formula (III), $R^4$ is —$CH_2NH_2$, $R^6$ is H, and $R^7$ is H. In an exemplary embodiment, the compound is Formula (I), $R^3$, $R^{3a}$, W, X and Y are as described herein, Z is Formula (III), $R^4$ is H, $R^6$ is —$CH_2NH_2$, and $R^7$ is H. In an exemplary embodiment, the compound is Formula (I), $R^3$, $R^{3a}$, W, X and Y are as described herein, Z is Formula (III), $R^4$ is H, $R^6$ is H, and $R^7$ is —$CH_2NH_2$.

In an exemplary embodiment, the compound is Formula (I), $R^3$, $R^{3a}$, W, X and Y are as described herein, Z is Formula (II), $R^4$, $R^5$, and $R^7$ are each independently selected from H or $C_1$-$C_3$ alkoxy. In an exemplary embodiment, the compound is Formula (I), $R^3$, $R^{3a}$, W, X and Y are as described herein, Z is Formula (II), $R^4$, $R^5$, and $R^7$ are each independently selected from H or —$OCH_3$. In an exemplary embodiment, the compound is Formula (I), $R^3$, $R^{3a}$, W, X and Y are as described herein, Z is Formula (II), $R^4$ is —$OCH_3$, $R^5$ is H, and $R^7$ is H. In an exemplary embodiment, the compound is Formula (I), $R^3$, $R^{3a}$, W, X and Y are as described herein, Z is Formula (II), $R^4$ is H, $R^5$ is —$OCH_3$, and $R^7$ is H. In an exemplary embodiment, the compound is Formula (I), $R^3$, $R^{3a}$, W, X and Y are as described herein, Z is Formula (II), $R^4$ is H, $R^5$ is H, and $R^7$ is —$OCH_3$.

In an exemplary embodiment, the compound is Formula (I), $R^3$, $R^{3a}$, W, X and Y are as described herein, Z is Formula (III), $R^4$, $R^6$, and $R^7$ are each independently selected from H or $C_1$-$C_3$ alkoxy. In an exemplary embodiment, the compound is Formula (I), $R^3$, $R^{3a}$, W, X and Y are as described herein, Z is Formula (III), $R^4$, $R^6$, and $R^7$ are each independently selected from H or $OCH_3$. In an exemplary embodiment, the compound is Formula (I), $R^3$, $R^{3a}$, W, X and Y are as described herein, Z is Formula (III), $R^4$ is —$OCH_3$, $R^6$ is H, and $R^7$ is H. In an exemplary embodiment, the compound is Formula (I), $R^3$, $R^{3a}$, W, X and Y are as described herein, Z is Formula (III), $R^4$ is H, $R^6$ is —$OCH_3$, and $R^7$ is H. In an exemplary embodiment, the compound is Formula (I), $R^3$, $R^{3a}$, W, X and Y are as described herein, Z is Formula (III), $R^4$ is H, $R^6$ is H, and $R^7$ is —$OCH_3$.

In an exemplary embodiment, the compound is Formula (I), $R^3$, $R^{3a}$, W, X and Y are as described herein, Z is Formula (II), $R^4$ is H, $R^5$ is H, and $R^7$ is H. In an exemplary embodiment, the compound is Formula (I), W, X and Y are as described herein, Z is Formula (II), $R^3$ is H, $R^{3a}$ is H, $R^4$ is H, $R^5$ is H, and $R^7$ is H. In an exemplary embodiment, the compound is Formula (I), W, X and Y are as described herein, Z is Formula (II), $R^3$ is $CH_3$, $R^{3a}$ is H, $R^4$ is H, $R^5$ is H, and $R^7$ is H. In an exemplary embodiment, the compound is Formula (I), W, X and Y are as described herein, Z is Formula (II), $R^3$ is $CH_3$, $R^{3a}$ is $CH_3$, $R^4$ is H, $R^5$ is H, and $R^7$ is H. In an exemplary embodiment the compound is Formula (I), W, X and Y are as described herein, Z is Formula (II), $R^3$ is $CH_2NH_2$, $R^{3a}$ is H, $R^4$ is H, $R^5$ is H, and $R^7$ is H.

In an exemplary embodiment, the compound is Formula (I), $R^3$, $R^{3a}$, W, X and Y are as described herein, Z is Formula (III), $R^4$ is H, $R^6$ is H, and $R^7$ is H. In an exemplary embodiment, the compound is Formula (I), W, X and Y are as described herein, Z is Formula (III), $R^3$ is H, $R^{3a}$ is H, $R^4$ is H, $R^6$ is H, and $R^7$ is H. In an exemplary embodiment, the compound is Formula (I), W, X and Y are as described herein, Z is Formula (III), $R^3$ is $CH_3$, $R^{3a}$ is H, $R^4$ is H, $R^6$ is H, and $R^7$ is H. In an exemplary embodiment, the compound is Formula (I), W, X and Y are as described herein, Z is Formula (III), $R^3$ is $CH_3$, $R^{3a}$ is $CH_3$, $R^4$ is H, $R^6$ is H, and $R^7$ is H. In an exemplary embodiment, the compound is Formula (I), W, X and Y are as described herein, Z is Formula (III), $R^3$ is $CH_2NH_2$, $R^{3a}$ is H, $R^4$ is H, $R^6$ is H, and $R^7$ is H.

In an exemplary embodiment, the compound is Formula (I), $R^3$, $R^{3a}$, W, X and Y are as described herein, Z is Formula (II), $R^4$ is H, $R^5$ is H, and $R^7$ is F. In an exemplary embodiment, the compound is Formula (I), W, X and Y are as described herein, Z is Formula (II), $R^3$ is H, $R^{3a}$ is H, $R^4$ is H, $R^5$ is H, and $R^7$ is F. In an exemplary embodiment, the compound is Formula (I), W, X and Y are as described herein, Z is Formula (II), $R^3$ is $CH_3$, $R^{3a}$ is H, $R^4$ is H, $R^5$ is H, and $R^7$ is F. In an exemplary embodiment, the compound is Formula (I), W, X and Y are as described herein, Z is Formula (II), $R^3$ is $CH_3$, $R^{3a}$ is $CH_3$, $R^4$ is H, $R^5$ is H, and $R^7$ is F. In an exemplary embodiment, the compound is Formula (I), W, X and Y are as described herein, Z is Formula (II), $R^3$ is $CH_2NH_2$, $R^{3a}$ is H, $R^4$ is H, $R^5$ is H, and $R^7$ is F.

In an exemplary embodiment, the compound is Formula (I), $R^3$, $R^{3a}$, W, X and Y are as described herein, Z is Formula (III), $R^4$ is H, $R^6$ is H, and $R^7$ is F. In an exemplary embodiment, the compound is Formula (I), W, X and Y are as described herein, Z is Formula (III), $R^3$ is H, $R^{3a}$ is H, $R^4$ is H, $R^6$ is H, and $R^7$ is F. In an exemplary embodiment, the compound is Formula (I), W, X and Y are as described herein, Z is Formula (III), $R^3$ is $CH_3$, $R^{3a}$ is H, $R^4$ is H, $R^6$ is H, and $R^7$ is F. In an exemplary embodiment, the compound is Formula (I), W, X and Y are as described herein, Z is Formula (III), $R^3$ is $CH_3$, $R^{3a}$ is $CH_3$, $R^4$ is H, $R^6$ is H, and $R^7$ is F. In an exemplary embodiment, the compound is Formula (I), W, X and Y are as described herein, Z is Formula (III), $R^3$ is $CH_2NH_2$, $R^{3a}$ is H, $R^4$ is H, $R^6$ is H, and $R^7$ is F.

In an exemplary embodiment, the compound is Formula (I), $R^3$, $R^{3a}$, W, X and Y are as described herein, Z is Formula (II), $R^4$ is H, $R^5$ is F, and $R^7$ is H. In an exemplary embodiment, the compound is Formula (I), W, X and Y are as described herein, Z is Formula (II), $R^3$ is H, $R^{3a}$ is H, $R^4$ is H, $R^5$ is F, and $R^7$ is H. In an exemplary embodiment, the compound is Formula (I), W, X and Y are as described herein, Z is Formula (II), $R^3$ is $CH_3$, $R^{3a}$ is H, $R^4$ is H, $R^5$ is F, and $R^7$ is H. In an exemplary embodiment, the compound is Formula (I), W, X and Y are as described herein, Z is Formula (II), $R^3$ is $CH_3$, $R^{3a}$ is $CH_3$, $R^4$ is H, $R^5$ is F, and $R^7$ is H. In an exemplary embodiment, the compound is Formula (I), W, X and Y are as described herein, Z is Formula (II), $R^3$ is $CH_2NH_2$, $R^{3a}$ is H, $R^4$ is H, $R^5$ is F, and $R^7$ is H.

In an exemplary embodiment, the compound is Formula (I), $R^3$, $R^{3a}$, W, X and Y are as described herein, Z is Formula (III), $R^4$ is H, $R^6$ is F, and $R^7$ is H. In an exemplary embodiment, the compound is Formula (I), W, X and Y are as described herein, Z is Formula (III), $R^3$ is H, $R^{3a}$ is H, $R^4$ is H, $R^6$ is F, and $R^7$ is H. In an exemplary embodiment, the compound is Formula (I), W, X and Y are as described herein, Z is Formula (III), $R^3$ is $CH_3$, $R^{3a}$ is H, $R^4$ is H, $R^6$ is F, and $R^7$ is H. In an exemplary embodiment, the compound is Formula (I), W, X and Y are as described herein, Z is Formula (III), $R^3$ is $CH_3$, $R^{3a}$ is $CH_3$, $R^4$ is H, $R^6$ is F, and $R^7$ is H. In an exemplary embodiment, the compound is Formula (I), W, X and Y are as described herein, Z is Formula (III), $R^3$ is $CH_2NH_2$, $R^{3a}$ is H, $R^4$ is H, $R^6$ is F, and $R^7$ is H.

In an exemplary embodiment, the compound is Formula (I), $R^3$, $R^{3a}$, W, X and Y are as described herein, Z is Formula (II), $R^4$ is H, $R^5$ is H, and $R^7$ is CN. In an exemplary embodiment, the compound is Formula (I), W, X and Y are as described herein, Z is Formula (II), $R^3$ is H, $R^{3a}$ is H, $R^4$ is H, $R^5$ is H, and $R^7$ is CN. In an exemplary embodiment, the compound is Formula (I), W, X and Y are as described herein, Z is Formula (II), $R^3$ is $CH_3$, $R^{3a}$ is H, $R^4$ is H, $R^5$ is H, and $R^7$ is CN. In an exemplary embodiment, the compound is Formula (I), W, X and Y are as described herein, Z is Formula (II), $R^3$ is $CH_3$, $R^{3a}$ is $CH_3$, $R^4$ is H, $R^5$ is H, and $R^7$ is CN. In an exemplary embodiment, the compound is Formula (I), W, X and Y are as described herein, Z is Formula (II), $R^3$ is $CH_2NH_2$, $R^{3a}$ is H, $R^4$ is H, $R^5$ is H, and $R^7$ is CN.

In an exemplary embodiment, the compound is Formula (I), $R^3$, $R^{3a}$, W, X and Y are as described herein, Z is Formula (III), $R^4$ is H, $R^6$ is H, and $R^7$ is CN. In an exemplary embodiment, the compound is Formula (I), W, X and Y are as described herein, Z is Formula (III), $R^3$ is H, $R^{3a}$ is H, $R^4$ is H, $R^6$ is H, and $R^7$ is CN. In an exemplary embodiment, the compound is Formula (I), W, X and Y are as described herein, Z is Formula (III), $R^3$ is $CH_3$, $R^{3a}$ is H, $R^4$ is H, $R^6$ is H, and $R^7$ is CN. In an exemplary embodiment, the compound is Formula (I), W, X and Y are as described herein, Z is Formula (III), $R^3$ is $CH_3$, $R^{3a}$ is $CH_3$, $R^4$ is H, $R^6$ is H, and $R^7$ is CN. In an exemplary embodiment, the compound is Formula (I), W, X and Y are as described herein, Z is Formula (III), $R^3$ is $CH_2NH_2$, $R^{3a}$ is H, $R^4$ is H, $R^6$ is H, and $R^7$ is CN.

In an exemplary embodiment, the compound is Formula (I), $R^3$, $R^{3a}$, W, X and Y are as described herein, Z is Formula (II), $R^4$ is H, $R^5$ is —$OCH_3$, and $R^7$ is H. In an exemplary embodiment, the compound is Formula (I), W, X and Y are as described herein, Z is Formula (II), $R^3$ is H, $R^{3a}$ is H, $R^4$ is H, $R^5$ is —$OCH_3$, and $R^7$ is H. In an exemplary embodiment, the compound is Formula (I), W, X and Y are as described herein, Z is Formula (II), $R^3$ is $CH_3$, $R^{3a}$ is H, $R^4$ is H, $R^5$ is —$OCH_3$, and $R^7$ is H. In an exemplary embodiment, the compound is Formula (I), W, X and Y are as described herein, Z is Formula (II), $R^3$ is $CH_3$, $R^{3a}$ is $CH_3$, $R^4$ is H, $R^5$ is —$OCH_3$, and $R^7$ is H. In an exemplary embodiment, the compound is Formula (I), W, X and Y are as described herein, Z is Formula (II), $R^3$ is —$CH_2NH_2$, $R^{3a}$ is H, $R^4$ is H, $R^5$ is —$OCH_3$, and $R^7$ is H.

In an exemplary embodiment, the compound is Formula (I), $R^3$, $R^{3a}$, W, X and Y are as described herein, Z is Formula (III), $R^4$ is H, $R^6$ is —$OCH_3$, and $R^7$ is H. In an exemplary embodiment, the compound is Formula (I), W, X and Y are as described herein, Z is Formula (III), $R^3$ is H, $R^{3a}$ is H, $R^4$ is H, $R^6$ is —$OCH_3$, and $R^7$ is H. In an exemplary embodiment, the compound is Formula (I), W, X and Y are as described herein, Z is Formula (III), $R^3$ is $CH_3$, $R^{3a}$ is H, $R^4$ is H, $R^6$ is —$OCH_3$, and $R^7$ is H. In an exemplary embodiment, the compound is Formula (I), W, X and Y are as described herein, Z is Formula (III), $R^3$ is $CH_3$, $R^{3a}$ is $CH_3$, $R^4$ is H, $R^6$ is —$OCH_3$, and $R^7$ is H. In an exemplary embodiment, the compound is Formula (I), W, X and Y are as described herein, Z is Formula (III), $R^3$ is —$CH_2NH_2$, $R^{3a}$ is H, $R^4$ is H, $R^6$ is —$OCH_3$, and $R^7$ is H.

In an exemplary embodiment, the compound is Formula (I), $R^3$, $R^{3a}$, W, X and Y are as described herein, Z is Formula (II), $R^4$ is —$CH_2NH_2$, $R^5$ is H, and $R^7$ is H. In an exemplary embodiment, the compound is Formula (I), W, X and Y are as described herein, Z is Formula (II), $R^3$ is H, $R^{3a}$ is H, $R^4$ is —$CH_2NH_2$, $R^5$ is H, and $R^7$ is H. In an exemplary embodiment, the compound is Formula (I), W, X and Y are as described herein, Z is Formula (II), $R^3$ is $CH_3$, $R^{3a}$ is H, $R^4$ is —$CH_2NH_2$, $R^5$ is H, and $R^7$ is H. In an exemplary embodiment, the compound is Formula (I), W, X and Y are as described herein, Z is Formula (II), $R^3$ is $CH_3$, $R^{3a}$ is $CH_3$, $R^4$ is —$CH_2NH_2$, $R^5$ is H, and $R^7$ is H. In an exemplary embodiment, the compound is Formula (I), W, X and Y are as described herein, Z is Formula (II), $R^3$ is —$CH_2NH_2$, $R^{3a}$ is H, $R^4$ is —$CH_2NH_2$, $R^5$ is H, and $R^7$ is H.

In an exemplary embodiment, the compound is Formula (I), $R^3$, $R^{3a}$, W, X and Y are as described herein, Z is Formula (III), $R^4$ is —$CH_2NH_2$, $R^6$ is H, and $R^7$ is H. In an exemplary embodiment, the compound is Formula (I), W, X and Y are as described herein, Z is Formula (III), $R^3$ is H, $R^{3a}$ is H, $R^4$ is —$CH_2NH_2$, $R^6$ is H, and $R^7$ is H. In an exemplary embodiment, the compound is Formula (I), W, X and Y are as described herein, Z is Formula (III), $R^3$ is $CH_3$, $R^{3a}$ is H, $R^4$ is —$CH_2NH_2$, $R^6$ is H, and $R^7$ is H. In an exemplary embodiment, the compound is Formula (I), W, X and Y are as described herein, Z is Formula (III), $R^3$ is $CH_3$, $R^{3a}$ is $CH_3$, $R^4$ is —$CH_2NH_2$, $R^6$ is H, and $R^7$ is H. In an exemplary embodiment, the compound is Formula (I), W, X and Y are as described herein, Z is Formula (III), $R^3$ is $CH_2NH_2$, $R^{3a}$ is H, $R^4$ is $CH_2NH_2$, $R^6$ is H, and $R^7$ is H.

In an exemplary embodiment, the compound is Formula (I), W, X and Y are as described herein, and said Z is $$(IV)$$

wherein $R^3$, $R^{3a}$, $R^4$, and $R^7$ are each independently selected from the group consisting of $R^{10}$, —$OR^{10}$, —$NR^{10}R^{11}$, —$SR^{10}$, —$S(O)R^{10}$, —$S(O)_2R^{10}$, —$S(O)_2NR^{10}R^{11}$, —$C(O)R^{10}$, —$C(O)OR^{10}$, and —$C(O)NR^{10}R^{11}$ wherein $R^{10}$ and $R^{11}$ are each independently selected from the group consisting of H, halogen, cyano, nitro, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

In an exemplary embodiment, the compound is Formula (I), W, X and Y are as described herein, and said Z is (V)

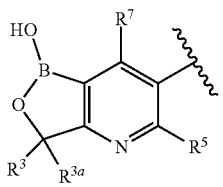

wherein $R^3$, $R^{3a}$, $R^5$, and $R^7$ are each independently selected from the group consisting of $R^{10}$, —$OR^{10}$, —$NR^{10}R^{11}$, —$SR^{10}$, —$S(O)R^{10}$, —$S(O)_2R^{10}$, —$S(O)_2NR^{10}R^{11}$, —$C(O)R^{10}$, —$C(O)OR^{10}$, and —$C(O)NR^{10}R^{11}$ wherein $R^{10}$ and $R^{11}$ are each independently selected from the group consisting of H, halogen, cyano, nitro, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

In an exemplary embodiment, the compound is Formula (I), W, X and Y are as described herein, and said Z is (VI)

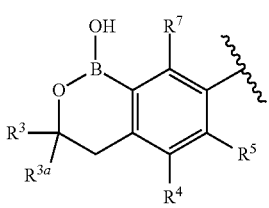

wherein $R^3$, $R^{3a}$, $R^4$, $R^5$, and $R^7$ are each independently selected from the group consisting of $R^{10}$, —$OR^{10}$, —$NR^{10}R^{11}$, —$S(O)R^{10}$, —$S(O)_2R^{10}$, —$S(O)_2NR^{10}R^{11}$, —$C(O)R^{10}$, —$C(O)OR^{10}$, and —$C(O)NR^{10}R^{11}$ wherein $R^{10}$ and $R^{11}$ are each independently selected from the group consisting of H, halogen, cyano, nitro, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

In an exemplary embodiment, the compound is Formula (I), W, X and Y are as described herein, and said Z is (VII)

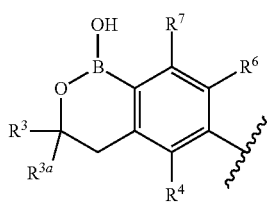

wherein $R^3$, $R^{3a}$, $R^4$, $R^6$, and $R^7$ are each independently selected from the group consisting of $R^{10}$, —$OR^{10}$, —$NR^{10}R^{11}$, —$S(O)R^{10}$, —$S(O)_2R^{10}$, —$S(O)_2NR^{10}R^{11}$, —$C(O)R^{10}$, —$C(O)OR^{10}$, and —$C(O)NR^{10}R^{11}$ wherein $R^{10}$ and $R^{11}$ are each independently selected from the group consisting of H, halogen, cyano, nitro, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

In an exemplary embodiment, the compound is Formula (I), W, X and Y are as described herein, and said Z is (VIII)

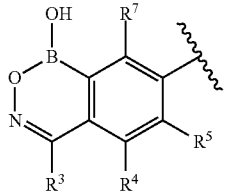

wherein $R^3$, $R^{3a}$, $R^4$, $R^5$, and $R^7$ are each independently selected from the group consisting of $R^{10}$, —$OR^{10}$, —$NR^{10}R^{11}$, —$S(O)R^{10}$, —$S(O)_2R^{10}$, —$S(O)_2NR^{10}R^{11}$, —$C(O)R^{10}$, —$C(O)OR^{10}$, and —$C(O)NR^{10}R^{11}$ wherein $R^{10}$ and $R^{11}$ are each independently selected from the group consisting of H, halogen, cyano, nitro, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

In an exemplary embodiment, the compound is Formula (I), W, X and Y are as described herein, and said Z is (IX)

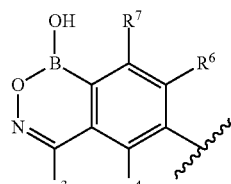

wherein $R^3$, $R^{3a}$, $R^4$, $R^6$, and $R^7$ are each independently selected from the group consisting of $R^{10}$, —$OR^{10}$, —$NR^{10}R^{11}$, —$SR^{10}$, —$S(O)R^{10}$, —$S(O)_2R^{10}$, —$S(O)_2NR^{10}R^{11}$, —$C(O)R^{10}$, —$C(O)OR^{10}$, and —$C(O)NR^{10}R^{11}$ wherein $R^{10}$ and $R^{11}$ are each independently selected from the group consisting of H, halogen, cyano, nitro, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

In an exemplary embodiment, the compound is Formula (I), W, X and Y are as described herein, and said Z is (X)

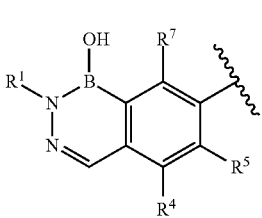

wherein $R^1$, $R^4$, $R^5$, and $R^7$ are each independently selected from the group consisting of $R^{10}$, —$OR^{10}$, —$NR^{10}R^{11}$, —$S(O)R^{10}$, —$S(O)_2R^{10}$, —$S(O)_2NR^{10}R^{11}$, —$C(O)R^{10}$, —$C(O)OR^{10}$, and —$C(O)NR^{10}R^{11}$ wherein $R^{10}$ and $R^{11}$ are each independently selected from the group consisting of H, halogen, cyano, nitro, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

In an exemplary embodiment, the compound is Formula (I), W, X and Y are as described herein, and said Z is

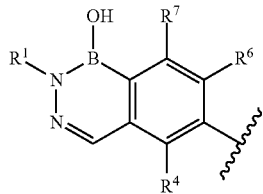

(XI)

wherein $R^1$, $R^4$, $R^6$, and $R^7$ are each independently selected from the group consisting of $R^{10}$, —$OR^{10}$, —$NR^{10}R^{11}$, —$S(O)R^{10}$, —$S(O)_2R^{10}$, —$S(O)_2NR^{10}R^{11}$, —$C(O)R^{10}$, —$C(O)OR^{10}$, and —$C(O)NR^{10}R^{11}$ wherein $R^{10}$ and $R^{11}$ are each independently selected from the group consisting of H, halogen, cyano, nitro, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

In an exemplary embodiment, the compound is Formula (I), W, X and Y are as described herein, and said Z is

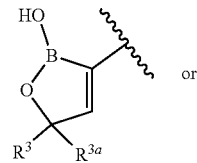

(XII)

or

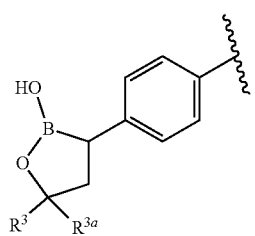

(XIII)

wherein $R^3$ and $R^{3a}$ are each independently selected from the group consisting of $R^{10}$, —$OR^{10}$, —$NR^{10}R^{11}$, —$S(O)R^{10}$, —$S(O)_2R^{10}$, —$S(O)_2NR^{10}R^{11}$, —$C(O)R^{10}$, —$C(O)OR^{10}$, and —$C(O)NR^{10}R^{11}$ wherein $R^{10}$ and $R^{11}$ are each independently selected from the group consisting of H, halogen, cyano, nitro, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

In an exemplary embodiment, the compound is Formula (I), W, X and Y are as described herein, and said Z is

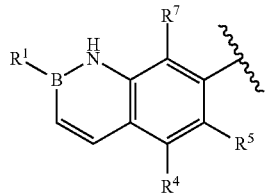

(XIV)

wherein $R^1$, $R^4$, $R^5$, and $R^7$ are each independently selected from the group consisting of $R^{10}$, —$OR^{10}$, —$NR^{10}R^{11}$, —$SR^{10}$, —$S(O)R^{10}$, —$S(O)_2R^{10}$, —$S(O)_2NR^{10}R^{11}$, —$C(O)R^{10}$, —$C(O)OR^{10}$, and —$C(O)NR^{10}R^{11}$ wherein $R^{10}$ and $R^{11}$ are each independently selected from the group consisting of H, halogen, cyano, nitro, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

In an exemplary embodiment, the compound is Formula (I), W is H, and X, Y, and Z are as described herein. In an exemplary embodiment, the compound is Formula (I), X and Z are as described herein, W is H, and Y is substituted alkylene. In an exemplary embodiment, the compound is Formula (I), X and Z are as described herein, W is H, and Y is unsubstituted alkylene. In an exemplary embodiment, the compound is Formula (I), X and Z are as described herein, W is H, and Y is methylene. In an exemplary embodiment, the compound is Formula (I), X and Z are as described herein, W is H, and Y is ethylene. In an exemplary embodiment, the compound is Formula (I), X and Z are as described herein, W is H, and Y is propylene. In an exemplary embodiment, the compound is Formula (I), X and Z are as described herein, W is H, and Y is substituted heteroalkylene. In an exemplary embodiment, the compound is Formula (I), X and Z are as described herein, W is H, and Y is unsubstituted heteroalkylene. In an exemplary embodiment, the compound is Formula (I), X and Z are as described herein, W is H, and Y is *—$OCH_2$—. In an exemplary embodiment, the compound is Formula (I), X and Z are as described herein, W is H, and Y is *—$SCH_2$—. In an exemplary embodiment, the compound is Formula (I), X and Z are as described herein, W is H, and Y is *—$NHCH_2$—. In an exemplary embodiment, the compound is Formula (I), X and Z are as described herein, W is H, and Y is *—$CH_2NH$—. In an exemplary embodiment, the compound is Formula (I), X and Z are as described herein, W is H, and Y is *—$C(O)NH$—. In an exemplary embodiment, the compound is Formula (I), X and Z are as described herein, W is H, and Y is *—$CH_2NHCH_2$— or 1-piperazinyl or *—$S(O)CH_2$— or *—$S(O)_2$—. In an exemplary embodiment, the compound is Formula (I), X and Z are as described herein, W is H, and Y is 1-piperazinyl. In an exemplary embodiment, the compound is Formula (I), X and Z are as described herein, W is H, and Y is *—$S(O)CH_2$—. In an exemplary embodiment, the compound is Formula (I), X and Z are as described herein, W is H, and Y is *—$S(O)_2$—. In an exemplary embodiment, the compound is Formula (I), X and Z are as described herein, W is H, and Y is *—$S(O)_2CH_2$—. In an exemplary embodiment, the compound is Formula (I), X and Z are as described herein, W is H, and Y is *—$NHC(O)OCH_2$—. In this paragraph, * represents the point of attachment to Z.

In an exemplary embodiment, the compound is Formula (I), W is H, X and Y are as described herein, and Z is substituted or unsubstituted heteroaryl, wherein said heteroaryl comprises an endocyclic boron. In an exemplary embodiment, the compound is Formula (I), W is H, X and Y are as described herein, and Z is substituted or unsubstituted heteroaryl, wherein said heteroaryl has one ring, and said ring comprises an endocyclic boron. In an exemplary embodiment, the compound is Formula (I), W is H, X and Y are as described herein, and Z is substituted or unsubstituted heteroaryl, wherein said heteroaryl has two rings, and one of the two rings comprises an endocyclic boron.

In an exemplary embodiment, the compound is Formula (I), W is H, X and Y are as described herein, and Z is substituted or unsubstituted heterocycloalkyl, wherein said heterocycloalkyl comprises an endocyclic boron. In an exemplary embodiment, the compound is Formula (I), W is H, X and Y are as described herein, and Z is substituted or unsubstituted heterocycloalkyl, wherein said heterocycloalkyl has one ring, and said ring comprises an endocyclic boron. In an exemplary embodiment, the compound is Formula (I), W is H, X and Y are as described herein, and Z is substituted or unsubstituted heterocycloalkyl, wherein said heterocycloalkyl has two rings, and one of the two rings comprises an endocyclic boron.

In an exemplary embodiment, the compound is Formula (I), W is H, X and Y are as described herein, and Z is substituted or unsubstituted benzoxaborole. In an exemplary embodiment, the compound is Formula (I), W is H, X and Y are as described herein, and Z is substituted or unsubstituted pyridinyloxaborole. In an exemplary embodiment, the compound is Formula (I), W is H, X and Y are as described herein, and Z is substituted or unsubstituted benzoxaborininol. In an exemplary embodiment, the compound is Formula (I), W is H, X and Y are as described herein, and Z is substituted or unsubstituted benzoxazaborininol. In an exemplary embodiment, the compound is Formula (I), W is H, X and Y are as described herein, and Z is substituted or unsubstituted benzodiazaborininol. In an exemplary embodiment, the compound is Formula (I), W is H, X and Y are as described herein, and Z is substituted or unsubstituted oxaborole. In an exemplary embodiment, the compound is Formula (I), W is H, X and Y are as described herein, and Z is substituted or unsubstituted dihydrobenzoazaborinine.

In an exemplary embodiment, the compound is Formula (I), X is as described herein, W is H, Z is substituted or unsubstituted heteroaryl, wherein said heteroaryl comprises an endocyclic boron, and Y is substituted alkylene. In an exemplary embodiment, the compound is Formula (I), X is as described herein, W is H, Z is substituted or unsubstituted heteroaryl, wherein said heteroaryl comprises an endocyclic boron, and Y is unsubstituted alkylene. In an exemplary embodiment, the compound is Formula (I), X is as described herein, W is H, Z is substituted or unsubstituted heteroaryl, wherein said heteroaryl comprises an endocyclic boron, and Y is methylene. In an exemplary embodiment, the compound is Formula (I), X is as described herein, W is H, Z is substituted or unsubstituted heteroaryl, wherein said heteroaryl comprises an endocyclic boron, and Y is ethylene. In an exemplary embodiment, the compound is Formula (I), X is as described herein, W is H, Z is substituted or unsubstituted heteroaryl, wherein said heteroaryl comprises an endocyclic boron, and Y is propylene. In an exemplary embodiment, the compound is Formula (I), X is as described herein, W is H, Z is substituted or unsubstituted heteroaryl, wherein said heteroaryl comprises an endocyclic boron, and Y is substituted heteroalkylene. In an exemplary embodiment, the compound is Formula (I), X is as described herein, W is H, Z is substituted or unsubstituted heteroaryl, wherein said heteroaryl comprises an endocyclic boron, and Y is unsubstituted heteroalkylene. In an exemplary embodiment, the compound is Formula (I), X is as described herein, W is H, Z is substituted or unsubstituted heteroaryl, wherein said heteroaryl comprises an endocyclic boron, and Y is *—OCH$_2$—. In an exemplary embodiment, the compound is Formula (I), X is as described herein, W is H, Z is substituted or unsubstituted heteroaryl, wherein said heteroaryl comprises an endocyclic boron, and Y is *—SCH$_2$—. In an exemplary embodiment, the compound is Formula (I), X is as described herein, W is H, Z is substituted or unsubstituted heteroaryl, wherein said heteroaryl comprises an endocyclic boron, and Y is *—NHCH$_2$—. In an exemplary embodiment, the compound is Formula (I), X is as described herein, W is H, Z is substituted or unsubstituted heteroaryl, wherein said heteroaryl comprises an endocyclic boron, and Y is *—CH$_2$NH—. In an exemplary embodiment, the compound is Formula (I), X is as described herein, W is H, Z is substituted or unsubstituted heteroaryl, wherein said heteroaryl comprises an endocyclic boron, and Y is *—C(O)NH—. In an exemplary embodiment, the compound is Formula (I), X is as described herein, W is H, Z is substituted or unsubstituted heteroaryl, wherein said heteroaryl comprises an endocyclic boron, and Y is *—CH$_2$NHCH$_2$— or 1-piperazinyl or *—S(O)CH$_2$— or *—S(O)$_2$—. In an exemplary embodiment, the compound is Formula (I), X is as described herein, W is H, Z is substituted or unsubstituted heteroaryl, wherein said heteroaryl comprises an endocyclic boron, and Y is 1-piperazinyl. In an exemplary embodiment, the compound is Formula (I), X is as described herein, W is H, Z is substituted or unsubstituted heteroaryl, wherein said heteroaryl comprises an endocyclic boron, and Y is *—S(O)CH$_2$—. In an exemplary embodiment, the compound is Formula (I), X is as described herein, W is H, Z is substituted or unsubstituted heteroaryl, wherein said heteroaryl comprises an endocyclic boron, and Y is *—S(O)$_2$—. In an exemplary embodiment, the compound is Formula (I), X is as described herein, W is H, Z is substituted or unsubstituted heteroaryl, wherein said heteroaryl comprises an endocyclic boron, and Y is *—S(O)$_2$CH$_2$—. In an exemplary embodiment, the compound is Formula (I), X is as described herein, W is H, Z is substituted or unsubstituted heteroaryl, wherein said heteroaryl comprises an endocyclic boron, and Y is *—NHC(O)OCH$_2$—. In this paragraph, * represents the point of attachment to Z.

In an exemplary embodiment, the compound is Formula (I), X is as described herein, W is H, Z is substituted or unsubstituted heteroaryl, wherein said heteroaryl has one ring, and said ring comprises an endocyclic boron, and Y is substituted alkylene. In an exemplary embodiment, the compound is Formula (I), X is as described herein, W is H, Z is substituted or unsubstituted heteroaryl, wherein said heteroaryl has one ring, and said ring comprises an endocyclic boron, and Y is unsubstituted alkylene. In an exemplary embodiment, the compound is Formula (I), X is as described herein, W is H, Z is substituted or unsubstituted heteroaryl, wherein said heteroaryl has one ring, and said ring comprises an endocyclic boron, and Y is methylene. In an exemplary embodiment, the compound is Formula (I), X is as described herein, W is H, Z is substituted or unsubstituted heteroaryl, wherein said heteroaryl has one ring, and said ring comprises an endocyclic boron, and Y is ethylene. In an exemplary embodiment, the compound is Formula (I), X is as described herein, W is H, Z is substituted or unsubstituted heteroaryl, wherein said heteroaryl has one ring, and said ring comprises an endocyclic boron, and Y is propylene. In an exemplary embodiment, the compound is Formula (I), X is as described herein, W is H, Z is substituted or unsubstituted heteroaryl, wherein said heteroaryl has one ring, and said ring comprises an endocyclic boron, and Y is substituted heteroalkylene. In an exemplary embodiment, the compound is Formula (I), X is as described herein, W is H, Z is substituted or unsubstituted heteroaryl, wherein said heteroaryl has one ring, and said ring comprises an endocyclic boron, and Y is unsubstituted heteroalkylene. In an exemplary embodiment, the compound is Formula (I), X is as described herein, W is H, Z is substituted or unsubstituted heteroaryl, wherein said heteroaryl has one ring, and said ring comprises an endocyclic boron, and Y is *—OCH$_2$—. In an exemplary embodiment, the compound is Formula (I), X is as described herein, W is H, Z is substituted or unsubstituted heteroaryl, wherein said heteroaryl has one ring, and said ring comprises an endocyclic boron, and Y is *—SCH$_2$—. In an exemplary embodiment, the compound is Formula (I), X is as described herein, W is H, Z is substituted or unsubstituted heteroaryl, wherein said heteroaryl has one ring, and said ring comprises an endocyclic boron, and Y is *—NHCH$_2$—. In an exemplary embodiment, the compound is Formula (I), X is as described herein, W is H, Z is substituted or unsubstituted heteroaryl, wherein said heteroaryl has one ring, and said ring comprises an endocyclic boron, and Y is *—CH$_2$NH—. In an exemplary embodiment, the compound is Formula (I), X is as described herein, W is H, Z is substituted or unsubstituted heteroaryl, wherein said heteroaryl has one ring, and said ring comprises an endocyclic boron, and Y is *—C(O)NH—. In an exemplary embodiment, the compound is Formula (I), X is as described herein, W is H, Z is substituted or unsubstituted heteroaryl, wherein said heteroaryl has one ring, and said ring comprises an endocyclic boron, and Y is *—CH$_2$NHCH$_2$— or 1-piperazinyl or *—S(O)CH$_2$— or *—S(O)$_2$—. In an exemplary embodiment, the compound is Formula (I), X is as described herein, W is H, Z is substituted or unsubstituted heteroaryl, wherein said heteroaryl has one ring, and said ring comprises an endocyclic boron, and Y is 1-piperazinyl. In an exemplary embodiment, the compound is Formula (I), X is as described herein, W is H, Z is substituted or unsubstituted heteroaryl, wherein said heteroaryl has one ring, and said ring comprises an endocyclic boron, and Y is *—S(O)CH$_2$—. In an exemplary embodiment, the compound is Formula (I), X is as described herein, W is H, Z is substituted or unsubstituted heteroaryl, wherein said heteroaryl has one ring, and said ring comprises an endocyclic boron, and Y is *—S(O)$_2$—. In an exemplary embodiment, the compound is Formula (I), X is as described herein, W is H, Z is substituted or unsubstituted heteroaryl, wherein said heteroaryl has one ring, and said ring comprises an endocyclic boron, and Y is *—S(O)$_2$CH$_2$—. In an exemplary embodiment, the compound is Formula (I), X is as described herein, W is H, Z is substituted or unsubstituted heteroaryl, wherein said heteroaryl has one ring, and said ring comprises an endocyclic boron, and Y is *—NHC(O)OCH$_2$—. In this paragraph, * represents the point of attachment to Z.

In an exemplary embodiment, the compound is Formula (I), X is as described herein, W is H, Z is substituted or unsubstituted heteroaryl, wherein said heteroaryl has two rings, and one of the two rings comprises an endocyclic boron, and Y is substituted alkylene. In an exemplary embodiment, the compound is Formula (I), X is as described herein, W is H, Z is substituted or unsubstituted heteroaryl, wherein said heteroaryl has two rings, and one of the two rings comprises an endocyclic boron, and Y is unsubstituted alkylene. In an exemplary embodiment, the compound is Formula (I), X is as described herein, W is H, Z is substituted or unsubstituted heteroaryl, wherein said heteroaryl has two rings, and one of the two rings comprises an endocyclic boron, and Y is methylene. In an exemplary embodiment, the compound is Formula (I), X is as described herein, W is H, Z is substituted or unsubstituted heteroaryl, wherein said heteroaryl has two rings, and one of the two rings comprises an endocyclic boron, and Y is ethylene. In an exemplary embodiment, the compound is Formula (I), X is as described herein, W is H, Z is substituted or unsubstituted heteroaryl, wherein said heteroaryl has two rings, and one of the two rings comprises an endocyclic boron, and Y is propylene. In an exemplary embodiment, the compound is Formula (I), X is as described herein, W is H, Z is substituted or unsubstituted heteroaryl, wherein said heteroaryl has two rings, and one of the two rings comprises an endocyclic boron, and Y is substituted heteroalkylene. In an exemplary embodiment, the compound is Formula (I), X is as described herein, W is H, Z is substituted or unsubstituted heteroaryl, wherein said heteroaryl has two rings, and one of the two rings comprises an endocyclic boron, and Y is unsubstituted heteroalkylene. In an exemplary embodiment, the compound is Formula (I), X is as described herein, W is H, Z is substituted or unsubstituted heteroaryl, wherein said heteroaryl has two rings, and one of the two rings comprises an endocyclic boron, and Y is *—OCH$_2$—. In an exemplary embodiment, the compound is Formula (I), X is as described herein, W is H, Z is substituted or unsubstituted heteroaryl, wherein said heteroaryl has two rings, and one of the two rings comprises an endocyclic boron, and Y is *—SCH$_2$—. In an exemplary embodiment, the compound is Formula (I), X is as described herein, W is H, Z is substituted or unsubstituted heteroaryl, wherein said heteroaryl has two rings, and one of the two rings comprises an endocyclic boron, and Y is *—NHCH$_2$—. In an exemplary embodiment, the compound is Formula (I), X is as described herein, W is H, Z is substituted or unsubstituted heteroaryl, wherein said heteroaryl has two rings, and one of the two rings comprises an endocyclic boron, and Y is *—CH$_2$NH—. In an exemplary embodiment, the compound is Formula (I), X is as described herein, W is H, Z is substituted or unsubstituted heteroaryl, wherein said heteroaryl has two rings, and one of the two rings comprises an endocyclic boron, and Y is *—C(O)NH—. In an exemplary embodiment, the compound is Formula (I), X is as described herein, W is H, Z is substituted or unsubstituted heteroaryl, wherein said heteroaryl has two rings, and one of the two rings comprises an endocyclic boron, and Y is *—CH$_2$NHCH$_2$— or 1-piperazinyl or *—S(O)CH$_2$— or *—S(O)$_2$—. In an exemplary embodiment, the compound is Formula (I), X is as described herein, W is H, Z is substituted or unsubstituted heteroaryl, wherein said heteroaryl has two rings, and one of the two rings comprises an endocyclic boron, and Y is 1-piperazinyl. In an exemplary embodiment, the compound is Formula (I), X is as described herein, W is H, Z is substituted or unsubstituted heteroaryl, wherein said heteroaryl has two rings, and one of the two rings comprises an endocyclic boron, and Y is *—S(O)CH$_2$—. In an exemplary embodiment, the compound is Formula (I), X is as described herein, W is H, Z is substituted or unsubstituted heteroaryl, wherein said heteroaryl has two rings, and one of the two rings comprises an endocyclic boron, and Y is *—S(O)$_2$—. In an exemplary embodiment, the compound is Formula (I), X is as described herein, W is H, Z is substituted or unsubstituted heteroaryl, wherein said heteroaryl has two rings, and one of the two rings comprises an endocyclic boron, and Y is *—S(O)$_2$CH$_2$—. In an exemplary embodiment, the compound is Formula (I), X is as described herein, W is H, Z is substituted or unsubstituted heteroaryl, wherein said heteroaryl has two rings, and one of the two rings comprises an endocyclic boron, and Y is *—NHC(O)OCH$_2$—. In this paragraph, * represents the point of attachment to Z.

In an exemplary embodiment, the compound is Formula (I), X is as described herein, W is H, Z is substituted or unsubstituted heterocycloalkyl, wherein said heterocycloalkyl comprises an endocyclic boron, and Y is substituted alkylene. In an exemplary embodiment, the compound is Formula (I), X is as described herein, W is H, Z is substituted or unsubstituted heterocycloalkyl, wherein said heterocycloalkyl comprises an endocyclic boron, and Y is unsubstituted alkylene. In an exemplary embodiment, the compound is Formula (I), X is as described herein, W is H, Z is substituted or unsubstituted heterocycloalkyl, wherein said heterocycloalkyl comprises an endocyclic boron, and Y is methylene. In an exemplary embodiment, the compound is Formula (I), X is as described herein, W is H, Z is substituted or unsubstituted heterocycloalkyl, wherein said heterocycloalkyl comprises an endocyclic boron, and Y is ethylene. In an exemplary embodiment, the compound is Formula (I), X is as described herein, W is H, Z is substituted or unsubstituted heterocycloalkyl, wherein said heterocycloalkyl comprises an endocyclic boron, and Y is propylene. In an exemplary embodiment, the compound is Formula (I), X is as described herein, W is H, Z is substituted or unsubstituted heterocycloalkyl, wherein said heterocycloalkyl comprises an endocyclic boron, and Y is substituted heteroalkylene. In an exemplary embodiment, the compound is Formula (I), X is as described herein, W is H, Z is substituted or unsubstituted heterocycloalkyl, wherein said heterocycloalkyl comprises an endocyclic boron, and Y is unsubstituted heteroalkylene. In an exemplary embodiment, the compound is Formula (I), X is as described herein, W is H, Z is substituted or unsubstituted heterocycloalkyl, wherein said heterocycloalkyl comprises an endocyclic boron, and Y is *—OCH$_2$—. In an exemplary embodiment, the compound is Formula (I), X is as described herein, W is H, Z is substituted or unsubstituted heterocycloalkyl, wherein said heterocycloalkyl comprises an endocyclic boron, and Y is *—SCH$_2$—. In an exemplary embodiment, the compound is Formula (I), X is as described herein, W is H, Z is substituted or unsubstituted heterocycloalkyl, wherein said heterocycloalkyl comprises an endocyclic boron, and Y is *—NHCH$_2$—. In an exemplary embodiment, the compound is Formula (I), X is as described herein, W is H, Z is substituted or unsubstituted heterocycloalkyl, wherein said heterocycloalkyl comprises an endocyclic boron, and Y is *—CH$_2$NH—. In an exemplary embodiment, the compound is Formula (I), X is as described herein, W is H, Z is substituted or unsubstituted heterocycloalkyl, wherein said heterocycloalkyl comprises an endocyclic boron, and Y is *—C(O)NH—. In an exemplary embodiment, the compound is Formula (I), X is as described herein, W is H, Z is substituted or unsubstituted heterocycloalkyl, wherein said heterocycloalkyl comprises an endocyclic boron, and Y is *—CH$_2$NHCH$_2$— or 1-piperazinyl or *—S(O)CH$_2$— or *—S(O)$_2$—. In an exemplary embodiment, the compound is Formula (I), X is as described herein, W is H, Z is substituted or unsubstituted heterocycloalkyl, wherein said heterocycloalkyl comprises an endocyclic boron, and Y is 1-piperazinyl. In an exemplary embodiment, the compound is Formula (I), X is as described herein, W is H, Z is substituted or unsubstituted heterocycloalkyl, wherein said heterocycloalkyl comprises an endocyclic boron, and Y is *—S(O)CH$_2$—. In an exemplary embodiment, the compound is Formula (I), X is as described herein, W is H, Z is substituted or unsubstituted heterocycloalkyl, wherein said heterocycloalkyl comprises an endocyclic boron, and Y is *—S(O)$_2$—. In an exemplary embodiment, the compound is Formula (I), X is as described herein, W is H, Z is substituted or unsubstituted heterocycloalkyl, wherein said heterocycloalkyl comprises an endocyclic boron, and Y is *—S(O)$_2$CH$_2$—. In an exemplary embodiment, the compound is Formula (I), X is as described herein, W is H, Z is substituted or unsubstituted heterocycloalkyl, wherein said heterocycloalkyl comprises an endocyclic boron, and Y is *—NHC(O)OCH$_2$—. In this paragraph, * represents the point of attachment to Z.

In an exemplary embodiment, the compound is Formula (I), X is as described herein, W is H, Z is substituted or unsubstituted heterocycloalkyl, wherein said heterocycloalkyl has one ring, and said ring comprises an endocyclic boron, and Y is substituted alkylene. In an exemplary embodiment, the compound is Formula (I), X is as described herein, W is H, Z is substituted or unsubstituted heterocycloalkyl, wherein said heterocycloalkyl has one ring, and said ring comprises an endocyclic boron, and Y is unsubstituted alkylene. In an exemplary embodiment, the compound is Formula (I), X is as described herein, W is H, Z is substituted or unsubstituted heterocycloalkyl, wherein said heterocycloalkyl has one ring, and said ring comprises an endocyclic boron, and Y is methylene. In an exemplary embodiment, the compound is Formula (I), X is as described herein, W is H, Z is substituted or unsubstituted heterocycloalkyl, wherein said heterocycloalkyl has one ring, and said ring comprises an endocyclic boron, and Y is ethylene. In an exemplary embodiment, the compound is Formula (I), X is as described herein, W is H, Z is substituted or unsubstituted heterocycloalkyl, wherein said heterocycloalkyl has one ring, and said ring comprises an endocyclic boron, and Y is propylene. In an exemplary embodiment, the compound is Formula (I), X is as described herein, W is H, Z is substituted or unsubstituted heterocycloalkyl, wherein said heterocycloalkyl has one ring, and said ring comprises an endocyclic boron, and Y is substituted heteroalkylene. In an exemplary embodiment, the compound is Formula (I), X is as described herein, W is H, Z is substituted or unsubstituted heterocycloalkyl, wherein said heterocycloalkyl has one ring, and said ring comprises an endocyclic boron, and Y is unsubstituted heteroalkylene. In an exemplary embodiment, the compound is Formula (I), X is as described herein, W is H, Z is substituted or unsubstituted heterocycloalkyl, wherein said heterocycloalkyl has one ring, and said ring comprises an endocyclic boron, and Y is *—OCH$_2$—. In an exemplary embodiment, the compound is Formula (I), X is as described herein, W is H, Z is substituted or unsubstituted heterocycloalkyl, wherein said heterocycloalkyl has one ring, and said ring comprises an endocyclic boron, and Y is *—SCH$_2$—. In an exemplary embodiment, the compound is Formula (I), X is as described herein, W is H, Z is substituted or unsubstituted heterocycloalkyl, wherein said heterocycloalkyl has one ring, and said ring comprises an endocyclic boron, and Y is *—NHCH$_2$—. In an exemplary embodiment, the compound is Formula (I), X is as described herein, W is H, Z is substituted or unsubstituted heterocycloalkyl, wherein said heterocycloalkyl has one ring, and said ring comprises an endocyclic boron, and Y is *—CH$_2$NH—. In an exemplary embodiment, the compound is Formula (I), X is as described herein, W is H, Z is substituted or unsubstituted heterocycloalkyl, wherein said heterocycloalkyl has one ring, and said ring comprises an endocyclic boron, and Y is *—C(O)NH—. In an exemplary embodiment, the compound is Formula (I), X is as described herein, W is H, Z is substituted or unsubstituted heterocycloalkyl, wherein said heterocycloalkyl has one ring, and said ring comprises an endocyclic boron, and Y is *—CH$_2$NH— CH$_2$ or 1-piperazinyl or *—S(O)CH$_2$— or *—S(O)$_2$—. In an exemplary embodiment, the compound is Formula (I), X is as described herein, W is H, Z is substituted or unsubstituted heterocycloalkyl, wherein said heterocycloalkyl has one ring, and said ring comprises an endocyclic boron, and Y is 1-piperazinyl. In an exemplary embodiment, the compound is Formula (I), X is as described herein, W is H, Z is substituted or unsubstituted heterocycloalkyl, wherein said heterocycloalkyl has one ring, and said ring comprises an endocyclic boron, and Y is *—S(O)CH$_2$—. In an exemplary embodiment, the compound is Formula (I), X is as described herein, W is H, Z is substituted or unsubstituted heterocycloalkyl, wherein said heterocycloalkyl has one ring, and said ring comprises an endocyclic boron, and Y is *—S(O)$_2$—. In an exemplary embodiment, the compound is Formula (I), X is as described herein, W is H, Z is substituted or unsubstituted heterocycloalkyl, wherein said heterocycloalkyl has one ring, and said ring comprises an endocyclic boron, and Y is *—S(O)$_2$CH$_2$—. In an exemplary embodiment, the compound is Formula (I), X is as described herein, W is H, Z is substituted or unsubstituted heterocycloalkyl, wherein said heterocycloalkyl has one ring, and said ring comprises an endocyclic boron, and Y is *—NHC(O)OCH$_2$—. In this paragraph, * represents the point of attachment to Z.

In an exemplary embodiment, the compound is Formula (I), X is as described herein, W is H, Z is substituted or unsubstituted heterocycloalkyl, wherein said heterocycloalkyl has two rings, and one of the two rings comprises an endocyclic boron, and Y is substituted alkylene. In an exemplary embodiment, the compound is Formula (I), X is as described herein, W is H, Z is substituted or unsubstituted heterocycloalkyl, wherein said heterocycloalkyl has two rings, and one of the two rings comprises an endocyclic boron, and Y is unsubstituted alkylene. In an exemplary embodiment, the compound is Formula (I), X is as described herein, W is H, Z is substituted or unsubstituted heterocycloalkyl, wherein said heterocycloalkyl has two rings, and one of the two rings comprises an endocyclic boron, and Y is methylene. In an exemplary embodiment, the compound is Formula (I), X is as described herein, W is H, Z is substituted or unsubstituted heterocycloalkyl, wherein said heterocycloalkyl has two rings, and one of the two rings comprises an endocyclic boron, and Y is ethylene. In an exemplary embodiment, the compound is Formula (I), X is as described herein, W is H, Z is substituted or unsubstituted heterocycloalkyl, wherein said heterocycloalkyl has two rings, and one of the two rings comprises an endocyclic boron, and Y is propylene. In an exemplary embodiment, the compound is Formula (I), X is as described herein, W is H, Z is substituted or unsubstituted heterocycloalkyl, wherein said heterocycloalkyl has two rings, and one of the two rings comprises an endocyclic boron, and Y is substituted heteroalkylene. In an exemplary embodiment, the compound is Formula (I), X is as described herein, W is H, Z is substituted or unsubstituted heterocycloalkyl, wherein said heterocycloalkyl has two rings, and one of the two rings comprises an endocyclic boron, and Y is unsubstituted heteroalkylene. In an exemplary embodiment, the compound is Formula (I), X is as described herein, W is H, Z is substituted or unsubstituted heterocycloalkyl, wherein said heterocycloalkyl has two rings, and one of the two rings comprises an endocyclic boron, and Y is *—OCH$_2$—. In an exemplary embodiment, the compound is Formula (I), X is as described herein, W is H, Z is substituted or unsubstituted heterocycloalkyl, wherein said heterocycloalkyl has two rings, and one of the two rings comprises an endocyclic boron, and Y is *—SCH$_2$—. In an exemplary embodiment, the compound is Formula (I), X is as described herein, W is H, Z is substituted or unsubstituted heterocycloalkyl, wherein said heterocycloalkyl has two rings, and one of the two rings comprises an endocyclic boron, and Y is *—NHCH$_2$—. In an exemplary embodiment, the compound is Formula (I), X is as described herein, W is H, Z is substituted or unsubstituted heterocycloalkyl, wherein said heterocycloalkyl has two rings, and one of the two rings comprises an endocyclic boron, and Y is *—CH$_2$NH—. In an exemplary embodiment, the compound is Formula (I), X is as described herein, W is H, Z is substituted or unsubstituted heterocycloalkyl, wherein said heterocycloalkyl has two rings, and one of the two rings comprises an endocyclic boron, and Y is *—C(O)NH—. In an exemplary embodiment, the compound is Formula (I), X is as described herein, W is H, Z is substituted or unsubstituted heterocycloalkyl, wherein said heterocycloalkyl has two rings, and one of the two rings comprises an endocyclic boron, and Y is *—CH$_2$NHCH$_2$— or 1-piperazinyl or *—S(O)CH$_2$— or *—S(O)$_2$—. In an exemplary embodiment, the compound is Formula (I), X is as described herein, W is H, Z is substituted or unsubstituted heterocycloalkyl, wherein said heterocycloalkyl has two rings, and one of the two rings comprises an endocyclic boron, and Y is 1-piperazinyl. In an exemplary embodiment, the compound is Formula (I), X is as described herein, W is H, Z is substituted or unsubstituted heterocycloalkyl, wherein said heterocycloalkyl has two rings, and one of the two rings comprises an endocyclic boron, and Y is *—S(O)CH$_2$—. In an exemplary embodiment, the compound is Formula (I), X is as described herein, W is H, Z is substituted or unsubstituted heterocycloalkyl, wherein said heterocycloalkyl has two rings, and one of the two rings comprises an endocyclic boron, and Y is *—S(O)$_2$—. In an exemplary embodiment, the compound is Formula (I), X is as described herein, W is H, Z is substituted or unsubstituted heterocycloalkyl, wherein said heterocycloalkyl has two rings, and one of the two rings comprises an endocyclic boron, and Y is *—S(O)$_2$— CH$_2$—. In an exemplary embodiment, the compound is Formula (I), X is as described herein, W is H, Z is substituted or unsubstituted heterocycloalkyl, wherein said heterocycloalkyl has two rings, and one of the two rings comprises an endocyclic boron, and Y is *—NHC(O)OCH$_2$—. In this paragraph, * represents the point of attachment to Z.

In an exemplary embodiment, the compound is Formula (I), X is as described herein, W is H, Z is a benzoxaborole described herein, and Y is substituted alkylene. In an exemplary embodiment, the compound is Formula (I), X is as described herein, W is H, Z is a benzoxaborole described herein, and Y is unsubstituted alkylene. In an exemplary embodiment, the compound is Formula (I), X is as described herein, W is H, Z is a benzoxaborole described herein, and Y is methylene. In an exemplary embodiment, the compound is Formula (I), X is as described herein, W is H, Z is a benzoxaborole described herein, and Y is ethylene. In an exemplary embodiment, the compound is Formula (I), X is as described herein, W is H, Z is a benzoxaborole described herein, and Y is propylene. In an exemplary embodiment, the compound is Formula (I), X is as described herein, W is H, Z is a benzoxaborole described herein, and Y is substituted heteroalkylene. In an exemplary embodiment, the compound is Formula (I), X is as described herein, W is H, Z is a benzoxaborole described herein, and Y is unsubstituted heteroalkylene. In an exemplary embodiment, the compound is Formula (I), X is as described herein, W is H, Z is a benzoxaborole described herein, and Y is *—OCH$_2$—. In an exemplary embodiment, the compound is Formula (I), X is as described herein, W is H, Z is a benzoxaborole described herein, and Y is *—SCH$_2$—. In an exemplary embodiment, the compound is Formula (I), X is as described herein, W is H, Z is a benzoxaborole described herein, and Y is *—NHCH$_2$—. In an exemplary embodiment, the compound is Formula (I), X is as described herein, W is H, Z is a benzoxaborole described herein, and Y is *—CH$_2$NH—. In an exemplary embodiment, the compound is Formula (I), X is as described herein, W is H, Z is a benzoxaborole described herein, and Y is *—C(O)NH—. In an exemplary embodiment, the compound is Formula (I), X is as described herein, W is H, Z is a benzoxaborole described herein, and Y is *—CH$_2$NHCH$_2$— or 1-piperazinyl or *—S(O)CH$_2$— or *—S(O)$_2$—. In an exemplary embodiment, the compound is Formula (I), X is as described herein, W is H, Z is a benzoxaborole described herein, and Y is 1-piperazinyl. In an exemplary embodiment, the compound is Formula (I), X is as described herein, W is H, Z is a benzoxaborole described herein, and Y is *—S(O)CH$_2$—. In an exemplary embodiment, the compound is Formula (I), X is as described herein, W is H, Z is a benzoxaborole described herein, and Y is *—S(O)$_2$—. In an exemplary embodiment, the compound is Formula (I), X is as described herein, W is H, Z is a benzoxaborole described herein, and Y is *—S(O)$_2$CH$_2$—. In an exemplary embodiment, the compound is Formula (I), X is as described herein, W is H, Z is a benzoxaborole described herein, and Y is *—NHC(O)OCH$_2$—. In this paragraph, * represents the point of attachment to Z.

In an exemplary embodiment, the compound is Formula (I), X is as described herein, W is H, Z is Formula (II), R$^3$ is H, R$^{3a}$ is H, R$^4$ is H, R$^5$ is H, and R$^7$ is H, and Y is substituted alkylene. In an exemplary embodiment, the compound is Formula (I), X is as described herein, W is H, Z is Formula (II), R$^3$ is H, R$^{3a}$ is H, R$^4$ is H, R$^5$ is H, and R$^7$ is H, and Y is unsubstituted alkylene. In an exemplary embodiment, the compound is Formula (I), X is as described herein, W is H, Z is Formula (II), R$^3$ is H, R$^{3a}$ is H, R$^4$ is H, R$^5$ is H, and R$^7$ is H, and Y is methylene. In an exemplary embodiment, the compound is Formula (I), X is as described herein, W is H, Z is Formula (II), R$^3$ is H, R$^{3a}$ is H, R$^4$ is H, R$^5$ is H, and R$^7$ is H, and Y is ethylene. In an exemplary embodiment, the compound is Formula (I), X is as described herein, W is H, Z is Formula (II), R$^3$ is H, R$^{3a}$ is H, R$^4$ is H, R$^5$ is H, and R$^7$ is H, and Y is propylene. In an exemplary embodiment, the compound is Formula (I), X is as described herein, W is H, Z is Formula (II), R$^3$ is H, R$^{3a}$ is H, R$^4$ is H, R$^5$ is H, and R$^7$ is H, and Y is substituted heteroalkylene. In an exemplary embodiment, the compound is Formula (I), X is as described herein, W is H, Z is Formula (II), R$^3$ is H, R$^{3a}$ is H, R$^4$ is H, R$^5$ is H, and R$^7$ is H, and Y is unsubstituted heteroalkylene. In an exemplary embodiment, the compound is Formula (I), X is as described herein, W is H, Z is Formula (II), R$^3$ is H, R$^{3a}$ is H, R$^4$ is H, R$^5$ is H, and R$^7$ is H, and Y is *—OCH$_2$—. In an exemplary embodiment, the compound is Formula (I), X is as described herein, W is H, Z is Formula (II), R$^3$ is H, R$^{3a}$ is H, R$^4$ is H, R$^5$ is H, and R$^7$ is H, and Y is *—SCH$_2$—. In an exemplary embodiment, the compound is Formula (I), X is as described herein, W is H, Z is Formula (II), R$^3$ is H, R$^{3a}$ is H, R$^4$ is H, R$^5$ is H, and R$^7$ is H, and Y is *—NHCH$_2$—. In an exemplary embodiment, the compound is Formula (I), X is as described herein, W is H, Z is Formula (II), R$^3$ is H, R$^{3a}$ is H, R$^4$ is H, R$^5$ is H, and R$^7$ is H, and Y is *—CH$_2$NH—. In an exemplary embodiment, the compound is Formula (I), X is as described herein, W is H, Z is Formula (II), R$^3$ is H, R$^{3a}$ is H, R$^4$ is H, R$^5$ is H, and R$^7$ is H, and Y is *—C(O)NH—. In an exemplary embodiment, the compound is Formula (I), X is as described herein, W is H, Z is Formula (II), R$^3$ is H, R$^{3a}$ is H, R$^4$ is H, R$^5$ is H, and R$^7$ is H, and Y is *—CH$_2$NH— CH$_2$ or 1-piperazinyl or *—S(O)CH$_2$— or *—S(O)$_2$—. In an exemplary embodiment, the compound is Formula (I), X is as described herein, W is H, Z is Formula (II), R$^3$ is H, R$^{3a}$ is H, R$^4$ is H, R$^5$ is H, and R$^7$ is H, and Y is 1-piperazinyl. In an exemplary embodiment, the compound is Formula (I), X is as described herein, W is H, Z is Formula (II), R$^3$ is H, R$^{3a}$ is H, R$^4$ is H, R$^5$ is H, and R$^7$ is H, and Y is *—S(O)CH$_2$—. In an exemplary embodiment, the compound is Formula (I), X is as described herein, W is H, Z is Formula (II), R$^3$ is H, R$^{3a}$ is H, R$^4$ is H, R$^5$ is H, and R$^7$ is H, and Y is *—S(O)$_2$—. In an exemplary embodiment, the compound is Formula (I), X is as described herein, W is H, Z is Formula (II), R$^3$ is H, R$^{3a}$ is H, R$^4$ is H, R$^5$ is H, and R$^7$ is H, and Y is *—S(O)$_2$CH$_2$—. In an exemplary embodiment, the compound is Formula (I), X is as described herein, W is H, Z is Formula (II), R$^3$ is H, R$^{3a}$ is H, R$^4$ is H, R$^5$ is H, and R$^7$ is H, and Y is *—NHC(O)OCH$_2$—. In this paragraph, * represents the point of attachment to Z.

In an exemplary embodiment, the compound is Formula (I), X is as described herein, W is H, Z is Formula (III), R$^3$ is H, R$^{3a}$ is H, R$^4$ is H, R$^6$ is H, and R$^7$ is H, and Y is substituted alkylene. In an exemplary embodiment, the compound is Formula (I), X is as described herein, W is H, Z is Formula (III), R$^3$ is H, R$^{3a}$ is H, R$^4$ is H, R$^6$ is H, and R$^7$ is H, and Y is unsubstituted alkylene. In an exemplary embodiment, the compound is Formula (I), X is as described herein, W is H, Z is Formula (III), R$^3$ is H, R$^{3a}$ is H, R$^4$ is H, R$^6$ is H, and R$^7$ is H, and Y is methylene. In an exemplary embodiment, the compound is Formula (I), X is as described herein, W is H, Z is Formula (III), R$^3$ is H, R$^{3a}$ is H, R$^4$ is H, R$^6$ is H, and R$^7$ is H, and Y is ethylene. In an exemplary embodiment, the compound is Formula (I), X is as described herein, W is H, Z is Formula (III), R$^3$ is H, R$^{3a}$ is H, R$^4$ is H, R$^6$ is H, and R$^7$ is H, and Y is propylene. In an exemplary embodiment, the compound is Formula (I), X is as described herein, W is H, Z is Formula (III), R$^3$ is H, R$^{3a}$ is H, R$^4$ is H, R$^6$ is H, and R$^7$ is H, and Y is substituted heteroalkylene. In an exemplary embodiment, the compound is Formula (I), X is as described herein, W is H, Z is Formula (III), R$^3$ is H, R$^{3a}$ is H, R$^4$ is H, R$^6$ is H, and R$^7$ is H, and Y is unsubstituted heteroalkylene. In an exemplary embodiment, the compound is Formula (I), X is as described herein, W is H, Z is Formula (III), R$^3$ is H, R$^{3a}$ is H, R$^4$ is H, R$^6$ is H, and R$^7$ is H, and Y is *—OCH$_2$—. In an exemplary embodiment, the compound is Formula (I), X is as described herein, W is H, Z is Formula (III), R$^3$ is H, R$^{3a}$ is H, R$^4$ is H, R$^6$ is H, and R$^7$ is H, and Y is *—SCH$_2$—. In an exemplary embodiment, the compound is Formula (I), X is as described herein, W is H, Z is Formula (III), R$^3$ is H, R$^{3a}$ is H, R$^4$ is H, R$^6$ is H, and R$^7$ is H, and Y is *—NHCH$_2$—. In an exemplary embodiment, the compound is Formula (I), X is as described herein, W is H, Z is Formula (III), R$^3$ is H, R$^{3a}$ is H, R$^4$ is H, R$^6$ is H, and R$^7$ is H, and Y is *—CH$_2$NH—. In an exemplary embodiment, the compound is Formula (I), X is as described herein, W is H, Z is Formula (III), R$^3$ is H, R$^{3a}$ is H, R$^4$ is H, R$^6$ is H, and R$^7$ is H, and Y is *—C(O)NH—. In an exemplary embodiment, the compound is Formula (I), X is as described herein, W is H, Z is Formula (III), R$^3$ is H, R$^{3a}$ is H, R$^4$ is H, R$^6$ is H, and R$^7$ is H, and Y is *—CH$_2$NHCH$_2$— or 1-piperazinyl or *—S(O)CH$_2$— or *—S(O)$_2$—. In an exemplary embodiment, the compound is Formula (I), X is as described herein, W is H, Z is Formula (III), $R^3$ is H, $R^{3a}$ is H, $R^4$ is H, $R^6$ is H, and $R^7$ is H, and Y is 1-piperazinyl.

In an exemplary embodiment, the compound is Formula (I), X is as described herein, W is H, Z is Formula (III), $R^3$ is H, $R^{3a}$ is H, $R^4$ is H, $R^6$ is H, and $R^7$ is H, and Y is *—S(O)CH$_2$—. In an exemplary embodiment, the compound is Formula (I), X is as described herein, W is H, Z is Formula (III), $R^3$ is H, $R^{3a}$ is H, $R^4$ is H, $R^6$ is H, and $R^7$ is H, and Y is *—S(O)$_2$—. In an exemplary embodiment, the compound is Formula (I), X is as described herein, W is H, Z is Formula (III), $R^3$ is H, $R^{3a}$ is H, $R^4$ is H, $R^6$ is H, and $R^7$ is H, and Y is *—S(O)$_2$CH$_2$—. In an exemplary embodiment, the compound is Formula (I), X is as described herein, W is H, Z is Formula (III), $R^3$ is H, $R^{3a}$ is H, $R^4$ is H, $R^6$ is H, and $R^7$ is H, and Y is *—NHC(O)OCH$_2$—. In this paragraph, * represents the point of attachment to Z.

In an exemplary embodiment, the compound is Formula (I), X is as described herein, W is H, Z is Formula (II), $R^3$ is H, $R^{3a}$ is H, $R^4$ is H, $R^5$ is H, and $R^7$ is F, and Y is substituted alkylene. In an exemplary embodiment, the compound is Formula (I), X is as described herein, W is H, Z is Formula (II), $R^3$ is H, $R^{3a}$ is H, $R^4$ is H, $R^5$ is H, and $R^7$ is F, and Y is unsubstituted alkylene. In an exemplary embodiment, the compound is Formula (I), X is as described herein, W is H, Z is Formula (II), $R^3$ is H, $R^{3a}$ is H, $R^4$ is H, $R^5$ is H, and $R^7$ is F, and Y is methylene. In an exemplary embodiment, the compound is Formula (I), X is as described herein, W is H, Z is Formula (II), $R^3$ is H, $R^{3a}$ is H, $R^4$ is H, $R^5$ is H, and $R^7$ is F, and Y is ethylene. In an exemplary embodiment, the compound is Formula (I), X is as described herein, W is H, Z is Formula (II), $R^3$ is H, $R^{3a}$ is H, $R^4$ is H, $R^5$ is H, and $R^7$ is F, and Y is propylene. In an exemplary embodiment, the compound is Formula (I), X is as described herein, W is H, Z is Formula (II), $R^3$ is H, $R^{3a}$ is H, $R^4$ is H, $R^5$ is H, and $R^7$ is F, and Y is substituted heteroalkylene. In an exemplary embodiment, the compound is Formula (I), X is as described herein, W is H, Z is Formula (II), $R^3$ is H, $R^{3a}$ is H, $R^4$ is H, $R^5$ is H, and $R^7$ is F, and Y is unsubstituted heteroalkylene. In an exemplary embodiment, the compound is Formula (I), X is as described herein, W is H, Z is Formula (II), $R^3$ is H, $R^{3a}$ is H, $R^4$ is H, $R^5$ is H, and $R^7$ is F, and Y is *—OCH$_2$—. In an exemplary embodiment, the compound is Formula (I), X is as described herein, W is H, Z is Formula (II), $R^3$ is H, $R^{3a}$ is H, $R^4$ is H, $R^5$ is H, and $R^7$ is F, and Y is *—SCH$_2$—. In an exemplary embodiment, the compound is Formula (I), X is as described herein, W is H, Z is Formula (II), $R^3$ is H, $R^{3a}$ is H, $R^4$ is H, $R^5$ is H, and $R^7$ is F, and Y is *—NHCH$_2$—. In an exemplary embodiment, the compound is Formula (I), X is as described herein, W is H, Z is Formula (II), $R^3$ is H, $R^{3a}$ is H, $R^4$ is H, $R^5$ is H, and $R^7$ is F, and Y is *—CH$_2$NH—. In an exemplary embodiment, the compound is Formula (I), X is as described herein, W is H, Z is Formula (II), $R^3$ is H, $R^{3a}$ is H, $R^4$ is H, $R^5$ is H, and $R^7$ is F, and Y is *—C(O)NH—. In an exemplary embodiment, the compound is Formula (I), X is as described herein, W is H, Z is Formula (II), $R^3$ is H, $R^{3a}$ is H, $R^4$ is H, $R^5$ is H, and $R^7$ is F, and Y is *—CH$_2$NHCH$_2$— or 1-piperazinyl or *—S(O)CH$_2$— or *—S(O)$_2$—. In an exemplary embodiment, the compound is Formula (I), X is as described herein, W is H, Z is Formula (II), $R^3$ is H, $R^{3a}$ is H, $R^4$ is H, $R^5$ is H, and $R^7$ is F, and Y is 1-piperazinyl. In an exemplary embodiment, the compound is Formula (I), X is as described herein, W is H, Z is Formula (II), $R^3$ is H, $R^{3a}$ is H, $R^4$ is H, $R^5$ is H, and $R^7$ is F, and Y is *—S(O)CH$_2$—. In an exemplary embodiment, the compound is Formula (I), X is as described herein, W is H, Z is Formula (II), $R^3$ is H, $R^{3a}$ is H, $R^4$ is H, $R^5$ is H, and $R^7$ is F, and Y is *—S(O)$_2$—. In an exemplary embodiment, the compound is Formula (I), X is as described herein, W is H, Z is Formula (II), $R^3$ is H, $R^{3a}$ is H, $R^4$ is H, $R^5$ is H, and $R^7$ is F, and Y is *—S(O)$_2$CH$_2$—. In an exemplary embodiment, the compound is Formula (I), X is as described herein, W is H, Z is Formula (II), $R^3$ is H, $R^{3a}$ is H, $R^4$ is H, $R^5$ is H, and $R^7$ is F, and Y is *—NHC(O)OCH$_2$—. In this paragraph, * represents the point of attachment to Z.

In an exemplary embodiment, the compound is Formula (I), X is as described herein, W is H, Z is Formula (III), $R^3$ is H, $R^{3a}$ is H, $R^4$ is H, $R^6$ is H, and $R^7$ is F, and Y is substituted alkylene. In an exemplary embodiment, the compound is Formula (I), X is as described herein, W is H, Z is Formula (III), $R^3$ is H, $R^{3a}$ is H, $R^4$ is H, $R^6$ is H, and $R^7$ is F, and Y is unsubstituted alkylene. In an exemplary embodiment, the compound is Formula (I), X is as described herein, W is H, Z is Formula (III), $R^3$ is H, $R^{3a}$ is H, $R^4$ is H, $R^6$ is H, and $R^7$ is F, and Y is methylene. In an exemplary embodiment, the compound is Formula (I), X is as described herein, W is H, Z is Formula (III), $R^3$ is H, $R^{3a}$ is H, $R^4$ is H, $R^6$ is H, and $R^7$ is F, and Y is ethylene. In an exemplary embodiment, the compound is Formula (I), X is as described herein, W is H, Z is Formula (III), $R^3$ is H, $R^{3a}$ is H, $R^4$ is H, $R^6$ is H, and $R^7$ is F, and Y is propylene. In an exemplary embodiment, the compound is Formula (I), X is as described herein, W is H, Z is Formula (III), $R^3$ is H, $R^{3a}$ is H, $R^4$ is H, $R^6$ is H, and $R^7$ is F, and Y is substituted heteroalkylene. In an exemplary embodiment, the compound is Formula (I), X is as described herein, W is H, Z is Formula (III), $R^3$ is H, $R^{3a}$ is H, $R^4$ is H, $R^6$ is H, and $R^7$ is F, and Y is unsubstituted heteroalkylene. In an exemplary embodiment, the compound is Formula (I), X is as described herein, W is H, Z is Formula (III), $R^3$ is H, $R^{3a}$ is H, $R^4$ is H, $R^6$ is H, and $R^7$ is F, and Y is *—OCH$_2$—. In an exemplary embodiment, the compound is Formula (I), X is as described herein, W is H, Z is Formula (III), $R^3$ is H, $R^{3a}$ is H, $R^4$ is H, $R^6$ is H, and $R^7$ is F, and Y is *—SCH$_2$—. In an exemplary embodiment, the compound is Formula (I), X is as described herein, W is H, Z is Formula (III), $R^3$ is H, $R^{3a}$ is H, $R^4$ is H, $R^6$ is H, and $R^7$ is F, and Y is *—NHCH$_2$—. In an exemplary embodiment, the compound is Formula (I), X is as described herein, W is H, Z is Formula (III), $R^3$ is H, $R^{3a}$ is H, $R^4$ is H, $R^6$ is H, and $R^7$ is F, and Y is *—CH$_2$NH—. In an exemplary embodiment, the compound is Formula (I), X is as described herein, W is H, Z is Formula (III), $R^3$ is H, $R^{3a}$ is H, $R^4$ is H, $R^6$ is H, and $R^7$ is F, and Y is *—C(O)NH—. In an exemplary embodiment, the compound is Formula (I), X is as described herein, W is H, Z is Formula (III), $R^3$ is H, $R^{3a}$ is H, $R^4$ is H, $R^6$ is H, and $R^7$ is F, and Y is *—CH$_2$NHCH$_2$— or 1-piperazinyl or *—S(O)CH$_2$— or *—S(O)$_2$—. In an exemplary embodiment, the compound is Formula (I), X is as described herein, W is H, Z is Formula (III), $R^3$ is H, $R^{3a}$ is H, $R^4$ is H, $R^6$ is H, and $R^7$ is F, and Y is 1-piperazinyl. In an exemplary embodiment, the compound is Formula (I), X is as described herein, W is H, Z is Formula (III), $R^3$ is H, $R^{3a}$ is H, $R^4$ is H, $R^6$ is H, and $R^7$ is F, and Y is *—S(O)CH$_2$—. In an exemplary embodiment, the compound is Formula (I), X is as described herein, W is H, Z is Formula (III), $R^3$ is H, $R^{3a}$ is H, $R^4$ is H, $R^6$ is H, and $R^7$ is F, and Y is *—S(O)$_2$—. In an exemplary embodiment, the compound is Formula (I), X is as described herein, W is H, Z is Formula (III), $R^3$ is H, $R^{3a}$ is H, $R^4$ is H, $R^6$ is H, and $R^7$ is F, and Y is *—S(O)$_2$CH$_2$—. In an exemplary embodiment, the compound is Formula (I), X is as described herein, W is H, Z is Formula (III), $R^3$ is H, $R^{3a}$ is H, $R^4$ is H, $R^6$ is H, and $R^7$ is F, and Y is *—NHC(O)OCH$_2$—. In this paragraph, * represents the point of attachment to Z.

In an exemplary embodiment, the compound is Formula (I), X is as described herein, W is H, Z is a pyridinyloxaborole described herein, and Y is substituted alkylene. In an exemplary embodiment, the compound is Formula (I), X is as described herein, W is H, Z is a pyridinyloxaborole described herein, and Y is unsubstituted alkylene. In an exemplary embodiment, the compound is Formula (I), X is as described herein, W is H, Z is a pyridinyloxaborole described herein, and Y is methylene. In an exemplary embodiment, the compound is Formula (I), X is as described herein, W is H, Z is a pyridinyloxaborole described herein, and Y is ethylene. In an exemplary embodiment, the compound is Formula (I), X is as described herein, W is H, Z is a pyridinyloxaborol described herein, and Y is propylene. In an exemplary embodiment, the compound is Formula (I), X is as described herein, W is H, Z is a pyridinyloxaborole described herein, and Y is substituted heteroalkylene. In an exemplary embodiment, the compound is Formula (I), X is as described herein, W is H, Z is a pyridinyloxaborole described herein, and Y is unsubstituted heteroalkylene. In an exemplary embodiment, the compound is Formula (I), X is as described herein, W is H, Z is a pyridinyloxaborole described herein, and Y is *—OCH$_2$—. In an exemplary embodiment, the compound is Formula (I), X is as described herein, W is H, Z is a pyridinyloxaborole described herein, and Y is *—SCH$_2$—. In an exemplary embodiment, the compound is Formula (I), X is as described herein, W is H, Z is a pyridinyloxaborole described herein, and Y is *—NHCH$_2$—. In an exemplary embodiment, the compound is Formula (I), X is as described herein, W is H, Z is a pyridinyloxaborole described herein, and Y is *—CH$_2$NH—. In an exemplary embodiment, the compound is Formula (I), X is as described herein, W is H, Z is a pyridinyloxaborole described herein, and Y is *—C(O)NH—. In an exemplary embodiment, the compound is Formula (I), X is as described herein, W is H, Z is a pyridinyloxaborole described herein, and Y is *—CH$_2$NHCH$_2$— or 1-piperazinyl or *—S(O)CH$_2$— or *—S(O)$_2$—. In an exemplary embodiment, the compound is Formula (I), X is as described herein, W is H, Z is a pyridinyloxaborole described herein, and Y is 1-piperazinyl. In an exemplary embodiment, the compound is Formula (I), X is as described herein, W is H, Z is a pyridinyloxaborole described herein, and Y is *—S(O)CH$_2$—. In an exemplary embodiment, the compound is Formula (I), X is as described herein, W is H, Z is a pyridinyloxaborole described herein, and Y is *—S(O)$_2$—. In an exemplary embodiment, the compound is Formula (I), X is as described herein, W is H, Z is a pyridinyloxaborole described herein, and Y is *—S(O)$_2$CH$_2$—. In an exemplary embodiment, the compound is Formula (I), X is as described herein, W is H, Z is a pyridinyloxaborole described herein, and Y is *—NHC(O)OCH$_2$—. In this paragraph, * represents the point of attachment to Z.

In an exemplary embodiment, the compound is Formula (I), X is as described herein, W is H, Z is a benzoxaborininol described herein, and Y is substituted alkylene. In an exemplary embodiment, the compound is Formula (I), X is as described herein, W is H, Z is a benzoxaborininol described herein, and Y is unsubstituted alkylene. In an exemplary embodiment, the compound is Formula (I), X is as described herein, W is H, Z is a benzoxaborininol described herein, and Y is methylene. In an exemplary embodiment, the compound is Formula (I), X is as described herein, W is H, Z is a benzoxaborininol described herein, and Y is ethylene. In an exemplary embodiment, the compound is Formula (I), X is as described herein, W is H, Z is a benzoxaborininol described herein, and Y is propylene. In an exemplary embodiment, the compound is Formula (I), X is as described herein, W is H, Z is a benzoxaborininol described herein, and Y is substituted heteroalkylene. In an exemplary embodiment, the compound is Formula (I), X is as described herein, W is H, Z is a benzoxaborininol described herein, and Y is unsubstituted heteroalkylene. In an exemplary embodiment, the compound is Formula (I), X is as described herein, W is H, Z is a benzoxaborininol described herein, and Y is *—OCH$_2$—. In an exemplary embodiment, the compound is Formula (I), X is as described herein, W is H, Z is a benzoxaborininol described herein, and Y is *—SCH$_2$—. In an exemplary embodiment, the compound is Formula (I), X is as described herein, W is H, Z is a benzoxaborininol described herein, and Y is *—NHCH$_2$—. In an exemplary embodiment, the compound is Formula (I), X is as described herein, W is H, Z is a benzoxaborininol described herein, and Y is *—CH$_2$NH—. In an exemplary embodiment, the compound is Formula (I), X is as described herein, W is H, Z is a benzoxaborininol described herein, and Y is *—C(O)NH—. In an exemplary embodiment, the compound is Formula (I), X is as described herein, W is H, Z is a benzoxaborininol described herein, and Y is *—CH$_2$NHCH$_2$— or 1-piperazinyl or *—S(O)CH$_2$— or *—S(O)$_2$—. In an exemplary embodiment, the compound is Formula (I), X is as described herein, W is H, Z is a benzoxaborininol described herein, and Y is 1-piperazinyl. In an exemplary embodiment, the compound is Formula (I), X is as described herein, W is H, Z is a benzoxaborininol described herein, and Y is *—S(O)CH$_2$—. In an exemplary embodiment, the compound is Formula (I), X is as described herein, W is H, Z is a benzoxaborininol described herein, and Y is *—S(O)$_2$—. In an exemplary embodiment, the compound is Formula (I), X is as described herein, W is H, Z is a benzoxaborininol described herein, and Y is *—S(O)$_2$CH$_2$—. In an exemplary embodiment, the compound is Formula (I), X is as described herein, W is H, Z is a benzoxaborininol described herein, and Y is *—NHC(O)OCH$_2$—. In this paragraph, * represents the point of attachment to Z.

In an exemplary embodiment, the compound is Formula (I), X is as described herein, W is H, Z is a benzoxazaborininol described herein, and Y is substituted alkylene. In an exemplary embodiment, the compound is Formula (I), X is as described herein, W is H, Z is a benzoxazaborininol described herein, and Y is unsubstituted alkylene. In an exemplary embodiment, the compound is Formula (I), X is as described herein, W is H, Z is a benzoxazaborininol described herein, and Y is methylene. In an exemplary embodiment, the compound is Formula (I), X is as described herein, W is H, Z is a benzoxazaborininol described herein, and Y is ethylene. In an exemplary embodiment, the compound is Formula (I), X is as described herein, W is H, Z is a benzoxazaborininol described herein, and Y is propylene. In an exemplary embodiment, the compound is Formula (I), X is as described herein, W is H, Z is a benzoxazaborininol described herein, and Y is substituted heteroalkylene. In an exemplary embodiment, the compound is Formula (I), X is as described herein, W is H, Z is a benzoxazaborininol described herein, and Y is unsubstituted heteroalkylene. In an exemplary embodiment, the compound is Formula (I), X is as described herein, W is H, Z is a benzoxazaborininol described herein, and Y is *—OCH$_2$—. In an exemplary embodiment, the compound is Formula (I), X is as described herein, W is H, Z is a benzoxazaborininol described herein, and Y is *—SCH$_2$—. In an exemplary embodiment, the compound is Formula (I), X is as described herein, W is H, Z is a benzoxazaborininol described herein, and Y is *—NHCH$_2$—. In an exemplary embodiment, the compound is Formula (I), X is as described herein, W is H, Z is a benzoxazaborininol described herein, and Y is *—CH$_2$NH—. In an exemplary embodiment, the compound is Formula (I), X is as described herein, W is H, Z is a benzoxazaborininol described herein, and Y is *—C(O)NH—. In an exemplary embodiment, the compound is Formula (I), X is as described herein, W is H, Z is a benzoxazaborininol described herein, and Y is *—CH$_2$NHCH$_2$— or 1-piperazinyl or *—S(O)CH$_2$— or *—S(O)$_2$—. In an exemplary embodiment, the compound is Formula (I), X is as described herein, W is H, Z is a benzoxazaborininol described herein, and Y is 1-piperazinyl. In an exemplary embodiment, the compound is Formula (I), X is as described herein, W is H, Z is a benzoxazaborininol described herein, and Y is *—S(O)CH$_2$—. In an exemplary embodiment, the compound is Formula (I), X is as described herein, W is H, Z is a benzoxazaborininol described herein, and Y is *—S(O)$_2$—. In an exemplary embodiment, the compound is Formula (I), X is as described herein, W is H, Z is a benzoxazaborininol described herein, and Y is *—S(O)$_2$CH$_2$—. In an exemplary embodiment, the compound is Formula (I), X is as described herein, W is H, Z is a benzoxazaborininol described herein, and Y is *—NHC(O)OCH$_2$—. In this paragraph, * represents the point of attachment to Z.

In an exemplary embodiment, the compound is Formula (I), X is as described herein, W is H, Z is a benzodiazaborininol described herein, and Y is substituted alkylene. In an exemplary embodiment, the compound is Formula (I), X is as described herein, W is H, Z is a benzodiazaborininol described herein, and Y is unsubstituted alkylene. In an exemplary embodiment, the compound is Formula (I), X is as described herein, W is H, Z is a benzodiazaborininol described herein, and Y is methylene. In an exemplary embodiment, the compound is Formula (I), X is as described herein, W is H, Z is a benzodiazaborininol described herein, and Y is ethylene. In an exemplary embodiment, the compound is Formula (I), X is as described herein, W is H, Z is a benzodiazaborininol described herein, and Y is propylene. In an exemplary embodiment, the compound is Formula (I), X is as described herein, W is H, Z is a benzodiazaborininol described herein, and Y is substituted heteroalkylene. In an exemplary embodiment, the compound is Formula (I), X is as described herein, W is H, Z is a benzodiazaborininol described herein, and Y is unsubstituted heteroalkylene. In an exemplary embodiment, the compound is Formula (I), X is as described herein, W is H, Z is a benzodiazaborininol described herein, and Y is *—OCH$_2$—. In an exemplary embodiment, the compound is Formula (I), X is as described herein, W is H, Z is a benzodiazaborininol described herein, and Y is *—SCH$_2$—. In an exemplary embodiment, the compound is Formula (I), X is as described herein, W is H, Z is a benzodiazaborininol described herein, and Y is *—NHCH$_2$—. In an exemplary embodiment, the compound is Formula (I), X is as described herein, W is H, Z is a benzodiazaborininol described herein, and Y is *—CH$_2$NH—. In an exemplary embodiment, the compound is Formula (I), X is as described herein, W is H, Z is a benzodiazaborininol described herein, and Y is *—C(O)NH—. In an exemplary embodiment, the compound is Formula (I), X is as described herein, W is H, Z is a benzodiazaborininol described herein, and Y is *—CH$_2$NHCH$_2$— or 1-piperazinyl or *—S(O)CH$_2$— or *—S(O)$_2$—. In an exemplary embodiment, the compound is Formula (I), X is as described herein, W is H, Z is a benzodiazaborininol described herein, and Y is 1-piperazinyl. In an exemplary embodiment, the compound is Formula (I), X is as described herein, W is H, Z is a benzodiazaborininol described herein, and Y is *—S(O)CH$_2$—. In an exemplary embodiment, the compound is Formula (I), X is as described herein, W is H, Z is a benzodiazaborininol described herein, and Y is *—S(O)$_2$—. In an exemplary embodiment, the compound is Formula (I), X is as described herein, W is H, Z is a benzodiazaborininol described herein, and Y is *—S(O)$_2$CH$_2$—. In an exemplary embodiment, the compound is Formula (I), X is as described herein, W is H, Z is a benzodiazaborininol described herein, and Y is *—NHC(O)OCH$_2$—. In this paragraph, * represents the point of attachment to Z.

In an exemplary embodiment, the compound is Formula (I), X is as described herein, W is H, Z is an oxaborole described herein, and Y is substituted alkylene. In an exemplary embodiment, the compound is Formula (I), X is as described herein, W is H, Z is an oxaborole described herein, and Y is unsubstituted alkylene. In an exemplary embodiment, the compound is Formula (I), X is as described herein, W is H, Z is an oxaborole described herein, and Y is methylene. In an exemplary embodiment, the compound is Formula (I), X is as described herein, W is H, Z is an oxaborole described herein, and Y is ethylene. In an exemplary embodiment, the compound is Formula (I), X is as described herein, W is H, Z is an oxaborole described herein, and Y is propylene. In an exemplary embodiment, the compound is Formula (I), X is as described herein, W is H, Z is an oxaborole described herein, and Y is substituted heteroalkylene. In an exemplary embodiment, the compound is Formula (I), X is as described herein, W is H, Z is an oxaborole described herein, and Y is unsubstituted heteroalkylene. In an exemplary embodiment, the compound is Formula (I), X is as described herein, W is H, Z is an oxaborole described herein, and Y is *—OCH$_2$—. In an exemplary embodiment, the compound is Formula (I), X is as described herein, W is H, Z is an oxaborole described herein, and Y is *—SCH$_2$—. In an exemplary embodiment, the compound is Formula (I), X is as described herein, W is H, Z is an oxaborole described herein, and Y is *—NHCH$_2$—. In an exemplary embodiment, the compound is Formula (I), X is as described herein, W is H, Z is an oxaborole described herein, and Y is *—CH$_2$NH—. In an exemplary embodiment, the compound is Formula (I), X is as described herein, W is H, Z is an oxaborole described herein, and Y is *—C(O)NH—. In an exemplary embodiment, the compound is Formula (I), X is as described herein, W is H, Z is an oxaborole described herein, and Y is *—CH$_2$NHCH$_2$— or 1-piperazinyl or *—S(O)CH$_2$— or *—S(O)$_2$—. In an exemplary embodiment, the compound is Formula (I), X is as described herein, W is H, Z is an oxaborole described herein, and Y is 1-piperazinyl. In an exemplary embodiment, the compound is Formula (I), X is as described herein, W is H, Z is an oxaborole described herein, and Y is *—S(O)CH$_2$—. In an exemplary embodiment, the compound is Formula (I), X is as described herein, W is H, Z is an oxaborole described herein, and Y is *—S(O)$_2$—. In an exemplary embodiment, the compound is Formula (I), X is as described herein, W is H, Z is an oxaborole described herein, and Y is *—S(O)$_2$CH$_2$—. In an exemplary embodiment, the compound is Formula (I), X is as described herein, W is H, Z is an oxaborole described herein, and Y is *—NHC(O)OCH$_2$—. In this paragraph, * represents the point of attachment to Z.

In an exemplary embodiment, the compound is Formula (I), X is as described herein, W is H, Z is a dihydrobenzoazaborinine described herein, and Y is substituted alkylene. In an exemplary embodiment, the compound is Formula (I), X is as described herein, W is H, Z is a dihydrobenzoazaborinine described herein, and Y is unsubstituted alkylene. In an exemplary embodiment, the compound is Formula (I), X is as described herein, W is H, Z is a dihydrobenzoazaborinine described herein, and Y is methylene. In an exemplary embodiment, the compound is Formula (I), X is as described herein, W is H, Z is a dihydrobenzoazaborinine described herein, and Y is ethylene. In an exemplary embodiment, the compound is Formula (I), X is as described herein, W is H, Z is a dihydrobenzoazaborinine described herein, and Y is propylene. In an exemplary embodiment, the compound is Formula (I), X is as described herein, W is H, Z is a dihydrobenzoazaborinine described herein, and Y is substituted heteroalkylene. In an exemplary embodiment, the compound is Formula (I), X is as described herein, W is H, Z is a dihydrobenzoazaborinine described herein, and Y is unsubstituted heteroalkylene. In an exemplary embodiment, the compound is Formula (I), X is as described herein, W is H, Z is a dihydrobenzoazaborinine described herein, and Y is *—OCH$_2$—. In an exemplary embodiment, the compound is Formula (I), X is as described herein, W is H, Z is a dihydrobenzoazaborinine described herein, and Y is *—SCH$_2$—. In an exemplary embodiment, the compound is Formula (I), X is as described herein, W is H, Z is a dihydrobenzoazaborinine described herein, and Y is *—NHCH$_2$—. In an exemplary embodiment, the compound is Formula (I), X is as described herein, W is H, Z is a dihydrobenzoazaborinine described herein, and Y is *—CH$_2$NH—. In an exemplary embodiment, the compound is Formula (I), X is as described herein, W is H, Z is a dihydrobenzoazaborinine described herein, and Y is *—C(O)NH—. In an exemplary embodiment, the compound is Formula (I), X is as described herein, W is H, Z is a dihydrobenzoazaborinine described herein, and Y is *—CH$_2$NHCH$_2$— or 1-piperazinyl or *—S(O)CH$_2$— or *—S(O)$_2$—. In an exemplary embodiment, the compound is Formula (I), X is as described herein, W is H, Z is a dihydrobenzoazaborinine described herein, and Y is 1-piperazinyl. In an exemplary embodiment, the compound is Formula (I), X is as described herein, W is H, Z is a dihydrobenzoazaborinine described herein, and Y is *—S(O)CH$_2$—. In an exemplary embodiment, the compound is Formula (I), X is as described herein, W is H, Z is a dihydrobenzoazaborinine described herein, and Y is *—S(O)$_2$—. In an exemplary embodiment, the compound is Formula (I), X is as described herein, W is H, Z is a dihydrobenzoazaborinine described herein, and Y is *—S(O)$_2$CH$_2$—. In an exemplary embodiment, the compound is Formula (I), X is as described herein, W is H, Z is a dihydrobenzoazaborinine described herein, and Y is *—NHC(O)OCH$_2$—. In this paragraph, * represents the point of attachment to Z.

The compounds of the invention can form a hydrate with water, solvates with alcohols such as methanol, ethanol, propanol, and the like; adducts with amino compounds, such as ammonia, methylamine, ethylamine, and the like; adducts with acids, such as formic acid, acetic acid and the like; complexes with ethanolamine, quinoline, amino acids, and the like.

In an exemplary embodiment, the invention provides a compound described herein, or a salt, hydrate or solvate thereof, or a combination thereof. In an exemplary embodiment, the invention provides a compound described herein, or a salt, hydrate or solvate thereof. In an exemplary embodiment, the invention provides a compound described herein, or a salt thereof. In an exemplary embodiment, the salt is a pharmaceutically acceptable salt. In an exemplary embodiment, the invention provides a compound described herein, or a hydrate thereof. In an exemplary embodiment, the invention provides a compound described herein, or a solvate thereof. In an exemplary embodiment, the invention provides a compound described herein, or a prodrug thereof. In an exemplary embodiment, the invention provides a salt of a compound described herein. In an exemplary embodiment, the invention provides a pharmaceutically acceptable salt of a compound described herein. In an exemplary embodiment, the invention provides a hydrate of a compound described herein. In an exemplary embodiment, the invention provides a solvate of a compound described herein. In an exemplary embodiment, the invention provides a prodrug of a compound described herein.

In an exemplary embodiment, alkyl is linear alkyl. In another exemplary embodiment, alkyl is branched alkyl.

In an exemplary embodiment, heteroalkyl is linear heteroalkyl. In another exemplary embodiment, heteroalkyl is branched heteroalkyl.

III. b) Combinations Comprising Additional Therapeutically Active Agents

The compounds of the invention may also be used in combination with at least one other therapeutically active agent. The invention thus provides, in a further aspect, a combination comprising a compound of the invention together with at least one other therapeutically active agent, or a salt, prodrug, hydrate or solvate thereof. In an exemplary embodiment, the compound of the invention is a compound described herein, or a salt thereof. In an exemplary embodiment, the additional therapeutically active agent is a compound of the invention. In an exemplary embodiment, the additional therapeutic agent includes a boron atom. In an exemplary embodiment, the additional therapeutic agent does not contain a boron atom. In an exemplary embodiment, the additional therapeutic agent is a compound described in section III a).

When a compound of the invention is used in combination with a second therapeutic agent active against the same disease state, the dose of each compound may differ from that when the compound is used alone. Appropriate doses will be readily appreciated by those skilled in the art. It will be appreciated that the amount of a compound of the invention required for use in treatment will vary with the nature of the condition being treated and the age and the condition of the patient and will be ultimately at the discretion of the attendant physician or veterinarian.

The individual components of such combinations may be administered either simultaneously or sequentially in a unit dosage form. The unit dosage form may be a single or multiple unit dosage forms. In an exemplary embodiment, the invention provides a combination in a single unit dosage form. An example of a single unit dosage form is a capsule wherein both the compound of the invention and the additional therapeutic agent are contained within the same capsule. In an exemplary embodiment, the invention provides a combination in a two unit dosage form. An example of a two unit dosage form is a first capsule which contains the compound of the invention and a second capsule which contains the additional therapeutic agent. Thus the term 'single unit' or 'two unit' or 'multiple unit' refers to the object which the animal (for example, a human) ingests, not to the interior components of the object. Appropriate doses of known therapeutic agents will be readily appreciated by those skilled in the art.

The combinations referred to herein may conveniently be presented for use in the form of a pharmaceutical formulation. Thus, an exemplary embodiment of the invention is a pharmaceutical formulation comprising a) a compound of the invention; b) an additional therapeutic agent and c) a pharmaceutically acceptable excipient. In an exemplary embodiment, the pharmaceutical formulation is a unit dosage form. In an exemplary embodiment, the pharmaceutical formulation is a single unit dosage form. In an exemplary embodiment, the pharmaceutical formulation is a single unit dosage form which includes a compound of the invention; an antibacterial and a pharmaceutically acceptable excipient. In an exemplary embodiment, the pharmaceutical formulation is a single unit dosage form which includes a compound of the invention; an antibacterial and at least one pharmaceutically acceptable excipient. In an exemplary embodiment, the pharmaceutical formulation is a two unit dosage form. In an exemplary embodiment, the pharmaceutical formulation is a two unit dosage form comprising a first unit dosage form and a second unit dosage form, wherein the first unit dosage form includes a) a compound of the invention and b) a first pharmaceutically acceptable excipient; and the second unit dosage form includes c) an additional therapeutic agent and d) a second pharmaceutically acceptable excipient. In an exemplary embodiment, the pharmaceutical formulation is a two unit dosage form comprising a first unit dosage form and a second unit dosage form, wherein the first unit dosage form includes a) a compound of the invention and b) a first pharmaceutically acceptable excipient; and the second unit dosage form includes c) an antibacterial and d) a second pharmaceutically acceptable excipient.

III. c) Preparation of Compounds of the Invention

Compounds of the invention can be prepared using commercially available starting materials, known intermediates, or by using the synthetic methods published in references described and incorporated by reference herein, such as U.S. patent application Ser. No. 12/142,692 and U.S. Pat. Pubs. US20060234981, US20070155699 and US20070293457.

The following general procedures were used as indicated in generating the examples and can be applied, using the knowledge of one of skill in the art, to other appropriate compounds to obtain additional analogues. Benzoxaborole, benzoxaborininol, and benzodiazaborininol are shown below for exemplary purposes. The procedures are adaptable to any of the boron ring systems described herein.

General Procedures for Creating Modified Pleuromutilins:

A general method of creating a modified pleuromutilin is provided below:

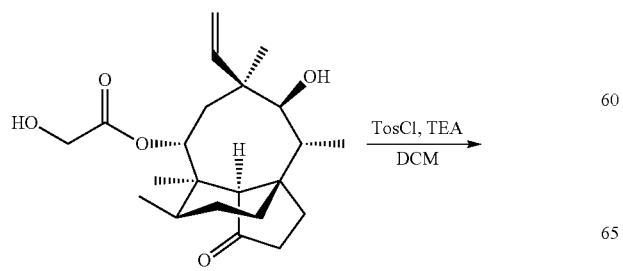

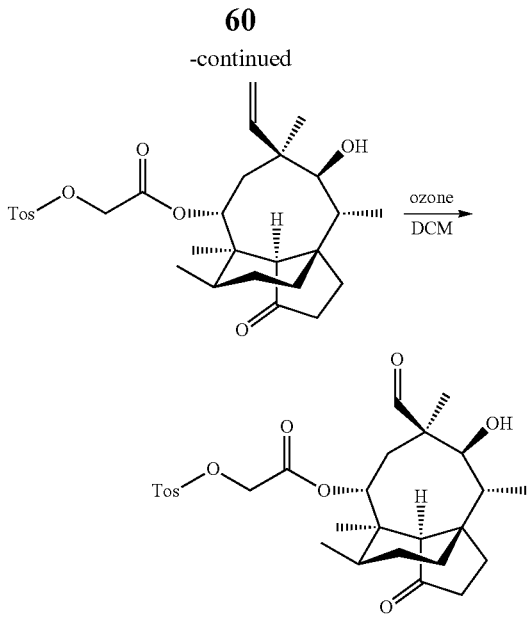

Another general method of creating a modified pleuromutilin is provided below:

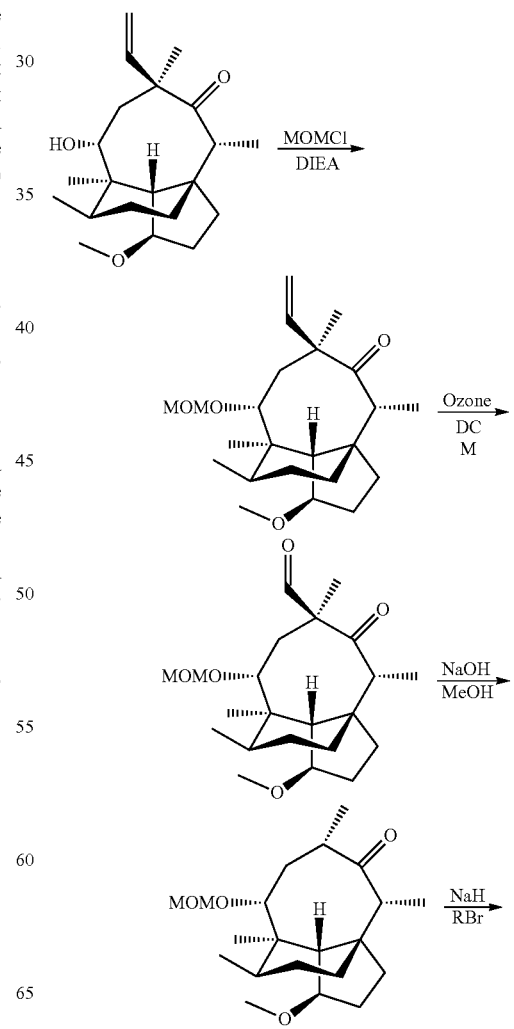

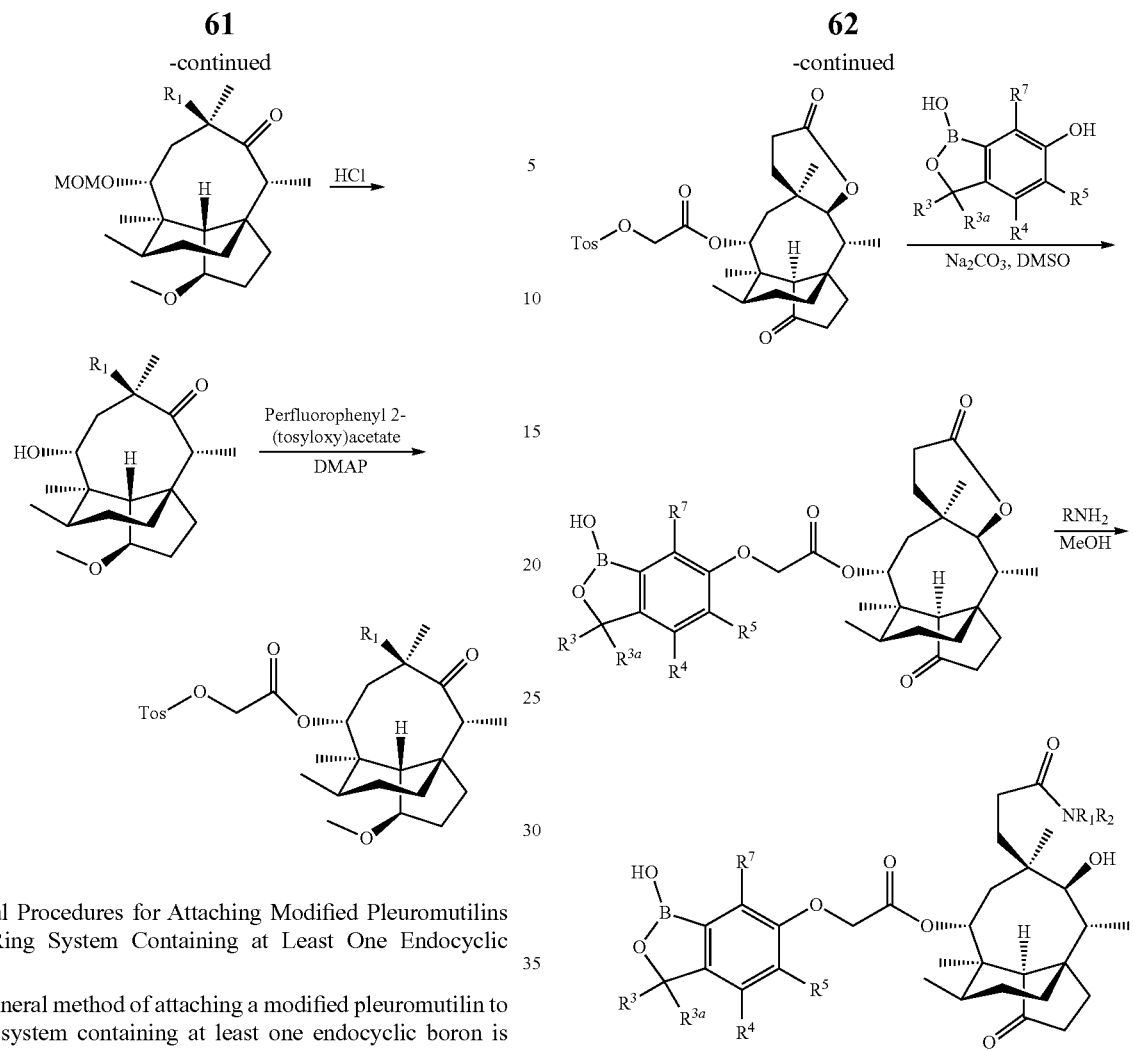

General Procedures for Attaching Modified Pleuromutilins to a Ring System Containing at Least One Endocyclic Boron:

A general method of attaching a modified pleuromutilin to a ring system containing at least one endocyclic boron is provided below.

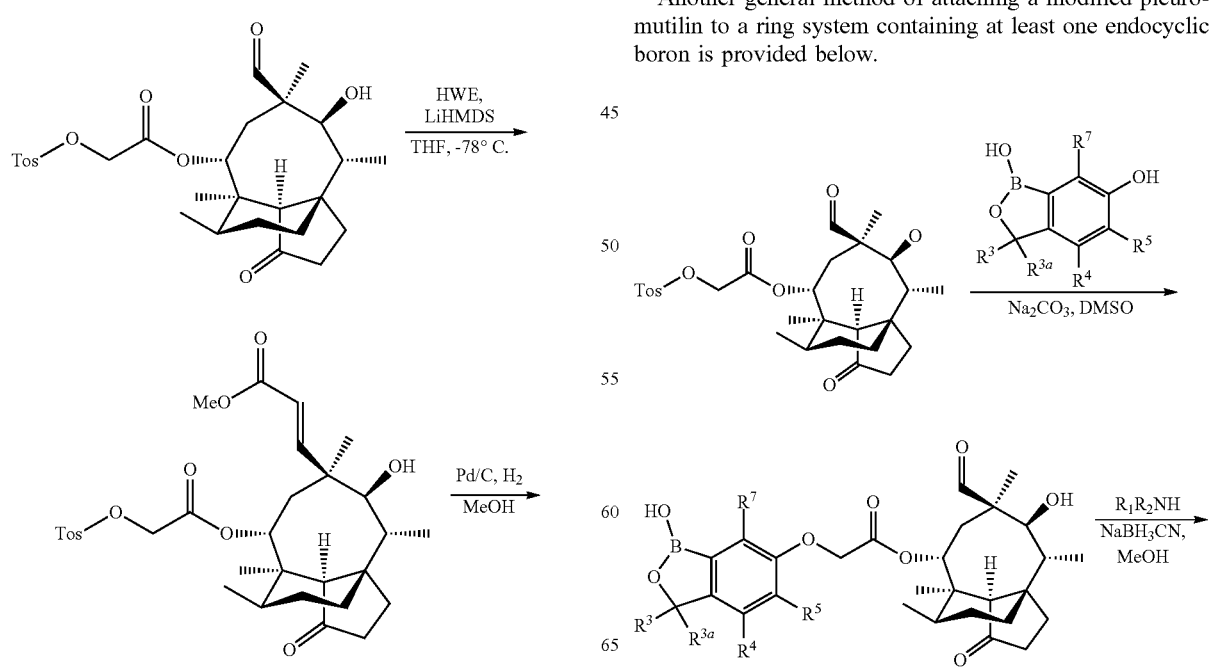

Another general method of attaching a modified pleuromutilin to a ring system containing at least one endocyclic boron is provided below.

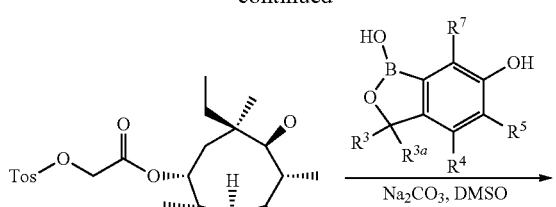

-continued

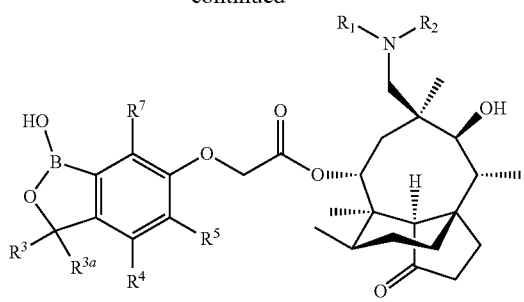

Another general method of attaching a modified pleuromutilin to a ring system containing at least one endocyclic boron is provided below.

Another general method of attaching a modified pleuromutilin to a ring system containing at least one endocyclic boron is provided below.

-continued

Another general method of attaching a modified pleuromutilin to a ring system containing at least one endocyclic boron is provided below.

Another general method of attaching a modified pleuromutilin to a ring system containing at least one endocyclic boron is provided below.

General Procedures for Modifying a Pleuromutilin Containing a Ring System with at Least One Endocyclic Boron:

A general method of modifying a pleuromutilin containing a ring system with at least one endocyclic boron is provided below:

Another general method of modifying a pleuromutilin containing a ring system with at least one endocyclic boron is provided below:

Another general method of modifying a pleuromutilin containing a ring system with at least one endocyclic boron is provided below:

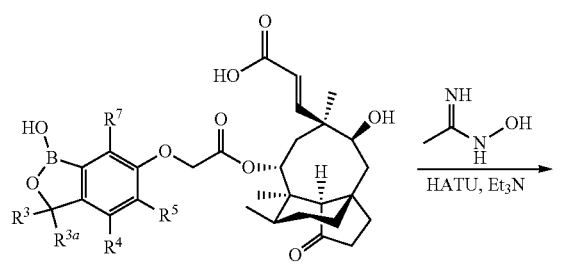
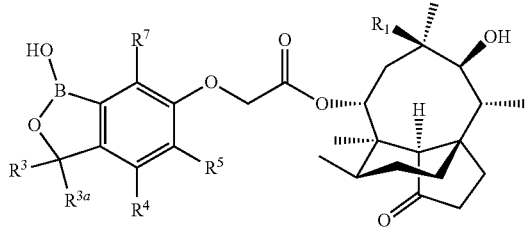

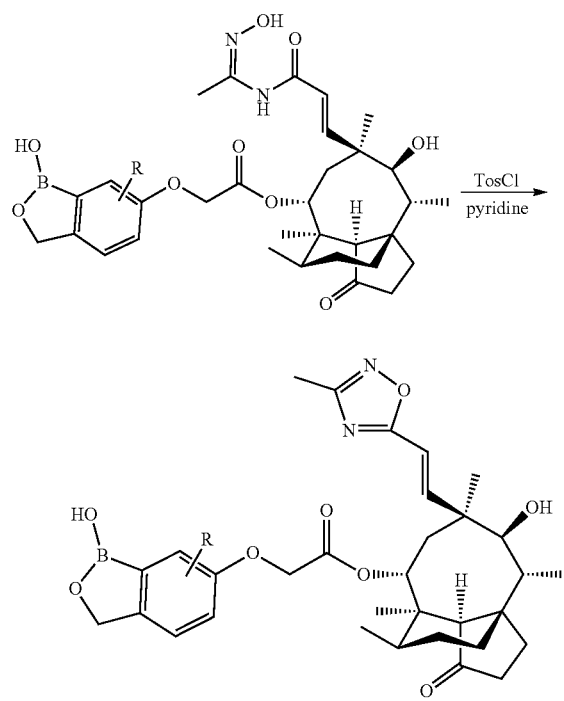

Another general method of modifying a pleuromutilin containing a ring system with at least one endocyclic boron is provided below:

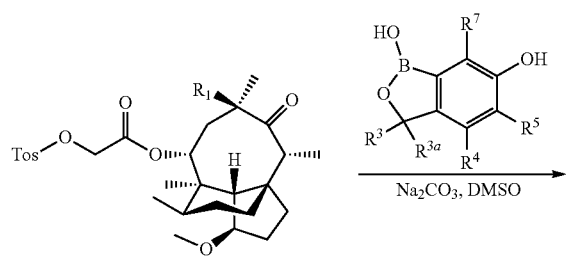

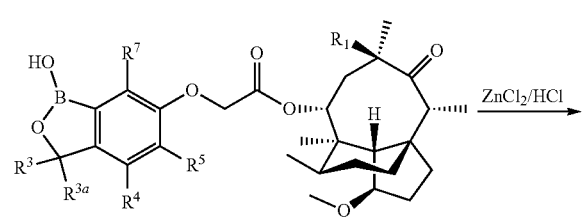

IV. Methods

In another aspect, the compounds of the invention and/or combinations of the invention can be utilized to inhibit protein synthesis in a bacteria. In another aspect, the compounds of the invention and/or combinations of the invention exhibit potency against microorganisms, such as bacteria, and worms, and therefore have the potential to kill and/or inhibit the growth of them. In another aspect, the compounds of the invention and/or combinations of the invention exhibit potency against microorganisms, such as bacteria, and worms, and therefore have the potential to achieve therapeutic efficacy in infections by these microorganisms and/or worms in the animals described herein. In an exemplary embodiment, the bacteria is Gram-positive. In another exemplary embodiment, the bacteria is a symbiont with another organism. In another exemplary embodiment, the bacteria is a symbiont with a worm. In another exemplary embodiment, the bacteria is a symbiont with an arthropod.

IV. A) Inhibiting Microorganism Growth or Killing Microorganisms

The compounds of the invention and/or combinations of the invention exhibit potency against microorganisms, such as bacteria, and therefore have the potential to treat, and/or prevent a microorganism infection, or kill and/or inhibit the growth of microorganisms.

In a further aspect, the invention provides a method of inhibiting the growth of and/or killing a bacteria, the method comprising contacting the bacteria with a compound of the invention, or a pharmaceutically acceptable salt or a hydrate or a solvate thereof, thereby inhibiting the growth of and/or killing the bacteria. In an exemplary embodiment, the bacteria is contacting with a therapeutically effective amount of the compound of the invention. In an exemplary embodiment, the bacteria is contacting with a prophylactically effective amount of the compound of the invention.

In a further aspect, the invention provides a method of treating and/or preventing a microorganism infection, or a method of killing and/or inhibiting the growth of a microorganism, said method comprising contacting said microorganism with an effective amount of a compound of the invention, thereby killing and/or inhibiting the growth of the microorganism. In a further aspect, the invention provides a method of treating and/or preventing a microorganism infection, or a method of killing and/or inhibiting the growth of a microorganism, said method comprising contacting said microorganism with an effective amount of a combination of the invention, thereby killing and/or inhibiting the growth of the microorganism.

In a further aspect, the invention provides a method of treating and/or preventing a microorganism infection, or a method of killing and/or inhibiting the growth of a microorganism, said method comprising contacting said microorganism with a compound of the invention, thereby killing and/or inhibiting the growth of the microorganism. In a further aspect, the invention provides a method of treating and/or preventing a microorganism infection, or a method of killing and/or inhibiting the growth of a microorganism, said method comprising contacting said microorganism with an effective amount of a compound of the invention, thereby killing and/or inhibiting the growth of the microorganism. In a further aspect, the invention provides a method of treating and/or preventing a microorganism infection, or a method of killing and/or inhibiting the growth of a microorganism, said method comprising: contacting said microorganism with an effective amount of a combination of the invention, thereby killing and/or inhibiting the growth of the microorganism.

In a further aspect, the invention provides a method of treating a bacterial infection comprising administering to an animal suffering from the infection an effective amount of a compound of the invention or a combination of the invention, or a pharmaceutically acceptable salt thereof, thereby treating the bacterial infection. In an exemplary embodiment, the invention provides a method of treating a bacterial infection comprising administering to an animal suffering from the infection an effective amount of a compound of the invention, or a pharmaceutically acceptable salt thereof, and an effective amount of an antibacterial, or a pharmaceutically acceptable salt thereof, thereby treating the bacterial infection.

In a further aspect, the invention provides a method of preventing a bacterial infection comprising administering to an animal a prophylactic amount of a compound of the invention or a combination of the invention, or a pharmaceutically acceptable salt thereof, thereby treating the bacterial infection. In an exemplary embodiment, the invention provides a method of preventing a bacterial infection comprising administering to an animal a prophylactic amount of a compound of the invention, or a pharmaceutically acceptable salt thereof.

In an exemplary embodiment, the microorganism is a bacteria. In an exemplary embodiment, the compound or combination is described herein, or a salt, prodrug, hydrate or solvate thereof, or a combination thereof. In an exemplary embodiment, the invention provides a compound or combination described herein, or a salt, hydrate or solvate thereof. In an exemplary embodiment, the invention provides a compound or combination described herein, or a prodrug thereof. In an exemplary embodiment, the invention provides a compound or combination described herein, or a salt thereof. In another exemplary embodiment, the compound or combination of the invention is a compound or combination described herein, or a pharmaceutically acceptable salt thereof. In another exemplary embodiment, the compound or compound of the combination is described by a formula listed herein, or a pharmaceutically acceptable salt thereof. In an exemplary embodiment, the compound is part of a combination described herein. In an exemplary embodiment, the compound is part of a pharmaceutical formulation described herein. In another exemplary embodiment, the contacting occurs under conditions which permit entry of the compound into the organism. Such conditions are known to one skilled in the art and are described herein.

In another aspect, the microorganism is inside, and/or on the surface of an animal. In an exemplary embodiment, the animal is selected from the group consisting of human, cattle, deer, reindeer, goat, honey bee, pig, sheep, horse, cow, bull, dog, guinea pig, gerbil, rabbit, cat, camel, yak, elephant, ostrich, otter, chicken, duck, goose, guinea fowl, pigeon, swan, and turkey. In another exemplary embodiment, the animal is a human.

In an exemplary embodiment, the microorganism infection is treated and or prevented, and/or the microorganism is killed or its growth is inhibited, through oral administration of the compound of the invention and/or the combination of the invention. In an exemplary embodiment, the microorganism infection is treated and or prevented, and/or the microorganism is killed or its growth is inhibited through intravenous administration of the compound of the invention and/or the combination of the invention.

In an exemplary embodiment, the microorganism is a bacteria. In an exemplary embodiment, an infection is caused by and/or associated with a microorganism, particularly a bacteria. In an exemplary embodiment, the bacteria is a Gram-positive bacteria. In another exemplary embodiment, the Gram-positive bacteria is selected from the group consisting of *Staphylococcus* species, *Streptococcus* species, *Bacillus* species, *Mycobacterium* species, *Corynebacterium* species (*Propionibacterium* species), *Clostridium* species, *Actinomyces* species, *Enterococcus* species, *Streptomyces* species, *Listeria* species. In another exemplary embodiment, the Gram-positive bacteria is selected from the group consisting of *Propionibacterium acnes*, *Staphylococcus aureus*, *Staphylococcus epidermidis*, *Staphylococcus saprophyticus*, *Staphylococcus haemolyticus*, *Streptococcus pyogenes*, *Streptococcus agalactiae*, *Streptococcus pneumoniae*, *Enterococcus faecalis*, *Enterococcus faecium*, *Bacillus anthraces*, *Mycobacterium avium-intracellulare*, *Mycobacterium tuberculosis*, *Acinetobacter baumanii*, *Corynebacterium diphtheria*, *Clostridium perfringens*, *Clostridium botulinum*, *Clostridium tetani*, *Clostridium difficile*, and *Listeria monocytogenes*. In another exemplary embodiment, the Gram-positive bacteria is selected from the group consisting of *Staphylococcus aureus*, *Staphylococcus epidermidis*, *Streptococcus pneumoniae*, *Streptococcus pyogenes*, *Enterococcus faecalis*, *Enterococcus faecium*, *Clostridium difficile* and *Propionibacter acnes*. In an exemplary embodiment, the bacteria is a coagulase positive Staphylococci. In an exemplary embodiment, the bacteria is a coagulase negative Staphylococci.

In an exemplary embodiment, the compounds of the invention exhibit potency against bacteria which are associated with worms. In an exemplary embodiment, the compounds of the invention exhibit potency against bacteria which live inside of worms. In an exemplary embodiment, the invention provides a method of killing and/or inhibiting the growth of a bacteria which is associated with a worm, comprising contacting the bacteria with an effective amount of the compound of the invention, thereby killing and/or inhibiting the growth of the bacteria. In an exemplary embodiment, the bacteria is of the *Wolbachia* genus. In an exemplary embodiment, the bacteria is *Wolbachia pipientis*.

IV. b) Inhibiting Worm Growth or Killing Worms

The compounds of the present invention exhibit potency against certain worms as a consequence of their ability to kill the endosymbiotic bacteria of the *Wolbachia* genus, and therefore have the potential to kill and/or inhibit the growth of such worms. The invention therefore provides a method of killing a worm, comprising contacting the worm with an effective amount of the compound of the invention, thereby killing the worm. The invention provides a method of inhibiting the growth of a worm, comprising contacting the worm with an effective amount of the compound of the invention, thereby inhibiting the growth of the worm. In an exemplary embodiment, the worm is female. In an exemplary embodiment, the worm is male. In an exemplary embodiment, the worm is a hermaphrodite. In an exemplary embodiment, the worm is an egg. In an exemplary embodiment, the worm is an unfertilized egg. In an exemplary embodiment, the worm is fertilized egg. In an exemplary embodiment, the worm is a larvae. In an exemplary embodiment, the worm is mature. In an exemplary embodiment, the worm is fully mature. In an exemplary embodiment, the worm is contacted with the compound of the invention inside an animal. In an exemplary embodiment, the worm is contacted with the compound of the invention outside of an animal.

In an exemplary embodiment, the worm is a parasitic worm. In an exemplary embodiment, the worm is a helminth. In an exemplary embodiment, the worm is a nematode. In an exemplary embodiment, the nematode is a filarid. In an exemplary embodiment, the nematode is a member of Filarioidea. In an exemplary embodiment, the nematode is a member of Onchocercinae. In an exemplary embodiment, the nematode is a member of Dirofilaranae. In an exemplary embodiment, the nematode is a filarid. In an exemplary embodiment, the nematode is a filarial worm. In an exemplary embodiment, the nematode is a member of the genus *Wuchereria*. In an exemplary embodiment, the nematode is *Wuchereria bancrofti*. In an exemplary embodiment, the nematode is a member of the genus *Brugia*. In an exemplary embodiment, the nematode is *Brugia malayi*. In an exemplary embodiment, the nematode is *Brugia timori*. In an exemplary embodiment, the *Brugia* is a microfilariae. In an exemplary embodiment, the *Brugia* is a larvae. In an exemplary embodiment, the *Brugia* is mature. In an exemplary embodiment, the *Brugia* is contacted by the compound of the invention in the skin of the animal. In an exemplary embodiment, the *Brugia* is contacted by the compound of the invention in the lymphatic system of the animal. In an exemplary embodiment, the *Brugia* is contacted by the compound of the invention in the blood of the animal. In an exemplary embodiment, the *Brugia* is contacted by the compound of the invention in the muscle of the animal. In an exemplary embodiment, the *Brugia* is contacted by the compound of the invention in the salivary gland of the animal.

In an exemplary embodiment, the nematode is a member of the genus *Mansonella*. In an exemplary embodiment, the nematode is selected from the group consisting of *Mansonella streptocerca*, *Mansonella perstans*, and *Mansonella ozzardi*. In an exemplary embodiment, the nematode is a member of the genus *Onchocerca*. In an exemplary embodiment, the nematode is *Onchocerca volvulus*. In an exemplary embodiment, the nematode is *Onchocerca ochengi*.

In an exemplary embodiment, the nematode is a heartworm. In an exemplary embodiment, the nematode is a member of the genus *Dirofilaria*. In an exemplary embodiment, the nematode is *Dirofilaria immitis*. In an exemplary embodiment, the nematode is *Dirofilaria tenuis* or *Dirofilaria repens*.

IV. c) Diseases

The compounds of the invention and/or combinations of the invention exhibit potency against microorganisms, such as bacteria, and therefore have the potential to achieve therapeutic efficacy in the animals described herein. The compounds of the invention and/or combinations of the invention exhibit potency against worms, and therefore have the potential to achieve therapeutic efficacy in the animals described herein.

In another aspect, the invention provides a method of treating and/or preventing a disease. In an exemplary embodiment, the method includes administering to the animal a therapeutically and/or prophylactically effective amount of a compound of the invention, sufficient to treat and/or prevent the disease. In an exemplary embodiment, the method includes administering to the animal a therapeutically and/or prophylactically effective amount of a combination of the invention, sufficient to treat and/or prevent the disease. In an exemplary embodiment, the animal being administered the compound is not otherwise in need of treatment with a compound of the invention.

In an exemplary embodiment, the compound of the invention or the combination of the invention can be used in human or veterinary medical therapy, particularly in the treatment or prophylaxis of bacterial-associated disease. In an exemplary embodiment, the compound of the invention or the combination of the invention can be used in human or veterinary medical therapy, particularly in the treatment of a Gram-positive bacterial-associated disease. In an exemplary embodiment, the compound of the invention or the combination of the invention can be used in human or veterinary medical therapy, particularly in the prophylaxis of a Gram-positive bacterial-associated disease. In an exemplary embodiment, the compound of the invention or the combination of the invention can be used in human or veterinary medical therapy, particularly in the treatment of a *Wolbachia*-associated disease. In an exemplary embodiment, the compound of the invention or the combination of the invention can be used in human or veterinary medical therapy, particularly in the prophylaxis of a *Wolbachia*-associated disease. In another exemplary embodiment, the disease is pneumonia. In another exemplary embodiment, the disease is hospital-acquired pneumonia. In another exemplary embodiment, the disease is hospital-associated pneumonia. In another exemplary embodiment, the disease is community-acquired pneumonia. In another exemplary embodiment, the disease is a acute bacterial skin and skin-structure infection (ABSSSI). In another exemplary embodiment, the disease is bacteremia. In another exemplary embodiment, the disease is endocarditis. In another exemplary embodiment, the disease is osteomyelitis. In an exemplary embodiment, the disease is associated with a *Staphylococcus* species. In another exemplary embodiment, the disease is selected from the group consisting of pneumonia, gastroenteritis, toxic shock syndrome, community acquired pneumonia (CAP), meningitis, septic arthritis, urinary tract infection, bacteremia, endocarditis, osteomylitis, skin and skin-structure infection. In an exemplary embodiment, the disease is associated with a *Streptococcus* species. In another exemplary embodiment, the disease is selected from the group consisting of strep throat, skin infections, necrotizing fasciitis, toxic shock syndrome, pneumonia, otitis media and sinusitis. In an exemplary embodiment, the disease is associated with an *Actinomyces* species. In another exemplary embodiment, the disease is actinomycosis. In an exemplary embodiment, the disease is associated with a *Norcardia* species. In another exemplary embodiment, the disease is pneumonia. In an exemplary embodiment, the disease is associated with a *Corynebacterium* species. In another exemplary embodiment, the disease is diptheria. In an exemplary embodiment, the disease is associated with a *Listeria* species. In another exemplary embodiment, the disease is meningitis. In an exemplary embodiment, the disease is associated with a *Bacillus* species. In another exemplary embodiment, the disease is anthrax or food poisoning. In an exemplary embodiment, the disease is associated with a *Clostridium* species. In another exemplary embodiment, the disease is selected from the group consisting of botulism, tetanus, gas gangrene and diarrhea. In an exemplary embodiment, the disease is associated with a *Mycobacterium* species. In another exemplary embodiment, the disease is tuberculosis or leprosy. In an exemplary embodiment, the disease is associated with a *Listeria* species. In an exemplary embodiment, the disease is associated with a *Wolbachia* species. In an exemplary embodiment, the disease is associated with *Wolbachia pipientis*. In an exemplary embodiment, the disease is selected from the group consisting of candidiasis, aspergillosis, coccidioidomycosis, cryptococcosis, histoplasmosis, blastomycosis, paracoccidioidomycosis, zygomycosis, phaeohyphomycosis and rhinosporidiosis.

In an exemplary embodiment, the compound of the invention can be used in human medical therapy, particularly in the treatment of worm-associated disease. In an exemplary embodiment, the compound of the invention can be used in human medical therapy, particularly in the prophylaxis of worm-associated disease. In an exemplary embodiment, the compound of the invention can be used in veterinary medical therapy, particularly in the treatment of worm-associated disease. In an exemplary embodiment, the compound of the invention can be used in veterinary medical therapy, particularly in the prophylaxis of worm-associated disease. In an exemplary embodiment, the compound of the invention can be used in human medical therapy, particularly in the treatment of helminth-associated disease. In an exemplary embodiment, the compound of the invention can be used in human medical therapy, particularly in the prophylaxis of helminth-associated disease. In an exemplary embodiment, the compound of the invention can be used in veterinary medical therapy, particularly in the treatment of helminth-associated disease. In an exemplary embodiment, the compound of the invention can be used in veterinary medical therapy, particularly in the prophylaxis of helminth-associated disease. In an exemplary embodiment, the disease is associated with a worm. In an exemplary embodiment, the disease is caused by a worm. In an exemplary embodiment, the disease is associated with a worm described herein. In an exemplary embodiment, the disease is associated with a nematode. In an exemplary embodiment, the disease is associated with a nematode described herein. In an exemplary embodiment, the nematode is *Wuchereria bancrofti*. In an exemplary embodiment, the nematode is *Brugia malayi*. In an exemplary embodiment, the nematode is *Brugia timori*. In an exemplary embodiment, the nematode is *Dirofilaria immitis*. In an exemplary embodiment, the disease is a member selected from enterobiasis, filariasis, and onchocerciasis. In an exemplary embodiment, the disease is lymphatic filariasis. In an exemplary embodiment, the disease is bancroftian filariasis. In an exemplary embodiment, the disease is lymphadenitis. In an exemplary embodiment, the disease is lymphangitis. In an exemplary embodiment, the disease is lymphedema. In an exemplary embodiment, the disease is subcutaneous filariasis. In an exemplary embodiment, the disease is serious cavity filariasis. In an exemplary embodiment, the disease is elephantiasis. In an exemplary embodiment, the disease is elephantiasis tropica. In an exemplary embodiment, the disease is onchocerciasis.

In another exemplary embodiment, the animal is selected from the group consisting of human, cattle, deer, reindeer, goat, honey bee, pig, sheep, horse, cow, bull, dog, guinea pig, gerbil, rabbit, cat, camel, yak, elephant, ostrich, otter, chicken, duck, goose, guinea fowl, pigeon, swan, and turkey. In another exemplary embodiment, the animal is a human. In another exemplary embodiment, the animal is selected from the group consisting of a human, cattle, goat, pig, sheep, horse, cow, bull, dog, guinea pig, gerbil, rabbit, cat, chicken and turkey. In another exemplary embodiment, the disease is a systemic disease. In another exemplary embodiment, the disease is a topical disease.

In an exemplary embodiment, the disease is treated through oral administration of a compound of the invention and/or a combination of the invention. In an exemplary embodiment, the disease is treated through intravenous administration of a compound of the invention and/or a combination of the invention. In an exemplary embodiment, the disease is treated through intramuscular administration of a compound of the invention and/or a combination of the invention. In an exemplary embodiment, the disease is treated through topical administration of a compound of the invention and/or a combination of the invention.

In an exemplary embodiment, for any of the methods described herein, a compound of the invention, a combination of the invention, a compound described herein or a pharmaceutically acceptable salt thereof, or combination described herein, and/or a pharmaceutical formulation described herein can be used.

V. Pharmaceutical Formulations

In another aspect, the invention is a pharmaceutical formulation which includes: (a) a pharmaceutically acceptable excipient; and (b) a compound of the invention. In another aspect, the pharmaceutical formulation includes: (a) a pharmaceutically acceptable excipient; and (b) a compound according to a formula described herein. In another aspect, the pharmaceutical formulation includes: (a) a pharmaceutically acceptable excipient; and (b) a compound described herein, or a salt, prodrug, hydrate or solvate thereof. In another aspect, the pharmaceutical formulation includes: (a) a pharmaceutically acceptable excipient; and (b) a compound described herein, or a salt, hydrate or solvate thereof. In another aspect, the pharmaceutical formulation includes: (a) a pharmaceutically acceptable excipient; and (b) a compound described herein, or a salt, hydrate or solvate thereof. In another aspect, the pharmaceutical formulation includes: (a) a pharmaceutically acceptable excipient; and (b) a salt of a compound described herein. In an exemplary embodiment, the salt is a pharmaceutically acceptable salt. In another aspect, the pharmaceutical formulation includes: (a) a pharmaceutically acceptable excipient; and (b) a prodrug of a compound described herein. In another aspect, the pharmaceutical formulation includes: (a) a pharmaceutically acceptable excipient; and (b) a compound described herein. In an exemplary embodiment, the pharmaceutical formulation is a unit dosage form. In an exemplary embodiment, the pharmaceutical formulation is a single unit dosage form.

Information regarding excipients of use in the formulations of the invention can be found in *Remington: The Science and Practice of Pharmacy*, 21st Ed., Pharmaceutical Press (2011) which is incorporated herein by reference.

Exemplary embodiments are summarized herein below.

In an exemplary embodiment, the invention provides a compound, or a salt or a hydrate or a solvate thereof, having a structure according to the following formula:

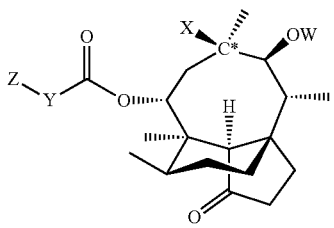

wherein W is H or a bond to X; X is

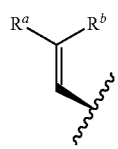

wherein $R^a$ and $R^b$ are each independently selected from the group consisting of $R^{15}$, $-OR^{15}$, $-NR^{15}R^{16}$, $-SR^{15}$, $-S(O)R^{15}$, $-S(O)_2R^{15}$, $-S(O)_2NR^{15}R^{16}$, $-C(O)R^{15}$, $-C(O)OR^{15}$, and $-C(O)NR^{15}R^{16}$ wherein $R^{15}$ and $R^{16}$ are each independently selected from the group consisting of H, halogen, cyano, nitro, $-OR^{17}$, $-NR^{17}R^{18}$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, wherein $R^{17}$ and $R^{18}$ are each independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, and wherein $R^{15}$ and $R^{16}$, and/or $R^{17}$ and $R^{18}$, along with the nitrogen to which they are connected, are optionally joined to form a substituted or unsubstituted 4- to 8-membered ring, with the proviso that $R^a$ and $R^b$ are not both H; or X is

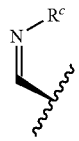

wherein $R^c$ is $-OR^{15}$, $-NR^{15}R^{16}$, $-SR^{15}$, $-S(O)R^{15}$, $-S(O)_2R^{15}$, $-S(O)_2NR^{15}R^{16}$, $-C(O)R^{15}$, $-C(O)OR^{15}$, and $-C(O)NR^{15}R^{16}$ wherein $R^{15}$ and $R^{16}$ are each independently selected from the group consisting of H, halogen, cyano, nitro, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, and wherein $R^{15}$ and $R^{16}$, along with the nitrogen to which they are connected, are optionally joined to form a substituted or unsubstituted 4- to 8-membered ring; or X is

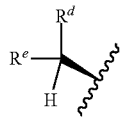

wherein $R^d$ and $R^e$ are each independently selected from the group consisting of H, halogen, cyano, nitro, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, $-OR^{15}$, $-NR^{15}R^{16}$, $-SR^{15}$, $-S(O)R^{15}$, $-S(O)_2R^{15}$, $-S(O)_2NR^{15}R^{16}$, $-C(O)R^{15}$, $-C(O)OR^{15}$, and $-C(O)NR^{15}R^{16}$, wherein $R^{15}$ and $R^{16}$ are each independently selected from the group consisting of H, halogen, cyano, nitro, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl and wherein $R^d$ and $R^e$, along with the atom to which they are connected, are optionally joined to form a substituted or unsubstituted 3- to 8-membered ring and wherein $R^{15}$ and $R^{16}$, along with the nitrogen to which they are connected, are optionally joined to form a substituted or unsubstituted 4- to 8-membered ring with the proviso that $R^d$ and $R^e$ are not both H, wherein X optionally comprises an attachment point to W; Y is selected from the group consisting of a bond, O, S, NH, substituted or unsubstituted alkylene, and substituted or unsubstituted heteroalkylene; and Z is a substituted or unsubstituted heterocyclic ring or ring system containing at least one endocyclic boron.

In an exemplary embodiment, according to the above paragraph, the compound, or a salt or a hydrate or a solvate thereof, wherein said X is

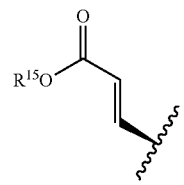

wherein $R^{15}$ is selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

In an exemplary embodiment, according to any of the above paragraphs, for the compound, or a salt or a hydrate or a solvate thereof, wherein said X is

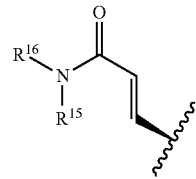

wherein $R^{15}$ and $R^{16}$ are each independently selected from the group consisting of H, $-NR^{17}R^{18}$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, wherein $R^{17}$ and $R^{18}$ are each independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, and wherein $R^{15}$ and $R^{16}$, and/or $R^{17}$ and $R^{18}$, along with the nitrogen to which they are connected, are optionally joined to form a substituted or unsubstituted 4- to 8-membered ring.

In an exemplary embodiment, according to any of the above paragraphs, for the compound, or a salt or a hydrate or a solvate thereof, wherein said X is

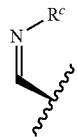

wherein $R^c$ is selected from the group consisting of H, substituted or unsubstituted alkyl, and $-OR^{15}$ wherein $R^{15}$ is H or substituted or unsubstituted alkyl.

In an exemplary embodiment, according to any of the above paragraphs, for the compound, or a salt or a hydrate or a solvate thereof, wherein said X is

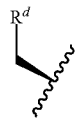

wherein $R^d$ is selected from the group consisting of halogen, substituted or unsubstituted alkyl, substituted or unsubstituted heterocycloalkyl, substituted or unsubstituted aryl, $-OR^{15}$, $-SR^{15}$, $-S(O)R^{15}$, $-NR^{15}R^{16}$, $-C(O)R^{15}$, $-CH_2C(O)OR^{15}$, and $-CH_2C(O)NR^{15}R^{16}$ wherein $R^{15}$ and $R^{16}$ are each independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl and wherein $R^{15}$ and $R^{16}$, along with the nitrogen to which they are connected, are optionally joined to form a substituted or unsubstituted 4- to 8-membered ring.

In an exemplary embodiment, according to any of the above paragraphs, the compound, or a salt or a hydrate or a solvate thereof, wherein $R^d$ comprises said attachment point to W.

In an exemplary embodiment, according to any of the above paragraphs, the compound, or a salt or a hydrate or a solvate thereof, wherein said Y is *$-OCH_2-$ or *$-SCH_2-$ or *$-NHCH_2-$ or *$-CH_2NH-$ or *$-C(O)NH-$, wherein * represents the attachment point to said Z.

In an exemplary embodiment, according to any of the above paragraphs, the compound, or a salt or a hydrate or a solvate thereof, wherein said Z is selected from the group consisting of substituted or unsubstituted benzoxaborole, substituted or unsubstituted pyridinyloxaborole, substituted or unsubstituted benzoxaborininol, substituted or unsubstituted benzoxazaborininol, substituted or unsubstituted benzodiazaborininol, and substituted or unsubstituted oxaborole.

In an exemplary embodiment, according to any of the above paragraphs, the compound, or a salt or a hydrate or a solvate thereof, wherein said Z is

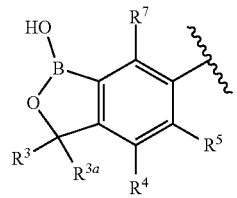

wherein $R^3$, $R^{3a}$, $R^4$, $R^5$, and $R^7$ are each independently selected from the group consisting of $R^{10}$, $-OR^{10}$, $-NR^{10}R^{11}$, $-SR^{10}$, $-S(O)R^{10}$, $-S(O)_2R^{10}$, $-S(O)_2NR^{10}R^{11}$, $-C(O)R^{10}$, $-C(O)OR^{10}$, and $-C(O)NR^{10}R^{11}$ wherein $R^{10}$ and $R^{11}$ are each independently selected from the group consisting of H, halogen, cyano, nitro, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

In an exemplary embodiment, according to any of the above paragraphs, the compound, or a salt or a hydrate or a solvate thereof, wherein said Z is

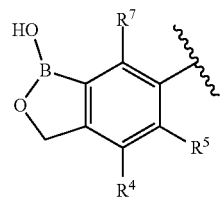

wherein $R^4$, $R^5$, and $R^7$ are each independently selected from the group consisting of $R^{10}$, $-OR^{10}$, $-NR^{10}R^{11}$, wherein $R^{10}$ and $R^{11}$ are each independently selected from the group consisting of H, halogen, cyano, nitro, substituted or unsubstituted alkyl, and substituted or unsubstituted heteroalkyl.

In an exemplary embodiment, according to any of the above paragraphs, the compound, or a salt or a hydrate or a solvate thereof, compound of claim 10, or a salt or a hydrate or a solvate thereof, wherein said Z is

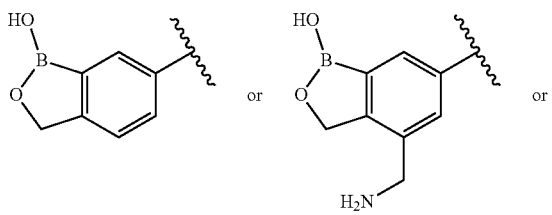

or

-continued

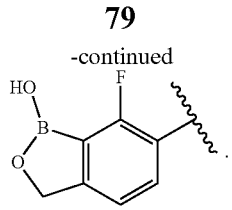

In an exemplary embodiment, according to any of the above paragraphs, the compound, or a salt or a hydrate or a solvate thereof, which is (3aR,4R,5R,7S,8S,9R,9aS,12R)-8-hydroxy-7-(hydroxymethyl)-4,7,9,12-tetramethyl-3-oxo-decahydro-4,9a-propanocyclopenta[8]annulen-5-yl 2-((7-fluoro-1-hydroxy-1,3-dihydrobenzo[c][1,2]oxaborol-6-yl)oxy)acetate.

In an exemplary embodiment, according to any of the above paragraphs, the compound, or a salt or a hydrate or a solvate thereof, which is (3aR,4R,5R,7R,8S,9R,9aS,12R)-8-hydroxy-4,7,9,12-tetramethyl-7-((R)-oxiran-2-yl)-3-oxo-decahydro-4,9a-propanocyclopenta[8]annulen-5-yl 2-((7-fluoro-1-hydroxy-1,3-dihydrobenzo[c][1,2]oxaborol-6-yl)oxy)acetate.

In an exemplary embodiment, according to any of the above paragraphs, the compound, or a salt or a hydrate or a solvate thereof, which is (3aR,4R,5R,7S,8S,9R,9aS,12R)-8-hydroxy-4,7,9,12-tetramethyl-7-((E)-2-(3-methyl-1,2,4-oxadiazol-5-yl)vinyl)-3-oxodecahydro-4,9a-propanocyclopenta[8]annulen-5-yl 2-((7-fluoro-1-hydroxy-1,3-dihydrobenzo[c][1,2]oxaborol-6-yl)oxy)acetate.

In an exemplary embodiment, the invention provides a combination comprising: the compound of a preceding claim, or a pharmaceutically acceptable salt thereof, together with at least one other therapeutically active agent.

In an exemplary embodiment, according to the above combination paragraph, wherein the other therapeutically active agent is an anti-bacterial agent.

In an exemplary embodiment, the invention provides a pharmaceutical formulation comprising: a) the compound of a preceding claim, or a pharmaceutically acceptable salt or a hydrate or a solvate thereof; and b) a pharmaceutically acceptable excipient.

In an exemplary embodiment, according to the above pharmaceutical formulation paragraph, the pharmaceutical formulation is an oral formulation or an intravenous formulation.

In an exemplary embodiment, according to any of the above paragraphs, the salt of the compound according to any of the above paragraphs is a pharmaceutically acceptable salt.

In an exemplary embodiment, the invention is a method of inhibiting protein synthesis in a bacteria, the method comprising contacting the bacteria with the compound in any of the above paragraphs, or a pharmaceutically acceptable salt or a hydrate or a solvate thereof, thereby inhibiting protein synthesis in the bacteria.

In an exemplary embodiment, the invention is a method of inhibiting the growth of and/or killing a bacteria, the method comprising contacting the bacteria with the compound in any of the above paragraphs, or a pharmaceutically acceptable salt or a hydrate or a solvate thereof, thereby inhibiting the growth of and/or killing the bacteria.

In an exemplary embodiment, according to any of the above method paragraphs, wherein the bacteria is Gram-positive.

In an exemplary embodiment, according to any of the above method paragraphs, wherein the bacteria is Staphylococcus aureus or Streptococcus pneumoniae.

In an exemplary embodiment, according to any of the above method paragraphs, wherein the bacteria is methicillin-resistant Staphylococcus aureus.

In an exemplary embodiment, according to any of the above method paragraphs, wherein the bacteria is of the Wolbachia genus.

In an exemplary embodiment, according to any of the above method paragraphs, wherein the bacteria is Wolbachia pipientis.

In an exemplary embodiment, the invention is a method of treating a disease in an animal in need of the treatment, the method comprising administering to the animal a therapeutically effective amount of the compound in any of the above paragraphs, or a pharmaceutically acceptable salt or a hydrate or a solvate thereof, thereby treating the disease.

In an exemplary embodiment, according to the above method paragraph, wherein the disease is associated with a Gram-positive bacteria.

In an exemplary embodiment, according to any of the above method paragraphs, wherein the disease is pneumonia.

In an exemplary embodiment, according to any of the above method paragraphs, wherein the disease is onchocerciasis.

In an exemplary embodiment, according to any of the above method paragraphs, the animal is a human.

In an exemplary embodiment, according to any of the above method paragraphs, there is a proviso that the animal is not otherwise in need of treatment with a compound of the invention.

The invention is further illustrated by the Examples that follow. The Examples are not intended to define or limit the scope of the invention.

EXAMPLES

Proton NMR are recorded on Varian AS 300 spectrometer and chemical shifts are reported as δ (ppm) down field from tetramethylsilane. Mass spectra are determined on Micromass Quattro II.

Example 1

1. (4aR,6R,7R,7aR,10aS,11R,11aS,14R)-4a,7,11,14-tetramethyl-2,8-dioxododecahydro-2H-7,10a-propanocyclopenta[6,7]cycloocta[1,2-b]pyran-6-yl 2-((7-fluoro-1-hydroxy-1,3-dihydrobenzo[c][1,2]oxaborol-6-yl)oxy)acetate
2. (3aR,4R,5R,7R,8S,9R,9aS,12R)-7-(3-amino-3-oxopropyl)-8-hydroxy-4,7,9,12-tetramethyl-3-oxodecahydro-4,9a-propanocyclopenta[8]annulen-5-yl 2-((7-fluoro-1-hydroxy-1,3-dihydrobenzo[c][1,2]oxaborol-6-yl)oxy)acetate
3. (3aR,4R,5R,7R,8S,9R,9aS,12R)-8-hydroxy-4,7,9,12-tetramethyl-7-(3-(methylamino)-3-oxopropyl)-3-oxodecahydro-4,9a-propanocyclopenta[8]annulen-5-yl 2-((7-fluoro-1-hydroxy-1,3-dihydrobenzo[c][1,2]oxaborol-6-yl)oxy)acetate
4. (3aR,4R,5R,7R,8S,9R,9aS,12R)-7-(3-(ethylamino)-3-oxopropyl)-8-hydroxy-4,7,9,12-tetramethyl-3-oxodecahydro-4,9a-propanocyclopenta[8]annulen-5-yl 2-((7-fluoro-1-hydroxy-1,3-dihydrobenzo[c][1,2]oxaborol-6-yl)oxy)acetate
5. (3aR,4R,5R,7R,8S,9R,9aS,12R)-7-(3-(butylamino)-3-oxopropyl)-8-hydroxy-4,7,9,12-tetramethyl-3-oxodecahydro-4,9a-propanocyclopenta[8]annulen-5-yl 2-((7-fluoro-1-hydroxy-1,3-dihydrobenzo[c][1,2]oxaborol-6-yl)oxy)acetate 6. (3aR,4R,5R,7R,8S,9R,9aS,12R)-7-(3-(cyclopropylamino)-3-oxopropyl)-8-hydroxy-4,7,9,12-tetramethyl-3-oxodecahydro-4,9a-propanocyclopenta[8]annulen-5-yl 2-((7-fluoro-1-hydroxy-1,3-dihydrobenzo[c][1,2]oxaborol-6-yl)oxy)acetate 7. (3aR,4R,5R,7R,8S,9R,9aS,12R)-8-hydroxy-7-(3-(3-hydroxypyrrolidin-1-yl)-3-oxopropyl)-4,7,9,12-tetramethyl-3-oxodecahydro-4,9a-propanocyclopenta[8]annulen-5-yl 2-((7-fluoro-1-hydroxy-1,3-dihydrobenzo[c][1,2]oxaborol-6-yl)oxy)acetate 8. (3aR,4R,5R,7R,8S,9R,9aS,12R)-8-hydroxy-7-(3-((S)-3-hydroxypyrrolidin-1-yl)-3-oxopropyl)-4,7,9,12-tetramethyl-3-oxodecahydro-4,9a-propanocyclopenta[8]annulen-5-yl 2-((7-fluoro-1-hydroxy-1,3-dihydrobenzo[c][1,2]oxaborol-6-yl)oxy)acetate

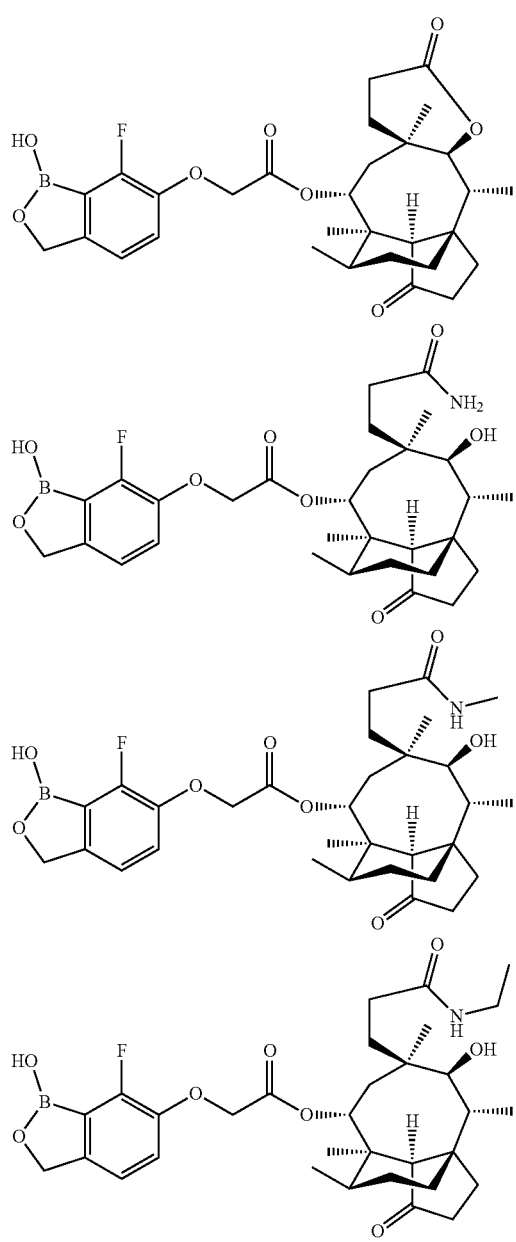

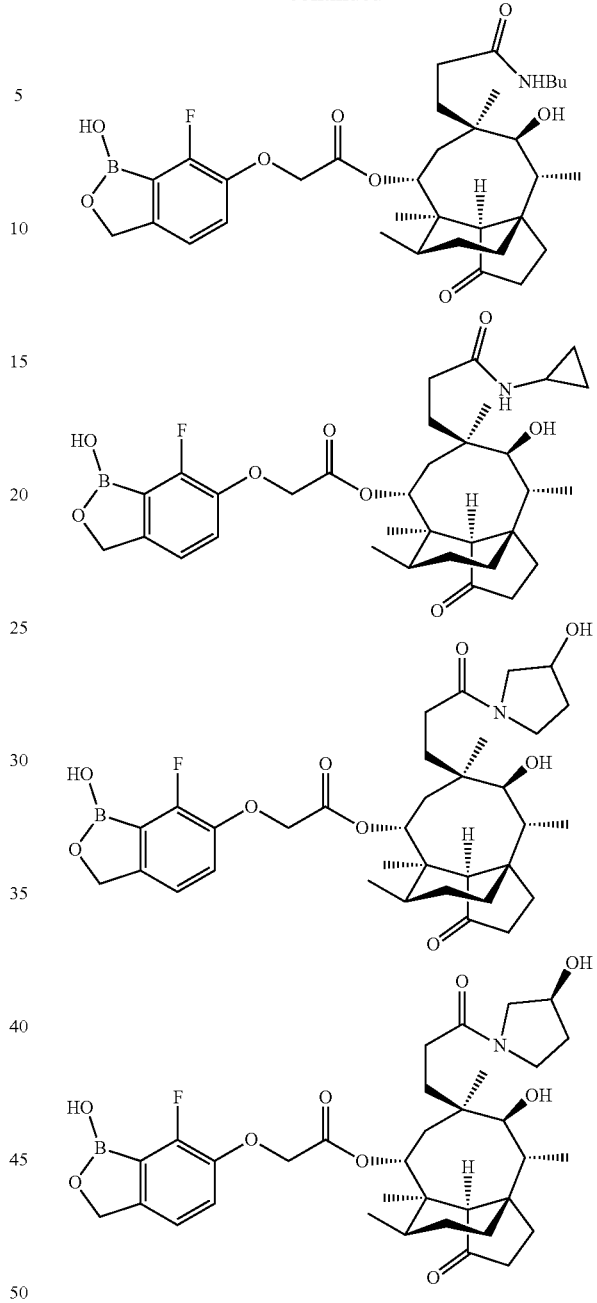

TosCl (55.5 g, 291.3 mmol, 1.1 eq) was added to a solution of (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-hydroxyacetate (104.0 g, 274.8 mmol, 1.0 eq), TEA (36.2 g, 357.2 mmol, 1.3 eq) and Py. (3.0 g, 38.5 mmol, 0.1 eq) in DCM (500 mL) at 0° C. The mixture was stirred at 15° C. for 3 hours. The mixture was filtered, the filtrate was treated with 2N aq. HCl till pH<4. The aqueous layer was treated with DCM (50 mL×3). The combined organic phase was treated with brine 100 mL×1, dried over Na$_2$SO$_4$ and concentrated in vacuo. The crude product was dissolved in DCM 300 mL, petroleum ether (100 mL) was added to the mixture. Yellow solid was precipitated and filtered to give (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-(tosyloxy)

acetate (93.0 g, 174.6 mmol, 63.5% yield) as yellow solid. ¹H NMR (DMSO-d₆, 400 MHz) δ 7.80 (d, J=8.2 Hz, 2H), 7.47 (d, J=8.0 Hz, 2H), 6.05 (dd, J=17.8, 11.2 Hz, 1H), 5.53 (d, J=8.4 Hz, 1H), 4.96-5.09 (m, 2H), 4.59-4.81 (m, 2H), 3.40 (d, J=5.6 Hz, 1H), 2.41 (s, 2H), 2.39 (s, 1H), 1.95-2.24 (m, 6H), 1.41-1.75 (m, 4H), 1.30 (s, 3H), 1.18-1.27 (m, 3H), 1.03 (s, 3H), 0.92-0.99 (m, 1H), 0.81 (d, J=7.0 Hz, 3H), 0.50 (d, J=7.0 Hz, 3H).

(3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-(tosyloxy)acetate (30.0 g, 56.3 mmol, 1.0 eq) in DCM (2.0 L) was bubbled into ozone (2.7 g, 56.3 mmol, 1.0 eq) at −78° C. for 2 hours. The mixture was bubbled with nitrogen for 10 mins and quenched by the addition of TEA (57.0 g, 563.2 mmol, 10.0 eq) at −78° C., the blue solution turned to colorless. The mixture was warmed to room temperature; wet starch potassium iodide paper didn't change. The solvent was concentrated, 2N HCl aq. solution was added to the mixture until pH<4. The aqueous solution was treated with DCM (100 mL×3). The combined organic was washed with brine 200 mL×1, dried over Na₂SO₄ and concentrated in vacuo to give 3aR,4R,5R,7R,8S,9R,9aS,12R)-7-formyl-8-hydroxy-4,7,9,12-tetramethyl-3-oxodecahydro-4,9a-propanocyclopenta[8]annulen-5-yl 2-(tosyloxy)acetate (29.0 g, 54.2 mmol, 96.3% yield) as white foam.

LiHMDS (1 M, 14.96 mL, 1.00 eq) was added to a solution of methyl 2-diethoxyphosphorylacetate (3.46 g, 16.46 mmol, 1.10 eq) in THF (100.00 mL) at −78° C., the mixture was stirred at this temperature for 1 hour, then (3aR,4R,5R,7R,8S,9R,9aS,12R)-7-formyl-8-hydroxy-4,7,9,12-tetramethyl-3-oxodecahydro-4,9a-propanocyclopenta[8]annulen-5-yl 2-(tosyloxy)acetate (8.0 g, 15.0 mmol, 1.0 eq) in 5 mL THF was added to the mixture dropwise at −78° C. Then the mixture warmed to 15° C., and stirred at 15° C. for 3 hours. 100 mL water was added to the mixture, the aqueous phase was treated with EtOAc (50 mL×3). The combined organic phase was washed with brine 50 mL×1, dried over Na₂SO₄ and concentrated in vacuo to give crude product, which was purified by flash column chromatography (petroleum ether/EtOAc=3:1) to give (E)-methyl 3-((3aR,4R,5R,7S,8S,9R,9aS,12R)-8-hydroxy-4,7,9,12-tetramethyl-3-oxo-5-(2-(tosyloxy)acetoxy)decahydro-4,9a-propanocyclopenta[8]annulen-7-yl)acrylate (6.4 g, 10.8 mmol, 72.4% yield) as white foam.

(E)-methyl3-((3aR,4R,5R,7S,8S,9R,9aS,12R)-8-hydroxy-4,7,9,12-tetramethyl-3-oxo-5-(2-(tosyloxy)acetoxy)decahydro-4,9a-propanocyclopenta[8]annulen-7-yl)acrylate (6.4 g, 10.8 mmol, 1.0 eq) and Pd/C (2.0 g) in MeOH (200.0 mL) were stirred at 50° C. for 60 hours under 50 Psi hydrogen atmosphere. The mixture was filtered and the filtrate was concentrated in vacuo to give crude (4aR,6R,7R,7aR,10aS,11R,11aS,14R)-4a,7,11,14-tetramethyl-2,8-dioxododecahydro-2H-7,10a-propanocyclopenta[6,7]cycloocta[1,2-b]pyran-6-yl 2-(tosyloxy)acetate (5.5 g, 9.8 mmol, 90.6% yield) as white foam.

(4aR,6R,7R,7aR,10aS,11R,11aS,14R)-4a,7,11,14-tetramethyl-2,8-dioxododecahydro-2H-7,10a-propanocyclopenta[6,7]cycloocta[1,2-b]pyran-6-yl 2-(tosyloxy)acetate (2.2 g, 3.9 mmol, 1.0 eq), 7-fluoro-1-hydroxy-3H-2,1-benzoxaborol-6-ol (658.9 mg, 3.9 mmol, 1.0 eq) and Na₂CO₃ (1.3 g, 11.8 mmol, 3.0 eq) in DMSO (30.0 mL) were heated to 30-40° C. for 12 hours. Water (20 mL) was added to the mixture, white solid was precipitated. The mixture was filtered to give crude product (~2.5 g crude). ~500 mg crude product was purified by prep-HPLC (column: Luna C18 100×30 mm, 5 μm; liquid phase: [A-TFA/H₂O=0.075% v/v; B-ACN] B %: 35%-50%, 18 mini). The solvent was concentrated to about 15 mL, and dried by lyophilizer to give (4aR,6R,7R,7aR,10aS,11R,11aS,14R)-4a,7,11,14-tetramethyl-2,8-dioxododecahydro-2H-7,10a-propanocyclopenta[6,7]cycloocta[1,2-b]pyran-6-yl2-((7-fluoro-1-hydroxy-1,3-dihydrobenzo[c][1,2]oxaborol-6-yl)oxy)acetate (53 mg) as white solid. Ⅲ NMR (DMSO-d₆, 400 MHz) δ 9.27 (s, 1H), 7.24 (t, J=8.0 Hz, 1H), 7.11 (d, J=8.0 Hz, 1H), 5.54 (d, J=7.6 Hz, 1H), 4.92 (s, 2H), 4.83 (s, 2H), 4.39 (d, J=5.6 Hz, 1H), 2.42 (s, 1H), 2.35-2.00 (m, 4H), 1.86-1.23 (m, 12H), 1.21-0.95 (m, 6H), 0.88 (d, J=6.6 Hz, 3H), 0.65 (d, J=7.1 Hz, 3H). MS (ESI): mass calcd. for $C_{30}H_{38}BFO_8$ 556.4, m/z found 573.3 [M+18-H]⁻. HPLC: 100% in 220 nm; 100% in 254 nm.

(4aR,6R,7R,7aR,10aS,11R,11aS,14R)-4a,7,11,14-tetramethyl-2,8-dioxododecahydro-2H-7,10a-propanocyclopenta[6,7]cycloocta[1,2-b]pyran-6-yl2-((7-fluoro-1-hydroxy-1,3-dihydrobenzo[c][1,2]oxaborol-6-yl)oxy)acetate (300.0 mg, 539.2 umol, 1.0 eq) in amine (15.0 eq) and MeOH (10 mL) were stirred at 50° C. for 12 hours. The mixture was concentrated in vacuo to give crude product, which was purified by prep-HPLC (Instrument: Gilson 281 semi-preparative HPLC system Mobile phase: A: 6.6 mM NH₄HCO₃ in H₂O; B: ACN Column: Durashell C18 150×25 mm, 5 μm, 100 A Flow rate: 20 ml/min; Monitor wavelength: 220&254 nm Gradient: 10-100 B %, time: 0-18.4) to give product (3aR,4R,5R,7R,8S,9R,9aS,12R)-7-(3-amino-3-oxopropyl)-8-hydroxy-4,7,9,12-tetramethyl-3-oxodecahydro-4,9a-propanocyclopenta[8]annulen-5-yl2-((7-fluoro-1-hydroxy-1,3-dihydrobenzo[c][1,2]oxaborol-6-yl)oxy)acetate (66.0 mg, 109.1 umol, 20.2% yield, 94.7% purity) as white solid. ¹H NMR (DMSO-d₆, 400 MHz) δ 9.25 (br. s., 1H), 7.26-7.16 (m, 2H), 7.14-7.08 (m, 1H), 6.68 (br. s., 1H), 5.55 (d, J=7.9 Hz, 1H), 4.92 (s, 1H), 4.85-4.75 (m, 2H), 4.46 (d, J=6.2 Hz, 1H), 3.37 (br. s., 1H), 2.30-1.97 (m, 4H), 1.78-1.11 (m, 12H), 1.09-0.74 (m, 11H), 0.64 (d, J=7.1 Hz, 3H). MS (ESI): mass calcd. for $C_{30}H_{41}BFNO_8$ 573.3, m/z found 572.3 [M−H]⁻. HPLC: 94.7% in 220 nm; 54.2% in 254 nm.

(3aR,4R,5R,7R,8S,9R,9aS,12R)-8-hydroxy-4,7,9,12-tetramethyl-7-(3-(methylamino)-3-oxopropyl)-3-oxodecahydro-4,9a-propanocyclopenta[8]annulen-5-yl2-((7-fluoro-1-hydroxy-1,3-dihydrobenzo[c][1,2]oxaborol-6-yl)oxy)acetate: Prep-HPLC condition: The residue was purified by prep-HPLC (column: Luna C8 100×30 mm, 5 μm; liquid phase: [A-TFA/H₂O=0.075% v/v; B-ACN] B %: 30%-60%, 12 min]). The solvent was concentrated to about 20 mL solution left and dried over lyophilize to give (3aR,4R,5R,7R,8S,9R,9aS,12R)-8-hydroxy-4,7,9,12-tetramethyl-7-(3-(methylamino)-3-oxopropyl)-3-oxodecahydro-4,9a-propanocyclopenta[8]annulen-5-yl2-((7-fluoro-1-hydroxy-1,3-dihydrobenzo[c][1,2]oxaborol-6-yl)oxy)acetate (73.0 mg, 120.1 μmol, 22.3% yield, 96.7% purity) as white solid. ¹H NMR (DMSO-d₆, 400 MHz) δ 7.71 (br. s., 1H), 7.21-7.15 (m, 2H), 7.12-7.00 (m, 1H), 5.55 (br. s., 1H), 4.92 (s, 1H), 4.80-4.40 (m, 2H), 4.40 (s, 1H), 3.35 (d, J=4.4 Hz, 1H), 2.55-3.21 (m, 3H), 2.19-2.05 (m, 7H), 1.68-1.28 (m, 12H), 0.85-0.80 (m, 8H), 0.65-0.63 (m, 3H). MS (ESI): mass calcd. for $C_{31}H_{43}BFNO_8$ 587.3, m/z found 586.3 [M−H]⁻. HPLC: 96.7% in 220 nm; 100% in 254 nm.

(3aR,4R,5R,7R,8S,9R,9aS,12R)-7-(3-(ethylamino)-3-oxopropyl)-8-hydroxy-4,7,9,12-tetramethyl-3-oxodecahydro-4,9a-propanocyclopenta[8]annulen-5-yl2-((7-fluoro-1-hydroxy-1,3-dihydrobenzo[c][1,2]oxaborol-6-yl)oxy)acetate: Prep-HPLC condition: (column: Waters Xbridge 150×25 mm, 5 μm; liquid phase: [A-10 mM NH₄HCO₃ in H₂O; B-ACN] B %: 25%-45%, 12 min]). The mixture was concentrated to about 15 mL, and dried by lyophilizer to give (3aR,4R,5R,7R,8S,9R,9aS,12R)-7-(3-(ethylamino)-3-oxopropyl)-8-hydroxy-4,7,9,12-tetramethyl-3-oxodecahydro-4,9a-propanocyclopenta[8]annulen-5-yl2-((7-fluoro-1-hydroxy-1,3-dihydrobenzo[c][1,2]oxaborol-6-yl)oxy)acetate (89.00 mg, 147.96 μmol, 20.58% yield) as white solid. $^1$H NMR (DMSO-d$_6$, 400 MHz) δ 9.25 (br. s., 1H), 7.75 (t, J=5.2 Hz, 1H), 7.20 (t, J=8.0 Hz, 1H), 7.10 (d, J=8.0 Hz, 1H), 5.55 (d, J=8.4 Hz, 1H), 4.92 (s, 2H), 4.80 (s, 2H), 4.43 (d, J=6.2 Hz, 1H), 3.38-3.33 (m, 1H), 3.08-2.98 (m, 2H), 2.27-1.95 (m, 7H), 1.77-1.57 (m, 4H), 1.53-1.22 (m, 9H), 1.07-0.77 (m, 9H), 0.64 (d, J=6.6 Hz, 3H). MS (ESI): mass calcd. for C$_{32}$H$_{45}$BFNO$_8$ 601.3, m/z found 602.3 [M+H]$^+$. HPLC: 96.1% in 220 nm; 100% in 254 nm.

(3aR,4R,5R,7R,8S,9R,9aS,12R)-7-(3-(butylamino)-3-oxopropyl)-8-hydroxy-4,7,9,12-tetramethyl-3-oxodecahydro-4,9a-propanocyclopenta[8]annulen-5-yl 2-((7-fluoro-1-hydroxy-1,3-dihydrobenzo[c][1,2]oxaborol-6-yl)oxy)acetate: Prep-HPLC condition: (column: Waters Xbridge 150×25 mm, 5 μm; liquid phase: [A-10 mM NH$_4$HCO$_3$ in H$_2$O; B-ACN] B %: 25%-55%, 12 min]). The mixture was concentrated to about 15 mL, and dried by lyophilizer to give to give (3aR,4R,5R,7R,8S,9R,9aS,12R)-7-(3-(butylamino)-3-oxopropyl)-8-hydroxy-4,7,9,12-tetramethyl-3-oxodecahydro-4,9a-propanocyclopenta[8]annulen-5-yl2-((7-fluoro-1-hydroxy-1,3-dihydrobenzo[c][1,2]oxaborol-6-yl)oxy)acetate (83.0 mg, 126.1 μmol, 23.4% yield, 95.7% purity) as white solid. $^1$H NMR (DMSO-d$_6$, 400 MHz) δ 9.24 (br. s., 1H), 7.71 (t, J=5.6 Hz, 1H), 7.23-7.16 (m, 1H), 7.10 (d, J=8.4 Hz, 1H), 5.55 (d, J=8.4 Hz, 1H), 4.92 (s, 1H), 4.80 (s, 1H), 4.43 (d, J=6.2 Hz, 1H), 3.36 (d, J=6.2 Hz, 1H), 3.10-2.91 (m, 2H), 2.25-1.93 (m, 7H), 1.77-1.17 (m, 15H), 0.92-0.77 (m, 9H), 0.64 (d, J=7.1 Hz, 3H). MS (ESI): mass calcd. for C$_{34}$H$_{49}$BFNO$_8$ 629.4, m/z found 628.4 [M−H]$^-$. HPLC: 95.67% in 220 nm; 100% in 254 nm.

(3aR,4R,5R,7R,8S,9R,9aS,12R)-7-(3-(cyclopropylamino)-3-oxopropyl)-8-hydroxy-4,7,9,12-tetramethyl-3-oxodecahydro-4,9a-propanocyclopenta[8]annulen-5-yl2-((7-fluoro-1-hydroxy-1,3-dihydrobenzo[c][1,2]oxaborol-6-yl)oxy)acetate: Prep-HPLC condition: (column: Waters Xbridge 150×25 mm, 5 μm; liquid phase: [A-10 mM NH$_4$HCO$_3$ in H$_2$O; B-ACN] B %: 30%-55%, 12 min]). The mixture was concentrated to about 15 mL, and dried by lyophilizer to give to give (3aR,4R,5R,7R,8S,9R,9aS,12R)-7-(3-(cyclopropylamino)-3-oxopropyl)-8-hydroxy-4,7,9,12-tetramethyl-3-oxodecahydro-4,9a-propanocyclopenta[8]annulen-5-yl2-((7-fluoro-1-hydroxy-1,3-dihydrobenzo[c][1,2]oxaborol-6-yl)oxy)acetate (50.0 mg, 81.5 μmol, 6.5% yield) as white solid. $^1$H NMR (DMSO-d$_6$, 400 MHz) δ 9.26 (br. s., 1H), 7.82 (d, J=4.0 Hz, 1H), 7.19 (t, J=7.9 Hz, 1H), 7.13-7.08 (m, 1H), 5.55 (d, J=8.0 Hz, 1H), 4.92 (s, 2H), 4.84-4.76 (m, 2H), 4.41 (d, J=6.2 Hz, 1H), 4.02-3.82 (m, 1H), 3.37-3.33 (m, 1H), 2.63-2.54 (m, 2H), 2.26-1.92 (m, 8H), 1.75-1.21 (m, 6H), 1.11-0.76 (m, 8H), 0.69-0.61 (m, 3H), 0.60-0.54 (m, 3H), 0.38-0.31 (m, 3H). MS (ESI): mass calcd. for C$_{33}$H$_{45}$BFNO$_8$ 613.3, m/z found 612.3 [M−H]$^-$. HPLC: 93.1% in 220 nm; 100% in 254 nm.

(3aR,4R,5R,7R,8S,9R,9aS,12R)-8-hydroxy-7-(3-(3-hydroxypyrrolidin-1-yl)-3-oxopropyl)-4,7,9,12-tetramethyl-3-oxodecahydro-4,9a-propanocyclopenta[8]annulen-5-yl2-((7-fluoro-1-hydroxy-1,3-dihydrobenzo[c][1,2]oxaborol-6-yl)oxy)acetate: Prep-HPLC condition: ((column: Luna C18 100×30 mm, 5 μm; liquid phase: [A-TFA/H$_2$O=0.075% v/v; B-ACN] B %: 28%-58%, 12 min])). The mixture was dried over lyophilizer to give to give (3aR,4R,5R,7R,8S,9R,9aS,12R)-8-hydroxy-7-(3-(3-hydroxypyrrolidin-1-yl)-3-oxopropyl)-4,7,9,12-tetramethyl-3-oxodecahydro-4,9a-propanocyclopenta[8]annulen-5-yl2-((7-fluoro-1-hydroxy-1,3-dihydrobenzo[c][1,2]oxaborol-6-yl)oxy)acetate (72.0 mg, 106.0 μmol, 16.8% yield, 94.72% purity) as white solid. $^1$H NMR (DMSO-d$_6$, 400 MHz,) δ 9.46-9.09 (m, 2H), 7.21 (t, J=8.2 Hz, 1H), 7.10 (d, J=8.0 Hz, 1H), 5.55 (d, J=7.6 Hz, 1H), 4.92 (br. s., 2H), 4.87-4.73 (m, 2H), 4.41 (br. s., 1H), 4.34-4.20 (m, 2H), 3.52 (d, J=4.4 Hz, 2H), 3.42-3.18 (m, 4H), 2.31-1.99 (m, 7H), 1.96-1.21 (m, 15H), 0.95-0.77 (m, 6H), 0.64 (d, J=6.6 Hz, 3H). MS (ESI): mass calcd. for C$_{34}$H$_{47}$BFNO$_9$ 643.3, m/z found 642.4 [M−H]$^-$. HPLC: 94.7% in 220 nm; 100% in 254 nm.

(3aR,4R,5R,7R,8S,9R,9aS,12R)-8-hydroxy-7-(3-((S)-3-hydroxypyrrolidin-1-yl)-3-oxopropyl)-4,7,9,12-tetramethyl-3-oxodecahydro-4,9a-propanocyclopenta[8]annulen-5-yl2-((7-fluoro-1-hydroxy-1,3-dihydrobenzo[c][1,2]oxaborol-6-yl)oxy)acetate: Prep-HPLC condition: (column: Luna C18 100×30 mm, 5 μm; liquid phase: [A-TFA/H$_2$O=0.075% v/v; B-ACN] B %: 28%-58%,12 min]). The mixture was dried over lyophilizer to give to give (3aR,4R,5R,7R,8S,9R,9aS,12R)-8-hydroxy-7-(3-((S)-3-hydroxypyrrolidin-1-yl)-3-oxopropyl)-4,7,9,12-tetramethyl-3-oxodecahydro-4,9a-propanocyclopenta[8]annulen-5-yl2-((7-fluoro-1-hydroxy-1,3-dihydrobenzo[c][1,2]oxaborol-6-yl)oxy)acetate: (67.0 mg, 101.6 μmol, 16.2% yield, 97.61% purity) as white solid. $^1$H NMR (DMSO-d$_6$, 400 MHz) δ 7.21 (t, J=8.2 Hz, 1H), 7.10 (d, J=8.0 Hz, 1H), 5.55 (d, J=8.0 Hz, 1H), 4.92 (br. s., 2H), 4.86-4.76 (m, 3H), 4.45-4.17 (m, 2H), 3.59-3.46 (m, 2H), 3.42-3.18 (m, 4H), 2.32-1.58 (m, 14H), 1.56-1.21 (m, 8H), 1.08-0.76 (m, 6H), 0.64 (d, J=6.6 Hz, 3H). MS (ESI): mass calcd. for C$_{34}$H$_{47}$BFNO$_9$ 643.3, m/z found 642.3 [M−H]$^-$. HPLC: 97.6% in 220 nm; 100% in 254 nm.

9. (3aS,5R,6R,6aR,9aS,10R,10aS,13R)-2-hydroxy-3a,6,10,13-tetramethyl-7-oxododecahydro-6,9a-propanocyclopenta[6,7]cyclooeta[1,2-b]furan-5-yl 2-((7-fluoro-1-hydroxy-1,3-dihydrobenzo[c][1,2]oxaborol-6-yl)oxy)acetate Ozone (51.4 mg, 1.1 mmol, 1.0 eq) was bubbled into a solution of (3R,3aS,4R,5R,7R,9R,9aR,12R)-7-allyl-3-methoxy-4,7,9,12-tetramethyl-8-oxodecahydro-4,9a-propanocyclopenta[8]annulen-5-yl 2-(tosyloxy)acetate (600.0 mg, 1.1 mmol, 1.0 eq) in DCM (50 mL) at −78° C. The mixture was stirred at −78° C. till TLC showed (3R,3aS,4R,5R,7R,9R,9aR,12R)-7-allyl-3-methoxy-4,7,9,12-tetramethyl-8-oxodecahydro-4,9a-propanocyclopenta[8]annulen-5-yl 2-(tosyloxy)acetate consumed, and one new spot was detected. The reaction was quenched by addition of TEA (1.1 g, 10.7 mmol, 1.5 mL, 10.0 eq) till wet potassium iodide starch didn't change. The solvent was warmed to room temperature, and concentrated. The mixture was treated with DCM (50 mL) and 2N HCl till pH<4. The aqueous phase was treated with DCM (20 mL×3). The combined organic phase was dried over Na$_2$SO$_4$ and concentrated in vacuo to give (3R,3aS,4R,5R,7S,9R,9aR,12R)-3-methoxy-4,7,9,12-tetramethyl-8-oxo-7-(2-oxoethyl)decahydro-4,9a-propanocyclopenta[8]annulen-5-yl 2-(tosyloxy)acetate (600.0 mg, crude) as yellow oil.

7-fluoro-1-hydroxy-3H-2,1-benzoxaborol-6-ol (179.7 mg, 1.1 mmol, 1.0 eq), (3R,3aS,4R,5R,7S,9R,9aR,12R)-3-methoxy-4,7,9,12-tetramethyl-8-oxo-7-(2-oxoethyl)decahydro-4,9a-propanocyclopenta[8]annulen-5-yl 2-(tosyloxy)acetate (600.0 mg, 1.1 mmol, 1.0 eq) and $Na_2CO_3$ (340.2 mg, 3.2 mmol, 3.0 eq) in DMSO (20 mL) were stirred at 30-40° C. for 12 hours. HPLC and LCMS showed major as desired. The reaction was quenched by addition of 50 mL water, and adjusted with 2N HCl till pH<4. White solid was precipitated and filtered to give crude product (3R,3aS,4R,5R,7S,9R,9aR,12R)-3-methoxy-4,7,9,12-tetramethyl-8-oxo-7-(2-oxoethyl)decahydro-4,9a-propanocyclopenta[8]annulen-5-yl 2-((7-fluoro-1-hydroxy-1,3-dihydrobenzo[c][1,2]oxaborol-6-yl)oxy)acetate (600.0 mg, crude) as brown solid. MS (ESI): mass calcd. for $C_{30}H_{40}BFO_8$ 558.28, m/z found 557 (M−H)⁻.

$ZnCl_2$ saturated in conc HCl (1.1 mmol, 10.0 mL) was added to a solution of (3R,3aS,4R,5R,7S,9R,9aR,12R)-3-methoxy-4,7,9,12-tetramethyl-8-oxo-7-(2-oxoethyl)decahydro-4,9a-propanocyclopenta[8]annulen-5-yl 2-((7-fluoro-1-hydroxy-1,3-dihydrobenzo[c][1,2] oxaborol-6-yl)oxy)acetate (600.0 mg, 1.1 mmol, 1.0 eq) in THF (20.0 mL). The mixture was stirred at 20° C. for 4 hours, HPLC showed (3R,3aS,4R,5R,7S,9R,9aR,12R)-3-methoxy-4,7,9,12-tetramethyl-8-oxo-7-(2-oxoethyl)decahydro-4,9a-propanocyclopenta[8]annulen-5-yl 2-((7-fluoro-1-hydroxy-1,3-dihydrobenzo[c][1,2]oxaborol-6-yl)oxy)acetate consumed, two new peaks were detected. The mixture was treated with DCM 50 mL and the aqueous phase was treated with DCM (20 mL×2). The combined organic phase was dried over $Na_2SO_4$ and concentrated in vacuo. The crude product was purified by prep-HPLC (column: Luna C18 100×30 mm, 5 μm; liquid phase: [A-TFA/$H_2O$=0.075% v/v; B-ACN, B %: 53%-83%, 12 min]). The mixture was concentrated to about 20 mL solution left and lyophilized to give (3aS,5R,6R,6aR,9aS,10R,10aS,13R)-2-hydroxy-3a,6,10,13-tetramethyl-7-oxododecahydro-6,9a-propanocyclopenta[6,7]cycloocta[1,2-b]furan-5-yl 2-((7-fluoro-1-hydroxy-1,3-dihydrobenzo[c][1,2]oxaborol-6-yl)oxy)acetate (24.0 mg, 42.0 μmol, 3.9% yield) as white solid. ¹H NMR (DMSO-$d_6$, 400 MHz) δ 9.40-9.14 (m, 1H), 7.26-7.19 (m, 1H), 7.12 (d, J=8.0 Hz, 1H), 5.59 (d, J=9.2 Hz, 1H), 5.29 (t, J=6.0 Hz, 1H), 4.92 (s, 2H), 4.88-4.75 (m, 3H), 3.50 (d, J=10.0 Hz, 1H), 2.26-1.94 (m, 6H), 1.76-1.61 (m, 2H), 1.59-1.21 (m, 11H), 1.07-0.92 (m, 5H), 0.68 (d, J=6.4 Hz, 3H). MS (ESI): mass calcd. for $C_{29}H_{38}BFO_8$ 544.26, m/z found 543[M−H]⁻. HPLC: 95.4% (220 nm), 91.2% (254 nm).

10. (3aR,4R,5R,7R,8S,9R,9aS,12R)-7-benzyl-8-hydroxy-4,7,9,12-tetramethyl-3-oxodecahydro-4,9a-propanocyclopenta[8]annulen-5-yl 2-((7-fluoro-1-hydroxy-1,3-dihydrobenzo[c][1,2]oxaborol-6-yl)oxy)acetate

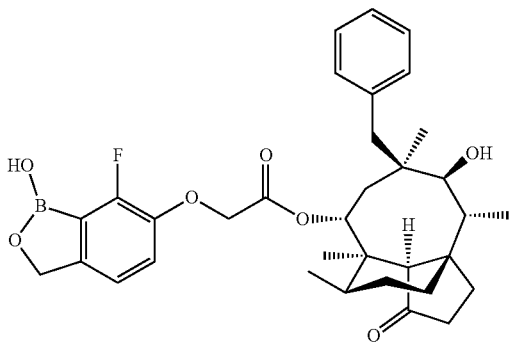

To a solution of (3R,3aS,4R,5R,7S,9R,9aR,12R)-3-methoxy-5-(methoxymethoxy)-4,7,9,12-tetramethyloctahydro-4,9a-propanocyclopenta[8]annulen-8(9H)-one (2.0 g, 5.7 mmol, 1.0 eq) in THF (20 mL) was added NaH (907.2 mg, 22.7 mmol, 60% purity, 4.0 eq) at 0° C. The mixture was stirred at 50° C. for 1 hr. Then bromoethylbenzene (5.8 g, 34.0 mmol, 4.0 mL, 6.0 eq) was added to the mixture and stirred at 50° C. for 12 hrs. The mixture was cooled to 20° C. $H_2O$ (60 mL) was added to the mixture. The mixture was extracted with ethyl acetate (40 mL×3). The combined organic phase was washed with brine (20 mL), dried with anhydrous $Na_2SO_4$, filtered and concentrated in vacuum to give a crude product, which was purified by silica gel chromatography (Petroleum ether) to afford (3R,3aS,4R,5R,7R,9R,9aR,12R)-7-benzyl-3-methoxy-5-(methoxymethoxy)-4,7,9,12-tetramethyloctahydro-4,9a-propanocyclopenta[8]annulen-8(9H)-one (2.1 g, 4.7 mmol, 83.7% yield) as white solid.

To a solution of (3R,3aS,4R,5R,7R,9R,9aR,12R)-7-benzyl-3-methoxy-5-(methoxymethoxy)-4,7,9,12-tetramethyloctahydro-4,9a-propanocyclopenta[8]annulen-8(9H)-one (2.0 g, 4.5 mmol, 1.0 eq) in MeOH (10.0 mL) was added HCl (2 M, 10.0 mL, 4.4 eq) in one portion at 25° C. The mixture was stirred at 25° C. for 24 hrs. New peak was detected, but the starting material was remained by HPLC. $H_2O$ (50 mL) was added to the mixture, which was extracted with EtOAc (50 mL×3). The combined organic layers were washed with brine (30 mL) and dried over $Na_2SO_4$. After filtration via filter paper, the organic layer was concentrated under reduced pressure to provide a crude product, which was purified by silica gel chromatography (petroleum ether/ethyl acetate=50/1) to afford (3R,3aS,4R,5R,7R,9R,9aR,12R)-7-benzyl-5-hydroxy-3-methoxy-4,7,9,12-tetramethyloctahydro-4,9a-propanocyclopenta[8]annulen-8(9H)-one (800.0 mg, 2.0 mmol, 44.4% yield) as light solid. ¹H NMR (CDCl₃, 400 MHz) δ 7.31 (d, J=7.2 Hz, 2H), 7.27-7.23 (m, 2H), 4.82 (dd, J=6.4, 9.2 Hz, 1H), 3.53-3.43 (m, 1H), 3.30-3.14 (m, 5H), 2.52-2.45 (m, 1H), 2.27-2.18 (m, 1H), 2.15-2.04 (m, 2H), 2.03-1.91 (m, 1H), 1.56 (m, 4H), 1.44 (d, J=6.4 Hz, 2H), 1.30-1.09 (m, 10H), 1.05 (d, J=6.4 Hz, 3H), 0.93 (s, 3H).

To a solution of (3R,3aS,4R,5R,7R,9R,9aR,12R)-7-benzyl-5-hydroxy-3-methoxy-4,7,9,12-tetramethyloctahydro-4,9a-propanocyclopenta[8]annulen-8(9H)-one (804.6 mg, 2.0 mmol, 1.0 eq) and perfluorophenyl 2-(tosyloxy)acetate (2.4 g, 6.1 mmol, 3.0 eq) in THF (25.0 mL) was added DMAP (493.3 mg, 4.0 mmol, 2.0 eq) at 25° C. The mixture was stirred at 25° C. for 18 hrs. $H_2O$ (60 mL) was added the mixture. The aqueous layer was extracted with EtOAc (30 mL×3). The combined organic layers were washed with brine (20 mL) and dried over $Na_2SO_4$. After filtration via filter paper, the organic layer was concentrated under reduced pressure to provide a crude product, which was purified by silica gel chromatography (petroleum ether/ethyl acetate=5/1) to afford (3R,3aS,4R,5R,7R,9R,9aR,12R)-7-benzyl-3-methoxy-4,7,9,12-tetramethyl-8-oxodecahydro-4,9a-propanocyclopenta[8]annulen-5-yl 2-(tosyloxy)acetate (600.0 mg, 982.3 μmol, 48.6% yield) as a light yellow solid. ¹H NMR (CDCl₃, 400 MHz) δ 7.87 (d, J=8.0 Hz, 2H), 7.38-7.29 (m, 2H), 7.26-7.18 (m, 3H), 7.07 (d, J=6.4 Hz, 2H), 6.12 (d, J=10.0 Hz, 1H), 4.82 (dd, J=6.4, 9.5 Hz, 1H), 4.61 (s, 2H), 3.76 (t, J=6.4 Hz, 3H), 3.54-3.36 (m, 2H), 3.11-2.98 (m, 2H), 2.39-2.16 (m, 3H), 2.05 (br. s., 2H), 1.87 (m, 3H), 1.62-1.42 (m, 9H), 1.05 (d, J=6.4 Hz, 2H), 1.01 (d, J=6.4 Hz, 3H), 0.78 (d, J=7.2 Hz, 3H).

To a solution of (3R,3aS,4R,5R,7R,9R,9aR,12R)-7-benzyl-3-methoxy-4,7,9,12-tetramethyl-8-oxodecahydro-4,9a- propanocyclopenta[8]annulen-5-yl 2-(tosyloxy)acetate (600.0 mg, 982.3 µmol, 1.1 eq) in DMSO (10.0 mL) was added Na$_2$CO$_3$ (94.7 mg, 893.0 µmol, 1.0 eq), KI (148.2 mg, 893.0 µmol, 1.0 eq) and 7-fluorobenzo[c][1,2]oxaborole-1,6(3H)-diol at 25° C. under N$_2$. The reaction mixture was stirred at 25° C. for 5 hrs. H$_2$O (80 mL) was added the mixture, which was acidified with aqueous HCl (2 M) till pH=5-6 to precipitate a white solid. The reaction mixture was filtered and the filter cake was washed with H$_2$O (20 mL×4) to give a white solid, which was dissolved in DCM (20 mL) and dried over Na$_2$SO$_4$. After filtration via filter paper, the organic layer was concentrated under reduced pressure to provide (3R,3aS,4R,5R,7R,9R,9aR,12R)-7-benzyl-3-methoxy-4,7,9,12-tetramethyl-8-oxodecahydro-4,9a-propanocyclopenta[8]annulen-5-yl 2-((7-fluoro-1-hydroxyl-1,3-dihydrobenzo[c][1,2]oxaborol-6-yl)oxy)acetate (500.0 mg, crude) as a light yellow solid.

To a mixture of (3R,3aS,4R,5R,7R,9R,9aR,12R)-7-benzyl-3-methoxy-4,7,9,12-tetramethyl-8-oxodecahydro-4,9a-propanocyclopenta[8]annulen-5-yl 2-((7-fluoro-1-hydroxy-1,3-dihydrobenzo[c][1,2]oxaborol-6-yl)oxy)acetate (500.0 mg, 824.4 µmol, 1.0 eq) in THF (5.0 mL) was added ZnCl$_2$ (10.0 mL saturated in con.HCl) in one portion at 25° C. The mixture was stirred at 25° C. for 15 hrs. HPLC and LCMS showed the reaction was complete. The mixture was added H$_2$O (20 mL). The aqueous phase was extracted with DCM (20 mL×3). The combined organic phase was washed with brine (10 mL×2), dried with anhydrous Na$_2$SO$_4$, filtered and concentrated in vacuum to give crude product, which was purified by prep-HPLC (column: Luna C18 100×30 mm, 5 µm; liquid phase: [A-TFA/H$_2$O=0.075% v/v; B-ACN] B %: 45%-75%, 12 mini). After prep-HPLC purification, the eluent was concentrated to remove organic solvent. The residual aqueous solution was lyophilized to give product (3aR,4R,5R,7R,8S,9R,9aS,12R)-7-benzyl-8-hydroxy-4,7,9,12-tetramethyl-3-oxodecahydro-4,9a-propanocyclopenta[8]annulen-5-yl 2-((7-fluoro-1-hydroxy-1,3-dihydrobenzo[c][1,2] oxaborol-6-yl)oxy)acetate (130.0 mg, 214.5 µmol, 26.0% yield, 97.8% purity) as white solid. $^1$H NMR (DMSO-d$_6$, 400 MHz) δ 7.37-7.29 (m, 1H), 7.21-7.08 (m, 4H), 7.05 (d, J=8.0 Hz, 1H), 6.95 (d, J=7.2 Hz, 2H), 5.92 (d, J=8.4 Hz, 1H), 4.99-4.83 (m, 4H), 2.80-2.73 (m, 2H), 2.39 (br. s., 1H), 2.26-2.00 (m, 4H), 1.85-1.58 (m, 3H), 1.55-1.44 (m, 2H), 1.37-1.11 (m, 6H), 1.08-0.97 (m, 1H), 0.94-0.81 (m, 4H), 0.67 (d, J=5.6 Hz, 3H), 0.55 (s, 3H). MS (ESI): mass calcd. for C$_{34}$H$_{42}$BFO$_7$ 592.5, m/z found 591.3 [M−H]$^-$. HPLC: 97.75% (220 nm), 100% (254 nm).

11. (3aR,4R,5R,7R,8S,9R,9aS,12R)-7-(chloromethyl)-8-hydroxy-4,7,9,12-tetramethyl-3-oxodecahydro-4,9a-propanocyclopenta[8]annulen-5-yl 2-((7-fluoro-1-hydroxy-1,3-dihydrobenzo[c][1,2]oxaborol-6-yl)oxy)acetate

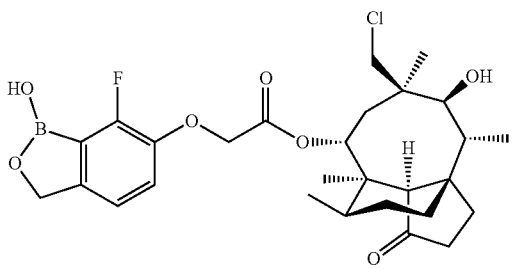

KHMDS (1M, 51.1 mL, 6.0 eq) was added to a solution of (3R,3aS,4R,5R,7S,9R,9aR,12R)-3-methoxy-5-(methoxymethoxy)-4,7,9,12-tetramethyloctahydro-4,9a-propanocyclopenta[8]annulen-8(9H)-one (3.0 g, 8.5 mmol, 1.0 eq) in THF (20 mL) at −78° C., half an hour later chloro(iodo)methane (7.5 g, 42.6 mmol, 3.1 mL, 5.0 eq) was added to the mixture and stirred at 25° C. for 12 hrs. The reaction was quenched by addition of 100 mL water, and treated with EtOAc (30 mL×3). The combined organic phase was dried over Na$_2$SO$_4$ and concentrated in vacuo. The crude product was purified by flash column chromatography (Petroleum ether:EtOAc)=100:1 to give (3R,3aS,4R,5R,7R,9R,9aR,12R)-7-(chloromethyl)-3-methoxy-5-(methoxymethoxy)-4,7,9,12-tetramethyloctahydro-4,9a-propanocyclopenta[8]annulen-8(9H)-one (2.4 g, 6.0 mmol, 70.3% yield) as yellow solid. $^1$H NMR (CDCl$_3$, 400 MHz,) δ 4.75 (d, J=6.4 Hz, 1H), 4.69 (d, J=6.4 Hz, 1H), 4.34 (d, J=9.6 Hz, 1H), 4.16 (d, J=11.6 Hz, 1H), 3.60 (d, J=11.6 Hz, 1H), 3.47 (m, 1H), 3.41-3.38 (m, 3H), 3.22 (s, 3H), 3.04 (q, J=6.5 Hz, 1H), 2.48 (dd, J=9.6, 16.0 Hz, 1H), 2.29-2.19 (m, 1H), 2.08-1.93 (m, 3H), 1.89 (d, J=16.0 Hz, 1H), 1.69 (d, J=11.2 Hz, 1H), 1.52 (d, J=4.0 Hz, 2H), 1.40-1.09 (m, 9H), 1.06 (d, J=6.4 Hz, 3H), 0.96 (d, J=7.2 Hz, 3H).

(3R,3aS,4R,5R,7R,9R,9aR,12R)-7-(chloromethyl)-3-methoxy-5-(methoxymethoxy)-4,7,9,12-tetramethyloctahydro-4,9a-propanocyclopenta[8]annulen-8(9H)-one (1.0 g, 2.5 mmol, 1.0 eq) in HCl (2M, 218.4 uL, 2.5 eq) and MeOH (100 mL) were stirred at 15° C. for 12 hour. The mixture was treated with DCM (100 mL) and water 100 mL. The aqueous phase was treated with DCM (50 mL×2). The combined organic phase was dried over Na$_2$SO$_4$ and concentrated in vacuo. The crude product was purified by flash column chromatography (petroleum ether/EtOAc=20/1-5/1) to give (3R,3aS,4R,5R,7R,9R,9aR,12R)-7-(chloromethyl)-5-hydroxy-3-methoxy-4,7,9,12-tetramethyloctahydro-4,9a-propanocyclopenta[8]annulen-8(9H)-one (800.0 mg, 2.2 mmol, 90.0% yield) as white solid. $^1$H NMR (CDCl$_3$, 400 MHz,) δ 4.58 (dd, J=9.6, 6.0 Hz, 1H), 4.06 (d, J=11.6 Hz, 1H), 3.63 (d, J=11.6 Hz, 1H), 3.38-3.50 (m, 1H), 3.22 (s, 3H), 3.01 (q, J=6.8 Hz, 1H), 2.50 (dd, J=15.2, 9.6 Hz, 1H), 2.20-2.29 (m, 1H), 1.93-2.09 (m, 2H), 1.65-1.78 (m, 3H), 1.53 (d, J=5.2 Hz, 2H), 1.26-1.20 (m, 4H), 1.21 (s, 3H), 1.14 (s, 3H), 1.08 (d, J=7.2 Hz, 3H), 1.04 (d, J=6.4 Hz, 3H).

(3R,3 aS,4R,5R,7R,9R,9aR,12R)-7-(chloromethyl)-5-hydroxy-3-methoxy-4,7,9,12-tetramethyloctahydro-4,9a-propanocyclopenta[8]annulen-8(9H)-one (800.0 mg, 2.2 mmol, 1.0 eq), perfluorophenyl 2-(tosyloxy)acetate (1.2 g, 2.9 mmol, 1.3 eq) and DMAP (273.8 mg, 2.2 mmol, 1.0 eq) in THF (15 mL) were stirred at 20° C. for 12 hr. The solvent was concentrated in vacuo directly. The crude product was purified by flash column chromatography (Petroleum ether/EtOAc=1/0-5/1) to give (3R,3aS,4R,5R,7R,9R,9aR,12R)-7-(chloromethyl)-3-methoxy-4,7,9,12-tetramethyl-8-oxodecahydro-4,9a-propanocyclopenta[8]annulen-5-yl 2-(tosyloxy) acetate (850.0 mg, 1.5 mmol, 66.7% yield) as yellow iol. $^1$H NMR (CDCl$_3$, 400 MHz) δ 7.85 (d, J=8.4 Hz, 2H), 7.38 (d, J=8.4 Hz, 2H), 5.74 (d, J=10.0 Hz, 1H), 4.62-4.56 (m, 1H), 4.54 (s, 2H), 4.37 (d, J=12.0 Hz, 1H), 3.39 (d, J=11.6 Hz, 2H), 3.23-3.18 (m, 3H), 3.05 (d, J=6.0 Hz, 1H), 2.54 (dd, J=10.0, 16.0 Hz, 1H), 2.48 (s, 3H), 2.30-2.20 (m, 1H), 2.09-1.93 (m, 3H), 1.72 (d, J=11.2 Hz, 1H), 1.56-1.44 (m, 3H), 1.38-1.19 (m, 8H), 1.17 (s, 3H), 1.07 (d, J=6.4 Hz, 3H), 0.74 (d, J=7.2 Hz, 3H).

Na$_2$CO$_3$ (419.0 mg, 4.0 mmol, 3.0 eq) was added to a solution of (3R,3aS,4R,5R,7R,9R,9aR,12R)-7-(chloromethyl)-3-methoxy-4,7,9,12-tetramethyl-8-oxodecahydro-4,9a-propanocyclopenta[8]annulen-5-yl 2-(tosyloxy)acetate (750.0 mg, 1.3 mmol, 1.0 eq) and 7-fluoro-1-hydroxy-3H-2,1-benzoxaborol-6-ol (221.3 mg, 1.3 mmol, 1.0 eq) in DMSO (20 mL). The mixture was stirred at 30° C. for 12 hrs. The reaction was quenched by addition of 50 mL water, and adjusted by addition of 2N HCl until pH<4, white solid was precipitated and filtered to give crude product to give (3R,3aS,4R,5R,7R,9R,9aR,12R)-7-(chloromethyl)-3-methoxy-4,7,9,12-tetramethyl-8-oxodecahydro-4,9a-propanocyclopenta[8]annulen-5-yl 2-((7-fluoro-1-hydroxy-1,3-dihydrobenzo[c][1,2] oxaborol-6-yl)oxy)acetate (710.0 mg, crude) as yellow solid.

ZnCl$_2$ saturated in Con HCl (1.2 mmol, 15.0 mL, 1.0 eq) was added to a solution of (3R,3aS,4R,5R,7R,9R,9aR,12R)-7-(chloromethyl)-3-methoxy-4,7,9,12-tetramethyl-8-oxo-decahydro-4,9a-propanocyclopenta[8]annulen-5-yl 2-((7-fluoro-1-hydroxy-1,3-dihydrobenzo[c][1,2] oxaborol-6-yl)oxy)acetate (700.0 mg, 1.2 mmol, 1.0 eq) in THF (20 mL) at 20° C. for 12 hrs. The reaction was treated with water 50 mL and 50 mL DCM. The aqueous solution was treated with DCM (30 mL×3). The combined organic phase was dried over Na$_2$SO$_4$ and concentrated in vacuo. The crude product was purified by prep-HPLC (column: Luna C18 100×30 mm, 5 μm; liquid phase: [A-TFA/H$_2$O=0.075% v/v; B-ACN, B %: 30%-60%, 12 min]). The solvent was concentrated to 30 mL solution left and lyophilized to give (3aR,4R,5R,7R,8S,9R,9aS,12R)-7-(chloromethyl)-8-hydroxy-4,7,9,12-tetramethyl-3-oxodecahydro-4,9a-propanocyclopenta[8]annulen-5-yl 2-((7-fluoro-1-hydroxy-1,3-dihydrobenzo[c][1,2] oxaborol-6-yl)oxy)acetate (226.00 mg, 410.28 μmol, 33.09% yield, 100% purity) as white solid. $^1$H NMR (DMSO-d$_6$, 400 MHz) δ 9.13 (s, 1H), 7.21 (t, J=8.0 Hz, 1H), 7.07 (d, J=8.0 Hz, 1H), 5.65 (d, J=8.0 Hz, 1H), 4.92 (s, 2H), 4.87-4.73 (m, 2H), 3.89 (d, J=11.2 Hz, 1H), 3.72 (d, J=10.4 Hz, 1H), 3.55 (d, J=6.4 Hz, 1H), 2.41 (s., 1H), 2.24-1.99 (m, 3H), 1.88 (dd, J=8.0, 16.8 Hz, 1H), 1.73-1.22 (m, 12H), 1.02 (s, 3H), 0.82 (d, J=6.4 Hz, 3H), 0.64 (d, J=7.2 Hz, 3H). MS (ESI): mass calcd. for C$_{28}$H$_{37}$BClFO$_7$ 550.23, m/z found 549.4 (M−H)$^-$. HPLC: 100% (220 nm), 100% (254 nm).

12. methyl (E)-3-((3aR,4R,5R,7S,8S,9R,9aS,12R)-5-(2-((7-fluoro-1-hydroxy-1,3-dihydrobenzo[c][1,2]oxaborol-6-yl)oxy)acetoxy)-8-hydroxy-4,7,9,12-tetramethyl-3-oxodecahydro-4,9a-propanocyclopenta[8]annulen-7-yl)acrylate 13. (E)-3-((3aR,4R,5R,7S,8S,9aS,12R)-5-(2-((7-fluoro-1-hydroxy-1,3-dihydrobenzo[c][1,2]oxaborol-6-yl)oxy)acetoxy)-8-hydroxy-4,7,12-trimethyl-3-oxodecahydro-4,9a-propanocyclopenta[8]annulen-7-yl)acrylic acid

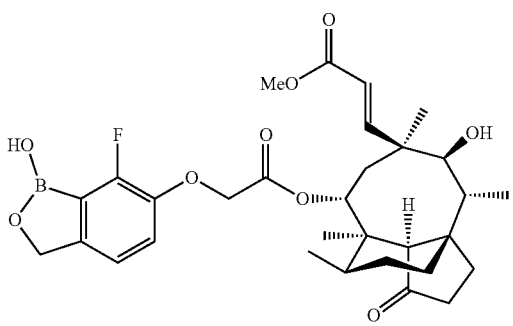

-continued

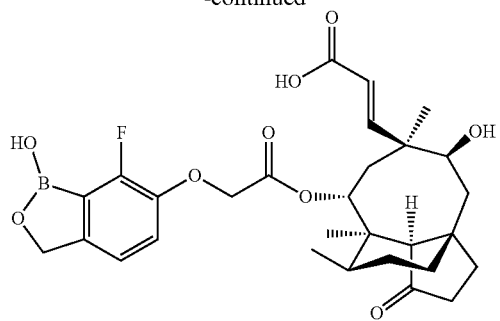

(E)-methyl3-((3aR,4R,5R,7S,8S,9R,9aS,12R)-8-hydroxy-4,7,9,12-tetramethyl-3-oxo-5-(2-(tosyloxy)acetoxy)decahydro-4,9a-propanocyclopenta[8]annulen-7-yl)acrylate (400.0 mg, 677.1 μmol, 1.0 eq), 7-fluoro-1-hydroxy-3H-2,1-benzoxaborol-6-ol (113.7 mg, 677.1 μmol, 1.0 eq) and Na$_2$CO$_3$ (215.3 mg, 2.0 mmol, 3.0 eq) in DMSO (10.0 mL) were heated to 30-40° C. for 12 hours. Water (30 mL) was added to the mixture, white solid was precipitated. The mixture was filtered to give crude product, which was purified by prep-HPLC (column: Luna C18 100×30 mm, 5 μm; liquid phase: [A-TFA/H$_2$O=0.075% v/v; B-ACN] B %: 42%-57%, 12 min]). The mixture was concentrated to about 20 mL solution left and dried over lyophilizer to give (E)-methyl3-((3aR,4R,5R,7S,8S,9R,9aS,12R)-5-(2-((7-fluoro-1-hydroxy-1,3-dihydrobenzo[c][1,2]oxaborol-6-yl)oxy)acetoxy)-8-hydroxy-4,7,9,12-tetramethyl-3-oxodecahydro-4,9a-propanocyclopenta[8]annulen-7-yl)acrylate (126.0 mg, 214.8 μmol, 31.7% yield, 100% purity) as white solid and 53 mg delivered. $^1$H NMR (DMSO-d$_6$, 400 MHz) δ 7.21 (t, J=8.2 Hz, 1H), 7.12-7.04 (m, 2H), 5.70 (d, J=16.3 Hz, 1H), 5.56 (d, J=7.9 Hz, 1H), 4.91 (d, J=1.8 Hz, 2H), 4.86-4.75 (m, 2H), 3.65 (s, 3H), 2.25-1.96 (m, 4H), 1.76-1.19 (m, 10H), 1.16-0.92 (m, 5H), 0.89-0.74 (m, 6H), 0.64 (d, J=6.6 Hz, 3H). MS (ESI): mass calcd. for C$_{31}$H$_{40}$BFO$_9$ 586.3, m/z found 585.3 [M−H]$^-$. HPLC: 99.9% in 220 nm; 100% in 254 nm.

(E)-methyl3-((3aR,4R,5R,7S,8S,9R,9aS,12R)-5-(2-((7-fluoro-1-hydroxy-1,3-dihydrobenzo[c][1,2]oxaborol-6-yl)oxy)acetoxy)-8-hydroxy-4,7,9,12-tetramethyl-3-oxodecahydro-4,9a-propanocyclopenta[8]annulen-7-yl)acrylate (73.0 mg, 124.5 μmol, 1.0 eq) and LiOH.H$_2$O (10.4 mg, 249.0 μmol, 2.0 eq) in MeOH (5.0 mL) and H$_2$O (5.0 mL) were stirred at 15° C. for 12 hours. 10 mL water was added to the mixture, the aqueous phase was adjusted to pH<5, white solid was precipitated. The mixture was filtered to give crude product, which was purified by prep-HPLC (column: Luna C18 100×30 mm, 5 μm; liquid phase: [A-TFA/H$_2$O=0.075% v/v; B-ACN] B %: 32%-47%,15 min]), the mixture was concentrated to about 15 mL solution left. The product was dried over lyophilizer to give (E)-3-((3aR,4R,5R,7S,8S,9R,9aS,12R)-5-(2-((7-fluoro-1-hydroxy-1,3-dihydrobenzo[c][1,2]oxaborol-6-yl)oxy)acetoxy)-8-hydroxy-4,7,9,12-tetramethyl-3-oxodecahydro-4,9a-propanocyclopenta[8]annulen-7-yl)acrylic acid (21.0 mg, 36.2 μmol, 29.1% yield, 98.7% purity) as white solid. NMR (DMSO-d$_6$, 400 MHz) δ 9.26 (s, 1H), 7.24-7.18 (m, 1H), 7.09 (d, J=8.4 Hz, 1H), 6.99 (d, J=16.3 Hz, 1H), 5.61 (d, J=16 Hz, 1H), 5.56 (d, J=8.4 Hz, 1H), 4.91 (s, 2H), 4.88-4.76 (m, 2H), 4.58 (d, J=6.2 Hz, 1H), 3.62 (t, J=6.4 Hz, 1H), 2.26-2.00 (m, 4H), 1.76-1.22 (m, 11H), 1.08 (s, 4H), 0.87-0.78 (m, 4H), 0.64 (d, J=7.1 Hz, 3H). MS (ESI): mass 14. (3aR,4R,5R,7S,8S,9R,9aS,12R)-7-((E)-3-amino-3-oxoprop-1-en-1-yl)-8-hydroxy-4,7,9,12-tetramethyl-3-oxodecahydro-4,9a-propanocyclopenta[8]annulen-5-yl 2-((7-fluoro-1-hydroxy-1,3-dihydrobenzo[c][1,2]oxaborol-6-yl)oxy)acetate 15. (3aR,4R,5R,7S,8S,9R,9aS,12R)-8-hydroxy-4,7,9,12-tetramethyl-7-((E)-3-(methylamino)-3-oxoprop-1-en-1-yl)-3-oxodecahydro-4,9a-propanocyclopenta[8]annulen-5-yl 2-((7-fluoro-1-hydroxy-1,3-dihydrobenzo[c][1,2]oxaborol-6-yl)oxy)acetate

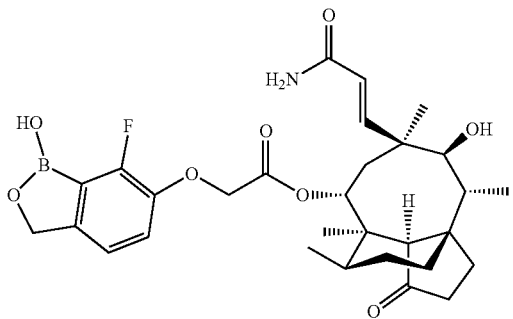

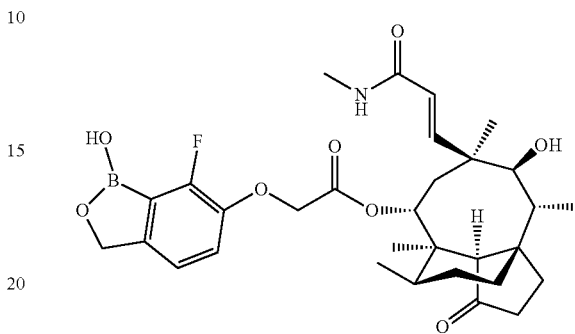

To a mixture of (E)-3-((3aR,4R,5R,7S,8S,9R,9aS,12R)-5-(2-((7-fluoro-1-hydroxy-1,3-dihydrobenzo[c][1,2]oxaborol-6-yl)oxy)acetoxy)-8-hydroxy-4,7,9,12-tetramethyl-3-oxodecahydro-4,9a-propanocyclopenta[8]annulen-7-yl) acrylic acid (0.4 g, 700.0 μmol, 1.0 eq), HATU (0.3 g, 768.7 μmol, 1.1 eq) and TEA (141.4 mg, 1.4 mmol, 2.0 eq) in DMF (5.0 mL) was added ammonia; hydrochloride (74.8 mg, 1.4 mmol, 2.0 eq) in one portion at 25° C. The mixture was stirred at 25° C. for 4 hours. HPLC and LCMS showed the reaction was complete. The mixture was added $H_2O$ (10 mL). The aqueous phase was acidified with aqueous HCl (2M) till pH=3-4 and extracted with DCM (15 mL×3). The combined organic layers were washed with saturated brine (10 mL) and dried over $Na_2SO_4$. The organic layer was filtered and concentrated under reduced pressure to provide crude product, which was purified by prep-HPLC (column: Phenomenex luna C18 130×25 mm, 5 μm; liquid phase: [A: 10 mM $NH_4HCO_3$ in $H_2O$; B-ACN] B %: 20%-45%, 12 mini). After prep-HPLC purification, the eluent was concentrated to remove organic solvents. The residual aqueous solution was lyophilized to give (3aR,4R,5R,7S,8S,9R,9aS,12R)-7-((E)-3-amino-3-oxoprop-1-en-1-yl)-8-hydroxy-4,7,9,12-tetramethyl-3-oxodecahydro-4,9a-propanocyclopenta[8]annulen-5-yl 2-((7-fluoro-1-hydroxy-1,3-dihydrobenzo[c][1,2]oxaborol-6-yl)oxy)acetate (100.0 mg, 173.9 μmol, 24.9% yield) as a white solid. $^1$H NMR (DMSO-$d_6$, 400 MHz) δ 9.28 (s, 1H), 7.28 (br. s., 1H), 7.21 (t, J=8.0 Hz, 1H), 7.06-7.15 (m, 1H), 6.72-6.86 (m, 2H), 5.76 (d, J=15.6 Hz, 1H), 5.58 (d, J=8.0 Hz, 1H), 4.92 (s, 2H), 4.78-4.86 (m, 2H), 4.51 (d, J=6.0 Hz, 1H), 3.56-3.62 (m, 1H), 2.00-2.26 (m, 3H), 1.47-1.74 (m, 4H), 1.22-1.46 (m, 6H), 1.00-1.13 (m, 4H), 0.89-0.96 (m, 2H), 0.82 (d, J=7.0 Hz, 3H), 0.65 (d, J=6.4 Hz, 3H). MS (ESI): mass calcd. for $C_{30}H_{39}BFNO_8$ 571.44, m/z found 570.3 [M–H]$^−$. HPLC: 99.4% (220 nm), 100% (254 nm).

To a mixture of (E)-3-((3aR,4R,5R,7S,8S,9R,9aS,12R)-5-(2-((7-fluoro-1-hydroxy-1,3-dihydrobenzo[c][1,2]oxaborol-6-yl)oxy)acetoxy)-8-hydroxy-4,7,9,12-tetramethyl-3-oxodecahydro-4,9a-propanocyclopenta[8]annulen-7-yl) acrylic acid (300.0 mg, 524.1 μmol, 1.0 eq), HATU (219.2 mg, 576.5 μmol, 1.1 eq) and TEA (106.1 mg, 1.1 mmol, 2.0 eq) in DMF (5 mL) was added methanamine; hydrochloride (70.8 mg, 1.1 mmol, 2.0 eq) in one portion at 25° C. The mixture was stirred at 25° C. for 4 hours. HPLC and LCMS showed the reaction was complete. The mixture was added $H_2O$ (10 mL). The aqueous phase was acidified with aqueous HCl (2M) till pH=3-4 and extracted with DCM (15 mL×3). The combined organic layers were washed with saturated brine (10 mL) and dried over $Na_2SO_4$. The organic layer was filtered and concentrated under reduced pressure to provide crude product, which and ET5616-20-P1 (110 mg) were combined and purified by prep-HPLC (column: Phenomenex luna C18 130×25 mm, 5 μm; liquid phase: [A A-10 mM $NH_4HCO_3$ in $H_2O$; B-ACN] B %:20%-45%, 12 mini). After prep-HPLC purification, the eluent was concentrated to remove organic solvents. The residual aqueous solution was lyophilized to give (3aR,4R,5R,7S,8S,9R,9aS,12R)-8-hydroxy-4,7,9,12-tetramethyl-7-((E)-3-(methylamino)-3-oxoprop-1-en-1-yl)-3-oxodecahydro-4,9a-propanocyclopenta[8]annulen-5-yl 2-((7-fluoro-1-hydroxy-1,3-dihydrobenzo[c][1,2]oxaborol-6-yl)oxy)acetate (280.0 mg) as a white solid. $^1$H NMR (DMSO-$d_6$, 400 MHz) δ 7.78 (d, J=4.4 Hz, 1H), 7.20 (t, J=8.0 Hz, 1H), 7.05-7.15 (m, 1H), 6.76 (d, J=16.0 Hz, 1H), 5.74 (d, J=16.0 Hz, 1H), 5.57 (d, J=8.0 Hz, 1H), 4.89-4.96 (m, 2H), 4.76-4.86 (m, 2H), 4.49 (d, J=6.0 Hz, 1H), 3.59 (t, J=6.0 Hz, 1H), 2.64 (d, J=4.4 Hz, 3H), 2.01-2.26 (m, 4H), 1.48-1.72 (m, 4H), 1.23-1.43 (m, 6H), 1.01-1.11 (m, 3H), 0.88-0.95 (m, 1H), 0.82 (d, J=6.4 Hz, 3H), 0.62-0.68 (d, J=7.0 Hz, 3H). MS (ESI): mass calcd. for $C_{31}H_{41}BFNO_8$ 585.47, m/z found 584.3 [M–H]$^−$. HPLC: 99.3% (220 nm), 100% (254 nm).

16. (3aR,4R,5R,7S,8S,9R,9aS,12R)-8-hydroxy-7-((E)-3-(methoxyamino)-3-oxoprop-1-en-1-yl)-4,7,9,12-tetramethyl-3-oxodecahydro-4,9a-propanocyclopenta[8]annulen-5-yl 2-((7-fluoro-1-hydroxy-1,3-dihydrobenzo[c][1,2]oxaborol-6-yl)oxy)acetate

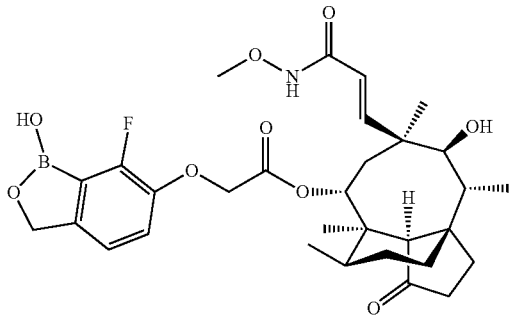

To a mixture of (E)-methyl 3-((3aR,4R,5R,7S,8S,9R,9aS,12R)-5-(2-((7-fluoro-1-hydroxy-1,3-dihydrobenzo[c][1,2]oxaborol-6-yl)oxy)acetoxy)-8-hydroxy-4,7,9,12-tetramethyl-3-oxodecahydro-4,9a-propanocyclopenta[8]annulen-7-yl)acrylate (8.0 g, 13.6 mmol, 1.0 eq) in MeOH (30 mL) and $H_2O$ (40 mL) was added $LiOH \cdot H_2O$ (1.1 g, 27.3 mmol, 2.0 eq) in one portion at 20° C. The mixture was stirred at 20° C. for 5 hours. HPLC showed the reaction was complete. $H_2O$ (30 mL) was added to the mixture which was acidified with aqueous HCl (2 M) till pH=5-6 to precipitate a white solid. The aqueous layer was extracted with EtOAc (50 mL×3). The combined organic layers were washed with brine (20 mL) and dried over $Na_2SO_4$. After filtration via filter paper, the organic layer was concentrated under reduced pressure to provide a crude product, which was purified by prep-HPLC (column: Phenomenex luna C18 250×50 mm, 10 μm; liquid phase: [A-TFA/$H_2O$=0.075% v/v; B-ACN] B %: 25%-55%, 20 mini). After prep-HPLC purification, the eluent was concentrated to remove organic solvent. The residual aqueous solution was lyophilized to give (E)-3-((3aR,4R,5R,7S,8S,9R,9aS,12R)-5-(2-((7-fluoro-1-hydroxy-1,3-dihydrobenzo[c][1,2]oxaborol-6-yl)oxy)acetoxy)-8-hydroxy-4,7,9,12-tetramethyl-3-oxodecahydro-4,9a-propanocyclopenta[8]annulen-7-yl)acrylic acid (3.0 g, 5.2 mmol, 38.4% yield) as a white solid.

To a mixture of (E)-3-((3aR,4R,5R,7S,8S,9R,9aS,12R)-5-(2-((7-fluoro-1-hydroxy-1,3-dihydrobenzo[c][1,2]oxaborol-6-yl)oxy)acetoxy)-8-hydroxy-4,7,9,12-tetramethyl-3-oxodecahydro-4,9a-propanocyclopenta[8]annulen-7-yl)acrylic acid (200.0 mg, 349.4 μmol, 1.0 eq), HATU (146.1 mg, 384.3 μmol, 1.1 eq), TEA (70.7 mg, 698.8 μmol, 2.0 eq) in DMF (10.0 mL) was added O-methylhydroxylamine hydrochloride (58.4 mg, 698.8 μmol, 2.0 eq) in one portion at 25° C. The mixture was stirred at 25° C. for 3 hours. HPLC showed the reaction was completed. $H_2O$ (30 mL) was added the mixture, which was acidified with aqueous HCl (2 M) till pH=5-6 to precipitate a white solid. The aqueous layer was extracted with EtOAc (20 mL×3). The combined organic layers were washed with brine (20 mL) and dried over $Na_2SO_4$. After filtration via filter paper, the organic layer was concentrated under reduced pressure to provide crude product, which was purified by prep-HPLC (column: Luna C18 100×30 mm, 5 μm; liquid phase: [A: TFA/$H_2O$=0.075% v/v; B-ACN] B %: 35%-65%, 12 mini). After prep-HPLC purification, the eluent was concentrated to remove organic solvent. The residual aqueous solution was lyophilized to give (3aR,4R,5R,7S,8S,9R,9aS,12R)-8-hydroxy-7-((E)-3-(methoxyamino)-3-oxoprop-1-en-1-yl)-4,7,9,12-tetramethyl-3-oxodecahydro-4,9a-propanocyclopenta[8]annulen-5-yl 2-((7-fluoro-1-hydroxy-1,3-dihydrobenzo[c][1,2]oxaborol-6-yl)oxy)acetate (75.0 mg, 118.1 μmol, 33.8% yield) as a white solid. $^1$H NMR (DMSO-$d_6$, 400 MHz) δ 7.17 (t, J=8.0 Hz, 1H), 7.05 (d, J=8.0 Hz, 1H), 6.83 (d, J=16.0 Hz, 1H), 5.52 (d, J=8.4 Hz, 2H), 4.88 (s, 2H), 4.71-4.84 (m, 2H), 3.57 (s, 5H), 1.96-2.21 (m, 5H), 1.64 (d, J=12.4 Hz, 2H), 1.39-1.53 (m, 2H), 1.19-1.38 (m, 6H), 0.86-1.09 (m, 5H), 0.77 (d, J=7.2 Hz, 3H), 0.61 (d, J=6.6 Hz, 3H). MS (ESI): mass calcd. for $C_{31}H_{41}BFNO_9$ 601.29, m/z found 602.4 [M+H]$^+$. HPLC: 94.7% (220 nm), 94.2% (254 nm).

17. tert-butyl 2-((E)-3-((3aR,4R,5R,7S,8S,9R,9aS,12R)-5-(2-((7-fluoro-1-hydroxy-1,3-dihydrobenzo[c][1,2]oxaborol-6-yl)oxy)acetoxy)-8-hydroxy-4,7,9,12-tetramethyl-3-oxodecahydro-4,9a-propanocyclopenta[8]annulen-7-yl)acryloyl)hydrazine-1-carboxylate 18. (3aR,4R,5R,7S,8S,9R,9aS,12R)-7-((E)-3-hydrazinyl-3-oxoprop-1-en-1-yl)-8-hydroxy-4,7,9,12-tetramethyl-3-oxodecahydro-4,9a-propanocyclopenta[8]annulen-5-yl 2-((7-fluoro-1-hydroxy-1,3-dihydrobenzo[c][1,2]oxaborol-6-yl)oxy)acetate

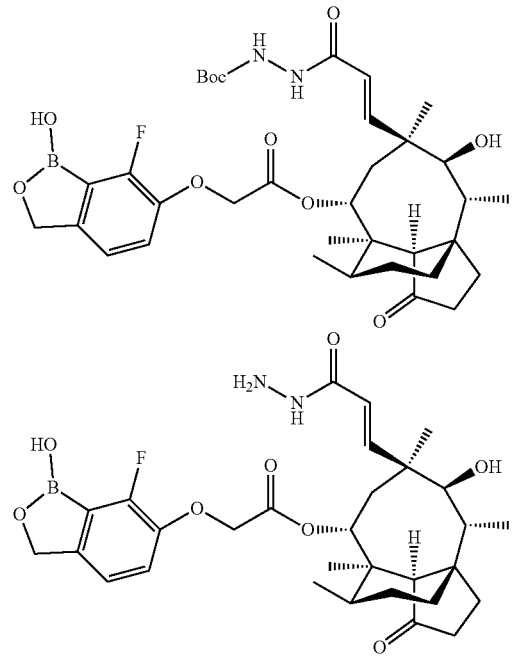

To a mixture of (E)-3-((3aR,4R,5R,7S,8S,9R,9aS,12R)-5-(2-((7-fluoro-1-hydroxy-1,3-dihydrobenzo[c][1,2]oxaborol-6-yl)oxy)acetoxy)-8-hydroxy-4,7,9,12-tetramethyl-3-oxodecahydro-4,9a-propanocyclopenta[8]annulen-7-yl) acrylic acid (1.0 g, 1.7 mmol, 1.0 eq), HATU (731.9 mg, 1.9 mmol, 1.1 eq) and TEA (354.2 mg, 3.5 mmol, 2.0 eq) in DMF (20 mL) was added tert-butyl N-aminocarbamate (462.6 mg, 3.5 mmol, 2.0 eq) in one portion at 25° C. The mixture was stirred at 25° C. for 3 hours. HPLC showed the reaction was completed. $H_2O$ (100 mL) was added the mixture, which was acidified with aqueous HCl (2 M) till pH=5-6 to precipitate a white solid. The aqueous layer was extracted with EtOAc (50 mL×3). The combined organic layers were washed with brine (30 mL) and dried over $Na_2SO_4$. After filtration via filter paper, the organic layer was concentrated under reduced pressure to provide crude product, which was purified by prep-HPLC (column: Phenomenex luna C18 130×25 mm, 5 μm; liquid phase: [A-10 mM $NH_4HCO_3$ in $H_2O$; B-ACN] B %: 20%-55%, 12 mini). After prep-HPLC purification, the eluent was concentrated to remove organic solvents. The residual aqueous solution was lyophilized to give tert-butyl 2-((E)-3-((3aR,4R,5R,7S,8S,9R,9aS,12R)-5-(2-((7-fluoro-1-hydroxy-1,3-dihydrobenzo[c][1,2]oxaborol-6-yl)oxy)acetoxy)-8-hydroxy-4,7,9,12-tetramethyl-3-oxodecahydro-4,9a-propanocyclopenta[8]annulen-7-yl)acryloyl)hydrazinecarboxylate (160.0 mg, 224.5 μmol, 12.8% yield) as a white solid. $^1$H NMR (DMSO-d$_6$, 400 MHz) δ 9.45 (br. s., 1H), 9.22 (s, 1H), 8.71 (br. s., 1H), 7.12-7.20 (m, 1H), 7.03-7.10 (m, 1H), 6.85 (d, J=16.0 Hz, 1H), 5.73 (d, J=15.4 Hz, 1H), 5.53 (d, J=7.6 Hz, 1H), 4.88 (s, 2H), 4.72-4.85 (m, 2H), 4.52 (d, J=6.2 Hz, 1H), 3.54-3.62 (m, 1H), 1.99-2.21 (m, 3H), 1.55-1.70 (m, 2H), 1.17-1.51 (m, 18H), 0.88-1.13 (m, 5H), 0.76-0.82 (d, J=7.2 Hz, 3H), 0.61 (d, J=7.2 Hz, 3H). MS (ESI): mass calcd. for $C_{35}H_{48}BFN_2O_{10}$ 686.34, m/z found 685.4 [M−H]$^-$. HPLC: 96.3% (220 nm), 100% (254 nm).

To a solution of tert-butyl 2-((E)-3-((3aR,4R,5R,7S,8S,9R,9aS,12R)-5-(2-((7-fluoro-1-hydroxy-1,3-dihydrobenzo[c][1,2]oxaborol-6-yl)oxy)acetoxy)-8-hydroxy-4,7,9,12-tetramethyl-3-oxodecahydro-4,9a-propanocyclopenta[8]annulen-7-yl)acryloyl)hydrazinecarboxylate (1.0 g, 1.5 mmol, 1.0 eq) in DCM was added HCl/EtOAc (4 M, 80.2 mL, 219.7 eq) at 25° C. The mixture was stirred at 25° C. for 3.5 hours. HPLC showed the reaction was complete. The reaction mixture was filtered and the filter cake was washed with 20 mL of ethyl acetate, dried in vacuum to give or afford product, which was purified by prep-HPLC (column: Luna C18 100×30 mm, 5 μm; liquid phase: [A-HCl/H$_2$O=0.040% v/v; BACN] B %: 25%-55%, 12 mini). After prep-HPLC purification, the eluent was concentrated to remove organic solvents. The residual aqueous solution was lyophilized to give (3aR,4R,5R,7S,8S,9R,9aS,12R)-7-((E)-3-hydrazinyl-3-oxoprop-1-en-1-yl)-8-hydroxy-4,7,9,12-tetramethyl-3-oxodecahydro-4,9a-propanocyclopenta[8]annulen-5-yl2-((7-fluoro-1-hydroxy-1,3-dihydrobenzo[c][1,2]oxa borol-6-yl)oxy)acetate (76.0 mg, 120.9 μmol, 8.3% yield) as a white solid. $^1$H NMR (DMSO-d$_6$, 400 MHz) δ 10.68 (br. s., 1H), 9.24 (br. s., 1H), 7.13-7.21 (m, 1H), 7.07 (d, J=8.4 Hz, 1H), 6.98 (d, J=16.0 Hz, 1H), 5.81 (d, J=16.0 Hz, 1H), 5.53 (d, J=8.0 Hz, 1H), 4.88 (s, 2H), 4.71-4.84 (m, 2H), 3.62 (d, J=5.6 Hz, 1H), 2.55-2.50 (m, 1H), 2.42 (d, J=1.8 Hz, 1H), 1.96-2.23 (m, 4H), 1.57-1.77 (m, 2H), 1.40-1.52 (m, 1H), 1.19-1.40 (m, 7H), 0.93-1.14 (m, 5H), 0.78 (d, J=7.2 Hz, 3H), 0.61 (d, J=7.2 Hz, 3H). MS (ESI): mass calcd. for $C_{30}H_{41}BClFN_2O_8$ 622.92, m/z found 585.3 [M−H]$^-$. HPLC: 99.7% (220 nm), 100% (254 nm).

19. (3aR,4R,5R,7R,8S,9R,9aS,12R)-7-ethyl-8-hydroxy-4,7,9,12-tetramethyl-3-oxodecahydro-4,9a-propanocyclopenta[8]annulen-5-yl 2-((7-fluoro-1-hydroxy-1,3-dihydrobenzo[c][1,2]oxaborol-6-yl)oxy)acetate

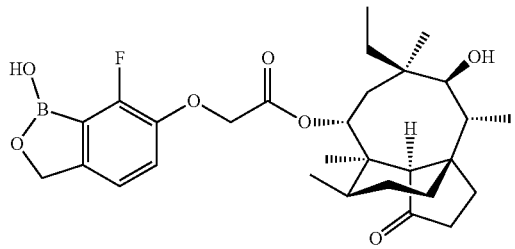

(3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-(tosyloxy)acetate (500.0 mg, 938.6 μmol, 1.0 eq) and Pd/C (300.0 mg, 938.6 μmol, 1.0 eq) in THF (30.0 mL) were stirred at 25° C. for 12 hours under 40 psi hydrogen atmosphere. The mixture was filtered and the filtrate was concentrated to give (3aR,4R,5R,7R,8S,9R,9aS,12R)-7-ethyl-8-hydroxy-4,7,9,12-tetramethyl-3-oxodecahydro-4,9a-propanocyclopenta[8]annulen-5-yl 2-(tosyloxy)acetate (500.0 mg, 902.8 μmol, 96.2% yield, 96.5% purity) as white foam. $^1$H NMR (CHLOROFORM-d, 400 MHz) δ 7.83 (d, J=8.4 Hz, 2H), 7.36 (d, J=8.4 Hz, 2H), 5.66 (d, J=7.9 Hz, 1H), 4.51 (s, 2H), 3.45-3.37 (m, 1H), 2.46 (s, 3H), 2.41-2.14 (m, 4H), 2.09 (br. s., 1H), 1.85-1.05 (m, 15H), 0.99-0.91 (m, 6H), 0.72 (t, J=7.5 Hz, 3H), 0.61 (d, J=7.1 Hz, 2H).

(3aR,4R,5R,7R,8S,9R,9aS,12R)-7-ethyl-8-hydroxy-4,7,9,12-tetramethyl-3-oxodecahydro-4,9a-propanocyclopenta[8]annulen-5-yl 2-(tosyloxy)acetate (300.0 mg, 561.1 μmol, 1.0 eq), 7-fluoro-1-hydroxy-3H-2,1-benzoxaborol-6-ol (94.22 mg, 561.06 μmol, 1.00 eq) and Na$_2$CO$_3$ (178.4 mg, 1.7 mmol, 3.0 eq) in DMSO (15.0 mL) were heated to 30-40° C. for 12 hours. Water (20 mL) was added to the mixture, white solid was precipitated. The mixture was filtered to give crude product, which was purified by prep-HPLC (column: Luna C18 100×30 mm, 5 μm; liquid phase: [A-TFA/H$_2$O=0.075% v/v; B-ACN] B %: 41%-61%, 12 min]) to give (3aR,4R,5R,7R,8S,9R,9aS,12R)-7-ethyl-8-hydroxy-4,7,9,12-tetramethyl-3-oxodecahydro-4,9a-propanocyclopenta[8]annulen-5-yl2-((7-fluoro-1-hydroxy-1,3-dihydrobenzo[c][1,2]oxaborol-6-yl)oxy)acetate (95.00 mg, 179.10 μmol, 31.92% yield, 100% purity) as white solid. $^1$H NMR (DMSO-d$_6$, 400 MHz) δ 9.26 (s, 1H), 7.24-7.21 (m, 1H), 7.12-7.06 (m, 1H), 5.58 (d, J=8.4 Hz, 1H), 4.92-4.83 (m, 2H), 4.84-4.80 (m, 2H), 4.40 (d, J=5.6 Hz, 1H), 3.34-3.32 (m, 1H), 2.37-2.18 (m., 1H), 2.24-2.00 (m, 3H), 1.80-0.93 (m, 20H), 0.88-0.77 (m, 3H), 0.66-0.56 (m, 3H). MS (ESI): mass calcd. for $C_{29}H_{40}BFO_7$ 530.3, m/z found 529.3 [M−H]$^-$. HPLC: 100% in 220 nm; 10% in 254 nm.

20. (3aR,4R,5R,7R,8S,9R,9aS,12R)-7-ethyl-8-hydroxy-4,7,9,12-tetramethyl-3-oxodecahydro-4,9a-propanocyclopenta[8]annulen-5-yl 2-((4-(aminomethyl)-1-hydroxy-1,3-dihydrobenzo[c][1,2]oxaborol-6-yl)oxy)acetate

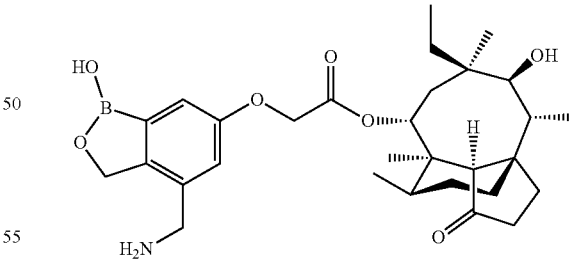

A solution of (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-((4-(aminomethyl)-1-hydroxy-1,3-dihydrobenzo[c][1,2]oxaborol-6-yl)oxy)acetate (40 mg, 0.074 mmol) in MeOH (5 mL) was hydrogenated using Pd/C (10%) (8 mg) as catalyst under atmospheric pressure for 6 h. The catalyst was removed by filtration, the solvent was removed and the residue was purified by Prep-HPLC to give (3aR,4R,5R,7R,8S,9R,9aS,12R)-7-ethyl-8-hydroxy-4,7,9,12-tetramethyl-3-oxodecahydro-4,9a-propanocyclopenta[8]annulen-5-yl 2-((4-(aminomethyl)-1-hydroxy-1,3-dihydrobenzo[c][1,2]oxaborol-6-yl)oxy)acetate (2.6 mg, yield 6.5%) as a white solid. $^1$H NMR (400 MHz, DMSO-d$_6$) δ 9.02 (s, 1H), 7.07 (s, 1H), 7.04 (s, 1H), 5.58 (d, J=4.8 Hz, 1H), 4.95 (s, 2H), 4.69 (q, J=20.8 Hz, 2H), 4.41 (d, J=6.0 Hz, 1H), 3.64 (s, 2H), 2.42-2.07 (m, 5H), 1.75-1.04 (m, 16H), 0.84-0.79 (m, 6H), 0.65 (d, J=6.8 Hz, 3H), 0.59 (t, J=7.2 Hz, 3H). HPLC purity: 100% (220 nm), 100% (254 nm); MS (ESI): mass calcd. for C$_{30}$H$_{44}$BNO$_7$ 541.32, m/z found 542.5 [M+H]$^+$.

21. (3aR,4R,5R,7R,8S,9R,9aS,12R)-7-allyl-8-hydroxy-4,7,9,12-tetramethyl-3-oxodecahydro-4,9a-propanocyclopenta[8]annulen-5-yl 2-((7-fluoro-1-hydroxy-1,3-dihydrobenzo[c][1,2]oxaborol-6-yl)oxy)acetate

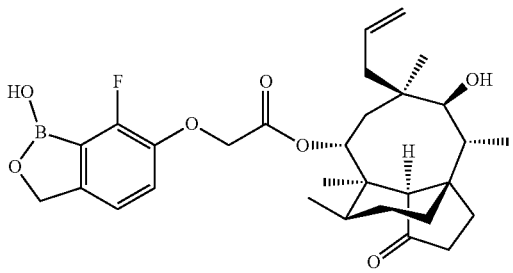

NaOH (6.1 g, 152.9 mmol, 3.0 eq) was added to a solution of (3R,3aS,4R,5R,7S,9R,9aR,12R)-3-methoxy-4,7,9,12-tetramethyl-8-oxo-7-vinyldecahydro-4,9a-propanocyclopenta[8]annulen-5-yl 2-hydroxyacetate (20.0 g, 51.0 mmol, 1.0 eq) in MeOH (100 mL) and H$_2$O (100 mL) at 15° C. The mixture was stirred at 15° C. for 12 hours. The solvent was concentrated in vacuo. 100 mL water was added to the mixture, and treated with EtOAc (100 mL×2). The combined organic phase was dried over Na$_2$SO$_4$ and concentrated in vacuo to give (3R,3aS,4R,5R,7S,9R,9aR,12R)-5-hydroxy-3-methoxy-4,7,9,12-tetramethyl-7-vinyloctahydro-4,9a-propanocyclopenta[8]annulen-8(9H)-one (17.0 g, crude) as brown oil. $^1$H NMR (CDCl$_3$, 400 MHz) δ 6.01 (dd, J=10.4, 17.6 Hz, 1H), 5.30-5.21 (m, 2H), 4.64 (dd, J=6.0, 9.2 Hz, 1H), 3.49 (m, 1H), 2.93 (q, J=6.4 Hz, 1H), 2.43 (dd, J=9.2, 15.2 Hz, 1H), 2.24-2.15 (m, 1H), 2.05-1.93 (m, 2H), 1.83 (d, J=15.6 Hz, 1H), 1.72 (d, J=11.0 Hz, 1H), 1.64-1.42 (m, 5H), 1.40-1.19 (m, 3H), 1.17 (d, J=7.6 Hz, 7H), 1.08 (d, J=7.2 Hz, 3H), 0.98 (d, J=6.4 Hz, 3H).

MOMCl (37.3 g, 463.4 mmol, 35.2 mL, 5.0 eq) was added to a solution of (3R,3aS,4R,5R,7 S,9R,9aR,12R)-5-hydroxy-3-methoxy-4,7,9,12-tetramethyl-7-vinyloctahydro-4,9a-propanocyclopenta[8] annulen-8(9H)-one (31.0 g, 92.7 mmol, 1.0 eq) and DIEA (71.9 g, 556.1 mmol, 97.1 mL, 6.0 eq) in DCM (200.0 mL) at 0° C., the mixture was stirred at 20° C. for 12 hours. The reaction was quenched by addition of 300 mL water, and adjusted to pH<5 with 2 N HCl and treated with DCM (100 mL×3). The combined organic phase was washed by brine 100 mL×1 and concentrated in vacuo to give (3R,3aS,4R,5R,7S,9R,9aR,12R)-3-methoxy-5-(methoxymethoxy)-4,7,9,12-tetramethyl-7-vinyloctahydro-4,9a-propanocyclopenta[8]annulen-8(9H)-one (35.0 g, crude) as yellow oil. $^1$H NMR (CDCl$_3$, 400 MHz) δ 6.34 (dd, J=10.8, 17.4 Hz, 1H), 5.26 (d, J=11.2 Hz, 1H), 5.05 (d, J=17.6 Hz, 1H), 4.80-4.68 (m, 2H), 4.34 (d, J=9.6 Hz, 1H), 3.50 (m, 1H), 3.43-3.40 (m, 3H), 3.23 (s, 2H), 2.91 (q, J=6.4 Hz, 1H), 2.40 (dd, J=9.6, 15.4 Hz, 1H), 2.24-2.14 (m, 1H), 2.05-1.91 (m, 3H), 1.68 (d, J=11.2 Hz, 1H), 1.57 (s, 3H), 1.48 (d, J=3.2 Hz, 2H), 1.37-1.23 (m, 2H), 1.20 (d, J=4.4 Hz, 6H), 1.16-1.04 (m, 2H), 0.98 (t, J=6.2 Hz, 6H).

Ozone (4.4 g, 92.5 mmol, 1.0 eq) was bubbled into a solution of (3R,3aS,4R,5R,7S,9R,9aR,12R)-3-methoxy-5-(methoxymethoxy)-4,7,9,12-tetramethyl-7-vinyloctahydro-4,9a-propanocyclopenta[8]annulen-8(9H)-one (35.0 g, 92.5 mmol, 1.0 eq) in DCM (2.5 L) at −78° C., the mixture was stirred at −78° C. till TLC showed that the starting material was consumed. The reaction was quenched by addition of TEA (93.6 g, 924.6 mmol, 128.2 mL, 10.0 eq) till wet potassium iodide starch didn't change. The solvent was warmed to room temperature, and concentrated. The mixture was treated with DCM (200 mL) and 2N HCl till pH<4. The aqueous phase was treated with DCM (100 mL×3). The combined organic phase was dried over Na$_2$SO$_4$ and concentrated in vacuo to give (3R,3aS,4R,5R,7S,9R,9aR,12R)-3-methoxy-5-(methoxymethoxy)-4,7,9,12-tetramethyl-8-oxodecahydro-4,9a-propanocyclopenta[8]annulene-7-carbaldehyde (35.0 g, crude) as yellow oil. $^1$H NMR (DMSO-d$_6$, 400 MHz) δ 9.60 (s, 1H), 4.78 (d, J=7.2 Hz, 1H), 4.70 (d, J=7.2 Hz, 1H), 4.23 (d, J=8.0 Hz, 1H), 3.45-3.36 (m, 4H), 3.22 (s, 3H), 2.92 (q, J=6.4 Hz, 1H), 2.52-2.35 (m, 2H), 2.26-2.14 (m, 1H), 2.07-1.87 (m, 2H), 1.70 (d, J=11.2 Hz, 1H), 1.60-1.40 (m, 3H), 1.22 (d, J=18.0 Hz, 9H), 1.07 (d, J=6.4 Hz, 3H), 0.93 (d, J=6.4 Hz, 3H).

NaOH (5.5 g, 138.0 mmol, 1.5 eq) was added to a solution of (3R,3aS,4R,5R,7S,9R,9aR,12R)-3-methoxy-5-(methoxymethoxy)-4,7,9,12-tetramethyl-8-oxodecahydro-4,9a-propanocyclopenta[8]annulene-7-carbaldehyde (35.0 g, 92.0 mmol, 1.0 eq) in MeOH (100 mL). The mixture was stirred at 20° C. for 0.5 hour. The solvent was evaporated and 200 mL water was added to the mixture, adjusted pH=6-7 with 2N HCl. The mixture was treated with DCM (100 mL×2). The combined organic phase was dried over Na$_2$SO$_4$ and concentrated in vacuo to give (3R,3aS,4R,5R,7S,9R,9aR,12R)-3-methoxy-5-(methoxymethoxy)-4,7,9,12-tetramethyloctahydro-4,9a-propanocyclopenta[8]annulen-8(9H)-one (32.0 g, crude) as yellow solid. $^1$H NMR (DMSO-d$_6$, 400 MHz,) δ 4.79-4.67 (m, 2H), 4.31 (d, J=9.2 Hz, 1H), 3.54-3.45 (m, 1H), 3.42 (s, 3H), 3.22-3.19 (m, 3H), 2.93 (d, J=6.4 Hz, 1H), 2.64 (m, 1H), 2.32-2.14 (m, 2H), 2.04-1.93 (m, 3H), 1.69 (d, J=11.0 Hz, 1H), 1.62-1.42 (m, 3H), 1.38-1.09 (m, 6H), 1.07 (d, J=6.0 Hz, 3H), 0.98 (m, 6H).

NaH (2.8 g, 56.7 mmol, 60%, 4.0 eq) was added to a solution of (3R,3aS,4R,5R,7S,9R,9aR,12R)-3-methoxy-5-(methoxymethoxy)-4,7,9,12-tetramethyloctahydro-4,9a-propanocyclopenta[8]annulen-8(9H)-one (5.0 g, 14.2 mmol, 1.0 eq) in THF (20 mL) at 50° C., half an hour later, allyl bromide (8.9 g, 70.9 mmol, 5.0 eq) was added to the mixture. The mixture was stirred at 50° C. for 12 hours. The reaction was quenched by addition of 50 ml water and was treated with EtOAc (30 mL×3). The combined organic phase was dried over Na$_2$SO$_4$ and concentrated in vacuo to give (3R,3aS,4R,5R,7R,9R,9aR,12R)-7-allyl-3-methoxy-5-(methoxymethoxy)-4,7,9,12-tetramethyloctahydro-4,9a-propanocyclopenta[8]annulen-8(9H)-one (5.3 g, crude) as yellow oil. $^1$H NMR (CDCl$_3$, 400 MHz) δ 5.58 (m, 1H), 5.14-5.01 (m, 2H), 4.77-4.66 (s, 2H), 4.38 (d, J=9.6 Hz, 1H), 3.54-3.34 (s, 3H), 3.29-3.14 (s, 3H), 3.05 (d, J=6.4 Hz, 1H), 2.75 (dd, J=7.2, 14.0 Hz, 1H), 2.44-2.13 (m, 3H), 2.07-1.88 (m, 1H), 1.82 (d, J=16.0 Hz, 1H), 1.70-1.44 (m, 5H), 1.36-1.10 (m, 10H), 1.07 (s, 3H), 0.98 (dd, J=6.4, 12.4 Hz, 3H).

(3R,3aS,4R,5R,7R,9R,9aR,12R)-7-allyl-3-methoxy-5-(methoxymethoxy)-4,7,9,12-tetramethyloctahydro-4,9a-propanocyclopenta[8]annulen-8(9H)-one (5.3 g, 13.5 mmol, 1.0 eq) in HCl (2 M, 6.7 mL, 1.0 eq) and MeOH (25 mL)

were stirred at 15° C. for 12 hours. The mixture was treated with DCM (50 mL) and water 100 mL, and the aqueous phase was treated with DCM (50 mL×2). The combined organic phase was dried over Na$_2$SO$_4$ and concentrated in vacuo to give crude product which was purified by flash column (petroleum ether/EtOAc=20/1-5/1) to give (3R,3aS,4R,5R,7R,9R,9aR,12R)-7-allyl-5-hydroxy-3-methoxy-4,7,9,12-tetramethyloctahydro-4,9a-propanocyclopenta[8]annulen-8(9H)-one (3.4 g, 9.8 mmol, 72.3% yield) as white solid. $^1$H NMR (CDCl$_3$, 400 MHz) δ 5.73-5.60 (m, 1H), 5.18-5.08 (m, 2H), 4.64 (dd, J=6.0, 9.6 Hz, 1H), 3.46 (m, 1H), 3.27-3.17 (m, 3H), 3.13-3.01 (m, 1H), 2.60-2.48 (m, 1H), 2.46-2.29 (m, 2H), 2.26-2.13 (m, 1H), 2.08-1.88 (m, 2H), 1.76-1.55 (m, 4H), 1.54-1.17 (m, 5H), 1.17-1.03 (m, 9H), 0.97 (d, J=6.5 Hz, 3H).

(3R,3aS,4R,5R,7R,9R,9aR,12R)-7-allyl-5-hydroxy-3-methoxy-4,7,9,12-tetramethyloctahydro-4,9a-propanocyclopenta[8]annulen-8(9H)-one (3.4 g, 9.8 mmol, 1.0 eq), perfluorophenyl 2-(tosyloxy)acetate (7.7 g, 19.5 mmol, 2.0 eq) and DMAP (1.2 g, 9.8 mmol, 1.0 eq) in THF (15.00 mL) were stirred at 20° C. for 12 hours. The solvent was concentrated in vacuo directly and the crude product was purified by flash column chromatography (Petroleum ether/EtOAc=1/0-5/1) to give (3R,3aS,4R,5R,7R,9R,9aR,12R)-7-allyl-3-methoxy-4,7,9,12-tetramethyl-8-oxodecahydro-4,9a-propanocyclopenta[8]annulen-5-yl 2-(tosyloxy)acetate (4.5 g, crude) as yellow oil. $^1$H NMR (CDCl$_3$, 400 MHz) δ 7.88-7.81 (m, 2H), 7.41-7.35 (m, 2H), 5.89 (d, J=9.6 Hz, 1H), 5.57-5.43 (m, 1H), 5.15-4.99 (m, 3H), 4.65 (dd, J=6.0, 10.0 Hz, 1H), 4.54 (s, 2H), 3.42 (m, 1H), 3.29-3.16 (m, 4H), 3.14-3.03 (m, 2H), 2.81 (dd, J=7.2, 14.8 Hz, 1H), 2.47 (s, 3H), 2.39 (dd, J=10.0, 15.2 Hz, 2H), 2.28-2.15 (m, 3H), 2.07-1.88 (m, 3H), 1.75-1.41 (m, 7H), 1.38-0.94 (m, 3H), 0.74 (d, J=6.4 Hz, 3H).

7-fluoro-1-hydroxy-3H-2,1-benzoxaborol-6-ol (179.7 mg, 1.1 mmol, 1.0 eq), (3R,3aS,4R,5R,7R,9R,9aR,12R)-7-allyl-3-methoxy-4,7,9,12-tetramethyl-8-oxodecahydro-4,9a-propanocyclopenta[8]annulen-5-yl 2-(tosyloxy)acetate (600 mg, 1.1 mmol, 1.0 eq) and Na$_2$CO$_3$ (340.2 mg, 3.2 mmol, 3.0 eq) in DMSO (20 mL) were stirred at 30-40° C. for 12 hours. The reaction was quenched by addition of 50 mL water and adjusted pH<4 with 2N HCl aqueous solution. White solid was precipitated and filtered to give crude product (3R,3aS,4R,5R,7R,9R,9aR,12R)-7-allyl-3-methoxy-4,7,9,12-tetramethyl-8-oxodecahydro-4,9a-propanocyclopenta[8]annulen-5-yl 2-((7-fluoro-1-hydroxy-1,3-dihydrobenzo[c][1,2]oxaborol-6-yl)oxy)acetate (590.0 mg, crude) as brown solid.

ZnCl$_2$ saturated in Con. HCl (1.1 mmol, 10.0 mL, 1.0 eq) was added to a mixture of (3R,3aS,4R,5R,7R,9R,9aR,12R)-7-allyl-3-methoxy-4,7,9,12-tetramethyl-8-oxodecahydro-4,9a-propanocyclopenta[8]annulen-5-yl 2-((7-fluoro-1-hydroxy-1,3-dihydrobenzo[c][1,2] oxaborol-6-yl)oxy)acetate (600.0 mg, 1.1 mmol, 1.0 eq) in THF (20 mL) at 15° C., the mixture was stirred at 15° C. for 2 hours. The mixture was treated with DCM 50 mL and water 50 mL, the aqueous phase was treated with DCM 20 mL×2. The combined organic phase was dried over Na$_2$SO$_4$ and concentrated in vacuo. The crude product was purified by prep-HPLC (column: Luna C18 100×30 mm, 5 μm; liquid phase: [A-TFA/H$_2$O=0.075% v/v; B-ACN, B %: 43%-73%, 12 min]). The mixture was concentrated to about 20 mL solution left and lyophilized to give (3aR,4R,5R,7R,8S,9R,9aS,12R)-7-allyl-8-hydroxy-4,7,9,12-tetramethyl-3-oxodecahydro-4,9a-propanocyclopenta[8]annulen-5-yl 2-((7-fluoro-1-hydroxy-1,3-dihydrobenzo[c][1,2]oxaborol-6-yl)oxy)acetate (133.0 mg, 243.9 μmol, 22.6% yield, 99.5% purity) as white solid. $^1$H NMR (DMSO-d$_6$, 400 MHz) δ 9.19 (s, 1H), 7.24 (t, J=8.0 Hz, 1H), 7.11 (d, J=8.0 Hz, 1H), 5.68 (d, J=8.4 Hz, 1H), 5.66-5.56 (m, 1H), 4.99-4.70 (m, 6H), 3.37 (d, J=5.6 Hz, 1H), 2.37 (br. s., 1H), 2.27-2.00 (m, 5H), 1.83 (dd, J=8.0, 15.6 Hz, 1H), 1.73-1.57 (m, 2H), 1.54-0.96 (m, 10H), 0.90-0.74 (m, 5H), 0.64 (d, J=6.4 Hz, 3H). MS (ESI): mass calcd. For C$_{30}$H$_{40}$BFO$_7$ 542.44, m/z found 541.3[M−H]$^-$. HPLC: 99.5% (220 nm), 90.7% (254 nm).

22. (3aR,4R,5R,7R,8S,9R,9aS,12R)-8-hydroxy-4,7,9,12-tetramethyl-3-oxo-7-(prop-2-yn-1-yl)decahydro-4,9a-propanocyclopenta[8]annulen-5-yl 2-((7-fluoro-1-hydroxy-1,3-dihydrobenzo[c][1,2]oxaborol-6-yl)oxy)acetate

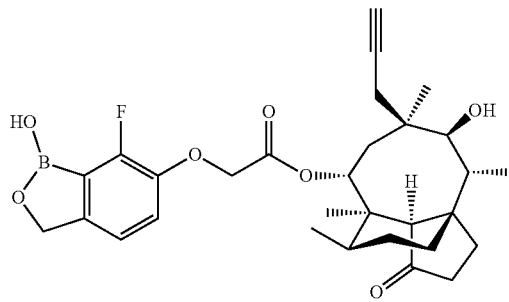

To a solution of (3R,3aS,4R,5R,7S,9R,9aR,12R)-3-methoxy-5-(methoxymethoxy)-4,7,9,12-tetramethyloctahydro-4,9a-propanocyclopenta[8]annulen-8(9H)-one (1.5 g, 4.3 mmol, 1.0 eq.) and 3-bromoprop-1-yne (3.8 g, 25.6 mmol, 2.75 mL, 6.0 eq.) in THF (50 mL) was added NaH (1.2 g, 29.8 mmol, 60% purity, 7.0 eq.). The mixture was stirred at 50° C. for 16 hours. TLC indicated the starting material was consumed. The reaction mixture was quenched by addition H$_2$O 50 mL, and then diluted with EtOAc 50 mL and extracted with EtOAc 150 mL (50 mL×3). The combined organic layers were washed with brine 100 mL, dried over Na$_2$SO$_4$, filtered and concentrated under reduced pressure to give a residue. The residue was purified by column chromatography (SiO$_2$, petroleum ether/ethyl acetate=20/1 to 10:1). (3R,3aS,4R,5R,7R,9R,9aR,12R)-3-methoxy-5-(methoxymethoxy)-4,7,9,12-tetramethyl-7-(prop-2-yn-1-yl)octahydro-4,9a-propanocyclopenta[8]annulen-8(9H)-one (1.5 g, 3.8 mmol, 90.2% yield) was obtained as colorless.

To a solution of (3R,3aS,4R,5R,7R,9R,9aR,12R)-3-methoxy-5-(methoxymethoxy)-4,7,9,12-tetramethyl-7-(prop-2-yn-1-yl) octahydro-4,9a-propanocyclopenta[8]annulen-8(9H)-one (1.5 g, 3.8 mmol, 1.0 eq.) in THF (70 mL) and CH$_3$OH (20 mL) was added HCl (4M, 10.0 mL). The mixture was stirred at 25° C. for 24 hrs. TLC indicated the starting material was consumed completely. The reaction mixture was quenched by addition H$_2$O 60 mL, and then extracted with DCM 150 mL (50 mL×3). The combined organic layers were washed with brine 100 mL, dried over Na$_2$SO$_4$, filtered and concentrated under reduced pressure to give a residue. The residue was purified by column chromatography (SiO$_2$, petroleum ether/ethyl acetate=20/1 to 5:1). (3R,3aS,4R,5R,7R,9R,9aR,12R)-5-hydroxy-3-methoxy-4,7,9,12-tetramethyl-7-(prop-2-yn-1-yl) octahydro-4,9a-propanocyclopenta[8]annulen-8(9H)-one (1.1 g, 3.0 mmol, 78.9% yield) was obtained as a white solid. $^1$H NMR (CDCl$_3$, 400 MHz) δ 4.58 (dd, J=5.6, 9.6 Hz, 1H), 3.49-3.41 (m, 1H), 3.22 (s, 3H), 3.02 (q, J=6.0 Hz, 1H), 2.76-2.67 (m, 1H), 2.51 (dd, J=2.4, 17.2 Hz, 1H), 2.42 (dd, J=9.6, 15.6 Hz, 1H), 2.26-2.17 (m, 1H), 2.09 (br. s., 1H), 2.06-1.94 (m, 2H), 1.74 (d, J=4.0 Hz, 1H), 1.71 (s, 1H), 1.57

(s, 4H), 1.51 (d, J=5.7 Hz, 2H), 1.38-1.31 (m, 1H), 1.26-1.19 (m, 3H), 1.17-1.11 (m, 3H), 1.08 (d, J=7.2 Hz, 3H), 1.02 (d, J=6.0 Hz, 3H).

To a solution of (3R,3aS,4R,5R,7R,9R,9aR,12R)-5-hydroxy-3-methoxy-4,7,9,12-tetramethyl-7-(prop-2-yn-1-yl) octahydro-4,9a-propanocyclopenta[8]annulen-8(9H)-one (1.1 g, 3.0 mmol, 1.0 eq.) and perfluorophenyl 2-(tosyloxy) acetate (2,3,4,5,6-pentafluoro-phenyl) 2-(p-tolylsulfonyloxy) acetate (1.8 g, 4.6 mmol, 1.5 eq.) in THF (50 mL) was added DMAP (370.1 mg, 3.0 mmol, 1.0 eq.). The mixture was stirred at 25° C. for 16 hours. TLC indicated the starting material was consumed completely. The reaction mixture was concentrated under reduced pressure to remove THF to give a residue. The residue was purified by column chromatography (SiO$_2$, petroleum ether/ethyl acetate=20/1 to 7:1) to give (3R,3aS,4R,5R,7R,9R,9aR,12R)-3-methoxy-4,7,9,12-tetramethyl-8-oxo-7-(prop-2-yn-1-yl)decahydro-4,9a-propanocyclopenta[8]annulen-5-yl 2-(tosyloxy)acetate (1.5 g, 2.7 mmol, 88.6% yield) as a white solid. $^1$H NMR (CDCl$_3$, 400 MHz) δ 7.85 (d, J=7.6 Hz, 2H), 7.38 (d, J=8.0 Hz, 2H), 5.77 (d, J=10.0 Hz, 1H), 4.54 (s, 2H), 3.45-3.37 (m, 1H), 3.22 (s, 3H), 3.12-3.01 (m, 2H), 2.50-2.37 (m, 1H), 2.33-2.21 (m, 2H), 2.06-1.95 (m, 3H), 1.71 (d, J=11.0 Hz, 1H), 1.60-1.45 (m, 2H), 1.30 (d, J=16.4 Hz, 2H), 1.22-1.12 (m, 8H), 1.10-1.03 (m, 4H), 0.87 (d, J=6.8 Hz, 3H), 0.73 (d, J=6.8 Hz, 3H).

To a solution of (3R,3aS,4R,5R,7R,9R,9aR,12R)-3-methoxy-4,7,9,12-tetramethyl-8-oxo-7-(prop-2-yn-1-yl) decahydro-4,9a-propanocyclopenta[8]annulen-5-yl 2-(tosyloxy)acetate (800.0 mg, 1.4 mmol, 1.0 eq.) and 7-fluoro-1-hydroxy-3H-2,1-benzoxaborol-6-ol (240.1 mg, 1.4 mmol, 1.0 eq.) in DMSO (10 mL) was added Na$_2$CO$_3$ (151.6 mg, 1.4 mmol, 1.0 eq.). The mixture was stirred at 40° C. for 16 hours. HPLC indicated the starting material was consumed completely. The reaction mixture was quenched by addition H$_2$O 50 mL, and then adjusted pH=7, filtered to give crude product to give (3R,3aS,4R,5R,7R,9R,9aR,12R)-3-methoxy-4,7,9,12-tetramethyl-8-oxo-7-(prop-2-yn-1-yl) decahydro-4,9a-propanocyclopenta[8]annulen-5-yl 2-((7-fluoro-1-hydroxy-1,3-dihydrobenzo[c][1,2]oxaborol-6-yl) oxy)acetate (900.0 mg, crude) as light gray solid, which was used into the next step without further purification.

To a solution of (3R,3aS,4R,5R,7R,9R,9aR,12R)-3-methoxy-4,7,9,12-tetramethyl-8-oxo-7-(prop-2-yn-1-yl) decahydro-4,9a-propanocyclopenta[8]annulen-5-yl 2-((7-fluoro-1-hydroxyl-1,3-dihydrobenzo[c][1,2]oxaborol-6-yl) oxy)acetate (500.0 mg, 901.8 μmol, 1.0 eq.) in THF (20 mL) was added ZnCl$_2$/HCl (901.8 μmol, 15.0 mL). The mixture was stirred at 25° C. for 2 hours. HPLC indicated the starting material was consumed completely. The reaction mixture was quenched by addition H$_2$O 50 mL, and then extracted with DCM 150 mL (50 mL×3). The combined organic layers were washed with brine 80 mL, dried over Na$_2$SO$_4$, filtered and concentrated under reduced pressure to give a residue. The residue was purified by prep-HPLC (column: Waters Xbridge 150×25 mm, 5 μm; liquid phase: [A-10 mM NH$_4$HCO$_3$ in H$_2$O; B-ACN, B %: 20%-50%, 12 min) (3aR,4R,5R,7R,8S,9R,9aS,12R)-8-hydroxy-4,7,9,12-tetramethyl-3-oxo-7-(prop-2-yn-1-yl)decahydro-4,9a-propanocyclopenta[8]annulen-5-yl 2-((7-fluoro-1-hydroxy-1,3-dihydrobenzo[c][1,2]oxaborol-6-yl)oxy)acetate (170.0 mg, 314.6 μmol, 34.9% yield) as a white solid. $^1$H NMR (DMSO-d$_6$, 400 MHz) δ 9.26 (s, 1H), 7.23 (t, J=8.0 Hz, 1H), 7.12 (s, 1H), 5.65 (d, J=7.6 Hz, 1H), 4.93 (s, 2H), 4.85-4.64 (m, 4H), 3.43 (br. s., 1H), 2.63 (br. s., 1H), 2.41-2.25 (m, 3H), 2.23-2.01 (m, 4H), 1.88 (dd, J=7.6, 15.6 Hz, 1H), 1.73-1.56 (m, 3H), 1.54-1.39 (m, 3H), 1.34-1.20 (m, 2H), 1.07-0.97 (m, 4H), 0.88-0.74 (m, 3H), 0.63 (d, J=6.0 Hz, 3H). MS (ESI): mass calcd. for C$_{30}$H$_{38}$BFO$_7$ 540.43, m/z found 539.4 [M−H]$^−$. HPLC: 96.49% (220 nm), 84.56% (254 nm).

23. (3aR,4R,5R,7S,8S,9R,9aS,12R)-8-hydroxy-7-(hydroxymethyl)-4,7,9,12-tetramethyl-3-oxodecahydro-4, 9a-propanocyclopenta[8]annulen-5-yl 2-((7-fluoro-1-hydroxy-1,3-dihydrobenzo[c][1,2]oxaborol-6-yl)oxy) acetate

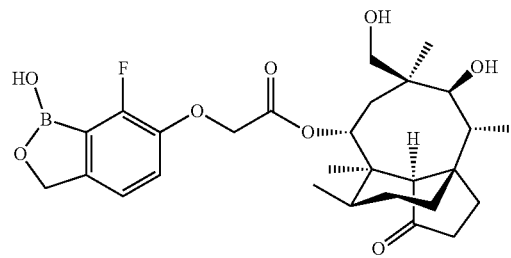

(3aR,4R,5R,7R,8S,9R,9aS,12R)-7-formyl-8-hydroxy-4, 7,9,12-tetramethyl-3-oxodecahydro-4,9a-propanocyclopenta[8]annulen-5-yl 2-(tosyloxy)acetate (300.0 mg, 561.1 μmol, 1.0 eq) and NaBH(OAc)$_3$ (237.8 mg, 1.1 mmol, 2.0 eq) in DCM (15.0 mL) were stirred at 20° C. for 2 hours. 20 mL water was added to the mixture, the aqueous layer was treated with DCM (10 mL×3), the combined organic phase was treated with brine, dried over Na$_2$SO$_4$ and concentrated in vacuo to give crude (3aR,4R,5R,7S,8S,9R,9aS,12R)-8-hydroxy-7-(hydroxymethyl)-4,7,9,12-tetramethyl-3-oxodecahydro-4,9a-propanocyclopenta[8]annulen-5-yl 2-(tosyloxy)acetate (300.0 mg, crude) as colorless oil.

(3aR,4R,5R,7S,8S,9R,9aS,12R)-8-hydroxy-7-(hydroxymethyl)-4,7,9,12-tetramethyl-3-oxodecahydro-4,9a-propanocyclopenta[8]annulen-5-yl 2-(tosyloxy)acetate (300.0 mg, 559.0 μmol, 1.0 eq), 7-fluoro-1-hydroxy-3H-2, 1-benzoxaborol-6-ol (93.9 mg, 559.0 μmol, 1.0 eq) and Na$_2$CO$_3$ (177.7 mg, 1.7 mmol, 3.0 eq) in DMSO (5.0 mL) were heated to 30-40° C. for 12 hours. 20 mL water was added to the mixture; white solid was precipitated and filtered to give crude product. The crude product was purified by prep-HPLC (column: Luna C18 100×30 mm, 5 μm; liquid phase: [A-TFA/H$_2$O=0.075% v/v; B-ACN] B %: 35%-70%, 12 min]) to give (3aR,4R,5R,7S,8S,9R,9aS, 12R)-8-hydroxy-7-(hydroxymethyl)-4,7,9,12-tetramethyl-3-oxodecahydro-4,9a-propanocyclopenta[8]annulen-5-yl2-((7-fluoro-1-hydroxy-1,3-dihydrobenzo[c][1,2]oxaborol-6-yl)oxy)acetate (47.0 mg, 88.3 μmol, 15.8% yield) as white solid. $^1$H NMR (DMSO-d$_6$, 400 MHz) δ 9.26 (s, 1H), 7.22-7.20 (m, 1H), 7.10-7.00 (m, 1H), 5.55-5.53 (m, 1H), 5.17-5.15 (m, 1H), 4.92 (s, 1H), 4.83-4.72 (m, 3H), 4.56-4.48 (m, 2H), 3.90 (d, J=11.0 Hz, 1H), 3.41 (d, J=6.2 Hz, 1H), 3.32 (d, J=11.0 Hz, 1H), 2.32-2.30 (m., 2H), 2.26-1.98 (m, 3H), 1.88-1.21 (m, 10H), 1.02 (s, 3H), 0.83 (d, J=7.1 Hz, 3H), 0.61 (d, J=6.6 Hz, 3H). MS (ESI): mass calcd. for C$_{28}$H$_{38}$BFO$_8$ 532.3, m/z found 531.3 [M−H]$^−$. HPLC: 100% in 220 nm; 100% in 254 nm.

24. (3aR,4R,5R,7S,8S,9R,9aS,12R)-8-hydroxy-7-(methoxymethyl)-4,7,9,12-tetramethyl-3-oxodecahydro-4,9a-propanocyclopenta[8]annulen-5-yl 2-((7-fluoro-1-hydroxy-1,3-dihydrobenzo[c][1,2]oxaborol-6-yl)oxy)acetate

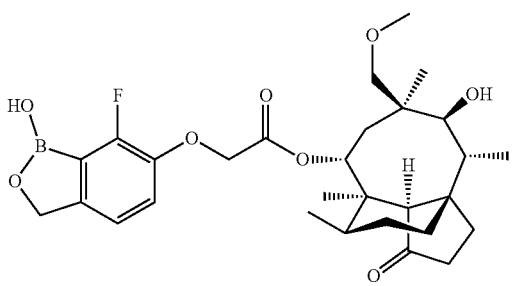

To a solution of (3R,3aS,4R,5R,7S,9R,9aR,12R)-3-methoxy-5-(methoxymethoxy)-4,7,9,12-tetramethyloctahydro-4,9a-propanocyclopenta[8]annulen-8(9H)-one (3.0 g, 8.5 mmol, 1.0 eq) in THF (20 mL) was added KHMDS (1M, 51.1 mL, 6.0 eq) at −78° C. over 30 mins, followed by MOMCl (3.4 g, 42.6 mmol, 3.2 mL, 5.0 eq). The mixture was stirred at 25° C. for 15 hrs. The reaction mixture was quenched by addition water 50 mL at 0° C., and then diluted with EtOAc 20 mL and extracted with EtOAc (50 mL×2). The combined organic layers were washed with brine (100 mL×2), dried over $Na_2SO_4$, filtered and concentrated under reduced pressure to give a residue. The residue was purified by column chromatography ($SiO_2$, petroleum ether/ethyl acetate=50/1 to 30:1) to afford (3R,3aS,4R,5R,7S,9R,9aR,12R)-3-methoxy-5-(methoxymethoxy)-7-(methoxymethyl)-4,7,9,12-tetramethyloctahydro-4,9a-propanocyclopenta[8]annulen-8(9H)-one (2.2 g, 5.6 mmol, 65.2% yield) as colorless oil.

To a solution of (3R,3aS,4R,5R,7S,9R,9aR,12R)-3-methoxy-5-(methoxymethoxy)-7-(methoxymethyl)-4,7,9,12-tetramethyloctahydro-4,9a-propanocyclopenta[8]annulen-8(9H)-one (2.2 g, 5.6 mmol, 1.0 eq) in THF (20 mL) and MeOH (5 mL) was added HCl (4M, 5 mL, 3.6 eq). The mixture was stirred at 25° C. for 20 hrs. The reaction mixture was quenched by addition water 50 mL at 20° C., and then diluted with EtOAc 20 mL and extracted with EtOAc (50 mL×2). The combined organic layers were washed with brine (100 mL×2), dried over $Na_2SO_4$, filtered and concentrated under reduced pressure to give a residue. The residue was purified by column chromatography ($SiO_2$, petroleum ether/ethyl acetate=30/1 to 10:1) to afford (3R,3aS,4R,5R,7S,9R,9aR,12R)-5-hydroxy-3-methoxy-7-(methoxymethyl)-4,7,9,12-tetramethyloctahydro-4,9a-propanocyclopenta[8]annulen-8(9H)-one (1.3 g, 3.7 mmol, 66.5% yield) as a white solid. $^1$H NMR ($CDCl_3$, 400 MHz) δ 4.66 (dd, J=5.6, 9.6 Hz, 1H), 3.89 (d, J=9.2 Hz, 1H), 3.49-3.41 (m, 1H), 3.33 (s, 3H), 3.21 (s, 3H), 3.06 (q, J=6.4 Hz, 1H), 2.38-2.19 (m, 2H), 2.07-1.94 (m, 2H), 1.72 (d, J=11.6 Hz, 1H), 1.64-1.45 (m, 5H), 1.40-1.16 (m, 4H), 1.14 (d, J=8.4 Hz, 7H), 1.08 (d, J=7.2 Hz, 3H), 0.96 (d, J=6.4 Hz, 3H).

To a solution of (3R,3aS,4R,5R,7S,9R,9aR,12R)-5-hydroxy-3-methoxy-7-(methoxymethyl)-4,7,9,12-tetramethyloctahydro-4,9a-propanocyclopenta[8]annulen-8(9H)-one (1.3 g, 3.7 mmol, 1.0 eq) and (2,3,4,5,6-pentafluorophenyl) 2-(p-tolylsulfonyloxy)acetate (2.2 g, 5.6 mmol, 1.5 eq) in THF (20 mL) was added DMAP (450.8 mg, 3.7 mmol, 1.0 eq). The mixture was stirred at 25° C. for 15 hrs. The solid was filtered and the filtrate was concentrated to give a residue. The residue was purified by column chromatography ($SiO_2$, petroleum ether/ethyl acetate=30/1 to 10:1) to afford (3R,3aS,4R,5R,7S,9R,9aR,12R)-3-methoxy-7-(methoxymethyl)-4,7,9,12-tetramethyl-8-oxodecahydro-4,9a-propanocyclopenta[8]annulen-5-yl 2-(tosyloxy)acetate (1.0 g, 1.8 mmol, 48.0% yield) as a white solid. $^1$H NMR ($CDCl_3$, 400 MHz) δ 7.85-7.80 (m, 2H), 7.36 (d, J=8.0 Hz, 2H), 5.78 (d, J=10.0 Hz, 1H), 4.50 (d, J=1.8 Hz, 2H), 4.10 (d, J=9.6 Hz, 1H), 3.46-3.36 (m, 1H), 3.29 (d, J=2.0 Hz, 3H), 3.19 (s, 3H), 3.10-3.03 (m, 1H), 2.45 (s, 3H), 2.36-2.18 (m, 3H), 2.00 (d, J=13.2 Hz, 2H), 1.68 (d, J=11.6 Hz, 1H), 1.54-1.38 (m, 3H), 1.35-1.00 (m, 10H), 0.95 (d, J=6.8 Hz, 3H), 0.71 (d, J=7.2 Hz, 3H).

A mixture of (3R,3aS,4R,5R,7S,9R,9aR,12R)-3-methoxy-7-(methoxymethyl)-4,7,9,12-tetramethyl-8-oxo-decahydro-4,9a-propanocyclopenta[8]annulen-5-yl 2-(tosyloxy)acetate (600.0 mg, 1.1 mmol, 1.0 eq), F—OHCBO (178.0 mg, 1.1 mmol, 1.0 eq), $Na_2CO_3$ (224.7 mg, 2.1 mmol, 2.0 eq) and KI (88.0 mg, 530.0 μmol, 0.5 eq) in DMSO (20 mL) was degassed and purged with $N_2$ for 3 times, and then the mixture was stirred at 40° C. for 4 hrs under $N_2$ atmosphere. The reaction mixture was quenched by addition water 50 mL at 0° C., then adjusted pH to 4-5 by 4N HCl, the solid was precipitated, filtered, the solid was washed with water for three times, then washed with petroleum ether for three times to afford (3R,3aS,4R,5R,7S,9R,9aR,12R)-3-methoxy-7-(methoxymethyl)-4,7,9,12-tetramethyl-8-oxo-decahydro-4,9a-propanocyclopenta[8]annulen-5-yl 2-((7-fluoro-1-hydroxy-1,3-dihydrobenzo[c][1,2]oxaborol-6-yl)oxy)acetate (500.0 mg, 892.1 μmol, 84.2% yield) as a pink solid.

To a solution of (3R,3aS,4R,5R,7S,9R,9aR,12R)-3-methoxy-7-(methoxymethyl)-4,7,9,12-tetramethyl-8-oxo-decahydro-4,9a-propanocyclopenta[8]annulen-5-yl 2-((7-fluoro-1-hydroxy-1,3-dihydrobenzo[c][1,2]oxaborol-6-yl)oxy)acetate (500.0 mg, 892.1 μmol, 1.0 eq) in THF (20 mL) was added $ZnCl_2$ in HCl (213.5 mmol, 10.0 mL, 239.3 eq). The mixture was stirred at 25° C. for 15 hrs. The reaction mixture was quenched by addition water 20 mL at 0° C., and then diluted with EtOAc 10 mL and extracted with EtOAc (20 mL×3). The combined organic layers were washed with brine (100 mL×1), dried over $Na_2SO_4$, filtered and concentrated under reduced pressure to give a residue. The residue was purified by prep-HPLC (column: Luna C18 100×30 mm, 5 μm; liquid phase: [A-TFA/$H_2O$=0.075% v/v; B-ACN, B %: 35%-75%, 12 min, MeCN was removed under reduced pressure, the residue was dried under freeze-drying to afford (3aR,4R,5R,7S,8S,9R,9aS,12R)-8-hydroxy-7-(methoxymethyl)-4,7,9,12-tetramethyl-3-oxodecahydro-4,9a-propanocyclopenta[8]annulen-5-yl 2-((7-fluoro-1-hydroxy-1,3-dihydrobenzo[c][1,2]oxaborol-6-yl)oxy)acetate (235.0 mg, 430.1 μmol, 48.2% yield) as a white solid. $^1$H NMR (DMSO-$d_6$, 400 MHz) δ 7.20 (t, J=8.0 Hz, 1H), 7.10 (d, J=8.4 Hz, 1H), 5.65 (d, J=8.4 Hz, 1H), 4.91 (s, 2H), 4.83-4.71 (m, 2H), 3.47-3.33 (m, 3H), 3.08 (s, 3H), 2.35 (br. s., 1H), 2.24-1.99 (m, 4H), 1.79-1.22 (m, 13H), 0.98 (s, 3H), 0.80 (d, J=7.2 Hz, 3H), 0.63 (d, J=7.2 Hz, 3H). MS (ESI): mass calcd. for $C_{29}H_{40}BFO_8$ 546.43, m/z found 545.3 [M−1]$^-$. HPLC: 99.7% (220 nm), 97.5% (254 nm).

25. (3aR,4R,5R,7R,8S,9R,9aS,12R)-8-hydroxy-7-(2-hydroxyethyl)-4,7,9,12-tetramethyl-3-oxodecahydro-4,9a-propanocyclopenta[8]annulen-5-yl 2-((7-fluoro-1-hydroxy-1,3-dihydrobenzo[c][1,2]oxaborol-6-yl)oxy)acetate

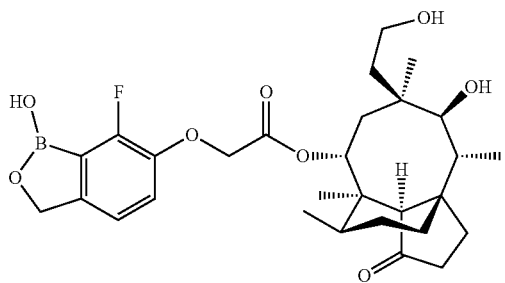

NaBH(OAc)$_3$ (453.6 mg, 2.1 mmol, 2.0 eq) was added to a solution of (3R,3aS,4R,5R,7S,9R,9aR,12R)-3-methoxy-4,7,9,12-tetramethyl-8-oxo-7-(2-oxoethyl)decahydro-4,9a-propanocyclopenta[8]annulen-5-yl 2-(tosyloxy)acetate (600.0 mg, 1.1 mmol, 1.0 eq) in DCM (20 mL) at 20° C. The mixture was stirred at this temperature for 12 hours. LCMS showed (3R,3aS,4R,5R,7S,9R,9aR,12R)-3-methoxy-4,7,9,12-tetramethyl-8-oxo-7-(2-oxoethyl)decahydro-4,9a-propanocyclopenta[8]annulen-5-yl 2-(tosyloxy)acetate consumed, one major peak was detected. The reaction was quenched by addition of 50 mL water, and treated with DCM (50 mL×3). The combined organic phase was dried over Na$_2$SO$_4$ and concentrated in vacuo to give (3R,3aS,4R,5R,7R,9R,9aR,12R)-7-(2-hydroxyethyl)-3-methoxy-4,7,9,12-tetramethyl-8-oxodecahydro-4,9a-propanocyclopenta[8]annulen-5-yl 2-(tosyloxy)acetate (600.0 mg, crude) as brown solid. MS (ESI): mass calcd. for C$_{30}$H$_{44}$O$_8$S 564.28, m/z found 563[M−H]$^-$.

7-fluoro-1-hydroxy-3H-2,1-benzoxaborol-6-ol (178.4 mg, 1.1 mmol, 1.0 eq), (3R,3aS,4R,5R,7R,9R,9aR,12R)-7-(2-hydroxyethyl)-3-methoxy-4,7,9,12-tetramethyl-8-oxodecahydro-4,9a-propanocyclopenta[8]annulen-5-yl 2-(tosyloxy)acetate (600.0 mg, 1.1 mmol, 1.0 eq) and Na$_2$CO$_3$ (337.8 mg, 3.2 mmol, 3.0 eq) in DMSO (20 mL) were stirred at 30-40° C. for 12 hours. The reaction was quenched by addition of 50 mL water, and adjusted by addition of 2N HCl till pH<4, white solid was precipitated and filtered to give (3R,3aS,4R,5R,7R,9R,9aR,12R)-7-(2-hydroxyethyl)-3-methoxy-4,7,9,12-tetramethyl-8-oxodecahydro-4,9a-propanocyclopenta[8]annulen-5-yl 2-((7-fluoro-1-hydroxy-1,3-dihydrobenzo[c][1,2]oxaborol-6-yl)oxy)acetate (600.00 mg, crude) as brown solid.

ZnCl$_2$ saturated in Con.HCl (1.1 mmol, 10.0 mL) was added to a solution of (3R,3aS,4R,5R,7R,9R,9aR,12R)-7-(2-hydroxyethyl)-3-methoxy-4,7,9,12-tetramethyl-8-oxodecahydro-4,9a-propanocyclopenta[8]annulen-5-yl 2-((7-fluoro-1-hydroxy-1,3-dihydrobenzo[c][1,2]oxaborol-6-yl)oxy)acetate (600.0 mg, 1.1 mmol, 1.0 eq) in THF (20 mL) at 20° C. The mixture was stirred at 20° C. for 6 hours. LCMS showed (3R,3aS,4R,5R,7R,9R,9aR,12R)-7-(2-hydroxyethyl)-3-methoxy-4,7,9,12-tetramethyl-8-oxodecahydro-4,9a-propanocyclopenta[8]annulen-5-yl 2-((7-fluoro-1-hydroxy-1,3-dihydrobenzo[c][1,2]oxaborol-6-yl)oxy)acetate consumed, one new peak MS=527 (M−H)$^-$. The mixture was treated with DCM 50 mL and 50 ml water, the aqueous phase was treated with DCM (30 mL×3). The combined organic phase was treated with Na$_2$SO$_4$ and concentrated in vacuo to give crude product. The crude product was purified by prep-HPLC (column: Luna C8 100×30 mm, 5 μm; liquid phase: [A-TFA/H$_2$O=0.075% v/v; B-ACN, B %: 50%-70%, 12 min]). The mixture was concentrated to 20 mL solution left and lyophilized to give (3aR,4R,5R,7R,8S,9R,9aS,12R)-8-hydroxy-7-(2-hydroxyethyl)-4,7,9,12-tetramethyl-3-oxodecahydro-4,9a-propanocyclopenta[8]annulen-5-yl 2-((7-fluoro-1-hydroxy-1,3-dihydrobenzo[c][1,2]oxaborol-6-yl)oxy)acetate (68.0 mg, 128.7 μmol, 12.0% yield) as white solid. $^1$H NMR (DMSO-d$_6$, 400 MHz) δ 9.27 (s, 1H), 7.27-7.21 (m, 1H), 7.10 (d, J=8.0 Hz, 1H), 5.71 (d, J=9.2 Hz, 1H), 5.18-5.06 (m, 2H), 4.92 (s, 2H), 4.87 (d, J=2.8 Hz, 2H), 3.67-3.63 (m, 3H), 2.41 (s, 1H), 2.25-1.88 (m, 5H), 1.66-1.62 (m, 2H), 1.42-1.29 (m, 8H), 1.03-1.00 (m, 4H), 0.81 (d, J=6.4 Hz, 3H), 0.67 (d, J=7.2 Hz, 3H). MS (ESI): mass calcd. for C$_{29}$H$_{40}$BFO$_8$ 546.28, m/z found 527[M−H$_2$O—H]$^-$. HPLC: 99.6% (220 nm), 100% (254 nm).

26. (3aR,4R,5R,7R,8S,9R,9aS,12R)-8-hydroxy-7-(2-methoxyethyl)-4,7,9,12-tetramethyl-3-oxodecahydro-4,9a-propanocyclopenta[8]annulen-5-yl 2-((7-fluoro-1-hydroxy-1,3-dihydrobenzo[c][1,2]oxaborol-6-yl)oxy)acetate

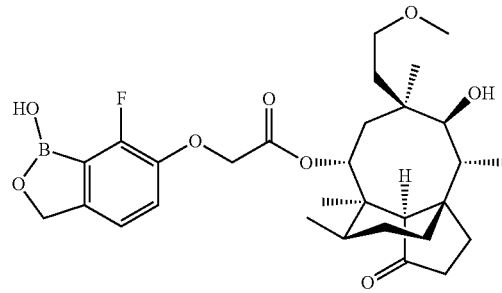

To a solution of (3R,3aS,4R,5R,7S,9R,9aR,12R)-3-methoxy-5-(methoxymethoxy)-4,7,9,12-tetramethyloctahydro-4,9a-propanocyclopenta[8]annulen-8(9H)-one (2.0 g, 5.7 mmol, 1.0 eq) in THF (30.0 mL) was added KHMDS (1 M, 34.0 mL, 6.0 eq) at −78° C. The mixture was stirred at −78° C. for 1 hour. Then 1-bromo-2-methoxy-ethane (3.9 g, 28.4 mmol, 2.7 mL, 5.0 eq) was added the mixture and stirred at 25° C. for 12 hours. TLC (petroleum ether/ethyl acetate=10/1, RF 0.35) showed the reaction was complete. H$_2$O (60 mL) was added to the mixture. The mixture was extracted with ethyl acetate (40 mL×3). The combined organic phase was washed with brine (20 mL), dried with anhydrous Na$_2$SO$_4$, filtered and concentrated in vacuum to give crude product, which was purified by silica gel chromatography (Petroleum ether) to afford (3R,3aS,4R,5R,7R,9R,9aR,12R)-3-methoxy-7-(2-methoxyethyl)-5-(methoxymethoxy)-4,7,9,12-tetramethyloctahydro-4,9a-propanocyclopenta[8]annulen-8(9H)-one (2.0 g, 4.9 mmol, 85.9% yield) as colorless oil.

To a mixture of (3R,3aS,4R,5R,7R,9R,9aR,12R)-3-methoxy-7-(2-methoxyethyl)-5-(methoxymethoxy)-4,7,9,12-tetramethyloctahydro-4,9a-propanocyclopenta[8]annulen-8(9H)-one (2.0 g, 4.9 mmol, 1.0 eq) in MeOH (10.0 mL) was added HCl (2 M, 10.0 mL, 4.1 eq) in one portion at 25° C. The mixture was stirred at 25° C. for 12 hours. TLC (petroleum ether/ethyl acetate=10/1, RF 0.3) showed the reaction was complete. H$_2$O (50 mL) was added the mixture, which was extracted with EtOAc (50 mL×3). The combined organic layers were washed with brine (30 mL) and dried over Na$_2$SO$_4$. After filtration via filter paper, the organic layer was concentrated under reduced pressure to provide crude product, which was purified by silica gel chromatography (petroleum ether/ethyl acetate=50/1) to afford product (3R,3aS,4R,5R,7R,9R,9aR,12R)-5-hydroxy-3-methoxy-7-(2-methoxyethyl)-4,7,9,12-tetramethyloctahydro-4,9a-propanocyclopenta[8]annulen-8(9H)-one (1.3 g, 3.6 mmol, 72.9% yield) as light yellow oil. $^1$H NMR (CDCl$_3$, 400 MHz) δ 4.62 (d, J=8.8 Hz, 1H), 3.57-3.40 (m, 2H), 3.33 (s, 3H), 3.21 (s, 3H), 3.16 (d, J=6.4 Hz, 1H), 2.38 (m, 1H), 2.24-1.91 (m, 4H), 1.89-1.45 (m, 8H), 1.19 (s, 3H), 1.14 (m, 3H), 1.11-1.04 (m, 6H), 0.98 (d, J=6.4 Hz, 3H).

To a solution of (3R,3aS,4R,5R,7R,9R,9aR,12R)-5-hydroxy-3-methoxy-7-(2-methoxyethyl)-4,7,9,12-tetramethyloctahydro-4,9a-propanocyclopenta[8]annulen-8(9H)-one (1.3 g, 3.5 mmol, 1.0 eq) and compound perfluorophenyl 2-(tosyloxy)acetate (1.8 g, 4.5 mmol, 1.3 eq) in THF (25.0 mL) was added DMAP (853.7 mg, 7.0 mmol, 2.0 eq) at 25° C. The mixture was stirred at 25° C. for 18 hours. H$_2$O (30 mL) was added the mixture. The aqueous layer was extracted with EtOAc (20 mL×3). The combined organic layers were washed with brine (10 mL) and dried over Na$_2$SO$_4$. After filtration via filter paper, the organic layer was concentrated under reduced pressure to provide crude product, which was purified by silica gel chromatography (petroleum ether/ethyl acetate=100/1, 20/1, 10/1) to afford product (3R,3aS,4R,5R,7R,9R,9aR,12R)-3-methoxy-7-(2-methoxyethyl)-4,7,9,12-tetramethyl-8-oxodecahydro-4,9a-propanocyclopenta[8]annulen-5-yl 2-(tosyloxy)acetate (560.0 mg, 967.6 μmol, 27.7% yield) as light yellow solid. NMR (CDCl$_3$, 400 MHz) δ 7.85 (d, J=7.9 Hz, 2H), 7.37 (d, J=7.9 Hz, 2H), 5.84 (d, J=10.1 Hz, 1H), 4.62 (d, J=9.3 Hz, 2H), 4.53 (s, 2H), 3.56-3.38 (m, 4H), 3.26 (s, 3H), 3.18-3.09 (m, 4H), 2.47 (s, 3H), 2.44-2.27 (m, 4H), 1.89-1.76 (m, 4H), 1.70 (d, J=11.6 Hz, 4H), 1.31-1.25 (m, 5H), 0.93-0.78 (m, 3H), 0.73 (d, J=6.6 Hz, 3H).

To a solution of compound 7-fluorobenzo[c][1,2]oxaborole-1,6(3H)-diol (145.0 mg, 863.5 μmol, 1.0 eq) and (3R,3aS,4R,5R,7R,9R,9aR,12R)-3-methoxy-7-(2-methoxyethyl)-4,7,9,12-tetramethyl-8-oxodecahydro-4,9a-propanocyclopenta[8]annulen-5-yl 2-(tosyloxy)acetate (549.7 mg, 949.8 μmol, 1.1 eq) in DMSO (10.0 mL) was added Na$_2$CO$_3$ (274.6 mg, 2.6 mmol, 3.0 eq) and KI (143.3 mg, 863.5 μmol, 1.0 eq) at 25° C. under N$_2$. The reaction mixture was stirred at 25° C. for 5 hours. H$_2$O (80 mL) was added the mixture, which was acidified with aqueous HCl (2 M) till pH=5-6 to precipitate a white solid. The reaction mixture was filtered and the filter cake was washed with H$_2$O (20 mL×4) to give a white solid, which was dissolved in DCM (20 mL) and dried over Na$_2$SO$_4$. After filtration via filter paper, the organic layer was concentrated under reduced pressure to provide product (3R,3aS,4R,5R,7R,9R,9aR,12R)-3-methoxy-7-(2-methoxyethyl)-4,7,9,12-tetramethyl-8-oxodecahydro-4,9a-propanocyclopenta[8]annulen-5-yl 2-((7-fluoro-1-hydroxy-1,3-dihydrobenzo[c][1,2]oxaborol-6-yl)oxy)acetate (450.0 mg, crude) as light yellow solid. The crude product was used directly in the next step.

To a mixture of (3R,3aS,4R,5R,7R,9R,9aR,12R)-3-methoxy-7-(2-methoxyethyl)-4,7,9,12-tetramethyl-8-oxodecahydro-4,9a-propanocyclopenta[8]annulen-5-yl 2-((7-fluoro-1-hydroxy-1,3-dihydrobenzo[c][1,2]oxaborol-6-yl)oxy)acetate (450.0 mg, 783.3 μmol, 1.0 eq) in THF (5.0 mL) was added ZnCl$_2$ (10.0 mL saturated in con.HCl) in one portion at 25° C. The mixture was stirred at 25° C. for 15 hours. HPLC and LCMS showed the reaction was complete. The mixture was added H$_2$O (20 mL). The aqueous phase was extracted with DCM (20 mL×3). The combined organic phase was washed with brine (10 mL×2), dried with anhydrous Na$_2$SO$_4$, filtered and concentrated in vacuum to give crude product, which was purified by prep-HPLC (column: Luna C18 100×30 mm, 5 μm; liquid phase: [A-TFA/H$_2$O=0.075% v/v; B-ACN] B %: 38%-68%, 12 min]). After prep-HPLC purification, the eluent was concentrated to remove organic solvent. The residual aqueous solution was lyophilized to give product (3 aR,4R,5R,7R,8 S,9R,9aS,12R)-8-hydroxy-7-(2-methoxyethyl)-4,7,9,12-tetramethyl-3-oxodecahydro-4,9a-propanocyclopenta[8]annulen-5-yl 2-((7-fluoro-1-hydroxy-1,3-dihydrobenzo[c][1,2]oxaborol-6-yl)oxy)acetate (48.0 mg, 84.8 μmol, 10.8% yield, 99.0% purity) as white solid. $^1$H NMR (DMSO-d$_6$ 400 MHz) δ 9.28 (s, 1H), 7.29-7.21 (m, 1H), 7.12 (d, J=8.0 Hz, 1H), 5.60 (d, J=8.0 Hz, 1H), 4.93 (s, 2H), 4.81 (d, J=4.2 Hz, 2H), 4.51 (d, J=6.4 Hz, 1H), 3.29 (m, 2H), 3.19 (d, J=6.0 Hz, 1H), 3.12 (s, 3H), 2.40-2.36 (m, 1H), 2.00 (s, 3H), 1.71-1.39 (m, 6H), 1.21-1.10 (m, 3H), 1.07-0.97 (m, 5H), 0.92 (s, 3H), 0.82 (d, J=6.4 Hz, 3H), 0.64 (d, J=6.4 Hz, 3H). MS (ESI): mass calcd. for C$_{30}$H$_{42}$BFO$_8$ 560.30, m/z found 559.3 [M–H]$^-$. HPLC: 99.0% (220 nm), 88.9% (254 nm).

27. (3aR,4R,5R,7R,8S,9R,9aS,12R)-8-hydroxy-4,7,9,12-tetramethyl-7-((R)-oxiran-2-yl)-3-oxodecahydro-4,9a-propanocyclopenta[8]annulen-5-yl 2-((7-fluoro-1-hydroxy-1,3-dihydrobenzo[c][1,2]oxaborol-6-yl)oxy)acetate 28. (3aR,4R,5R,7R,8S,9R,9aS,12R)-8-hydroxy-7-((R)-1-hydroxy-2-(methylamino)ethyl)-4,7,9,12-tetramethyl-3-oxodecahydro-4,9a-propanocyclopenta[8]annulen-5-yl 2-((7-fluoro-1-hydroxy-1,3-dihydrobenzo[c][1,2]oxaborol-6-yl)oxy)acetate

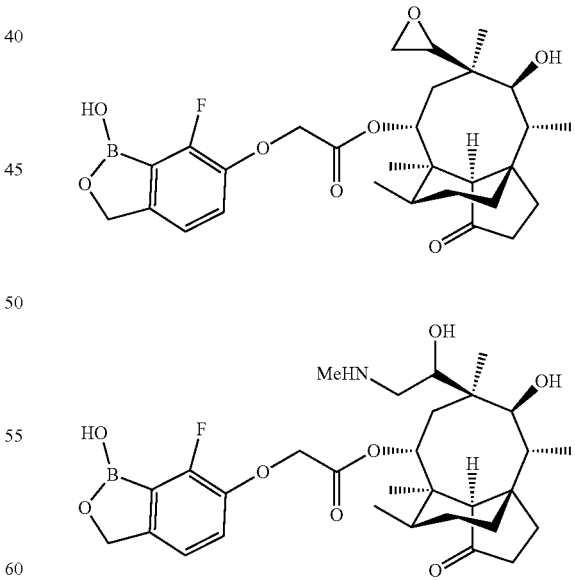

A mixture of (3aR,4R,5R,7S,8S,9R,9aS,12R)-8-hydroxy-4,7,9,12-tetramethyl-3-oxo-7-vinyldecahydro-4,9a-propanocyclopenta[8]annulen-5-yl 2-(tosyloxy)acetate (20.0 g, 37.5 mmol, 1.0 eq), m-CPBA (8.9 g, 41.3 mmol, 1.1 eq) in DCM (200.0 mL) was degassed and purged with N₂ for 3 times, and then the mixture was stirred at 25° C. for 12 hours under N₂ atmosphere. The mixture was poured into ice-water (w/w=1/1) (100 mL). The combined organic phase was washed with aq.NaHCO₃(20 mL) and brine (100 mL), dried with anhydrous Na₂SO₄, filtered and concentrated in vacuum. The residue was purified by silica gel chromatography (petroleum ether/Ethyl acetate=1/1) to give (3aR,4R,5R,7R,8S,9R,9aS,12R)-8-hydroxy-4,7,9,12-tetramethyl-7-((R)-oxiran-2-yl)-3-oxodecahydro-4,9a-propanocyclopenta[8]annulen-5-yl 2-(tosyloxy)acetate (11.0 g, 20.0 mmol, 53.4% yield) as a white solid.

A mixture of (3aR,4R,5R,7R,8S,9R,9aS,12R)-8-hydroxy-4,7,9,12-tetramethyl-7-((R)-oxiran-2-yl)-3-oxodecahydro-4,9a-propanocyclopenta[8]annulen-5-yl 2-(tosyloxy)acetate (2.0 g, 3.6 mmol, 1.0 eq.), 7-fluoro-1-hydroxy-3H-2,1-benzoxaborol-6-ol (612.9 mg, 3.6 mmol, 1.0 eq.), Na₂CO₃ (1.2 g, 10.9 mmol, 3.0 eq.) in DMSO (30.0 mL) was degassed and purged with N₂ for 3 times, and then the mixture was stirred at 30° C. for 12 hours under N₂ atmosphere. The mixture was poured into ice-water (w/w=1/1) (50 mL) and precipitating solid. The solid was collected to afford (3aR,4R,5R,7R,8S,9R,9aS,12R)-8-hydroxy-4,7,9,12-tetramethyl-7-((R)-oxiran-2-yl)-3-oxodecahydro-4,9a-propanocyclopenta[8]annulen-5-yl 2-((7-fluoro-1-hydroxy-1,3-dihydrobenzo[c][1,2]oxaborol-6-yl)oxy)acetate (1.7 g, crude) as a white solid. ¹H NMR (DMSO-d₆, 400 MHz) δ 9.27 (s, 1H), 7.25-7.19 (m, 1H), 7.13 (d, J=8.4 Hz, 1H), 5.6 (d, J=8.4 Hz, 1H), 4.97-4.90 (m, 2H), 4.89-4.75 (m, 2H), 4.35 (d, J=6.4 Hz, 1H), 3.48 (t, J=6.4 Hz, 1H), 3.13-3.10 (m, 1H), 2.43-2.37 (m, 1H), 2.30-1.99 (m, 5H), 1.76-1.57 (m, 3H), 1.55-1.23 (m, 6H), 1.18-0.97 (m, 3H), 0.93-0.75 (m, 6H), 0.64 (d, J=7.2 Hz, 3H) MS (ESI): mass calcd. for C₂₉H₃₈BFO₈ 544.26, m/z found 543.3 [M−H]⁻. HPLC: 96.6% (220 nm), 100.0% (254 nm).

A mixture of (3aR,4R,5R,7R,8S,9R,9aS,12R)-8-hydroxy-4,7,9,12-tetramethyl-7-((R)-oxiran-2-yl)-3-oxodecahydro-4,9a-propanocyclopenta[8]annulen-5-yl 2-((7-fluoro-1-hydroxy-1,3-dihydrobenzo[c][1,2]oxaborol-6-yl)oxy)acetate (500.0 mg, 918.4 µmol, 1.0 eq.), methanamine (950.8 mg, 9.2 mmol, 10.0 eq.) in MeOH (20.0 mL) was degassed and purged with N₂ for 3 times, and then the mixture was stirred at 40° C. for 12 hours under N₂ atmosphere. The solvent was concentrated under reduced pressure at 30° C. to give a residue, which was purified by prep-HPLC (column: Luna 250×50.0 mm, 10 µm; liquid phase: [A-H₂O+0.075% TFA; B-ACN] B %: 15%-45%, 20 min]) to give (3aR,4R,5R,7R,8S,9R,9aS,12R)-8-hydroxy-7-((R)-1-hydroxy-2-(methylamino)ethyl)-4,7,9,12-tetramethyl-3-oxodecahydro-4,9a-propanocyclopenta[8]annulen-5-yl 2-((7-fluoro-1-hydroxy-1,3-dihydrobenzo[c][1,2]oxaborol-6-yl)oxy)acetate (323.0 mg, 561.2 µmol, 61.1% yield) as a white solid. ¹H NMR (DMSO-d₆, 400 MHz) δ 7.25 (br. s., 1H), 7.12 (d, J=8.0 Hz, 1H), 5.44 (d, J=8.0 Hz, 1H), 4.94-4.80 (m, 4H), 4.52 (d, J=9.8 Hz, 1H), 3.60 (d, J=4.8 Hz, 1H), 2.85-2.76 (m, 1H), 2.68 (d, J=10.8 Hz, 1H), 2.40-2.30 (m, 4H), 2.27-1.88 (m, 4H), 1.73-1.44 (m, 4H), 1.38-1.13 (m, 7H), 0.99 (s, 4H), 0.89 (d, J=6.4 Hz, 3H), 0.62 (d, J=6.4 Hz, 3H) MS (ESI): mass calcd. for C₃₂H₄₄BF₄NO₁₀ 575.31, m/z found 576.4 [M+H]⁺. HPLC: 97.1% (220 nm), 93.6% (254 nm).

29. (3aR,4R,5R,7R,8S,9R,9aS,12R)-8-hydroxy-4,7,9,12-tetramethyl-7-((methylthio)methyl)-3-oxodecahydro-4,9a-propanocyclopenta[8]annulen-5-yl 2-((7-fluoro-1-hydroxy-1,3-dihydrobenzo[c][1,2]oxaborol-6-yl)oxy) acetate 30. (3aR,4R,5R,7R,8S,9R,9aS,12R)-8-hydroxy-4,7,9,12-tetramethyl-7-((methylsulfinyl)methyl)-3-oxodecahydro-4,9a-propanocyclopenta[8]annulen-5-yl 2-((7-fluoro-1-hydroxy-1,3-dihydrobenzo[c][1,2]oxaborol-6-yl)oxy) acetate

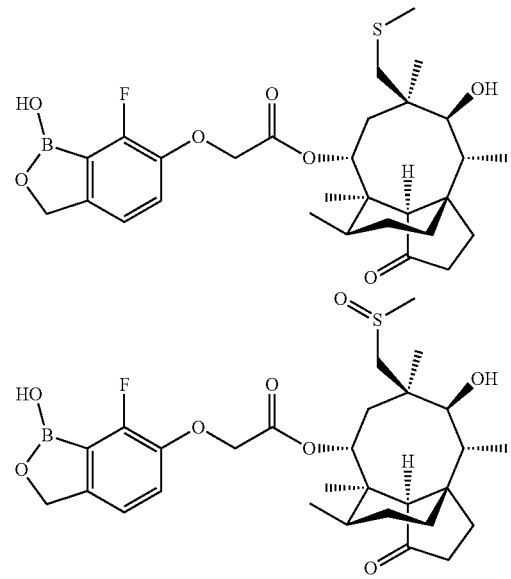

NaH (852.0 mg, 21.3 mmol, 60% purity, 5.0 eq) was added to a solution of (3R,3aS,4R,5R,7S,9R,9aR,12R)-3-methoxy-5-(methoxymethoxy)-4,7,9,12-tetramethyloctahydro-4,9a-propanocyclopenta[8]annulen-8(9H)-one (1.5 g, 4.3 mmol, 1.0 eq) in THF (20 mL) at 50° C., half an hour later chloro(methylsulfanyl)methane (2.5 g, 25.5 mmol, 2.1 mL, 6.0 eq) was added to the mixture and stirred at 50° C. for 12 hours. The reaction was quenched by addition of 100 mL water, and treated with EtOAc (30 mL×3). The combined organic phase was dried over Na₂SO₄ and concentrated in vacuo. The crude product was purified by flash column chromatography Petroleum ether:EtOAc=100:1 to give (3R,3aS,4R,5R,7R,9R,9aR,12R)-3-methoxy-5-(methoxymethoxy)-4,7,9,12-tetramethyl-7-((methylthio)methyl)octahydro-4,9a-propanocyclopenta[8]annulen-8(9H)-one (1.5 g, 3.6 mmol, 85.3% yield) as yellow oil. ¹H NMR (DMSO-d₆, 400 MHz) δ 4.73 (s, 2H), 4.34 (d, J=9.6 Hz, 1H), 3.50-3.38 (m, 4H), 3.24-3.19 (m, 3H), 3.05-2.96 (m, 2H), 2.80 (d, J=13.2 Hz, 1H), 2.37 (dd, J=9.6, 15.6 Hz, 1H), 2.27-2.18 (m, 1H), 2.17-2.13 (m, 3H), 2.07-1.89 (m, 5H), 1.67 (d, J=11.6 Hz, 1H), 1.54-1.44 (m, 4H), 1.19 (d, J=4.4 Hz, 7H), 1.04 (d, J=6.4 Hz, 3H), 0.99 (d, J=6.5 Hz, 3H).

(3R,3aS,4R,5R,7R,9R,9aR,12R)-3-methoxy-5-(methoxymethoxy)-4,7,9,12-tetramethyl-7-((methylthio) methyl)octahydro-4,9a-propanocyclopenta[8]annulen-8(9H)-one (1.9 g, 4.6 mmol, 1.0 eq) and HCl (2 M, 51.3 mL, 22.3 eq) in THF (10 mL) and MeOH (10 mL) were stirred at 20° C. for 12 hours. The mixture was treated with DCM 50 mL and water 100 mL. The aqueous phase was treated with DCM (50 mL×3). The combined organic phase was dried over Na₂SO₄ and concentrated in vacuo. The crude product was purified by flash column chromatography (Petroleum ether/EtOAc=100/1) to give (3R,3aS,4R,5R,7R,9R,9aR,12R)-5-hydroxy-3-methoxy-4,7,9,12-tetramethyl-7-((methylthio)methyl)octahydro-4,9a-propanocyclopenta[8]annulen-8(9H)-one (1.2 g, 3.4 mmol, 73.6% yield) as yellow oil.

DMAP (412.9 mg, 3.4 mmol, 1.0 eq) was added to a solution of (3R,3aS,4R,5R,7R,9R,9aR,12R)-5-hydroxy-3-methoxy-4,7,9,12-tetramethyl-7-((methylthio)methyl)octahydro-4,9a-propanocyclopenta[8]annulen-8(9H)-one (1.2 g, 3.4 mmol, 1.0 eq), perfluorophenyl 2-(tosyloxy)acetate (2.0 g, 5.1 mmol, 1.5 eq) in THF (30 mL). The mixture was stirred at 20° C. for 12 hours. The mixture was purified by flash column (petroleum ether/EtOAc=10/1) without any work-up to give (3R,3aS,4R,5R,7R,9R,9aR,12R)-3-methoxy-4,7,9,12-tetramethyl-7-((methylthio)methyl)-8-oxodecahydro-4,9a-propanocyclopenta[8]annulen-5-yl 2-(tosyloxy)acetate (1.5 g, 2.6 mmol, 76.4% yield) as yellow oil. $^1$H NMR (DMSO-$d_6$, 400 MHz) δ 7.85 (d, J=8.4 Hz, 2H), 7.40-7.35 (m, 2H), 5.82 (d, J=10.0 Hz, 1H), 4.60-4.53 (m, 2H), 3.46-3.37 (m, 2H), 3.22 (s, 4H), 3.16 (d, J=13.2 Hz, 1H), 3.09-3.00 (m, 2H), 2.89 (s, 1H), 2.76 (d, J=12.8 Hz, 1H), 2.50-2.44 (m, 3H), 2.43-2.33 (m, 2H), 2.07-1.91 (m, 3H), 1.54-1.44 (m, 3H), 1.22-1.00 (m, 12H), 0.73 (d, J=6.4 Hz, 3H).

$Na_2CO_3$ (286.3 mg, 2.7 mmol, 3.0 eq) was added to a solution of (3R,3aS,4R,5R,7R,9R,9aR,12R)-3-methoxy-4,7,9,12-tetramethyl-7-((methylthio)methyl)-8-oxodecahydro-4,9a-propanocyclopenta[8]annulen-5-yl 2-(tosyloxy)acetate (523.00 mg, 900.50 μmol, 1.0 eq) and 7-fluoro-1-hydroxy-3H-2,1-benzoxaborol-6-ol (151.2 mg, 900.5 μmol, 1.00 eq) in DMSO (20 mL). The mixture was stirred at 30-40° C. for 12 hours. The reaction was quenched by addition of 50 mL water, and adjusted by addition of 2N HCl till pH<4, white solid was precipitated and filtered to give crude (3R,3aS,4R,5R,7R,9R,9aR,12R)-3-methoxy-4,7,9,12-tetramethyl-7-((methylthio)methyl)-8-oxodecahydro-4,9a-propanocyclopenta[8]annulen-5-yl 2-((7-fluoro-1-hydroxy-1,3-dihydrobenzo[c][1,2]oxaborol-6-yl)oxy)acetate (520.0 mg, crude) as yellow solid.

$ZnCl_2$ saturated in Con HCl (867.3 μmol, 15.0 mL, 1.0 eq) was added to a solution of (3R,3aS,4R,5R,7R,9R,9aR,12R)-3-methoxy-4,7,9,12-tetramethyl-7-((methylthio)methyl)-8-oxodecahydro-4,9a-propanocyclopenta[8]annulen-5-yl 2-((7-fluoro-1-hydroxy-1,3-dihydrobenzo[c][1,2]oxaborol-6-yl)oxy)acetate (500.0 mg, 867.3 μmol, 1.0 eq) in THF (20.0 mL) at 20° C. for 12 hours. The reaction was treated with water 50 mL and 50 mL DCM. The aqueous solution was treated with DCM (30 mL×3). The combined organic phase was dried over $Na_2SO_4$ and concentrated in vacuo. The crude product was purified by prep-HPLC ((column: Luna C18 100×30 mm, 5 μm; liquid phase: [A-TFA/$H_2O$=0.075% v/v; B-ACN, B %: 30%-60%, 12 min]). The solvent was concentrated to 30 mL solution left and lyophilized to give (3aR,4R,5R,7R,8S,9R,9aS,12R)-8-hydroxy-4,7,9,12-tetramethyl-7-((methylthio)methyl)-3-oxodecahydro-4,9a-propanocyclopenta[8]annulen-5-yl 2-((7-fluoro-1-hydroxy-1,3-dihydrobenzo[c][1,2]oxaborol-6-yl)oxy)acetate (71.0 mg, 123.9 μmol, 14.3% yield, 98.1% purity) as white solid $^1$H NMR (DMSO-$d_6$, 400 MHz) δ 9.28 (s, 1H), 7.25 (t, J=8.0 Hz, 1H), 7.09 (d, J=8.0 Hz, 1H), 5.64 (d, J=7.6 Hz, 1H), 4.92 (s, 2H), 4.84-4.71 (m, 2H), 3.40 (d, J=6.0 Hz, 1H), 2.83-2.62 (m, 2H), 2.37 (br. s, 1H), 2.22-1.99 (m, 3H), 1.86 (s, 4H), 1.72-1.37 (m, 6H), 1.34-1.20 (m, 5H), 0.97-0.95 (m, 4H), 0.82 (d, J=7.2 Hz, 3H), 0.63 (d, J=6.4 Hz, 3H). MS (ESI): mass calcd. for $C_{29}H_{40}BFO_7S$ 562.26, m/z found 561.2 [M–H]$^-$. HPLC: 98.14% (220 nm), 94.91% (254 nm). and (3aR,4R,5R,7R,8S,9R,9aS,12R)-8-hydroxy-4,7,9,12-tetramethyl-7-((methylsulfinyl)methyl)-3-oxodecahydro-4,9a-propanocyclopenta[8]annulen-5-yl 2-((7-fluoro-1-hydroxy-1,3-dihydrobenzo[c][1,2]oxaborol-6-yl)oxy)acetate (96.0 mg, 154.7 μmol, 17.8% yield, 93.2% purity) as white solid. $^1$H NMR (DMSO-$d_6$, 400 MHz,) δ 7.46-7.22 (m, 1H), 7.16-7.05 (m, 1H), 5.85 (s, 1H), 5.46 (d, J=8.0 Hz, 1H), 4.99-4.59 (m, 5H), 3.36 (d, J=5.6 Hz, 2H), 2.99-2.79 (m, 2H), 2.43 (br. s., 1H), 2.35 (s, 2H), 2.24-1.98 (m, 4H), 1.80-1.12 (m, 12H), 1.03 (d, J=8.4 Hz, 1H), 0.83 (d, J=6.4 Hz, 3H), 0.63 (d, J=7.2 Hz, 3H). MS (ESI): mass calcd. for $C_{29}H_{40}BFO_8S$ 578.25, m/z found 577 [M–H]$^-$. HPLC: 93.2% (220 nm), 89.9% (254 nm).

31. (3aR,4R,5R,7R,8S,9R,9aS,12R)-7-formyl-8-hydroxy-4,7,9,12-tetramethyl-3-oxodecahydro-4,9a-propanocyclopenta[8]annulen-5-yl 2-((7-fluoro-1-hydroxy-1,3-dihydrobenzo[c][1,2]oxaborol-6-yl)oxy)acetate 32. (3aR,4R,5R,7S,8S,9R,9aS,12R)-8-hydroxy-4,7,9,12-tetramethyl-7-((methylamino)methyl)-3-oxodecahydro-4,9a-propanocyclopenta[8]annulen-5-yl 2-((7-fluoro-1-hydroxy-1,3-dihydrobenzo[c][1,2]oxaborol-6-yl)oxy) acetate 33. (3aR,4R,5R,7S,8S,9R,9aS,12R)-7-((dimethylamino)methyl)-8-hydroxy-4,7,9,12-tetramethyl-3-oxodecahydro-4,9a-propanocyclopenta[8]annulen-5-yl 2-((7-fluoro-1-hydroxy-1,3-dihydrobenzo[c][1,2]oxaborol-6-yl)oxy)acetate 34. (3aR,4R,5R,7S,8S,9R,9aS,12R)-7-((ethylamino)methyl)-8-hydroxy-4,7,9,12-tetramethyl-3-oxodecahydro-4,9a-propanocyclopenta[8]annulen-5-yl 2-((7-fluoro-1-hydroxy-1,3-dihydrobenzo[c][1,2]oxaborol-6-yl)oxy)acetate 35. (3aR,4R,5R,7S,8S,9R,9aS,12R)-8-hydroxy-4,7,9,12-tetramethyl-3-oxo-7-((propylamino)methyl)decahydro-4,9a-propanocyclopenta[8]annulen-5-yl 2-((7-fluoro-1-hydroxy-1,3-dihydrobenzo[c][1,2]oxaborol-6-yl)oxy) acetate 36. (3aR,4R,5R,7S,8S,9R,9aS,12R)-7-((butylamino)methyl)-8-hydroxy-4,7,9,12-tetramethyl-3-oxodecahydro-4,9a-propanocyclopenta[8]annulen-5-yl 2-((7-fluoro-1-hydroxy-1,3-dihydrobenzo[c][1,2]oxaborol-6-yl)oxy)acetate 37. (3aR,4R,5R,7S,8S,9R,9aS,12R)-7-((cyclopropylamino)methyl)-8-hydroxy-4,7,9,12-tetramethyl-3-oxodecahydro-4,9a-propanocyclopenta[8]annulen-5-yl 2-((7-fluoro-1-hydroxy-1,3-dihydrobenzo[c][1,2]oxaborol-6-yl)oxy)acetate

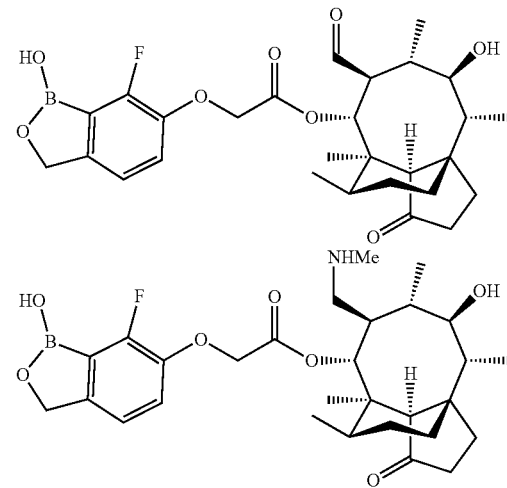

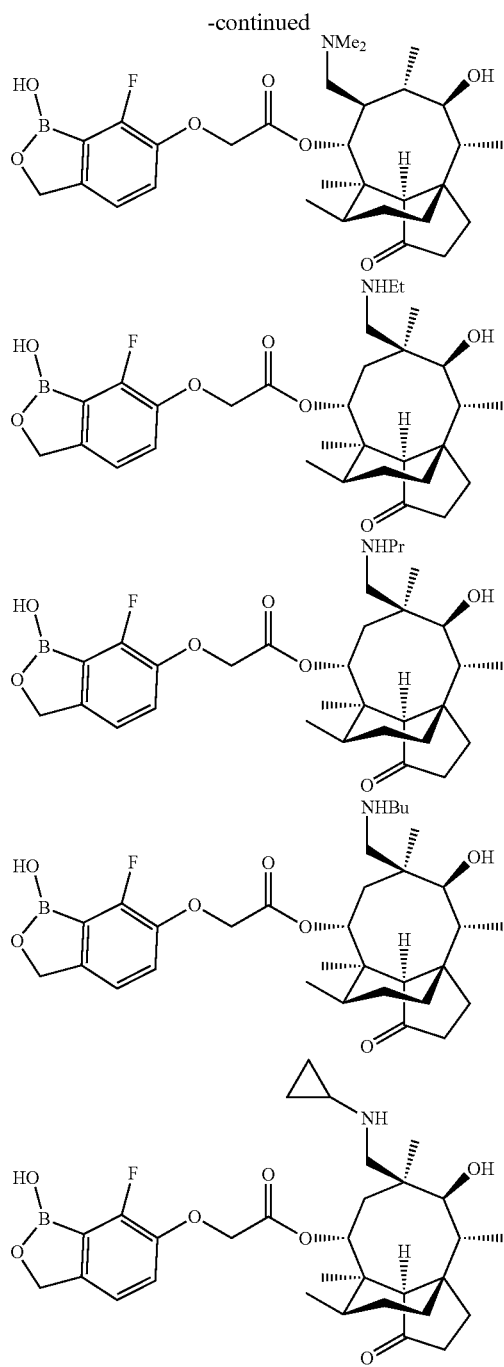

(3aR,4R,5R,7R,8S,9R,9aS,12R)-7-formyl-8-hydroxy-4,7,9,12-tetramethyl-3-oxodecahydro-4,9a-propanocyclopenta[8]annulen-5-yl 2-(tosyloxy)acetate (300.0 mg, 561.1 μmol, 1.0 eq), 7-fluoro-1-hydroxy-3H-2,1-benzoxaborol-6-ol (94.2 mg, 561.1 μmol, 1.0 eq) and $Na_2CO_3$ (178.41 mg, 1.68 mmol, 3.00 eq) in DMSO (10.0 mL) were heated to 30-40° C. for 12 hours. 20 mL water was added to the mixture, white solid precipitated and filtered to give crude product. The crude product was purified by prep-HPLC (column: Luna C18 100×30 mm, 5 μm; liquid phase: [A-TFA/$H_2O$=0.075% v/v; B-ACN] B %: 33%-53%, 12 min]) to give (3aR,4R,5R,7R,8S,9R,9aS,12R)-7-formyl-8-hydroxy-4,7,9,12-tetramethyl-3-oxodecahydro-4,9a-propanocyclopenta[8]annulen-5-yl 2-((7-fluoro-1-hydroxy-1,3-dihydrobenzo[c][1,2]oxaborol-6-yl)oxy)acetate (81.0 mg, 152.7 μmol, 27.2% yield, 10% purity) as white solid. $^1$H NMR (DMSO-$d_6$, 400 MHz) δ 9.67 (s, 1H), 9.27 (s, 1H), 7.24 (t, J=7.9 Hz, 1H), 7.11 (d, J=8.4 Hz, 1H), 5.42 (d, J=8.4 Hz, 1H), 4.92 (s, 2H), 4.86-4.75 (m, 3H), 3.57 (t, J=6.6 Hz, 1H), 2.43-2.03 (m, 4H), 1.76-1.21 (m, 10H), 1.09 (s, 3H), 0.95 (d, J=7.1 Hz, 3H), 0.89-0.80 (m, 2H), 0.62 (d, J=7.1 Hz, 3H). MS (ESI): mass calcd. for $C_{28}H_{36}BFO_8$ 530.3, m/z found 529.3 [M−H]$^-$. HPLC: 100% in 220 nm; 100% in 254 nm.

NaBH$_3$CN (142.2 mg, 2.3 mmol, 4.0 eq) was added to a solution of (3aR,4R,5R,7R,8S,9R,9aS,12R)-7-formyl-8-hydroxy-4,7,9,12-tetramethyl-3-oxodecahydro-4,9a-propanocyclopenta[8]annulen-5-yl 2-((7-fluoro-1-hydroxy-1,3-dihydrobenzo[c][1,2]oxaborol-6-yl)oxy)acetate (300.0 mg, 565.6 μmol, 1.0 eq) and Amine (4.0 eq) in MeOH (10.0 mL) and AcOH (1.0 mL). The mixture was stirred at 15° C. for 12 hours. 30 mL water was added to the mixture, and the mixture was treated with DCM (30 mL×3). The combined organic phase was concentrated to give crude product. The crude product was purified by prep-HPLC.

(3aR,4R,5R,7S,8S,9R,9aS,12R)-8-hydroxy-4,7,9,12-tetramethyl-7-((methylamino)methyl)-3-oxodecahydro-4,9a-propanocyclopenta[8]annulen-5-yl 2-((7-fluoro-1-hydroxy-1,3-dihydrobenzo[c][1,2]oxaborol-6-yl)oxy)acetate: Prep-HPLC conditions: (column: Luna C18 100×30 mm, 5 μm; liquid phase: [A-TFA/$H_2O$=0.075% v/v; B-ACN] B %: 26%-46%, 12 min]). The solvent was concentrated to about 15-20 mL solution left, and dried over lyophilizer to give (3aR,4R,5R,7S,8S,9R,9aS,12R)-8-hydroxy-4,7,9,12-tetramethyl-7-((methylamino)methyl)-3-oxodecahydro-4,9a-propanocyclopenta[8]annulen-5-yl2-((7-fluoro-1-hydroxy-1,3-dihydrobenzo[c][1,2]oxaborol-6-yl)oxy)acetate (52.0 mg, 95.3 μmol, 16.8% yield) as white TFA salt solid. $^1$H NMR DMSO-$d_6$, (400 MHz) δ 9.30 (br. s., 1H), 8.01 (br. s., 2H), 7.31 (t, J=8.0 Hz, 1H), 7.13 (d, J=7.8 Hz, 1H), 5.36 (d, J=8.0 Hz, 1H), 4.93 (s, 2H), 4.87-4.71 (m, 2H), 3.47 (d, J=5.3 Hz, 1H), 3.27 (d, J=8.8 Hz, 1H), 3.12 (d, J=10.5 Hz, 1H), 2.62-2.57 (m, 3H), 2.26-1.93 (m, 6H), 1.71-1.21 (m, 10H), 1.14-0.94 (m, 4H), 0.84 (d, J=6.3 Hz, 3H), 0.64 (d, J=7.0 Hz, 3H). MS (ESI): mass calcd. for $C_{31}H_{42}BF_4NO_9$ 545.3 m/z found 546.3 [M+H]$^+$. HPLC: 96.4% in 220 nm; 100% in 254 nm.

(3aR,4R,5R,7S,8S,9R,9aS,12R)-7-((dimethylamino)methyl)-8-hydroxy-4,7,9,12-tetramethyl-3-oxodecahydro-4,9a-propanocyclopenta[8]annulen-5-yl2-((7-fluoro-1-hydroxy-1,3-dihydrobenzo[c][1,2]oxaborol-6-yl)oxy)acetate: Prep-HPLC conditions: (column: Waters Xbridge Prep OBD 100×19 mm, 5 μm; liquid phase: [A-TFA/$H_2O$=0.075% v/v; B-ACN] B %: 22%-52%, 3 min]). The solvent was concentrated to about 20 mL solution left, and dried over lyophilizer to give (3 aR,4R,5R,7 S,8S,9R,9aS,12R)-7-((dimethylamino)methyl)-8-hydroxy-4,7,9,12-tetramethyl-3-oxodecahydro-4,9a-propanocyclopenta[8]annulen-5-yl2-((7-fluoro-1-hydroxy-1,3-dihydrobenzo[c][1,2]oxaborol-6-yl)oxy)acetate (64.0 mg, 114.4 μmol, 20.2% yield) as white TFA salt solid. $^1$H NMR (DMSO-$d_6$, 400 MHz) δ 9.29 (br. s., 1H), 8.81 (br. s., 1H), 7.27 (t, J=7.7 Hz, 1H), 7.12 (d, J=8.4 Hz, 1H), 5.94 (br. s., 1H), 5.35 (d, J=7.9 Hz, 1H), 4.93 (s, 2H), 4.83 (br. s., 2H), 3.72-3.40 (m, 4H), 3.10 (d, J=13.2 Hz, 1H), 2.86-2.84 (m, 4H), 2.41 (br. s., 1H), 2.27-1.99 (m, 4H), 1.77-1.18 (m, 12H), 1.12-0.96 (m, 2H), 0.88 (d, J=6.2 Hz, 3H), 0.65 (d, J=5.7 Hz, 3H). MS (ESI): mass calcd. for $C_{32}H_{44}BF_4NO_9$ 559.3 m/z found 560.3 [M+H]$^+$. HPLC: 96.8% in 220 nm; 100% in 254 nm.

(3 aR,4R,5R,7 S,8S,9R,9aS,12R)-7-((ethylamino)methyl)-8-hydroxy-4,7,9,12-tetramethyl-3-oxodecahydro-4, 9a-propanocyclopenta[8]annulen-5-yl2-((7-fluoro-1-hydroxy-1,3-dihydrobenzo[c][1,2]oxaborol-6-yl)oxy)acetate: Prep-HPLC conditions: (column: Luna C18 100×30 mm, 5 µm; liquid phase: [A-TFA/H$_2$O=0.075% v/v; B-ACN] B %: 10%-45%, 12 min]). The solvent was concentrated to about 20 mL left, and dried over lyophilizer to give (3aR,4R,5R,7S,8S,9R,9aS,12R)-7-((ethylamino)methyl)-8-hydroxy-4,7,9,12-tetramethyl-3-oxodecahydro-4,9a-propanocyclopenta[8]annulen-5-yl2-((7-fluoro-1-hydroxy-1,3-dihydrobenzo[c][1,2]oxaborol-6-yl)oxy)acetate (109.0 mg, 191.4 µmol, 33.8% yield, 98.2% purity) as white TFA salt solid. $^1$H NMR (DMSO-d$_6$, 400 MHz) δ 9.28 (br. s., 1H), 7.88 (br. s., 1H), 7.73 (br. s., 1H), 7.31 (t, J=8.2 Hz, 1H), 7.12 (d, J=8.4 Hz, 1H), 5.42 (br. s., 1H), 5.36 (d, J=8.4 Hz, 1H), 4.93 (s, 2H), 4.86-4.74 (m, 2H), 3.49 (d, J=5.7 Hz, 1H), 3.33-3.22 (m, 1H), 3.14-2.94 (m, 3H), 2.42 (br. s., 1H), 2.25-1.94 (m, 4H), 1.72-0.94 (m, 18H), 0.84 (d, J=7.1 Hz, 2H), 0.64 (d, J=7.1 Hz, 3H). MS (ESI): mass calcd. for C$_{32}$H$_{44}$BF$_4$NO$_9$ 559.3 m/z found 560.3 [M+H]$^+$. HPLC: 98.2% in 220 nm; 100% in 254 nm.

(3aR,4R,5R,7S,8S,9R,9aS,12R)-8-hydroxy-4,7,9,12-tetramethyl-3-oxo-7-((propylamino)methyl)decahydro-4,9a-propanocyclopenta[8]annulen-5-yl2-((7-fluoro-1-hydroxy-1,3-dihydrobenzo[c][1,2]oxaborol-6-yl)oxy)acetate: Prep-HPLC conditions: (column: Luna C18 100×30 mm, 5 µm; liquid phase: [A-TFA/H$_2$O=0.075% v/v; B-ACN] B %: 29%-49%,12 min]). The solvent was concentrated to about 15-20 mL solution left, and dried over lyophilizer to give (3aR,4R,5R,7S,8S,9R,9aS,12R)-8-hydroxy-4,7,9,12-tetramethyl-3-oxo-7-((propylamino)methyl)decahydro-4,9a-propanocyclopenta[8]annulen-5-yl2-((7-fluoro-1-hydroxy-1,3-dihydrobenzo[c][1,2]oxaborol-6-yl)oxy)acetate (171.0 mg, 294.9 µmol, 52.2% yield, 98.92% purity) as white TFA salt solid. $^1$H NMR (DMSO-d$_6$, 400 MHz,) δ 9.29 (br. s., 1H), 7.96 (br. s., 2H), 7.77 (br. s., 1H), 7.31 (t, J=7.9 Hz, 1H), 7.11 (d, J=7.9 Hz, 1H), 5.48 (br. s., 1H), 5.35 (d, J=7.9 Hz, 1H), 4.93 (s, 2H), 4.87-4.75 (m, 2H), 3.49 (d, J=5.7 Hz, 1H), 3.29 (t, J=10.1 Hz, 1H), 3.17-3.04 (m, 1H), 2.97-2.82 (m, 2H), 2.41 (br. s., 1H), 2.24-1.91 (m, 4H), 1.75-0.95 (m, 17H), 0.90-0.79 (m, 4H), 0.65 (d, J=7.1 Hz, 3H). MS (ESI): mass calcd. for C$_{33}$H$_{46}$BF$_4$NO$_9$ 573.3 m/z found 574.3 [M+H]$^+$. HPLC: 98.9% in 220 nm; 100% in 254 nm.

(3aR,4R,5R,7S,8S,9R,9aS,12R)-7-((cyclopropylamino)methyl)-8-hydroxy-4,7,9,12-tetramethyl-3-oxodecahydro-4,9a-propanocyclopenta[8]annulen-5-yl2-((7-fluoro-1-hydroxy-1,3-dihydrobenzo[c][1,2]oxaborol-6-yl)oxy)acetate: Prep-HPLC conditions: (column: Luna C18 100×30 mm, 5 µm; liquid phase: [A-TFA/H$_2$O=0.075% v/v; B-ACN] B %: 27%-47%, 12 min]). The solvent was concentrated to about 15-20 mL solution left, and dried over lyophilizer to give (3aR,4R,5R,7S,8S,9R,9aS,12R)-7-((cyclopropylamino)methyl)-8-hydroxy-4,7,9,12-tetramethyl-3-oxodecahydro-4,9a-propanocyclopenta[8]annulen-5-yl2-((7-fluoro-1-hydroxy-1,3-dihydrobenzo[c][1,2]oxaborol-6-yl)oxy)acetate (129.0 mg, 220.5 µmol, 39.0% yield, 97.7% purity) as white TFA salt solid. $^1$H NMR (DMSO-d$_6$, 400 MHz,) δ 9.29 (br. s., 1H), 8.29 (br. s., 1H), 7.99 (br. s., 1H), 7.32 (t, J=8.2 Hz, 1H), 7.12 (d, J=7.9 Hz, 1H), 5.42 (d, J=8.4 Hz, 2H), 4.93 (s, 2H), 4.87-4.75 (m, 2H), 3.48 (d, J=6.2 Hz, 1H), 3.39-3.22 (m, 2H), 2.73 (br. s., 1H), 2.42 (br. s., 1H), 2.25-1.91 (m, 5H), 1.74-1.22 (m, 10H), 1.13-0.92 (m, 6H), 0.89-0.68 (m, 6H), 0.65 (d, J=7.1 Hz, 3H). MS (ESI): mass calcd. for C$_{33}$H$_{44}$BF$_4$NO$_9$ 571.3 m/z found 572.3 [M+H]$^+$. HPLC: 97.7% in 220 nm; 100% in 254 nm.

(3aR,4R,5R,7S,8S,9R,9aS,12R)-7-((butylamino)methyl)-8-hydroxy-4,7,9,12-tetramethyl-3-oxodecahydro-4,9a-propanocyclopenta[8]annulen-5-yl2-((7-fluoro-1,3-dihydrobenzo[c][1,2]oxaborol-6-yl)oxy)acetate: Prep-HPLC conditions: (column: Luna C18 100×30 mm, 5 µm; liquid phase: [A-TFA/H$_2$O=0.075% v/v; B-ACN] B %: 32%-52%, 12 min]). The solvent was concentrated to about 15-20 mL solution left, and dried over lyophilizer to give (3aR,4R,5R,7S,8S,9R,9aS,12R)-7-((butylamino)methyl)-8-hydroxy-4,7,9,12-tetramethyl-3-oxodecahydro-4,9a-propanocyclopenta[8]annulen-5-yl2-((7-fluoro-1-hydroxy-1,3-dihydrobenzo[c][1,2]oxaborol-6-yl)oxy)acetate (111.0 mg, 186.2 µmol, 49.4% yield, 98.6% purity) as white TFA salt solid. $^1$H NMR (DMSO-d$_6$, 400 MHz) δ 9.28 (br. s., 1H), 7.97 (br. s., 1H), 7.76 (br. s., 1H), 7.31 (t, J=8.2 Hz, 1H), 7.11 (d, J=7.9 Hz, 1H), 5.35 (d, J=8.4 Hz, 1H), 4.92 (s, 2H), 4.86-4.75 (m, 2H), 3.49 (d, J=6.2 Hz, 1H), 3.28 (t, J=9.9 Hz, 1H), 3.18-3.06 (m, 1H), 2.93 (br. s., 2H), 2.42 (br. s., 1H), 2.25-1.91 (m, 5H), 1.73-1.20 (m, 15H), 1.17-0.96 (m, 4H), 0.90-0.79 (m, 5H), 0.65 (d, J=6.6 Hz, 3H). MS (ESI): mass calcd. for C$_{34}$H$_{48}$BF$_4$NO$_9$ 587.3 m/z found 588.5 [M+H]$^+$. HPLC: 98.6% in 220 nm; 91.6% in 254 nm.

38. (3aR,4R,5R,7S,8S,9R,9aS,12R)-7-(azetidin-1-ylmethyl)-8-hydroxy-4,7,9,12-tetramethyl-3-oxodecahydro-4,9a-propanocyclopenta[8]annulen-5-yl 2-((7-fluoro-1-hydroxy-1,3-dihydrobenzo[c][1,2]oxaborol-6-yl)oxy) acetate

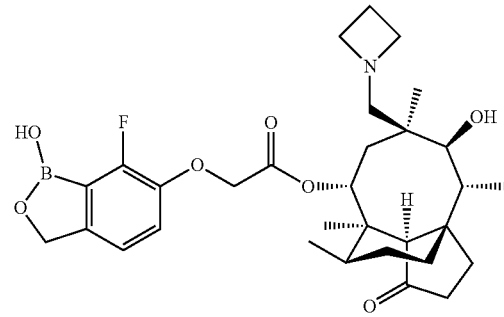

To a solution of (3aR,4R,5R,7R,8S,9R,9aS,12R)-7-formyl-8-hydroxy-4,7,9,12-tetramethyl-3-oxodecahydro-4,9a-propanocyclopenta[8]annulen-5-yl 2-((7-fluoro-1-hydroxy-1,3-dihydrobenzo[c][1,2]oxaborol-6-yl)oxy)acetate (500.0 mg, 942.7 µmol, 1.0 eq) in MeOH (10 mL) was added azetidine; hydrochloride (441.0 mg, 4.71 mmol, 5.00 eq), CH$_3$COOH (2.6 g, 43.7 mmol, 2.5 mL, 46 eq), NaBH$_3$CN (237.0 mg, 3.8 mmol, 4.0 eq) and sodium; triacetoxyboranuide (399.6 mg, 1.9 mmol, 2.0 eq) at 25° C. The mixture was stirred at 25° C. for 3 hrs. HPLC showed the reaction was completed. H$_2$O (20 mL) was added to the mixture. The aqueous layer was extracted with DCM (20 mL×3). The combined organic layers were washed with brine (20 mL) and dried over Na$_2$SO$_4$. After filtration via filter paper, the organic layer was concentrated under reduced pressure to provide crude product, which was combined and purified by prep-HPLC (column: Luna C8 100×30 mm, 5 µm; liquid phase: [A-TFA/H$_2$O=0.075% v/v; B-ACN] B %: 25%-55%, 12 min]). After prep-HPLC purification, the eluent was concentrated to remove organic solvent. The residual aqueous solution was lyophilized to give 1-(((3aR,4R,5R,7S,8S,9R,9aS,12R)-5-(2-((7-fluoro-1-hydroxy-1,3-dihydrobenzo[c][1,2]oxaborol-6-yl)oxy)acetoxy)-8-hydroxy-4,7,9,12-tetramethyl-3-oxodecahydro-4,9a-propanocyclopenta[8]annulen-7-yl)methyl)azetidin-1-ium 2,2,2-trifluoroacetate (160.0 mg, 20.5% yield) as a white solid. $^1$H NMR (DMSO-d$_6$, 400 MHz) δ 9.01 (br. s., 1H), 7.34 (t, J=8.0 Hz, 1H), 7.15

(d, J=8.0 Hz, 1H), 5.28 (d, J=8.0 Hz, 1H), 4.94 (s, 2H), 4.90-4.77 (m, 2H), 4.30-3.40 (m, 7H), 2.40 (s, 1H), 2.31-1.93 (m, 5H), 1.72-1.23 (m, 11H), 1.17-0.95 (m, 5H), 0.84 (d, J=6.4 Hz, 3H), 0.65 (d, J=6.4 Hz, 3H). HPLC: 98.2% (220 nm), 100% (254 nm). MS (ESI): mass calcd. for $C_{31}H_{43}BFNO_7$ 571.3, m/z found 572.4 [M+H]$^+$.

39. (3aR,4R,5R,7R,8S,9R,9aS,12R)-7-(2-(azetidin-1-yl)ethyl)-8-hydroxy-4,7,9,12-tetramethyl-3-oxodecahydro-4,9a-propanocyclopenta[8]annulen-5-yl 2-((7-fluoro-1-hydroxy-1,3-dihydrobenzo[c][1,2]oxaborol-6-yl)oxy)acetate

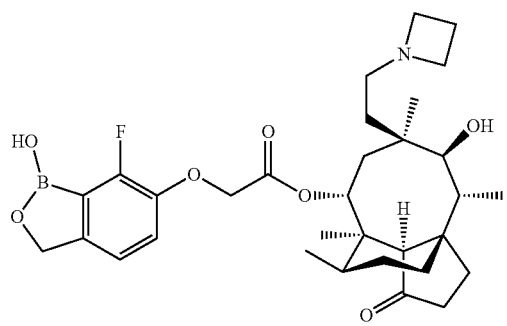

To a solution of (3R,3aS,4R,5R,7S,9R,9aR,12R)-3-methoxy-4,7,9,12-tetramethyl-8-oxo-7-(2-oxoethyl)decahydro-4,9a-propanocyclopenta[8]annulen-5-yl 2-((7-fluoro-1-hydroxy-1,3-dihydrobenzo[c][1,2]oxaborol-6-yl)oxy)acetate (300.0 mg, 537.2 μmol, 1.0 eq) in MeOH (5.0 mL) was added $CH_3COOH$ (525.0 mg, 8.7 mmol, 500.0 uL, 16.3 eq), azetidine; hydrochloride (251.3 mg, 2.7 mmol, 5.0 eq), $NaBH_3CN$ (135.0 mg, 2.2 mmol, 4.0 eq) and sodium triacetoxyboranuide (227.7 mg, 1.1 mmol, 2.0 eq) at 25° C. The mixture was stirred at 25° C. for 3 hrs. The mixture was added $H_2O$ (20 mL). The aqueous phase was extracted with DCM (20 mL×3). The combined organic phase was washed with brine (15 mL×2), dried with anhydrous $Na_2SO_4$, filtered and concentrated in vacuum to give compound (3R,3aS,4R,5R,7R,9R,9aR,12R)-7-(2-(azetidin-1-yl)ethyl)-3-methoxy-4,7,9,12-tetramethyl-8-oxodecahydro-4,9a-propanocyclopenta[8]annulen-5-yl 2-((7-fluoro-1-hydroxy-1,3-dihydrobenzo[c][1,2]oxaborol-6-yl)oxy)acetate (300.0 mg, crude) as a light yellow solid.

To a mixture of (3R,3aS,4R,5R,7R,9R,9aR,12R)-7-(2-(azetidin-1-yl)ethyl)-3-methoxy-4,7,9,12-tetramethyl-8-oxodecahydro-4,9a-propanocyclopenta[8]annulen-5-yl 2-((7-fluoro-1-hydroxy-1,3-dihydrobenzo[c][1,2]oxaborol-6-yl)oxy)acetate (300.0 mg, 500.4 μmol, 1.0 eq) in THF (5.0 mL) was added $ZnCl_2$ (29.1 mg, 10.0 mL, saturated in con.HCl) in one portion at 25° C. The mixture was stirred at 25° C. for 12 hrs. HPLC and LCMS showed the reaction was complete. The mixture was added $H_2O$ (20 mL). The aqueous phase was extracted with DCM (20 mL×3). The combined organic phase was washed with brine (10 mL×2), dried with anhydrous $Na_2SO_4$, filtered and concentrated in vacuum to give crude product, which was purified by prep-HPLC (column: Luna C18 100×30 mm, 5 μm; liquid phase: [A-HCl/$H_2O$=0.040% v/v; B-ACN] B %: 16%-46%, 11 min]). After prep-HPLC purification, the eluent was concentrated to remove organic solvent, and 0.2 mL of 4 N hydrochloride acid was added, the residual aqueous solution was lyophilized to give product (3aR,4R,5R,7R,8S,9R,9aS,12R)-7-(2-(azetidin-1-yl)ethyl)-8-hydroxy-4,7,9,12-tetramethyl-3-oxodecahydro-4,9a-propanocyclopenta[8]annulen-5-yl 2-((7-fluoro-1-hydroxy-1,3-dihydrobenzo[c][1,2]oxaborol-6-yl)oxy)acetate (83.0 mg, 131.2 μmol, 26.2% yield, 98.3% purity) as white solid. $^1$H NMR (DMSO-$d_6$, 400 MHz) δ 9.30 (br. s., 1H), 7.31 (t, J=8.0 Hz, 1H), 7.16 (d, J=8.0 Hz, 1H), 5.51 (d, J=8.0 Hz, 1H), 4.98-4.82 (m, 4H), 3.89-3.68 (m, 2H), 2.44-2.39 (m, 1H), 2.08 (m, 7H), 1.36 (s, 13H), 1.18-0.91 (m, 8H), 0.83 (d, J=6.5 Hz, 3H), 0.66 (d, J=6.5 Hz, 3H). MS (ESI): mass calcd. for $C_{32}H_{46}BClFNO_7$ 621.3, m/z found 586.3 [M+H]$^+$. HPLC: 98.3% (220 nm), 100% (254 nm).

40. (3aR,4R,5R,7R,8S,9R,9aS,12R)-8-hydroxy-4,7,9,12-tetramethyl-3-oxo-7-(2-(piperidin-1-yl)ethyl)decahydro-4,9a-propanocyclopenta[8]annulen-5-yl 2-((7-fluoro-1-hydroxy-1,3-dihydrobenzo[c][1,2]oxaborol-6-yl)oxy)acetate

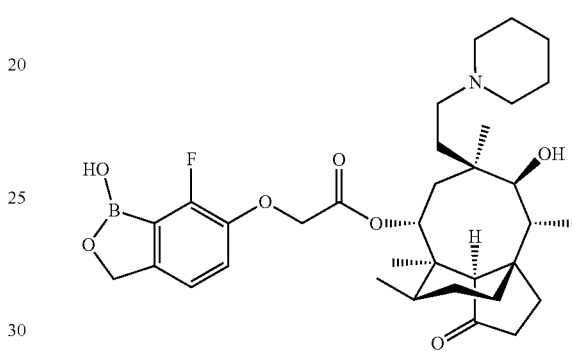

To a solution of (3R,3aS,4R,5R,7S,9R,9aR,12R)-3-methoxy-4,7,9,12-tetramethyl-8-oxo-7-(2-oxoethyl)decahydro-4,9a-propanocyclopenta[8]annulen-5-yl 2-((7-fluoro-1-hydroxy-1,3-dihydrobenzo[c][1,2]oxaborol-6-yl)oxy)acetate (300.0 mg, 537.2 μmol, 1.0 eq) in MeOH (5.0 mL) was added $CH_3COOH$ (525.0 mg, 8.7 mmol, 500.0 uL, 16.3 eq), sodium triacetoxyboranuide (227.7 mg, 1.1 mmol, 2.0 eq) and piperidine (228.7 mg, 2.7 mmol, 265.9 uL, 5.00 eq) at 25° C. The mixture was stirred at 25° C. for 3 hrs. The mixture was added $H_2O$ (20 mL). The aqueous phase was extracted with DCM (20 mL×3). The combined organic phase was washed with brine (15 mL×2), dried with anhydrous $Na_2SO_4$, filtered and concentrated in vacuum to give compound (3R,3aS,4R,5R,7R,9R,9aR,12R)-3-methoxy-4,7,9,12-tetramethyl-8-oxo-7-(2-(piperidin-1-yl)ethyl)decahydro-4,9a-propanocyclopenta[8]annulen-5-yl 2-((7-fluoro-1-hydroxy-1,3-dihydro benzo[c][1,2]oxaborol-6-yl)oxy)acetate (300.0 mg, crude) as a light yellow solid.

To a mixture of compound (3R,3aS,4R,5R,7R,9R,9aR,12R)-3-methoxy-4,7,9,12-tetramethyl-8-oxo-7-(2-(piperidin-1-yl)ethyl)decahydro-4,9a-propanocyclopenta[8]annulen-5-yl 2-((7-fluoro-1-hydroxy-1,3-dihydrobenzo[c][1,2]oxaborol-6-yl)oxy)acetate (300.0 mg, 478.0 μmol, 1.0 eq) in THF (5.0 mL) was added $ZnCl_2$ (29.1 mg, 10.0 mL, saturated in con.HCl) in one portion at 25° C. The mixture was stirred at 25° C. for 12 hrs. HPLC and LCMS showed the reaction was complete. The mixture was added $H_2O$ (20 mL). The aqueous phase was extracted with DCM (20 mL×3). The combined organic phase was washed with brine (10 mL×2), dried with anhydrous $Na_2SO_4$, filtered and concentrated in vacuum to give crude product, which was purified by prep-HPLC (column: Luna C18 100×30 mm, 5 μm; liquid phase: [A-HCl/$H_2O$=0.040% v/v; B-ACN] B %: 19%-49%, 11 mini). After prep-HPLC purification, the eluent was concentrated to remove organic solvent. The residual aqueous solution was lyophilized to give (3aR,4R,5R,7R,8S,9R,9aS,12R)-8-hydroxy-4,7,9,12-tetramethyl-3-oxo-7-(2-(piperidin-1-yl)ethyl)decahydro-4,9a-propanocyclopenta[8]annulen-5-yl 2-((7-fluoro-1-hydroxy-1,3-dihydrobenzo[c][1,2]oxaborol-6-yl)oxy) acetate (160.0 mg, 240.3 µmol, 50.3% yield, 97.6% purity) as colorless oil. $^1$H NMR (DMSO-d$_6$, 400 MHz) δ 9.27 (br. s., 1H), 7.28 (t, J=8.2 Hz, 1H), 7.12 (d, J=7.9 Hz, 1H), 5.46 (d, J=8.4 Hz, 1H), 4.95-4.77 (m, 4H), 3.62 (t, J=6.6 Hz, 5H), 2.05 (s, 2H), 1.95 (br. s., 1H), 1.81-1.68 (m, 6H), 1.66-1.53 (m, 9H), 1.51-1.24 (m, 9H), 0.97-0.88 (m, 3H), 0.81 (d, J=7.1 Hz, 3H), 0.64 (d, J=6.6 Hz, 3H). MS (ESI): mass calcd. for $C_{34}H_{50}BClFNO_7$ 649.3, m/z found 614.5 [M+H]$^+$. HPLC: 97.6% (220 nm), 100% (254 nm).

41. (3aR,4R,5R,7R,8S,9R,9aS,12R)-8-hydroxy-4,7,9,12-tetramethyl-7-(2-morpholinoethyl)-3-oxodecahydro-4,9a-propanocyclopenta[8]annulen-5-yl 2-((7-fluoro-1-hydroxy-1,3-dihydrobenzo[c][1,2]oxaborol-6-yl)oxy) acetate

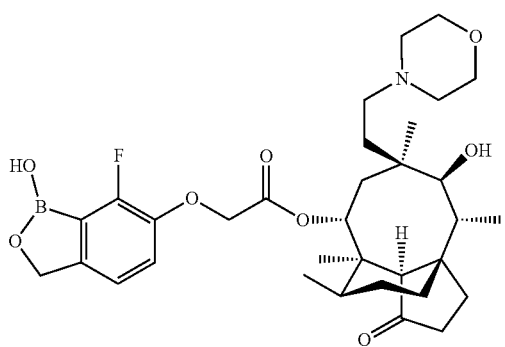

NaBH$_3$CN (112.5 mg, 1.8 mmol, 4.0 equiv) was added to a solution of (3R,3aS,4R,5R,7S,9R,9aR,12R)-3-methoxy-4,7,9,12-tetramethyl-8-oxo-7-(2-oxoethyl)decahydro-4,9a-propanocyclopenta[8]annulen-5-yl 2-((7-fluoro-1-hydroxy-1,3-dihydrobenzo[c][1,2] oxaborol-6-yl)oxy)acetate (250.0 mg, 447.7 µmol, 1.0 equiv) and morpholine (195.0 mg, 2.2 mmol, 196.9 uL, 5.0 equiv) in MeOH (20.0 mL) and AcOH (1.0 mL). The mixture was stirred at 20° C. for 12 hours. HPLC and LCMS showed major as desired. The mixture was treated with DCM 50 mL and water 100 mL. The aqueous phase was treated with DCM (50 mL×3). The combined organic phase was dried over Na$_2$SO$_4$ and concentrated in vacuo to give (3R,3aS,4R,5R,7R,9R,9aR,12R)-3-methoxy-4,7,9,12-tetramethyl-7-(2-morpholinoethyl)-8-oxodecahydro-4,9a-propanocyclopenta[8]annulen-5-yl 2-((7-fluoro-1-hydroxy-1,3-dihydrobenzo[c][1,2]oxaborol-6-yl)oxy)acetate (180.0 mg, 285.9 µmol, 63.9% yield) as yellow oil. MS (ESI): mass calcd. For $C_{34}H_{49}BFNO_8$ 629.3, m/z found 630 [M+H]$^+$ ZnCl$_2$ in saturated con.HCl (285.9 µmol, 5.0 mL, 1.0 equiv) was added to a solution of (3R,3aS,4R,5R,7R,9R,9aR,12R)-3-methoxy-4,7,9,12-tetramethyl-7-(2-morpholinoethyl)-8-oxodecahydro-4,9a-propanocyclopenta[8]annulen-5-yl 2-((7-fluoro-1-hydroxy-1,3-dihydrobenzo[c][1,2] oxaborol-6-yl)oxy)acetate (180.0 mg, 285.9 µmol, 1.0 equiv) in THF (15.0 mL) at 20° C. and stirred at 20° C. for 12 hours. The mixture was treated with DCM 50 mL and water 50 mL, the aqueous phase was extracted with DCM (30 mL×3). The organic phase was dried over Na$_2$SO$_4$ and concentrated in vacuo. The crude product was purified by prep-HPLC ((column: Luna C18 100×30 mm, 5 µm; liquid phase: [A-TFA/H$_2$O=0.075% v/v; B-ACN] B %: 25%-65%, 12 min])). The mixture was concentrated in vacuo till 20 mL solution left and 0.2 mL of 4 N hydrochloride acid was added, then the mixture was lyophilized to give (3aR,4R,5R,7R,8S,9R,9aS,12R)-8-hydroxy-4,7,9,12-tetramethyl-7-(2-morpholinoethyl)-3-oxodecahydro-4,9a-propanocyclopenta[8]annulen-5-yl 2-((7-fluoro-1-hydroxy-1,3-dihydrobenzo[c][1,2]oxaborol-6-yl)oxy)acetate (96.0 mg, 158.4 µmol, 55.4% yield, 97.2% purity) as white solid. $^1$H NMR (DMSO-d$_6$, 400 MHz) 10.20 (br. s., 1H), 9.28 (s, 1H), 7.31 (t, J=7.5 Hz, 1H), 7.15 (d, J=8.0 Hz, 1H), 5.52 (d, J=8.0 Hz, 1H), 5.02-4.74 (m, 4H), 4.38 (t, J=5.0 Hz, 2H), 3.64 (t, J=6.8 Hz, 2H), 3.41-3.34 (m, 4H), 2.40 (br. s., 1H), 2.25-1.85 (m, 3H), 1.81-1.70 (m, 4H), 1.69-1.39 (m, 9H), 1.34 (s, 4H), 0.97 (s, 3H), 0.93 (s, 3H), 0.83 (d, J=7.0 Hz, 3H), 0.64 (d, J=7.0 Hz, 3H). MS (ESI): mass calcd. for $C_{33}H_{48}BClFNO_8$ 651.3, m/z found 616.3 [M+H]$^+$ HPLC: 97.2% (220 nm); 100% (254 nm).

42. (3aR,4R,5R,7R,8S,9R,9aS,12R)-7-(2-(diethylamino)ethyl)-8-hydroxy-4,7,9,12-tetramethyl-3-oxodecahydro-4,9a-propanocyclopenta[8]annulen-5-yl 2-((7-fluoro-1-hydroxy-1,3-dihydrobenzo[c][1,2]oxaborol-6-yl)oxy) acetate

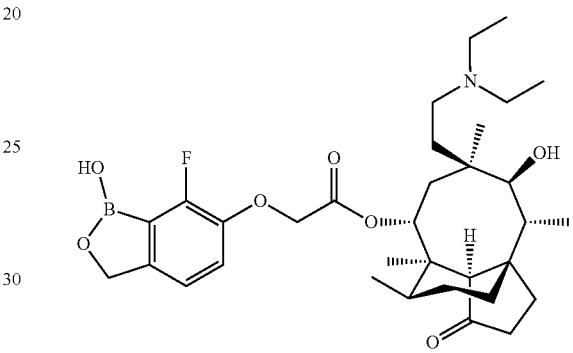

To a solution of (3R,3aS,4R,5R,7S,9R,9aR,12R)-3-methoxy-4,7,9,12-tetramethyl-8-oxo-7-(2-oxoethyl)decahydro-4,9a-propanocyclopenta[8]annulen-5-yl 2-((7-fluoro-1-hydroxy-1,3-dihydrobenzo[c][1,2]oxaborol-6-yl)oxy) acetate (300.0 mg, 537.2 µmol, 1.0 eq) in MeOH (5.0 mL) was CH$_3$COOH (525.0 mg, 8.7 mmol, 500.0 uL, 16.3 eq), N-ethylethanamine hydrochloride (294.4 mg, 2.7 mmol, 5.0 eq) and sodium triacetoxyboranuide (227.7 mg, 1.1 mmol, 2.0 eq) at 25° C. The mixture was stirred at 25° C. for 3 hrs. The mixture was added H$_2$O (20 mL). The aqueous phase was extracted with DCM (20 mL×3). The combined organic phase was washed with brine (15 mL×2), dried with anhydrous Na$_2$SO$_4$, filtered and concentrated in vacuum to give (3R,3aS,4R,5R,7R,9R,9aR,12R)-7-(2-(diethylamino)ethyl)-3-methoxy-4,7,9,12-tetramethyl-8-oxodecahydro-4,9a-propanocyclopenta[8]annulen-5-yl 2-((7-fluoro-1-hydroxy-1,3-dihydrobenzo[c][1,2]oxaborol-6-yl)oxy)acetate (300.0 mg, crude) as a light yellow solid.

To a mixture of (3R,3aS,4R,5R,7R,9R,9aR,12R)-7-(2-(diethylamino)ethyl)-3-methoxy-4,7,9,12-tetramethyl-8-oxodecahydro-4,9a-propanocyclopenta[8]annulen-5-yl 2-((7-fluoro-1-hydroxy-1,3-dihydrobenzo[c][1,2]oxaborol-6-yl)oxy)acetate (300.0 mg, 487.4 µmol, 1.0 eq) in THF (5.0 mL) was added ZnCl$_2$ (29.1 mg, 10.0 mL, saturated in con.HCl) in one portion at 25° C. The mixture was stirred at 25° C. for 12 hrs. HPLC and LCMS showed the reaction was complete. The mixture was added H$_2$O (20 mL). The aqueous phase was extracted with DCM (20 mL×3). The combined organic phase was washed with brine (10 mL×2), dried with anhydrous Na$_2$SO$_4$, filtered and concentrated in vacuum to give crude product, which was purified by prep-HPLC (column: Luna C18 100×30 mm, 5 µm; liquid phase: [A-HCl/H$_2$O=0.040% v/v; B-ACN] B %: 23%-53%, 11 min]). After prep-HPLC purification, the eluent was concentrated to remove organic solvent. The residual aqueous solution was lyophilized to give (3aR,4R,5R,7R,8S,9R,9aS,12R)-7-(2-(diethylamino)ethyl)-8-hydroxy-4,7,9,12-tetramethyl-3-oxodecahydro-4,9a-propanocyclopenta[8]annulen-5-yl 2-((7-fluoro-1-hydroxy-1,3-dihydrobenzo[c][1,2]oxaborol-6-yl)oxy)acetate (62.0 mg, 93.7 μmol, 19.2% yield, 96.5% purity) as white solid. $^1$H NMR (DMSO-$d_6$, 400 MHz) δ 7.21 (br. s., 1H), 7.08 (d, J=7.5 Hz, 1H), 4.89 (s, 3H), 4.80 (br. s., 2H), 4.38-4.28 (m, 3H), 3.62 (t, J=6.6 Hz, 4H), 1.78-1.66 (m, 3H), 1.65-1.53 (m, 4H), 1.53-1.36 (m, 9H), 1.35-1.21 (m, 3H), 0.97-0.76 (m, 12H), 0.62 (d, J=6.6 Hz, 3H). MS (ESI): mass calcd. for $C_{33}H_{50}BClFNO_7$ 637.3 m/z found 602.4 [M+1-1]$^+$. HPLC: 96.5% (220 nm), 100% (254 nm).

43. (3aR,4R,5R,7S,8S,9R,9aS,12R)-8-hydroxy-7-((hydroxyimino)methyl)-4,7,9,12-tetramethyl-3-oxodecahydro-4,9a-propanocyclopenta[8]annulen-5-yl 2-((7-fluoro-1-hydroxy-1,3-dihydrobenzo[c][1,2]oxaborol-6-yl)oxy)acetate

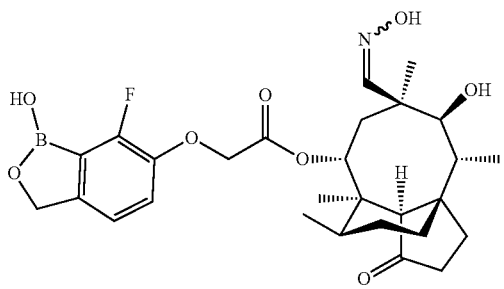

(3aR,4R,5R,7R,8S,9R,9aS,12R)-7-formyl-8-hydroxy-4,7,9,12-tetramethyl-3-oxodecahydro-4,9a-propanocyclopenta[8]annulen-5-yl 2-((7-fluoro-1-hydroxy-1,3-dihydrobenzo[c][1,2]oxaborol-6-yl)oxy)acetate (400.0 mg, 754.2 μmol, 1.0 eq) and NH$_2$OH.HCl (62.9 mg, 905.0 μmol, 1.2 eq) in H$_2$O (5.0 mL) and EtOH (10.0 mL) were stirred at 15° C. for 12 hours. HPLC and LCMS showed major as desired, (3aR,4R,5R,7R,8S,9R,9aS,12R)-7-formyl-8-hydroxy-4,7,9,12-tetramethyl-3-oxodecahydro-4,9a-propanocyclopenta[8]annulen-5-yl2-((7-fluoro-1-hydroxy-1,3-dihydrobenzo[c][1,2]oxaborol-6-yl)oxy)acetate consumed. 30 mL water was added to the mixture, white solid precipitated, the mixture was filtered to give crude product. The crude product was purified by prep-HPLC (column: Luna C8 100×30 mm, 5 μm; liquid phase: [A-TFA/H$_2$O=0.075% v/v; B-ACN] B %: 30%-50%, 12 min]). The solvent was concentrated to about 15 mL solution left, and dried by lyophilizer to give (3aR,4R,5R,7S,8S,9R,9aS,12R)-8-hydroxy-7-((hydroxyimino)methyl)-4,7,9,12-tetramethyl-3-oxodecahydro-4,9a-propanocyclopenta[8]annulen-5-yl2-((7-fluoro-1-hydroxy-1,3-dihydrobenzo[c][1,2]oxaborol-6-yl)oxy)acetate (99.0 mg, 174.3 μmol, 23.1% yield, 96.0% purity) as white solid. $^1$H NMR (DMSO-$d_6$, 400 MHz) δ 10.41 (br. s., 1H), 9.25 (br. s., 1H), 7.51 (s, 1H), 7.23 (t, J=7.9 Hz, 1H), 7.10 (d, J=7.9 Hz, 1H), 5.55 (d, J=7.9 Hz, 1H), 4.92 (s, 2H), 4.78 (s, 2H), 3.46 (d, J=6.6 Hz, 1H), 2.41 (br. s., 1H), 2.25-2.01 (m, 3H), 1.75-0.94 (m, 16H), 0.85 (d, J=7.1 Hz, 3H), 0.62 (d, J=6.6 Hz, 3H). MS (ESI): mass calcd. for $C_{28}H_{37}BFNO_8$ 545.26 m/z found 546.3 [M+H]$^+$. HPLC: 96.2% in 220 nm; 100% in 254 nm.

44. (3aR,4R,5R,7S,8S,9R,9aS,12R)-8-hydroxy-7-((methoxyimino)methyl)-4,7,9,12-tetramethyl-3-oxodecahydro-4,9a-propanocyclopenta[8]annulen-5-yl 2-((7-fluoro-1-hydroxy-1,3-dihydrobenzo[c][1,2]oxaborol-6-yl)oxy)acetate

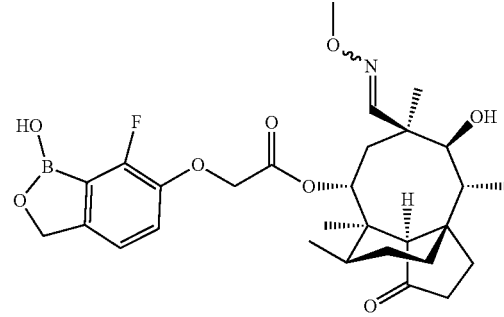

To a mixture of (3aR,4R,5R,7R,8S,9R,9aS,12R)-7-formyl-8-hydroxy-4,7,9,12-tetramethyl-3-oxodecahydro-4,9a-propanocyclopenta[8]annulen-5-yl 2-((7-fluoro-1-hydroxy-1,3-dihydrobenzo[c][1,2]oxaborol-6-yl)oxy)acetate (150.0 mg, 282.8 μmol, 1.0 eq.) and O-methyl hydroxylamine (35.4 mg, 424.2 μmol, 1.5 eq., HCl) in EtO H (5.0 mL) and water (10.0 mL) was stirred for 12 hours at 25° C. LCMS showed the reaction was completed and one main peak with desired MS was detected. The reaction mixture was diluted with EtOAc 20 mL and extracted with EtOAc (10 mL×2). The combined organic layers were washed with brine 15 mL, dried over Na$_2$SO$_4$, filtered and concentrated under reduced pressure to give a residue, which was purified by prep-HPLC (column: Luna 100×30.0 mm, 5 μm; liquid phase: [A-H$_2$O+0.075% TFA; B-ACN] B %: 47%-67%, 12 min]) to afford (3aR,4R,5R,7S,8S,9R,9aS,12R)-8-hydroxy-7-((methoxyimino)methyl)-4,7,9,12-tetramethyl-3-oxodecahydro-4,9a-propanocyclopenta[8]annulen-5-yl 2-((7-fluoro-1-hydroxy-1,3-dihydrobenzo[c][1,2]oxaborol-6-yl)oxy)acetate (50.0 mg, 89.4 μmol, 31.6% yield) as a white solid. $^1$H NMR (DMSO-$d_6$, 400 MHz,) δ 9.25 (br. s., 1H), 7.50 (s, 1H), 7.25 (t, J=8.0 Hz, 1H), 7.10 (d, J=8.4 Hz, 1H), 5.60 (d, J=8.0 Hz, 1H), 4.92 (s, 2H), 4.78 (s, 2H), 3.62 (s, 3H), 3.48 (d, J=5.6 Hz, 1H), 2.41 (br. s., 1H), 2.24-1.97 (m, 4H), 1.72-1.40 (m, 5H), 1.35-1.19 (m, 5H), 1.15-0.96 (m, 5H), 0.85 (d, J=6.4 Hz, 3H), 0.63 (d, J=5.6 Hz, 3H) MS (ESI): mass calcd. for $C_{29}H_{39}BFNO_8$ 559.28, m/z found 560.3 [M+H]$^+$. HPLC: 97.5% (220 nm), 100.0% (254 nm).

45. (3aR,4R,5R,7S,8S,9R,9aS,12R)-8-hydroxy-7-((methoxyamino)methyl)-4,7,9,12-tetramethyl-3-oxodecahydro-4,9a-propanocyclopenta[8]annulen-5-yl 2-((7-fluoro-1-hydroxy-1,3-dihydrobenzo[c][1,2]oxaborol-6-yl)oxy)acetate

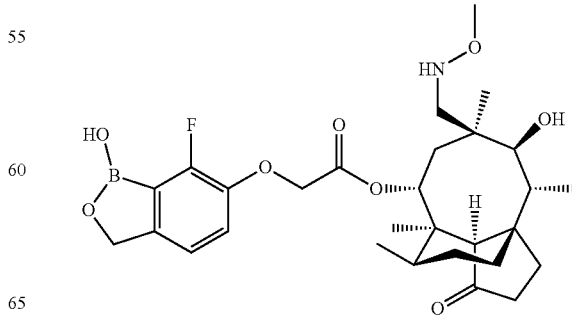

To a mixture of (3aR,4R,5R,7R,8S,9R,9aS,12R)-7-formyl-8-hydroxy-4,7,9,12-tetramethyl-3-oxodecahydro-4,9a-propanocyclopenta[8]annulen-5-yl 2-((7-fluoro-1-hydroxy-1,3-dihydro benzo[c][1,2]oxaborol-6-yl)oxy)acetate (150.0 mg, 282.8 μmol, 1.0 eq.) and O-methylhydroxylamine (35.43 mg, 424.2 μmol, 1.5 eq., HCl) in EtOH (5.0 mL) and water (10.0 mL) was stirred for 12 hours at 25° C. LCMS showed the reaction was completed and one main peak with desired MS was detected. The reaction mixture was diluted with EtOAc 20 mL and extracted with EtOAc (10 mL×2). The combined organic layers were washed with brine 15 mL, dried over $Na_2SO_4$, filtered and concentrated under reduced pressure to give a residue, which was purified by prep-HPLC (column: Luna 100×30.0 mm, 5 μm; liquid phase: [A-$H_2O$+0.075% TFA; B-ACN] B %: 47%-67%, 12 min]) to afford (3aR,4R,5R,7S,8S,9R,9aS,12R)-8-hydroxy-7-((Z)-(methoxyimino)methyl)-4,7,9,12-tetramethyl-3-oxodecahydro-4,9a-propanocyclopenta[8]annulen-5-yl 2-((7-fluoro-1-hydroxy-1,3-dihy-drobenzo[c][1,2]oxaborol-6-yl)oxy)acetate (50.0 mg, 89.4 μmol, 31.6% yield) as a white solid. $^1$H NMR (DMSO-$d_6$, 400 MHz) δ 9.24 (br. s., 1H), 7.50 (s, 1H), 7.25 (t, J=8.0 Hz, 1H), 7.10 (d, J=8.0 Hz, 1H), 5.60 (d, J=8.0 Hz, 1H), 4.92 (s, 2H), 4.78 (s, 2H), 3.62 (s, 3H), 3.48 (d, J=6.4 Hz, 1H), 2.40 (br. s., 1H), 2.24-1.98 (m, 4H), 1.74-1.42 (m, 5H), 1.38-1.17 (m, 6H), 1.10-0.98 (m, 4H), 0.85 (d, J=7.2 Hz, 3H), 0.62 (d, J=6.4 Hz, 3H). MS (ESI): mass calcd. for $C_{29}H_{39}BFNO_8$ 559.28, m/z found 560.3 [M+H]$^+$. HPLC: 97.5% (220 nm), 100.0% (254 nm).

To a solution of (3aR,4R,5R,7S,8S,9R,9aS,12R)-8-hydroxy-7-((Z)-(methoxyimino) methyl)-4,7,9,12-tetramethyl-3-oxodecahydro-4,9a-propanocyclopenta[8]annulen-5-yl 2-((7-fluoro-1-hydroxy-1,3-dihydrobenzo[c][1,2] oxaborol-6-yl)oxy)acetate (1.0 g, 1.8 mmol, 1.0 eq.) in EtOH (15.0 mL) was added pyridin-1-ium-1-ylboranuide (1.7 g, 17.9 mmol, 10.0 eq.). Subsequently, MeOH/HCl (4 M, 8.0 mL, 17.9 eq.) was added under $N_2$ atmosphere at 0° C. The mixture was stirred at 25° C. for 12 hours. The mixture was adjusted to pH-6 with saturated $NaHCO_3$ and extracted with ethyl acetate (20 mL×2). After concentrated in vacuo, the residue was purified by prep-HPLC (column: Luna 250×50.0 mm, 10 μm; liquid phase: [A-$H_2O$=0.075% TFA; B-ACN] B %: 20%-50%, 20 min]) to afford (3aR,4R,5R,7S,8S,9R,9aS,12R)-8-hydroxy-7-((methoxyamino)methyl)-4,7,9,12-tetramethyl-3-oxodecahydro-4,9a-propanocyclopenta[8]annulen-5-yl 2-((7-fluoro-1-hydroxy-1,3-dihydro-benzo[c][1,2]oxaborol-6-yl)oxy)acetate (432.0 mg, 769.4 μmol, 43.0% yield) as a white solid. $^1$H NMR (DMSO-$d_6$, 400 MHz) δ 7.28 (t, J=8.0 Hz, 1H), 7.12 (d, J=8.0 Hz, 1H), 5.45-5.36 (m, 1H), 4.93 (s, 2H), 4.81 (d, J=2.4 Hz, 2H), 4.31 (d, J=5.6 Hz, 1H), 3.77-3.71 (m, 4H), 3.50-3.44 (m, 1H), 3.26 (t, J=13.2 Hz, 1H), 2.40 (br. s., 1H), 2.23-1.93 (m, 4H), 1.77-1.23 (m, 10H), 1.19-0.97 (m, 4H), 0.87 (d, J=6.4 Hz, 3H), 0.65 (dd, J=3.2, 6.8 Hz, 3H). MS (ESI): mass calcd. for $C_{31}H_{42}BF_4NO_{10}$ 561.29, m/z found 562.4 [M+H]$^+$. HPLC: 95.4% (220 nm), 95.1% (254 nm).

46. (3aR,4R,5R,7S,8S,9R,9aS,12R)-8-hydroxy-7-((isopropoxyimino)methyl)-4,7,9,12-tetramethyl-3-oxodecahydro-4,9a-propanocyclopenta[8]annulen-5-yl 2-((7-fluoro-1-hydroxy-1,3-dihydrobenzo[c][1,2]oxaborol-6-yl)oxy)acetate

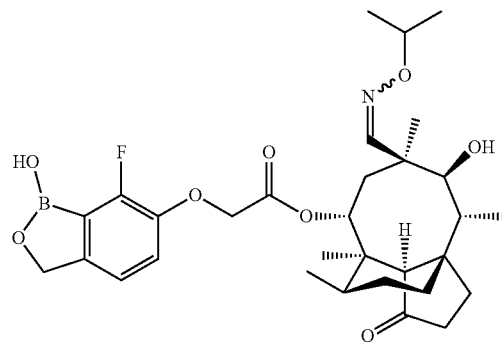

A mixture of (3aR,4R,5R,7R,8S,9R,9aS,12R)-7-formyl-8-hydroxy-4,7,9,12 tetramethyl-3-oxodecahydro-4,9a-propanocyclopenta[8]annulen-5-yl2-((7-fluoro-1-hydroxy-1,3-dihydrobenzo[c][1,2] oxaborol-6-yl)oxy)acetate (400.0 mg, 754.2 μmol, 1.0 eq.), O-isopropylhydroxylamine (100.0 mg, 905.0 μmol, 1.2 eq, HCl) in EtOH (15.0 mL) and $H_2O$ (10.0 mL) was degassed and purged with $N_2$ for 3 times, and then the mixture was stirred at 25° C. for 12 hours under $N_2$ atmosphere. The reaction mixture was diluted with EtOAc 20 mL and extracted with EtOAc (10 mL×2). The combined organic layers were washed with brine 15 mL, dried over $Na_2SO_4$, filtered and concentrated under reduced pressure to give a residue, which was purified by prep-HPLC (column: Luna 250×50.0 mm, 10 μm; liquid phase: [A-$H_2O$=0.075% TFA; B-ACN] B %: 40%-70%, 20 min]) to afford (3aR,4R,5R,7S,8S,9R,9aS,12R)-8-hydroxy-7-((isoprop-oxyimino) methyl)-4,7,9,12-tetramethyl-3-oxodecahydro-4,9a-propanocyclopenta[8]annulen-5-yl2-((7-fluoro-1-hydroxy-1,3-dihydrobenzo[c][1,2]oxaborol-6-yl)oxy)acetate (139.00 mg, 233.65 μmol, 30.98% yield, 98.75% purity) as a white solid. $^1$H NMR (DMSO-$d_6$, 400 MHz) δ 9.26 (br. s., 1H), 7.47 (s, 1H), 7.23 (t, J=8.0 Hz, 1H), 7.10 (d, J=8.0 Hz, 1H), 5.57 (d, J=8.0 Hz, 1H), 4.92 (s, 1H), 4.76 (s, 1H), 4.16 (dt, J=5.6, 12.1 Hz, 1H), 3.48 (d, J=5.2 Hz, 2H), 2.41 (br. s., 1H), 2.09 (d, J=15.6 Hz, 4H), 1.73-1.21 (m, 12H), 1.19-0.97 (m, 10H), 0.86 (d, J=6.4 Hz, 3H), 0.63 (d, J=6.4 Hz, 3H). MS (ESI): mass calcd. for $C_{31}H_{43}BFNO_8$ 587.48, m/z found 586.3 [M−H]$^−$. HPLC: 98.8% (220 nm), 85.1% (254 nm).

47. (3aR,4R,5R,7S,8S,9R,9aS,12R)-7-(aminomethyl)-8-hydroxy-4,7,9,12-tetramethyl-3-oxodecahydro-4,9a-propanocyclopenta[8]annulen-5-yl 2-((7-fluoro-1-hydroxy-1,3-dihydrobenzo[c][1,2]oxaborol-6-yl)oxy)acetate 48. (3aR,4R,5R,7S,8S,9R,9aS,12R)-7-(acetamidomethyl)-8-hydroxy-4,7,9,12-tetramethyl-3-oxodecahydro-4,9a-propanocyclopenta[8]annulen-5-yl 2-((7-fluoro-1-hydroxy-1,3-dihydrobenzo[c][1,2]oxaborol-6-yl)oxy)acetate

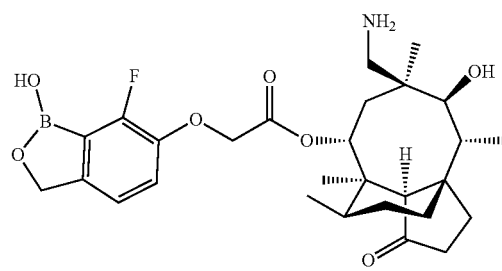

-continued

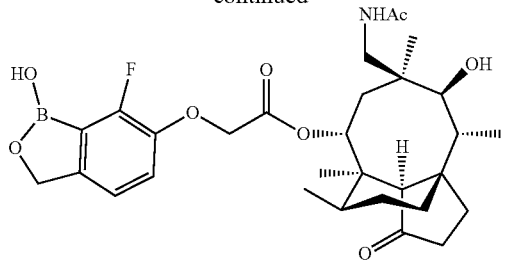

To a solution of (3aR,4R,5R,7S,8S,9R,9aS,12R)-8-hydroxy-7-((hydroxyimino)methyl)-4,7,9,12-tetramethyl-3-oxodecahydro-4,9a-propanocyclopenta[8]annulen-5-yl 2-((7-fluoro-1-hydroxy-1,3-dihydrobenzo[c][1,2]oxaborol-6-yl)oxy)acetate (570.0 mg, 1.0 mmol, 1.0 eq) in MeOH (10.0 mL) was added $R^a$—Ni (0.5 g) under $N_2$ atmosphere. The suspension was degassed and purged with $H_2$ for 3 times. The mixture was stirred under $H_2$ (50 psi) at 25° C. for 2 hours. The reaction mixture was filtered and the filter was concentrated to give a residue, which was purified by prep-HPLC (column: Luna 250×50.0 mm, 10 μm; liquid phase: [A-$H_2O$+0.075% TFA; B-ACN] B %: 15%-45%, 20 min]) to give (3aR,4R,5R,7S,8S,9R,9aS,12R)-7-(aminomethyl)-8-hydroxy-4,7,9,12-tetramethyl-3-oxodecahydro-4,9a-propanocyclopenta[8]annulen-5-yl 2-((7-fluoro-1-hydroxy-1,3-dihydro benzo[c][1,2]oxaborol-6-yl)oxy)acetate (300.0 mg, 464.8 μmol, 44.2% yield, TFA) as a light yellow solid. $^1$H NMR (DMSO-$d_6$, 400 MHz) δ 9.27 (br. s., 1H), 7.55 (br. s., 2H), 7.25 (t, J=7.6 Hz, 1H), 7.15-7.06 (m, 1H), 5.49-5.28 (m, 2H), 4.91 (br. s., 1H), 4.78 (br. s., 1H), 3.51 (br. s., 1H), 3.18 (br. s., 1H), 2.92 (br. s., 1H), 2.42 (d, J=8.4 Hz, 2H), 2.25-1.90 (m, 4H), 1.69-1.21 (m, 10H), 1.04 (br. s., 3H), 0.84 (d, J=5.6 Hz, 2H), 0.64 (d, J=6.4 Hz, 3H) MS (ESI): mass calcd. for $C_{30}H_{40}BF_4NO_9$ 531.28, m/z found 532.3 [M+H]$^+$. HPLC: 97.1% (220 nm), 93.6% (254 nm).

A mixture of (3aR,4R,5R,7S,8S,9R,9aS,12R)-7-(aminomethyl)-8-hydroxy-4,7,9,12-tetramethyl-3-oxodecahydro-4,9a-propanocyclopenta[8]annulen-5-yl 2-((7-fluoro-1-hydroxy-1,3-dihydrobenzo[c][1,2]oxaborol-6-yl)oxy)acetate (300.0 mg, 564.5 μmol, 1.0 eq.), $Ac_2O$ (63.4 mg, 620.9 μmol, 1.1 eq.), AcOH (67.8 mg, 1.1 mmol, 2.0 eq.) in DCM (20.0 mL) was degassed and purged with $N_2$ for 3 times, and then the mixture was stirred at 60° C. for 12 hours under $N_2$ atmosphere. LC-MS showed (3aR,4R,5R,7S,8S,9R,9aS,12R)-7-(aminomethyl)-8-hydroxy-4,7,9,12-tetramethyl-3-oxodecahydro-4,9a-propanocyclopenta[8]annulen-5-yl 2-((7-fluoro-1-hydroxy-1,3-dihydrobenzo[c][1,2]oxaborol-6-yl)oxy)acetate was consumed completely and one main peak with desired MS was detected. The solvent was removed. The residue was purified by prep-HPLC (column: Luna 250×50.0 mm, 10 m; liquid phase: [A-$H_2O$+0.075% TFA; B-ACN] B %: 25%-55%, 20 min]) to give (3aR,4R,5R,7S,8S,9R,9aS,12R)-7-(acetamidomethyl)-8-hydroxy-4,7,9,12-tetramethyl-3-oxodecahydro-4,9a-propanocyclopenta[8]annulen-5-yl 2-((7-fluoro-1-hydroxy-1,3-dihydrobenzo[c][1,2]oxaborol-6-yl)oxy)acetate (97.0 mg, 169.1 μmol, 29.9% yield) was obtained as a white solid. $^1$H NMR (DMSO-$d_6$, 400 MHz) δ 7.28 (t, J=8.4 Hz, 1H), 7.09 (d, J=8.4 Hz, 1H), 7.00-6.94 (m, 1H), 5.51 (d, J=8.4 Hz, 1H), 4.90 (s, 2H), 4.85-4.74 (m, 2H), 3.60 (dd, J=6.4, 13.8 Hz, 1H), 3.43 (d, J=5.6 Hz, 1H), 3.00 (dd, J=4.4, 13.8 Hz, 1H), 2.36 (br. s., 1H), 2.31 (br. s., 1H), 2.23-1.99 (m, 3H), 1.94-1.82 (m, 1H), 1.81-1.73 (m, 2H), 1.69-1.55 (m, 2H), 1.48 (br. s., 1H), 1.40-1.20 (m, 6H), 1.05-0.87 (m, 4H), 0.83 (d, J=6.4 Hz, 2H), 0.62 (d, J=6.4 Hz, 3H) MS (ESI): mass calcd. for $C_{30}H_{41}BFNO_8$ 573.29, m/z found 574.3 [M+H]$^+$. HPLC: 100.0% (220 nm), 100.0% (254 nm).

49. (3aR,4R,5R,7S,8S,9R,9aS,12R)-4,7,9,12-tetramethyl-7-(methylsulfonamidomethyl)-8-((methylsulfonyl)oxy)-3-oxodecahydro-4,9a-propanocyclopenta[8]annulen-5-yl 2-((7-fluoro-1-hydroxy-1,3-dihydrobenzo[c][1,2]oxaborol-6-yl)oxy)acetate
50. (3aR,4R,5R,7S,8S,9R,9aS,12R)-7-(aminomethyl)-4,7,9,12-tetramethyl-8-((methylsulfonyl)oxy)-3-oxodecahydro-4,9a-propanocyclopenta[8]annulen-5-yl 2-((7-fluoro-1-hydroxy-1,3-dihydrobenzo[c][1,2]oxaborol-6-yl)oxy)acetate

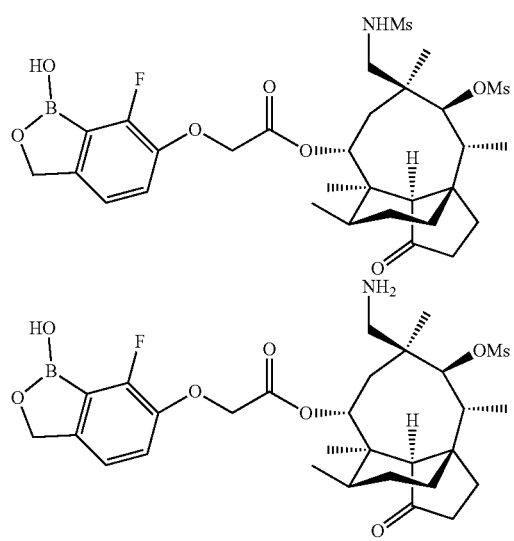

To a solution of (3aR,4R,5R,7S,8S,9R,9aS,12R)-7-(aminomethyl)-8-hydroxy-4,7,9,12-tetramethyl-3-oxodecahydro-4,9a-propanocyclopenta[8]annulen-5-yl2-((7-fluoro-1-hydroxy-1,3-dihydrobenzo[c][1,2]oxaborol-6-yl)oxy)acetate (100.0 mg, 188.2 μmol, 1.0 eq.) in THF (10.00 mL) was added $Na_2CO_3$ (79.8 mg, 752.7 μmol, 4.0 eq.) and MsCl (43.1 mg, 376.4 μmol, 2.0 eq.). The mixture was stirred at 0° C. for 1 hour. The reaction mixture was partitioned between EtOAc (10 mL) and water (10 mL). The organic phase was separated, washed with brine (10 mL), dried over $Na_2SO_4$, filtered and concentrated under reduced pressure to give a residue, which was purified by prep-HPLC (column: Luna 100×30.0 mm, 5 μm; liquid phase: [A-$H_2O$+0.075% TFA; B-ACN] B %: 41%-61%, 12 min]) to give (3aR,4R,5R,7S,8S,9R,9aS,12R)-4,7,9,12-tetramethyl-7-(methylsul fonamidomethyl)-8-((methylsulfonyl)oxy)-3-oxodecahydro-4,9a-propanocyclopenta[8]annulen-5-yl2-47-fluoro-1-hydroxy-1,3-dihydrobenzo[c][1,2]oxaborol-6-yl)oxy)acetate (19.0 mg, 27.6 μmol, 14.7% yield) as a white solid. $^1$H NMR (DMSO-$d_6$, 400 MHz) δ 9.27 (br. s., 1H), 7.34 (t, J=8.2 Hz, 1H), 7.12 (d, J=8.4 Hz, 1H), 6.42-6.36 (m, 1H), 5.53 (d, J=8.4 Hz, 1H), 4.93 (s, 2H), 4.80 (d, J=3.6 Hz, 2H), 4.74 (d, J=7.2 Hz, 1H), 3.40 (s., 1H), 3.20 (s, 3H), 3.16-3.07 (m, 1H), 2.85 (s, 3H), 2.41-2.38 (m, 1H), 2.23-2.00 (m, 5H), 1.96-1.84 (m, 1H), 1.68 (d, J=12.8 Hz, 1H), 1.59-1.24 (m, 8H), 1.05 (s, 3H), 0.97 (d, J=6.6 Hz, 3H), 0.64 (d, J=7.2 Hz, 3H). MS (ESI): mass calcd. for $C_{30}H_{43}BFNO_{11}S_2$ 687.24, m/z found 686.3 [M−H]$^-$. HPLC: 94.2% (220 nm), 52.7% (Weak absorbtion at 254 nm).

To a solution of (3aR,4R,5R,7S,8S,9R,9aS,12R)-7-(aminomethyl)-8-hydroxy-4,7,9,12-tetramethyl-3-oxodecahydro-4,9a-propanocyclopenta[8]annulen-5-yl2-((7-fluoro-1-hydroxy-1,3-dihydrobenzo[c][1,2]oxaborol-6-yl)oxy)acetate (600.0 mg, 1.1 mmol, 1.0 eq.) in THF (20 mL) was added NaHCO$_3$(284.8 mg, 3.4 mmol, 3.0 eq.) and MsCl (129.3 mg, 1.1 mmol, 1.0 eq.). The mixture was stirred at −78° C. for 1 hour. The reaction mixture was quenched by addition water (15 mL), and then extracted with EtOAc (15 mL×2). The combined organic layers were washed with brine (15 mL), dried over Na$_2$SO$_4$, filtered and concentrated under reduced pressure to give a residue, which was purified by prep-HPLC (column: Luna 250×50.0 mm, 5 μm; liquid phase: [A-H$_2$O+0.075% TFA; B-ACN] B %: 20%-50%, 20 min]) to give (3aR,4R,5R,7S,8S,9R,9aS,12R)-7-(aminomethyl)-4,7,9,12-tetramethyl-8-((methylsulfonyl)oxy)-3-oxodecahydro-4,9a-propanocyclopenta[8]annulen-5-yl2-((7-fluoro-1-hydroxy-1,3-dihydrobenzo[c][1,2]oxaborol-6-yl)oxy)acetate (242.0 mg, 334.5 μmol, 29.6% yield) as a white solid. $^1$H NMR (DMSO-d$_6$, 400 MHz) δ 9.29 (s, 1H), 7.74 (br. s., 2H), 7.31-7.27 (m, 1H), 7.13 (d, J=8.0 Hz, 1H), 5.32 (d, J=7.2 Hz, 1H), 4.80 (s, 1H), 4.76 (d, J=6.0 Hz, 1H), 4.83-4.72 (m, 3H), 3.41 (s., 1H), 3.24 (s, 3H), 3.02-2.90 (m, 1H), 2.55 (s, 1H), 2.39-2.10 (m, 4H), 1.95-1.80 (m, 1H), 1.75-1.59 (m, 2H), 1.50 (br. s., 1H), 1.34 (s, 8H), 1.16-1.05 (m, 4H), 0.97 (d, J=7.0 Hz, 3H), 0.66 (d, J=6.8 Hz, 3H). MS (ESI): mass calcd. for C$_{31}$H$_{42}$BF$_4$NO$_{11}$S 609.26, m/z found 608.3 [M−H]$^-$. HPLC: 99.9% (220 nm), 100% (254 nm).

51. (3aR,4R,5R,7S,8S,9R,9aS,12R)-8-hydroxy-4,7,9,12-tetramethyl-7-((E)-2-(5-methyl-1,3,4-oxadiazol-2-yl)vinyl)-3-oxodecahydro-4,9a-propanocyclopenta[8]annulen-5-yl 2-((7-fluoro-1-hydroxy-1,3-dihydrobenzo[c][1,2]oxaborol-6-yl)oxy)acetate

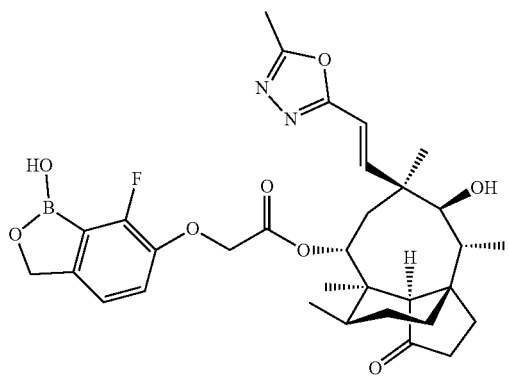

To a mixture of (E)-3-((3aR,4R,5R,7S,8S,9R,9aS,12R)-5-(2-((7-fluoro-1-hydroxy-1,3-dihydrobenzo[c][1,2]oxaborol-6-yl)oxy)acetoxy)-8-hydroxy-4,7,9,12-tetramethyl-3-oxodecahydro-4,9a-propanocyclopenta[8]annulen-7-yl)acrylic acid (500.0 mg, 873.5 μmol, 1.0 eq), HATU (365.3 mg, 960.8 μmol, 1.1 eq) and TEA (176.8 mg, 1.75 mmol, 242.15 uL, 2.00 eq) in DMF (10.00 mL) was added acetohydrazide (129.4 mg, 1.8 mmol, 2.00 eq) in one portion at 25° C. The mixture was stirred at 25° C. for 1 hr. H$_2$O (50 mL) was added the mixture, which was acidified with aqueous HCl (2 M) till PH=5-6 to precipitate a white solid. The reaction mixture was filtered and the cake was washed with 10 mL of H$_2$O, dried to give (3aR,4R,5R,7S,8S,9R,9aS,12R)-7-((E)-3-(2-acetylhydrazinyl)-3-oxoprop-1-en-1-yl)-8-hydroxy-4,7,9,12-tetramethyl-3-oxodecahydro-4,9a-propanocyclopenta[8]annulen-5-yl 2-((7-fluoro-1-hydroxy-1,3-dihydrobenzo[c] [1,2]oxaborol-6-yl)oxy)acetate (500.0 mg, crude) as white solid.

To a mixture of (3aR,4R,5R,7S,8S,9R,9aS,12R)-7-((E)-3-(2-acetylhydrazinyl)-3-oxoprop-1-en-1-yl)-8-hydroxy-4,7,9,12-tetramethyl-3-oxodecahydro-4,9a-propanocyclopenta[8]annulen-5-yl 2-((7-fluoro-1-hydroxy-1,3-dihydrobenzo[c][1,2]oxaborol-6-yl)oxy)acetate (500.0 mg, 795.6 μmol, 1.0 eq) in DCM (10.0 mL) was added TEA (161.0 mg, 1.6 mmol, 220.6 uL, 2.0 eq) and TosCl (151.7 mg, 795.6 μmol, 1.0 eq) in one portion at 25° C. The mixture was stirred at 25° C. for 20 hrs. H$_2$O (30 mL) was added the mixture, which was acidified with aqueous HCl (2 M) till pH=5-6 to precipitate a white solid. The aqueous layer was extracted with EtOAc (50 mL×3). The combined organic layers were washed with brine (10 mL) and dried over Na$_2$SO$_4$. After filtration via filter paper, the organic layer was concentrated under reduced pressure to provide crude product, which was purified by prep-HPLC (column: Luna C18 100×30 mm, 5 μm; liquid phase: [A-TFA/H$_2$O=0.075% v/v; BACN] B %: 33%-63%, 12 min]) and (column: Luna C18 100×30 mm, 5 μm; liquid phase: [A-TFA/H$_2$O=0.075% v/v; B-ACN] B %: 35%-65%, 12 min]). After prep-HPLC purification, the eluent was concentrated to remove organic solvent. The residual aqueous solution was lyophilized to give (3aR,4R,5R,7S,8S,9R,9aS,12R)-8-hydroxy-4,7,9,12-tetramethyl-7-((E)-2-(5-methyl-1,3,4-oxadiazol-2-yl)vinyl)-3-oxodecahydro-4,9a-propanocyclopenta[8]annulen-5-yl 2-((7-fluoro-1-hydroxy-1,3-dihydrobenzo[c][1,2]oxaborol-6-yl)oxy)acetate (20.0 mg, 28.8 μmol, 3.6% yield, 87.9% purity) as white solid. $^1$H NMR (DMSO-d$_6$,400 MHz) δ 7.22 (t, J=8.0 Hz, 1H), 7.09 (d, J=8.0 Hz, 1H), 6.87 (d, J=16.4 Hz, 1H), 6.28 (d, J=16.4 Hz, 1H), 5.59 (d, J=8.0 Hz, 1H), 4.93-4.74 (m, 4H), 3.68 (d, J=5.6 Hz, 1H), 2.44 (s, 1H), 2.28-2.00 (m, 4H), 1.73-1.59 (m, 2H), 1.54-1.44 (m, 1H), 1.42-1.23 (m, 7H), 1.17-0.87 (m, 7H), 0.81 (d, J=7.1 Hz, 3H), 0.63 (d, J=6.6 Hz, 3H). MS (ESI): mass calcd. for C$_{32}$H$_{40}$BFN$_2$O$_8$ 610.3, m/z found 609.3 [M−H]$^-$. HPLC: 87.9% (220 nm), 98.3% (254 nm).

52. (3aR,4R,5R,7S,8S,9R,9aS,12R)-8-hydroxy-4,7,9,12-tetramethyl-7-((E)-2-(3-methyl-1,2,4-oxadiazol-5-yl)vinyl)-3-oxodecahydro-4,9a-propanocyclopenta[8]annulen-5-yl 2-((7-fluoro-1-hydroxy-1,3-dihydrobenzo[c][1,2]oxaborol-6-yl)oxy)acetate

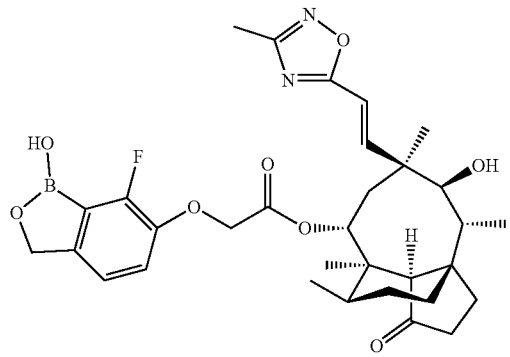

To a mixture of (E)-3-((3aR,4R,5R,7S,8S,9R,9aS,12R)-5-(2-((7-fluoro-1-hydroxy-1,3-dihydro benzo[c][1,2]oxaborol-6-yl)oxy)acetoxy)-8-hydroxy-4,7,9,12-tetramethyl-3-oxodecahydro-4,9a-propanocyclopenta[8]annulen-7-yl)acrylic acid (500.0 mg, 873.5 μmol, 1.0 eq), HATU (365.3 mg, 960.8 μmol, 1.1 eq) and TEA (176.8 mg, 1.7 mmol, 242.2 uL, 2.0 eq) in DMF (5.0 mL) was added N'-hydroxyacetamidine (129.4 mg, 1.7 mmol, 2.0 eq) in one portion at 25° C. The mixture was stirred at 25° C. for 2 hrs. $H_2O$ (50 mL) was added to the mixture, which was acidified with aqueous HCl (2 M) till pH=5-6 to precipitate a white solid. The reaction mixture was filtered and the filter cake was washed with 20 mL of $H_2O$, dried to give (3aR,4R,5R,7S,8S,9R,9aS,12R)-8-hydroxy-7-((E)-3-((Z)—N'-hydroxyacetimidamido)-3-oxoprop-1-en-1-yl)-4,7,9,12-tetramethyl-3-oxodecahydro-4,9a-propanocyclopenta[8]annulen-5-yl 2-((7-fluoro-1-hydroxy-1,3-dihydrobenzo[c] [1,2]oxaborol-6-yl)oxy)acetate (550.0 mg, crude) as white solid.

To a mixture of (3aR,4R,5R,7S,8S,9R,9aS,12R)-8-hydroxy-7-((E)-3-((Z)—N'-hydroxyacetimidamido)-3-oxoprop-1-en-1-yl)-4,7,9,12-tetramethyl-3-oxodecahydro-4,9a-propanocyclopenta[8]annulen-5-yl 2-((7-fluoro-1-hydroxy-1,3-dihydrobenzo[c] [1,2]oxaborol-6-yl)oxy) acetate (500.0 mg, 795.6 µmol, 1.0 eq) in THF (5.0 mL) was added TosCl (303.4 mg, 1.6 mmol, 2.0 eq) and pyridine (314.6 mg, 4.0 mmol, 321.1 uL, 5.0 eq) in one portion at 25° C. The mixture was stirred at 25° C. for 30 hrs. A new peak was detected, and some the starting material remained. $H_2O$ (20 mL) was added to the mixture, which was acidified with aqueous HCl (2 M) till pH=5-6 to precipitate a white solid. The aqueous layer was extracted with EtOAc (20 mL×3). The combined organic layers were washed with brine (10 mL) and dried over $Na_2SO_4$. After filtration via filter paper, the organic layer was concentrated under reduced pressure to provide a crude product, which was purified by prep-HPLC (column: Luna C18 100×30 mm, 5 µm; liquid phase: [A-TFA/$H_2O$=0.075% v/v; BACN] B %: 38%-68%, 12 min]). After prep-HPLC purification, the eluent was concentrated to remove organic solvents. The residual aqueous solution was lyophilized to give (3aR,4R,5R,7S,8S,9R,9aS,12R)-8-hydroxy-4,7,9,12-tetramethyl-7-((E)-2-(3-methyl-1,2,4-oxadiazol-5-yl)vinyl)-3-oxodecahydro-4,9a-propanocyclopenta[8]annulen-5-yl 2-((7-fluoro-1-hydroxy-1,3-dihydrobenzo[c][1,2]oxaborol-6-yl)oxy)acetate (26.0 mg, 38.4 µmol, 4.8% yield, 90.1% purity) as white solid. $^1$H NMR (DMSO-$d_6$, 400 MHz) δ 7.24-7.14 (m, 2H), 7.10-7.02 (m, 1H), 6.32 (d, J=16.3 Hz, 1H), 5.56 (d, J=7.9 Hz, 1H), 4.92-4.83 (m, 2H), 4.82-4.73 (m, 2H), 3.69 (d, J=6.2 Hz, 1H), 2.53 (br. s., 4H), 2.43 (d, J=1.8 Hz, 4H), 2.29 (s, 2H), 2.27-2.04 (m, 3H), 1.75-1.59 (m, 1H), 1.39-1.21 (m, 4H), 1.14 (s, 2H), 1.07-0.97 (m, 1H), 0.96-0.84 (m, 1H), 0.80 (d, J=7.1 Hz, 3H), 0.71 (s, 1H), 0.63 (d, J=7.1 Hz, 3H). MS (ESI): mass calcd. for $C_{32}H_{40}BFN_2O_8$ 610.5, m/z found 609.3 [M–H]$^-$. HPLC: 90.1% (220 nm), 98.6% (254 nm).

Example 2

Antibacterial MIC Assays

All MIC testing of bacteria followed the Clinical and Laboratory Standards Institute (CLSI) guidelines for antimicrobial testing of aerobic bacteria (Methods for Dilution Antimicrobial Susceptibility Tests for Bacteria that Grow Aerobically; Approved Standard Tenth Edition, M07-A10; Performance Standards for Antimicrobial Susceptibility Testing; Twenty-fifth Informational Supplement, M100-S25).

Briefly, the microbroth dilution MIC method was used to quantitatively measure the in vitro antibacterial activity of a compound against a given bacterial isolate. The following bacterial strains were evaluated: *Staphylococcus aureus*, MRSA (ATCC 33591) and *Streptococcus pneumoniae* (ATCC 49619). Bacteria were grown in cation-adjusted Mueller-Hinton broth, with additions as required per species growth requirements (e.g. 3% lysed horse blood for fastidious organisms such as *S. pneumoniae*). A direct colony suspension in saline was prepared from colonies on an overnight agar plate to achieve a turbidity equivalent to 0.5 McFarland standard, which was subsequently diluted into the assay plate to achieve 5×10$^5$ CFU/mL. Assays plates were prepared by 2-fold dilution of compound across the plate and included a positive growth control. After incubation at 35° C. for 16-20 hours, the MIC was determined as the lowest concentration of compound that inhibits growth of the bacteria as detected by the unaided eye.

Anti-*Wolbachia* High-Content Assay $C_{6/36}$ cells (ECACC #89051705, derived from *Aedes albopictus* larvae) were infected with *Wolbachia pipientis* derived from the supernatant of cultured *A. albopictus* Aa23 cells to create a stably *Wolbachia*-infected cell line $C_{6/36}$ (wAlbB). This cell line was subpassaged 6-8 days prior to plating out at a density of 2000 viable cells per well in a 384-well CellCarrier plate suspended in Liebovitz media supplemented with 20% fetal bovine serum, 2% tryptose phosphate broth and 1% non-essential amino acids. Compounds were dissolved and diluted in DMSO, and compound solution was added to each well to provide a final DMSO concentration <1% and a total volume of 100 µL per well.

Following 7 days of sterile incubation at 26° C., staining media containing SYTO 11 DNA dye was added to each well. After 15 minutes, all media was removed from each well and fresh media (no stain) was added. Imaging of each well was accomplished using a Perkin Elmer Operetta high-content imaging system. Five fields per well were imaged using a confocal 60× objective with the Fluorescein filter (excitation filter: 460-490 nm; emission filter: 500-550 nm). Images were analyzed using the Perkin Elmer Harmony software to score each intact cell on the basis of texture complexity of the cytoplasm. Full details can be found in: Clare, R. H. et al, J. Biomol. Screening, 2015, 20, 64-49.

Compound sample wells were analyzed and normalized (along with the positive controls) against the vehicle (untreated) control to give a percentage reduction of *Wolbachia*-infected cells. Using the cell number analysis, compounds with a host cell number amounting to less than 50% of the vehicle control were classified as toxic and retested at a reduced compound concentration. Dose-response curves were generated with percentage reduction of *Wolbachia*-infected cells versus compound concentration, using 5-10 compound serial dilutions. Data were analyzed and compound EC$_{50}$s determined using a 4 parameter logistic non-linear regression model. EC$_{50}$ is defined as the compound concentration producing a 50% reduction of *Wolbachia* in the $C_{6/36}$ cell line.

Antibacterial testing results for exemplary compounds of the invention are provided below. Units for MIC are µg/mL. Units for EC50 are µM. MIC of ≤0.25 is A, 0.5-2 is B, 4-32 is C, and ≥64 is D.

| Compound # | MIC *Staphylococcus aureus*, MRSA (ATCC 33591) | MIC *Streptococcus pneumoniae* (ATCC 49619) | EC50 *Wolbachia pipientis* in C6/36 cell line |
|---|---|---|---|
| 1. | B | C | >1 |
| 2. | C | C | >1 |
| 3. | B | B | >1 |
| 4. | B | B | 0.283 |
| 5. | B | B | 0.305 |

-continued

| Compound # | MIC Staphylococcus aureus, MRSA (ATCC 33591) | MIC Streptococcus pneumoniae (ATCC 49619) | EC50 Wolbachia pipientis in C6/36 cell line |
|---|---|---|---|
| 6. | B | B | 0.392 |
| 7. | C | B | |
| 8. | C | B | |
| 9. | C | C | |
| 10. | A | B | |
| 11. | A | B | |
| 12. | A | A | 0.081 |
| 13. | C | D | >1 |
| 14. | B | B | |
| 15. | B | B | |
| 16. | C | B | |
| 17. | C | B | |
| 18. | C | B | |
| 19. | A | B | 0.038 |
| 20. | A | B | 0.101 |
| 21. | A | B | |
| 22. | A | B | |
| 23. | A | C | >1 |
| 24. | A | C | |
| 25. | B | C | |
| 26. | A | C | |
| 27. | A | B | 0.148 |
| 28. | D | D | >1 |
| 29. | A | C | |
| 30. | B | C | |
| 31. | A | B | 0.278 |
| 32. | B | C | >1 |
| 33. | B | C | 0.328 |
| 34. | C | C | 0.474 |
| 35. | C | C | 0.357 |
| 36. | B | C | 0.116 |
| 37. | B | C | 0.372 |
| 38. | B | C | |
| 39. | C | C | |
| 40. | C | D | |
| 41. | C | C | |
| 42. | C | D | |
| 43. | A | C | >1 |
| 44. | A | C | 0.197 |
| 45. | B | C | |
| 46. | B | C | |
| 47. | B | C | >1 |
| 48. | B | C | >1 |
| 49. | C | D | >1 |
| 50. | C | C | |
| 51. | B | B | |
| 52. | A | A | |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A compound, or a salt or a hydrate or a solvate thereof, having a structure which is:

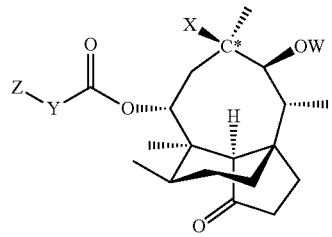

wherein
W is H or a bond to X;
X is

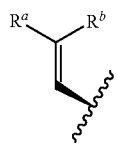

wherein
$R^a$ and $R^b$ are each independently selected from the group consisting of $R^{15}$, $-OR^{15}$, $-NR^{15}R^{16}$, $-SR^{15}$, $-S(O)R^{15}$, $-S(O)_2R^{15}$, $-S(O)_2NR^{15}R^{16}$, $-C(O)R^{15}$, $-C(O)OR^{15}$, and $-C(O)NR^{15}R^{16}$,
wherein $R^{15}$ and $R^{16}$ are each independently selected from the group consisting of H, halogen, cyano, nitro, $-OR^{17}$, $-NR^{17}R^{18}$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl,
wherein $R^{17}$ and $R^{18}$ are each independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl,
and wherein $R^{15}$ and $R^{16}$, and/or $R^{17}$ and $R^{18}$, along with the nitrogen to which they are connected, are optionally joined to form a substituted or unsubstituted 4- to 8-membered ring,
with the proviso that $R^a$ and $R^b$ are not both H;
or X is

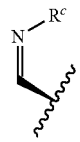

wherein
$R^c$ is $-OR^{15}$, $-NR^{15}R^{16}$, $-SR^{15}$, $-S(O)R^{15}$, $-S(O)_2R^{15}$, $-S(O)_2NR^{15}R^{16}$, $-C(O)R^{15}$, $-C(O)OR^{15}$, and $-C(O)NR^{15}R^{16}$,
wherein $R^{15}$ and $R^{16}$ are each independently selected from the group consisting of H, halogen, cyano, nitro, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, and wherein $R^{15}$ and $R^{16}$, along with the nitrogen to which they are connected, are optionally joined to form a substituted or unsubstituted 4- to 8-membered ring;

or X is

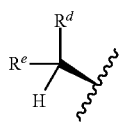

wherein
$R^d$ and $R^e$ are each independently selected from the group consisting of H, halogen, cyano, nitro, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, —$OR^{15}$, —$NR^{15}R^{16}$, —$S(O)R^{15}$, —$S(O)_2R^{15}$, —$S(O)_2NR^{15}R^{16}$, —$C(O)R^{15}$, —$C(O)OR^{15}$, and —$C(O)NR^{15}R^{16}$—, wherein $R^{15}$ and $R^{16}$ are each independently selected from the group consisting of H, halogen, cyano, nitro, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl, and wherein $R^d$ and $R^e$, along with the atom to which they are connected, are optionally joined to form a substituted or unsubstituted 3- to 8-membered ring, and wherein $R^{15}$ and $R^{16}$, along with the nitrogen to which they are connected, are optionally joined to form a substituted or unsubstituted 4- to 8-membered ring, with the proviso that $R^d$ and $R^e$ are not both H,
wherein X optionally comprises an attachment point to W;
Y is selected from the group consisting of a bond, —O—, —S—, —NH—, substituted or unsubstituted alkylene, and substituted or unsubstituted heteroalkylene;
Z is a substituted or unsubstituted heterocyclic ring or ring system containing at least one endocyclic boron; and
the substituted alkyl, substituted heteroalkyl, substituted cycloalkyl, substituted heterocycloalkyl, substituted alkylene, substituted heteroalkylene, s substituted aryl, and substituted heteroaryl are respectively alkyl, heteroalkyl, cycloalkyl, heterocycloalkyl, aryl, and heteroaryl respectively substituted with one or more substituents selected from the group consisting of —R', —OR', =O, NR', =N—OR', —NR'R", —SR', halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR""—C(NR'R"R'")=NR"", —NR""—C(NR'R")=NR'", —S(O)R', —S(O)$_2$R', —S(O)$_2$NR'R", —NR"SO$_2$R', —CN, —NO$_2$, —CH(Ph)$_2$, fluoro($C_1$-$C_4$)alkoxy, and fluoro($C_1$-$C_4$)alkyl, wherein R', R", R'", R"" and R""' are each independently selected from the group consisting of hydrogen, substituted or unsubstituted heteroalkyl, substituted or unsubstituted aryl, aryl substituted with 1-3 halogens, substituted or unsubstituted alkyl, alkoxy or thioalkoxy groups, and arylalkyl groups.

2. The compound of claim 1, or a salt or a hydrate or a solvate thereof, wherein said X is

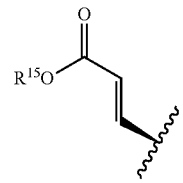

wherein
$R^{15}$ is selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

3. The compound of claim 1, or a salt or a hydrate or a solvate thereof, wherein said X is

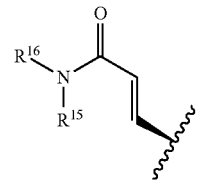

wherein
$R^{15}$ and $R^{16}$ are each independently selected from the group consisting of H, —$NR^{17}R^{18}$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl
wherein $R^{17}$ and $R^{18}$ are each independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl
and wherein $R^{15}$ and $R^{16}$, and/or $R^{17}$ and $R^{18}$, along with the nitrogen to which they are connected, are optionally joined to form a substituted or unsubstituted 4- to 8-membered ring.

4. The compound of claim 1, or a salt or a hydrate or a solvate thereof, wherein said X is

wherein
R$^c$ is selected from the group consisting of H, substituted or unsubstituted alkyl, and —OR$^{15}$
wherein R$^{15}$ is H or substituted or unsubstituted alkyl.

5. The compound of claim 1, or a salt or a hydrate or a solvate thereof, wherein said X is

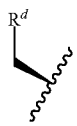

wherein
R$^d$ is selected from the group consisting of halogen, substituted or unsubstituted alkyl, substituted or unsubstituted heterocycloalkyl, substituted or unsubstituted aryl, —OR$^{15}$, —SR$^{15}$, —S(O)R$^{15}$, —NR$^{15}$R$^{16}$, —C(O)R$^{15}$, —CH$_2$C(O)OR$^{15}$, and —CH$_2$C(O)NR$^{15}$R$^{16}$
wherein R$^{15}$ and R$^{16}$ are each independently selected from the group consisting of H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl
and wherein R$^{15}$ and R$^{16}$, along with the nitrogen to which they are connected, are optionally joined to form a substituted or unsubstituted 4- to 8-membered ring.

6. The compound of claim 5, or a salt or a hydrate or a solvate thereof, wherein R$^d$ comprises said attachment point to W.

7. The compound of claim 1, or a salt or a hydrate or a solvate thereof, wherein said Y is *—OCH$_2$— or *—SCH$_2$— or *—NHCH$_2$— or *—CH$_2$NH— or *—C(O)NH—, wherein * represents the attachment point to said Z.

8. The compound of claim 1, or a salt or a hydrate or a solvate thereof, wherein said Z is selected from the group consisting of substituted or unsubstituted benzoxaborole, substituted or unsubstituted pyridinyloxaborole, substituted or unsubstituted benzoxaborininol, substituted or unsubstituted benzoxazaborininol, substituted or unsubstituted benzodiazaborininol, and substituted or unsubstituted oxaborole.

9. The compound of claim 8, or a salt or a hydrate or a solvate thereof, wherein said Z is

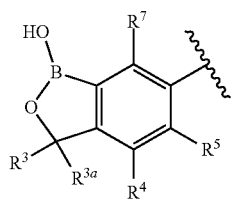

wherein
R$^3$, R$^{3a}$, R$^4$, R$^5$, and R$^7$ are each independently selected from the group consisting of R$^{10}$, —OR$^{10}$, —NR$^{10}$R$^{11}$, —SR$^{10}$, —S(O)R$^{10}$, —S(O)$_2$R$^{10}$, —S(O)$_2$NR$^{10}$R$^{11}$, —C(O)R$^{10}$, —C(O)OR$^{10}$, and —C(O)NR$^{10}$R$^{11}$ wherein
R$^{10}$ and R$^{11}$ are each independently selected from the group consisting of H, halogen, cyano, nitro, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

10. The compound of claim 9, or a salt or a hydrate or a solvate thereof, wherein said Z is

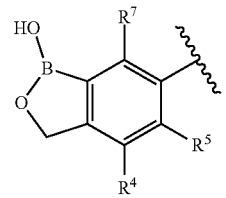

wherein
R$^4$, R$^5$, and W are each independently selected from the group consisting of R$^{10}$, —OR$^{10}$, —NR$^{10}$R$^{11}$,
wherein
R$^{10}$ and R$^{11}$ are each independently selected from the group consisting of H, halogen, cyano, nitro, substituted or unsubstituted alkyl, and substituted or unsubstituted heteroalkyl.

11. The compound of claim 10, or a salt or a hydrate or a solvate thereof, wherein said Z is

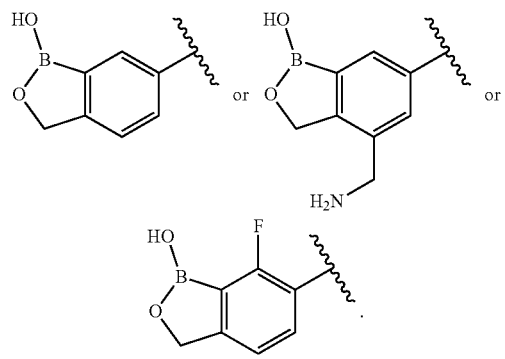

12. A combination comprising the compound of claim 1, or a pharmaceutically acceptable salt thereof, together with at least one other therapeutically active agent.

13. The combination of claim 12, or a pharmaceutically acceptable salt or a hydrate or a solvate thereof, wherein the other therapeutically active agent is an anti-bacterial agent.

14. A pharmaceutical formulation comprising:
a) the compound of claim 1, or a pharmaceutically acceptable salt or a hydrate or a solvate thereof; and
b) a pharmaceutically acceptable excipient.

15. A method of inhibiting protein synthesis in a bacteria, the method comprising contacting the bacteria with the compound of claim 1, or a pharmaceutically acceptable salt or a hydrate or a solvate thereof, thereby inhibiting protein synthesis in the bacteria.

16. A method of inhibiting the growth of and/or killing a bacteria, the method comprising contacting the bacteria with the compound of claim 1, or a pharmaceutically acceptable salt or a hydrate or a solvate thereof, thereby inhibiting the growth of and/or killing the bacteria.

17. The method of claim 15, wherein the bacteria is Gram-positive.

18. The method of claim 17, wherein the bacteria is selected from the group consisting of *Staphylococcus aureus, Streptococcus pneumoniae*, methicillin-resistant *Staphylococcus aureus, Wolbachia pipientis*, and bacteria of the *Wolbachia* genus.

19. A method of treating a disease associated with a Gram-positive bacteria, and/or a worm in an animal, the method comprising administering to the animal a therapeutically effective amount of the compound of claim 1, or a pharmaceutically acceptable salt or a hydrate or a solvate thereof, thereby treating the disease.

20. The method of claim 19, wherein the disease is associated with a Gram-positive bacteria.

21. The method of claim 19, wherein the disease is selected from the group consisting of pneumonia, hospital-acquired pneumonia, hospital-associated pneumonia, community-acquired pneumonia, acute bacterial skin and skin-structure infection (ABSSSI), bacteremia, endocarditis, osteomyelitis, gastroenteritis, toxic shock syndrome, meningitis, septic arthritis, urinary tract infection, skin and skin-structure infection, strep throat, necrotizing fasciitis, otitis media, sinusitis, actinomycosis, diptheria, anthrax, food poisoning, botulism, tetanus, gas gangrene, diarrhea, tuberculosis, leprosy, candidiasis, aspergillosis, coccidioidomycosis, cryptococcosis, histoplasmosis, blastomycosis, paracoccidioidomycosis, zygomycosis, phaeohyphomycosis, rhinosporidiosis, enterobiasis, filariasis, lymphatic filariasis, bancroftian filariasis, subcutaneous filariasis, serious cavity filariasis, elephantiasis, elephantiasis tropica, lymphadenitis, lymphangitis, lymphedema, and onchocerciasis.

* * * * *